United States Patent
Desnoyers et al.

(10) Patent No.: US 10,568,977 B2
(45) Date of Patent: Feb. 25, 2020

(54) ANTIBODIES THAT BIND ACTIVATABLE ANTIBODIES AND METHODS OF USE THEREOF

(71) Applicant: CytomX Therapeutics, Inc., South San Francisco, CA (US)

(72) Inventors: Luc Roland Desnoyers, San Francisco, CA (US); Tony W. Liang, San Mateo, CA (US); Annie Yang Weaver, San Mateo, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/660,215

(22) Filed: Jul. 26, 2017

(65) Prior Publication Data

US 2017/0326260 A1  Nov. 16, 2017

Related U.S. Application Data

(62) Division of application No. 14/567,467, filed on Dec. 11, 2014, now Pat. No. 9,737,623.

(60) Provisional application No. 61/914,489, filed on Dec. 11, 2013.

(51) Int. Cl.

| | | |
|---|---|---|
| G01N 33/53 | (2006.01) | |
| G01N 33/68 | (2006.01) | |
| C07K 16/42 | (2006.01) | |
| C07K 16/28 | (2006.01) | |
| A61K 51/10 | (2006.01) | |
| C07K 16/00 | (2006.01) | |
| A61K 39/00 | (2006.01) | |

(52) U.S. Cl.
CPC .......... *A61K 51/1078* (2013.01); *C07K 16/00* (2013.01); *C07K 16/2896* (2013.01); *C07K 16/42* (2013.01); *C07K 16/4291* (2013.01); *G01N 33/6854* (2013.01); *A61K 2039/505* (2013.01); *C07K 16/2863* (2013.01); *C07K 2317/24* (2013.01); *C07K 2317/34* (2013.01); *C07K 2317/76* (2013.01); *C07K 2319/00* (2013.01); *C07K 2319/50* (2013.01)

(58) Field of Classification Search
CPC ......... A61K 51/1078; A61K 2039/505; G01N 33/6854; C07K 16/42; C07K 2319/50; C07K 2319/00; C07K 2317/76; C07K 16/2863; C07K 2317/24
See application file for complete search history.

(56) References Cited

U.S. PATENT DOCUMENTS

| | | | |
|---|---|---|---|
| 4,522,811 A | 6/1985 | Eppstein et al. | |
| 5,525,491 A | 6/1996 | Huston et al. | |
| 7,465,790 B2 | 12/2008 | Waldmann et al. | |
| 7,666,817 B2 | 2/2010 | Daugherty et al. | |
| 8,034,959 B2 | 10/2011 | Ng et al. | |
| 8,226,945 B2 | 11/2012 | Ebens et al. | |
| 8,809,504 B2 | 8/2014 | Lauermann | |
| 8,895,702 B2 | 11/2014 | Williams et al. | |
| 9,120,853 B2 | 9/2015 | Lowman et al. | |
| 9,540,440 B2 | 1/2017 | Lowman et al. | |
| 9,545,442 B2 | 1/2017 | Lowman et al. | |
| 9,737,623 B2 | 8/2017 | Desnoyers et al. | |
| 9,889,211 B2 | 2/2018 | Lowman et al. | |
| 2002/0016481 A1 | 2/2002 | Sasaki et al. | |
| 2002/0016484 A1 | 2/2002 | Sasaki et al. | |
| 2002/0127564 A1 | 9/2002 | Nolan | |
| 2004/0109855 A1 | 6/2004 | Waldmann et al. | |
| 2007/0213511 A1 | 9/2007 | Kunz et al. | |
| 2008/0114153 A1 | 5/2008 | Steeves et al. | |
| 2008/0175847 A1 | 7/2008 | Yan et al. | |
| 2009/0148905 A1 | 6/2009 | Ashman et al. | |
| 2009/0304719 A1 | 12/2009 | Daugherty et al. | |
| 2010/0189651 A1 | 7/2010 | Stagliano et al. | |
| 2010/0189727 A1 | 7/2010 | Rodeck et al. | |
| 2011/0178279 A1 | 7/2011 | Williams et al. | |
| 2013/0004481 A1 | 1/2013 | Solca et al. | |
| 2013/0060010 A1 | 3/2013 | Williams et al. | |

FOREIGN PATENT DOCUMENTS

| | | | |
|---|---|---|---|
| EA | 2010/00704 A1 | 12/2010 | |
| EP | 1324771 B1 | 6/2011 | |
| JP | 2003-530852 A | 10/2003 | |
| WO | WO 94/11026 A2 | 5/1994 | |
| WO | WO 97/31024 A1 | 8/1997 | |
| WO | WO 98/11126 A1 | 3/1998 | |
| WO | WO 2001/79271 A1 | 10/2001 | |
| WO | WO 2001/79480 A1 | 10/2001 | |
| WO | WO 01/91798 A2 | 12/2001 | |
| WO | WO 2007/008712 A2 | 1/2007 | |
| WO | WO 2007/105027 A1 | 9/2007 | |
| WO | WO 2008/101177 A2 | 8/2008 | |

(Continued)

OTHER PUBLICATIONS

Yu et al., Investigative Ophthalmology & Visual Science 49(2):522-527 (Year: 2008).*
Lloyd et al., Protein Engineering, Design & Selection 22: 159-168 (Year: 2009).*
Edwards et al., J Mol Biol 334(1): 103-118 (Year: 2003).*
Paul, Fundamental Immunology, (textbook), pp. 292-295 (Year: 1993).*
Rudikoff et al., Proc. Natl. Acad. Sci. USA vol. 79 p. 1979-1983 (Year: 1982).*
Affara N., et al. "Delineating protease functions during cancer development", Methods Mol Biol, (2009), 539:1-32.

(Continued)

*Primary Examiner* — Phuong Huynh

(74) *Attorney, Agent, or Firm* — Cooley LLP; Ivor R. Elrifi; Madhuri Roy

(57) ABSTRACT

The invention relates generally to antibodies and antigen-binding fragments thereof that bind activatable antibodies and/or conjugated activatable antibodies and methods of making and using these antibodies that bind activatable antibodies and/or conjugated activatable antibodies.

20 Claims, 5 Drawing Sheets

Specification includes a Sequence Listing.

(56) References Cited

FOREIGN PATENT DOCUMENTS

| | | |
|---|---|---|
| WO | WO 2009/011572 A1 | 1/2009 |
| WO | WO 2009/025846 A2 | 2/2009 |
| WO | WO 2009/068649 A2 | 6/2009 |
| WO | WO 2009/140242 A1 | 11/2009 |
| WO | WO 2010/081173 A2 | 7/2010 |
| WO | WO 2010/129609 A2 | 11/2010 |
| WO | WO 2011/109789 A2 | 9/2011 |
| WO | WO 2013/043071 A1 | 3/2013 |
| WO | WO 2013/163631 A2 | 10/2013 |
| WO | WO 2014/107599 A2 | 7/2014 |
| WO | WO 2014/197612 A1 | 12/2014 |
| WO | WO 2015/013671 A1 | 1/2015 |

OTHER PUBLICATIONS

Azzopardi et al. "Cetuximab Pharmacokinetics Influences Progression-Free Survival of Metastatic Colorectal Cancer Patients", *Clinical Cancer Research*, (2011), vol. 17: 6329-37.

Baselga et al. "Phase I Studies of Anti-Epidermal Growth Factor Receptor Chimeric Antibody C225 Alone and in Combination with Cisplatin", Journal of Clinical Oncology, (2000), vol. 18(4): 904-914.

Benjamin R. et al. "Tolerance to rat monoclonal antibodies. Implications for serotherapy", *J Exp Med.*, (1986), 163(6):1539-52.

Boulware, J. et al. "Evolutionary optimization of peptide substrates for proteases that exhibit rapid hydrolysis kinetics", *Biotechnol Bioeng.*, (2010), 106.3:339-46 Article first published online: Feb. 10, 2010.

Brinks et al. "Preclinical models Used for Immunogenicity Prediction of Therapeutic Proteins", *Pharm. Res*, (May 2013), 30, pp. 1719-1728.

Chiller J. et al. "Cellular events during induction of immunologic unresponsiveness in adult mice", *J Immunol.*, (Jun. 1971), 106(6):1647-53.

Chirinos-Rojas C. et al. "Use of a solid-phase random peptide library to identify inhibitors of TNF-alpha mediated cytotoxicity in vitro", *Cytokine*, (Apr. 1997), 9(4):226-32.

Cwirla S. et al. "Peptides on phage: a vast library of peptides for identifying ligands", *Proc Natl Acad Sci USA*, (Aug. 1990), 87(16):6378-82.

Darragh et al., "Tumor detection by imaging proteolytic activity", *Cancer Res*, (2010), 70: 1505-1512.

Donaldson J. et al. "Design and Development of Masked Therapeutic Antibodies to Limit Off-target Effects", *Cancer Biol Ther*, (Nov. 7, 2009), vol. 8, No. 22 p. 2147-2152.

Francisco et al., "cAC10-vcMMAE, an anti-CD30-monomethyl auristatin E conjugate with potent and selected antitumor activity." *Blood*, (2003), 102:1458-1465.

Geysen H. et al. "Strategies for epitope analysis using peptide synthesis", *J Immunol Methods*, (Sep. 24, 1987), 102(2):259-74.

Gilliland L. et al. "Elimination of the immunogenicity of therapeutic antibodies", *J Immunol*, (Mar. 15, 1999), 162(6):3663-71.

Goldstein et al. "Biological Efficacy of a Chimeric Antibody to the Epidermal Growth Factor Receptor in a Human Tumor Xenograft", Model. Clin. Cancer Research, (1995), vol. 1:1311-18.

Gravanis I. et al. "The European Medicines Agency review of ofatumumab (Arzerra®) for the treatment of chronic lymphocytic leukemia in patients refractory to fludarabine and alemtuzumab: summary of the scientific assessment of the European medicines agency committee for medicinal products for human use", *Oncologist*, (2010), 15(12):1335-43.

Hale G. "Synthetic peptide mimotope of the CAMPATH-1 (CD52) antigen, a small glycosylphosphatidylinositol-anchored glycoprotein", *Immunotechnology*, (1995), 1(3-4):175-87.

Holliger P. "Diabodies: small bivalent and bispecific antibody fragments" *Proc Natl Acad Sci USA*, (Jul. 15, 1993), 90(14):6444-8.

Huston J. et al. "Protein engineering of antibody binding sites: recovery of specific activity in an anti-digoxin single-chain Fv analogue produced in *Escherichia coli*", *Proc Natl Acad Sci USA*, (Aug. 1988), 85(16):5879-83.

Hutchinson E., "Developing patterns", *Nature Rev Cancer*, (2006), vol. 6.

Hynes, N. et al. "ErbB receptors and signaling pathways in cancer", *Curr Opin Cell Biol*, (2009), 21, pp. 177-184.

Irving, "Probodies Empower a New Generation of Antibody Immunotherapies," presented at Keystone Symposia on Molecular and Cellular Biology, Feb. 2015.

James L. et al. "1.9 A structure of the therapeutic antibody CAMPATH-1H fab in complex with a synthetic peptide antigen", *J Mol Biol*, (Jun. 4, 1999), 289(2):293-301.

Jensen-Jarolim E "Peptide mimotopes displayed by phage inhibit antibody binding to bet v 1, the major birch pollen allergen, and induce specific IgG response in mice", *FASEB J.*, (Dec. 1998), 12(15):1635-42.

Katz B. "Structural and mechanistic determinants of affinity and specificity of ligands discovered or engineered by phage display", *Annu Rev Biophys Biomol Struct*, (1997), 26:27-45.

Krieckaert et al. "Methotrexate reduces immunogenicity in adalimumab treated rheumatoid arthritis patients in a dose dependent manner", *Ann Rheum. Dis.*, (2012), 71(11), p. 1914.

Krieckaert C. et al. "Therapy: Immunogenicity of biologic therapies—we need tolerance", *Nat Rev Rheumatol.*, (2010), 6(10):558-9.

Leitner A. et al. "A mimotope defined by phage display inhibits IgE binding to the plant *Panallergen profilin*", *Eur J Immunol.*, (Sep. 1998), 28(9):2921-7.

Li S et al. "Structural Basis for Inhibition of the Epidermal Growth Factor Receptor by Cetuximab", *Cancer Cell*, (Apr. 1, 2005), vol. 7, No. 4 p. 301-311.

Lichtenstein, "Comprehensive review:antitumor necrosis factor agents in inflammatory bowel disease and factors implicated in treatment response", *Ther Adv Gastroenterol*, (2013), 6(4) pp. 269-293.

Mitchison N. "The dosage requirements for immunological paralysis by soluble proteins", *Immunology*, (1968), 15(4):509-30.

Mook O. et al. "In situ localization of gelatinolytic activity in the extracellular matrix of metastases of colon cancer in rat liver using quenched fluorogenic DQ-gelatin", *J Histochem Cytochem*, (2003), 51: 821-829.

Moore J. "Antibodies to discontinuous or conformationally sensitive epitopes on the gp120 glycoprotein of human immunodeficiency virus type 1 are highly prevalent in sera of infected humans", *J Virol*, (1993), 67(2):863-75.

Murthy R., et al. "Legumain expression in relation to clinicopathologic and biological variables in colorectal cancer", *Clin Cancer Res*, 11 (2005): 2293-2299.

NCI Cancer Drug Information, Cetuximab, 2006, http://www.cancer.gov/cancertopics/duginfo/cetuximab, downloaded Jul. 18, 2014.

NEB website http://www.neb.com/neb/products/phd/phd.html, downloaded Jan. 11, 2012.

Nelson et al. "Development trends for human monoclonal antibody therapeutics", *Nature Reviews*, (2010), vol. 9:767-774.

Nielsen B., et al. "Urokinase plasminogen activator is localized in stromal cells in ductal breast cancer", *Lab Invest*, (2001), 81: 1485-1501.

Pirker et al., "Cetuximab plus chemotherapy in patients with advanced non-small-cell lung cancer (FLEX): an open-label randomized phase III trial", *Lancet*, (2009), vol. 373:1525-31.

Roitt I. et al., "Immunochemical Techniques", *Roitt's Essential Immunology* (Tenth Edition), Chapter 6, (2001), pp. 118-120.

Scott J. et al. "Searching for peptide ligands with an epitope library", *Science*, (Jul. 27, 1990), 249(4967):386-90.

Segaert et al. "Clinical signs, pathophysiology and management of skin toxicity during therapy with epidermal growth factor receptor inhibitors", *Ann Oncol.*, (2005), 16(9):1425-33.

Sethu et al. "Immunogenicity to Biologics: Mechanisms, Prediction and Reduction", *Arch. Immunol. Ther. Exp.*, (2012, Warszawa) 60, pp. 331-344.

Smith et al., "Phage Display", *Chem. Rev.*, (1997), 97, pp. 391-410.

(56) References Cited

OTHER PUBLICATIONS

Tabanero et al. "Pharmacogenomic and Pharmacoproteomic Studies of Cetuximab in Metastatic Colorectal Cancer Biomarker Analysis of a Phase I Dose-Escalation", *Study. J. Clin. Oncol.*, (2010), vol. 28(7):1181-89.

Weigle W. "Recent observations and concepts in immunological unresponsiveness and autoimmunity", *Clin Exp Immunol*, (Oct. 1971), 9(4):437-47.

Wolbink G. et al. "Dealing with immunogenicity of biologicals: assessment and clinical relevance", *Curr Opin Rheumatol*, (May 2009), 21(3):211-5.

Yan et al. "Antibody Based Therapy for Solid Tumors", *The Cancer Journal*, (2008), vol. 14 (3):178-183.

Yang Y. et al. "Generation and characterization of a target-selectively activated antibody against epidermal growth factor receptor with enhanced anti-tumor potency", *MAbs.* (2015), 7(2):440-50.

Bagshawe, K.D. (2006) "Antibody-directed enzyme prodrug therapy (ADEPT) for cancer" *Expert Rev Anticancer Ther*, 6(10):1421-1431.

"Cetuximab" (Updated Aug. 17, 2016) DrugBank Accession No. DB00002 [online]. Retrieved from: http://www.drugbank.ca/drugs/DB00002, on Dec. 16, 2016, 10 pages.

Chung, C.H. et al. (2008) "Cetuximab-induced anaphylaxis and lgE specific for galactose-alpha-1,3-galactose" *New England Journal of Medicine*, 358(11):1109-1117.

Desnoyers, L.R. et al. (Oct. 16, 2013) "Tumor-specific activation of an EGFR-targeting probody enhances therapeutic index" [online]. Retrieved from the Internet: www.sciencetranslationalmedicine.org, vol. 5, issue 207, 207ra144, 10 pages.

Desnoyers, L.R. et al. (Apr. 15, 2013) "Abstract 4570: Development of a proteolytically activatable EGFR Probody for cancer therapy" [online]. Retrieved from the Internet: http://cancerres.aacrjournals.org/content/73/8_Supplement/4570, on Oct. 15, 2015, 2 pages.

Dubel, S. (Ed.) *Handbook of Therapeutic Antibodies*. vol. 1, 2007, Wiley-VCH Verlag GmbH & Co. KGaA, Weinheim; pp. 95-102 and 119-126.

Kabat, E.A. et al. *Sequences of Proteins of Immunological Interest*. 5th Edition, vol. 1., NIH Publication 91-3242, 1991; pp. 310, 662.

Leibiger, H. et al. (1999) "Variable domain-linked oligosaccharides of a human monoclonal IgG: structure and influence on antigen binding" *Biochem J*, 338:529-538.

Morgan, C. and D. Fernandes (Oct. 2, 2009) "Designing Biobetter Monoclonal Antibody Therapeutics by Glycoengineering" [online]. Retrieved from the Internet: http://www.ludger.com/articles/ludger-m-00308-intpharmind-2009-biobetter-mAbs.pdf, 5 pages.

Schwarz, F. and M. Aebi (2011) "Mechanisms and principles of N-linked protein glycosylation" *Current Opinion In Structural Biology*, 21(5):576-582.

Wright, A. et al. (1991) "Antibody variable region glycosylation: position effects on antigen binding and carbohydrate structure" *The EMBO Journal*, 10(10):2717-2723.

Zeitlin, L. et al. (Dec. 20, 2011) "Enhanced potency of a fucose-free monoclonal antibody being developed as an Ebola virus immunoprotectant" *PNAS*, 108(51):20690-20694.

Zhong, X. and W. Somers (Feb. 4, 2012) "Recent Advances in Glycosylation Modifications in the Context of Therapeutic Glycoproteins" Chapter 10 in *Integrative Proteomics*.Dr. Hon-Chiu Leung (Ed.), InTech; pp. 184-196.

\* cited by examiner

ANTIBODIES THAT BIND ACTIVATABLE ANTIBODIES AND METHODS OF USE THEREOF

RELATED APPLICATIONS

This application is a divisional of U.S. patent application Ser. No. 14/567,467, filed Dec. 11, 2014, now U.S. Pat. No. 9,737,623, issued Aug. 22, 2017, which claims the benefit of U.S. Provisional Application No. 61/914,489, filed Dec. 11, 2013, the contents of each of which are incorporated herein by reference in its entirety.

INCORPORATION OF SEQUENCE LISTING

The contents of the text file named "CYTM_033D01US_ST25.txt," which was created on Jul. 26, 2017 and is 365 KB in size, are hereby incorporated by reference in their entirety.

FIELD OF THE INVENTION

The invention relates generally to antibodies and antigen-binding fragments thereof that bind activatable antibodies and/or conjugated activatable antibodies and methods of making and using these antibodies that bind activatable antibodies and/or conjugated activatable antibodies.

BACKGROUND OF THE INVENTION

Modified antibody-based therapies such as masked antibodies and activatable antibodies have proven effective treatments for a variety of diseases.

Accordingly, there exists a need for reagents to detect the level of such modified antibody-based therapeutics and to detect whether the modified antibody-based therapeutic is in an activated or non-activated state.

SUMMARY OF THE INVENTION

The invention provides antibodies and antigen-binding fragments thereof that bind one or more activatable antibodies that include an antibody or antigen-binding fragment thereof (AB) that specifically binds a target coupled to a masking moiety (MM), such that coupling of the MM reduces the ability of the antibody or antigen-binding fragment thereof to bind the target. In some embodiments, the MM is coupled to the AB via a sequence that includes a substrate for a protease, for example, a protease that is co-localized with the target at a treatment site in a subject. This substrate sequence is also referred to herein as a cleavable moiety (CM) sequence, and the terms substrate and CM are used interchangeably throughout.

In some embodiments, antibodies and antigen-binding fragments thereof of the disclosure bind one or more activatable antibodies that include an antibody or antigen-binding fragment thereof (AB) that specifically binds epidermal growth factor receptor (EGFR) coupled to a masking moiety (MM), such that coupling of the MM reduces the ability of the antibody or antigen-binding fragment thereof to bind EGFR. In some embodiments, the MM is coupled to the AB via a sequence that includes a substrate for a protease, for example, a protease that is co-localized with EGFR at a treatment site in a subject.

In some embodiments, antibodies and antigen-binding fragments thereof of the disclosure bind one or more activatable antibodies that include an antibody or antigen-binding fragment thereof (AB) that specifically binds a Jagged target, e.g., Jagged 1 and/or Jagged 2, coupled to a masking moiety (MM), such that coupling of the MM reduces the ability of the antibody or antigen-binding fragment thereof to bind the Jagged target. In some embodiments, the MM is coupled to the AB via a sequence that includes a substrate for a protease, for example, a protease that is co-localized with the Jagged target at a treatment site in a subject.

In some embodiments, antibodies and antigen-binding fragments thereof of the disclosure bind one or more activatable antibodies that include an antibody or antigen-binding fragment thereof (AB) that specifically binds interleukin 6 receptor (IL-6R) coupled to a masking moiety (MM), such that coupling of the MM reduces the ability of the antibody or antigen-binding fragment thereof to bind IL-6R. In some embodiments, the MM is coupled to the AB via a sequence that includes a substrate for a protease, for example, a protease that is co-localized with IL-6R at a treatment site in a subject.

The invention provides antibodies that bind conjugated activatable antibodies that include an antibody or antigen-binding fragment thereof (AB) that specifically binds a target coupled to a masking moiety (MM), such that coupling of the MM reduces the ability of the antibody or antigen-binding fragment thereof to bind the target, and wherein the activatable antibody is conjugated to one or more additional agents. In some embodiments of the conjugated activatable antibodies, the MM is coupled to the AB via a sequence that includes a substrate for a protease, for example, a protease that is co-localized with the target at a treatment site in a subject. In some embodiments, the agent is a therapeutic agent. In some embodiments, the agent is an antineoplastic agent. In some embodiments, the agent is a toxin or fragment thereof. In some embodiments, the agent is an agent selected from the group listed in Table 4. In some embodiments, the activatable antibody also includes a detectable moiety. In some embodiments, the detectable moiety is a diagnostic agent. In some embodiments, the detectable moiety is a conjugatable detection reagent. In some embodiments, the agent is conjugated to the AB via a linker. In some embodiments, the linker is a cleavable linker.

The invention provides antibodies that bind conjugated activatable antibodies that include an antibody or antigen-binding fragment thereof (AB) that specifically binds epidermal growth factor receptor (EGFR) coupled to a masking moiety (MM), such that coupling of the MM reduces the ability of the antibody or antigen-binding fragment thereof to bind EGFR, and wherein the activatable antibody is conjugated to one or more additional agents. In some embodiments of the conjugated activatable antibodies, the MM is coupled to the AB via a sequence that includes a substrate for a protease, for example, a protease that is co-localized with EGFR at a treatment site in a subject.

The invention provides antibodies that bind conjugated activatable antibodies that include an antibody or antigen-binding fragment thereof (AB) that specifically binds a Jagged target, e.g., Jagged 1 and/or Jagged 2, coupled to a masking moiety (MM), such that coupling of the MM reduces the ability of the antibody or antigen-binding fragment thereof to bind the Jagged target, and wherein the activatable antibody is conjugated to one or more additional agents. In some embodiments of the conjugated activatable antibodies, the MM is coupled to the AB via a sequence that includes a substrate for a protease, for example, a protease that is co-localized with the Jagged target at a treatment site in a subject.

The invention provides antibodies that bind conjugated activatable antibodies that include an antibody or antigen-binding fragment thereof (AB) that specifically binds interleukin 6 receptor (IL-6R) coupled to a masking moiety (MM), such that coupling of the MM reduces the ability of the antibody or antigen-binding fragment thereof to bind IL-6R, and wherein the activatable antibody is conjugated to one or more additional agents. In some embodiments of the conjugated activatable antibodies, the MM is coupled to the AB via a sequence that includes a substrate for a protease, for example, a protease that is co-localized with IL-6R at a treatment site in a subject.

The antibodies and antigen-binding fragments of the disclosure that bind activatable antibodies and/or conjugated activatable antibodies are collectively referred to herein as anti-AA antibodies and anti-AA antibody fragments.

In some embodiments, the antibody or fragment thereof that binds the activatable antibody is a monoclonal antibody, domain antibody, single chain, Fab fragment, a F(ab')$_2$ fragment, a scFv, a scAb, a dAb, a single domain heavy chain antibody, and a single domain light chain antibody. In some embodiments, such an antibody or fragment thereof that binds an activatable antibody is a rabbit, mouse, chimeric, humanized or fully human monoclonal antibody.

In some embodiments, the antibody or fragment thereof that binds an activatable antibody and/or conjugated activatable antibody has an equilibrium dissociation constant of about 100 nM or less for binding to the activatable antibody and/or conjugated activatable antibody.

In some embodiments, the antibody or fragment thereof that binds an activatable antibody and/or conjugated activatable antibody comprises a heavy chain amino acid sequence selected from the group consisting of SEQ ID NO: 2, 6, 10, 14, 76, and 105. In some embodiments, the antibody or fragment thereof that binds an activatable antibody and/or conjugated activatable antibody comprises a light chain amino acid sequence selected from the group consisting of SEQ ID NO: 4, 8, 12, 16, 86, 93, and 108. In some embodiments, the antibody or fragment thereof that binds an activatable antibody and/or conjugated activatable antibody comprises a heavy chain amino acid sequence selected from the group consisting of SEQ ID NO: 2, 6, 10, 14, 76, and 105, and a light chain amino acid sequence selected from the group consisting of SEQ ID NO: 4, 8, 12, 16, 86, 93, and 108.

In some embodiments, the antibody or fragment thereof that binds an activatable antibody and/or conjugated activatable antibody comprises a combination of a heavy chain and a light chain selected from the group consisting of a heavy chain comprising the amino acid sequence of SEQ ID NO: 2 and a light chain comprising the amino acid sequence of SEQ ID NO: 4; a heavy chain comprising the amino acid sequence of SEQ ID NO: 6 and a light chain comprising the amino acid sequence of SEQ ID NO: 8; a heavy chain comprising the amino acid sequence of SEQ ID NO: 10 and a light chain comprising the amino acid sequence of SEQ ID NO: 12; and a heavy chain comprising the amino acid sequence of SEQ ID NO: 14 and a light chain comprising the amino acid sequence of SEQ ID NO: 16.

In some embodiments, the antibody or fragment thereof that binds an activatable antibody and/or conjugated activatable antibody comprises a heavy chain amino acid sequence that is at least 90%, 91%, 92%, 93%, 94%, 95%, 96%, 97%, 98% or 99% identical to an amino acid sequence selected from the group consisting of SEQ ID NO: 2, 6, 10, 14, 76, and 105. In some embodiments, the antibody or fragment thereof that binds an activatable antibody and/or conjugated activatable antibody comprises a light chain amino acid that is at least 90%, 91%, 92%, 93%, 94%, 95%, 96%, 97%, 98% or 99% identical to an amino acid sequence selected from the group consisting of SEQ ID NO: 4, 8, 12, 16, 86, 93, and 108. In some embodiments, the antibody or fragment thereof that binds an activatable antibody and/or conjugated activatable antibody comprises a heavy chain amino acid sequence that is at least 90%, 91%, 92%, 93%, 94%, 95%, 96%, 97%, 98% or 99% identical to an amino acid sequence selected from the group consisting of SEQ ID NO: 2, 6, 10, 14, 76, and 105, and a light chain amino acid that is at least 90%, 91%, 92%, 93%, 94%, 95%, 96%, 97%, 98% or 99% identical to an amino acid sequence selected from the group consisting of SEQ ID NO: 4, 8, 12, 16, 86, 93, and 108.

In some embodiments, the antibody or fragment thereof that binds an activatable antibody and/or conjugated activatable antibody comprises a combination of a heavy chain and a light chain selected from the group consisting of a heavy chain comprising the amino acid sequence that is at least 90%, 91%, 92%, 93%, 94%, 95%, 96%, 97%, 98% or 99% identical to the amino acid sequence of SEQ ID NO: 2 and a light chain comprising the amino acid sequence that is at least 90%, 91%, 92%, 93%, 94%, 95%, 96%, 97%, 98% or 99% identical to the amino acid sequence of SEQ ID NO: 4; a heavy chain comprising the amino acid sequence that is at least 90%, 91%, 92%, 93%, 94%, 95%, 96%, 97%, 98% or 99% identical to the amino acid sequence of SEQ ID NO: 6 and a light chain comprising the amino acid sequence that is at least 90%, 91%, 92%, 93%, 94%, 95%, 96%, 97%, 98% or 99% identical to the amino acid sequence of SEQ ID NO: 8; a heavy chain comprising the amino acid sequence that is at least 90%, 91%, 92%, 93%, 94%, 95%, 96%, 97%, 98% or 99% identical to the amino acid sequence of SEQ ID NO: 10 and a light chain comprising the amino acid sequence that is at least 90%, 91%, 92%, 93%, 94%, 95%, 96%, 97%, 98% or 99% identical to the amino acid sequence of SEQ ID NO: 12; and a heavy chain comprising the amino acid sequence that is at least 90%, 91%, 92%, 93%, 94%, 95%, 96%, 97%, 98% or 99% identical to the amino acid sequence of SEQ ID NO: 14 and a light chain comprising the amino acid sequence that is at least 90%, 91%, 92%, 93%, 94%, 95%, 96%, 97%, 98% or 99% identical to the amino acid sequence of SEQ ID NO: 16.

In some embodiments, the antibody or fragment thereof that binds an activatable antibody and/or conjugated activatable antibody comprises a variable heavy chain amino acid sequence selected from the group consisting of SEQ ID NO: 42, 56, 60, 64, 77, and 106. In some embodiments, the antibody or fragment thereof that binds an activatable antibody and/or conjugated activatable antibody comprises a variable light chain amino acid sequence selected from the group consisting of SEQ ID NO: 44, 58, 62, 66, 87, 94, and 109. In some embodiments, the antibody or fragment thereof that binds an activatable antibody and/or conjugated activatable antibody comprises a variable heavy chain amino acid sequence selected from the group consisting of SEQ ID NO: 42, 56, 60, 64, 77, and 106, and a variable light chain amino acid sequence selected from the group consisting of SEQ ID NO: 44, 58, 62, 66, 87, 94, and 109.

In some embodiments, the antibody or fragment thereof that binds an activatable antibody and/or conjugated activatable antibody comprises a combination of a variable heavy chain and a variable light chain selected from the group consisting of a variable heavy chain comprising the amino acid sequence of SEQ ID NO: 42 and a variable light chain comprising the amino acid sequence of SEQ ID NO:

44; a variable heavy chain comprising the amino acid sequence of SEQ ID NO: 56 and a variable light chain comprising the amino acid sequence of SEQ ID NO: 58; a variable heavy chain comprising the amino acid sequence of SEQ ID NO: 60 and a variable light chain comprising the amino acid sequence of SEQ ID NO: 62; and a variable heavy chain comprising the amino acid sequence of SEQ ID NO: 64 and a variable light chain comprising the amino acid sequence of SEQ ID NO: 66.

In some embodiments, the antibody or fragment thereof that binds an activatable antibody and/or conjugated activatable antibody comprises a combination of a variable heavy chain and a variable light chain selected from the group consisting of a variable heavy chain comprising the amino acid sequence that is at least 90%, 91%, 92%, 93%, 94%, 95%, 96%, 97%, 98% or 99% identical to the amino acid sequence of SEQ ID NO: 42 and a variable light chain comprising the amino acid sequence that is at least 90%, 91%, 92%, 93%, 94%, 95%, 96%, 97%, 98% or 99% identical to the amino acid sequence of SEQ ID NO: 44; a variable heavy chain comprising the amino acid sequence that is at least 90%, 91%, 92%, 93%, 94%, 95%, 96%, 97%, 98% or 99% identical to the amino acid sequence of SEQ ID NO: 56 and a variable light chain comprising the amino acid sequence that is at least 90%, 91%, 92%, 93%, 94%, 95%, 96%, 97%, 98% or 99% identical to the amino acid sequence of SEQ ID NO: 58; a variable heavy chain comprising the amino acid sequence that is at least 90%, 91%, 92%, 93%, 94%, 95%, 96%, 97%, 98% or 99% identical to the amino acid sequence of SEQ ID NO: 60 and a variable light chain comprising the amino acid sequence that is at least 90%, 91%, 92%, 93%, 94%, 95%, 96%, 97%, 98% or 99% identical to the amino acid sequence of SEQ ID NO: 62; and a variable heavy chain comprising the amino acid sequence that is at least 90%, 91%, 92%, 93%, 94%, 95%, 96%, 97%, 98% or 99% identical to the amino acid sequence of SEQ ID NO: 64 and a variable light chain comprising the amino acid sequence that is at least 90%, 91%, 92%, 93%, 94%, 95%, 96%, 97%, 98% or 99% identical to the amino acid sequence of SEQ ID NO: 66.

In some embodiments, the antibody or fragment thereof that binds an activatable antibody and/or conjugated activatable antibody comprises a variable heavy chain amino acid sequence that is at least 90%, 91%, 92%, 93%, 94%, 95%, 96%, 97%, 98% or 99% identical to an amino acid sequence selected from the group consisting of SEQ ID NO: 42, 56, 60, 64, 77, and 106. In some embodiments, the antibody or fragment thereof that binds an activatable antibody and/or conjugated activatable antibody comprises a variable light chain amino acid that is at least 90%, 91%, 92%, 93%, 94%, 95%, 96%, 97%, 98% or 99% identical to an amino acid sequence selected from the group consisting of SEQ ID NO: 44, 58, 62, 66, 87, 94, and 109. In some embodiments, the antibody or fragment thereof that binds an activatable antibody and/or conjugated activatable antibody comprises a variable heavy chain amino acid sequence that is at least 90%, 91%, 92%, 93%, 94%, 95%, 96%, 97%, 98% or 99% identical to an amino acid sequence selected from the group consisting of SEQ ID NO: 42, 56, 60, 64, 77, and 106, and a variable light chain amino acid that is at least 90%, 91%, 92%, 93%, 94%, 95%, 96%, 97%, 98% or 99% identical to an amino acid sequence selected from the group consisting of SEQ ID NO: 44, 58, 62, 66, 87, 94, and 109.

In some embodiments, the antibody or fragment thereof that binds an activatable antibody and/or conjugated activatable antibody comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence that includes at least an amino acid sequence selected from the group consisting of SEQ ID NO: 67, 73, 78, 88, 95, and 101; a VH CD2 sequence that includes at least an amino acid sequence selected from the group consisting of SEQ ID NO: 68, 74, 79, 89, 96, and 102; a VH CDR3 sequence that includes at least an amino acid sequence selected from the group consisting of SEQ ID NO: 69, 80, 90, and 97; a VL CDR1 sequence that includes at least an amino acid sequence selected from the group consisting of SEQ ID NO: 70, 81, and 98; a VL CDR2 sequence that includes at least an amino acid sequence selected from the group consisting of SEQ ID NO: 71, 82, and 99; and a VL CDR3 sequence that includes at least an amino acid sequence selected from the group consisting of SEQ ID NO: 72, 83, 84, 91, 110, 100, and 103.

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to an amino acid sequence selected from the group consisting of SEQ ID NO: 67, 73, 78, 88, 95, and 101; a VH CD2 sequence that includes a sequence that is at least 90%, 91%, 92%, 93%, 94%, 95%, 96%, 97%, 98%, 99% or more identical to an amino acid sequence selected from the group consisting of SEQ ID NO: 68, 74, 79, 89, 96, and 102; a VH CDR3 sequence that includes a sequence that is at least 90%, 91%, 92%, 93%, 94%, 95%, 96%, 97%, 98%, 99% or more identical to an amino acid sequence selected from the group consisting of SEQ ID NO: 69, 80, 90, and 97; a VL CDR1 sequence that includes a sequence that is at least 90%, 91%, 92%, 93%, 94%, 95%, 96%, 97%, 98%, 99% or more identical to an amino acid sequence selected from the group consisting of SEQ ID NO: 70, 81, and 98; a VL CDR2 sequence that includes a sequence that is at least 90%, 91%, 92%, 93%, 94%, 95%, 96%, 97%, 98%, 99% or more identical to an amino acid sequence selected from the group consisting of SEQ ID NO: 71, 82, and 99; and a VL CDR3 sequence that includes a sequence that is at least 90%, 91%, 92%, 93%, 94%, 95%, 96%, 97%, 98%, 99% or more identical to an amino acid sequence selected from the group consisting of SEQ ID NO: 72, 83, 84, 91, 110, 100, and 103.

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises at least an amino acid sequence selected from the group consisting of SEQ ID NO: 67, 73, 78, 88, 95, and 101; the VH CD2 sequence comprises at least an amino acid sequence selected from the group consisting of SEQ ID NO: 68, 74, 79, 89, 96, and 102; the VH CDR3 sequence comprises at least an amino acid sequence selected from the group consisting of SEQ ID NO: 69, 80, 90, and 97; the VL CDR1 sequence comprises at least an amino acid sequence selected from the group consisting of SEQ ID NO: 70, 81, and 98; the VL CDR2 sequence comprises at least an amino acid sequence selected from the group consisting of SEQ ID NO: 71, 82, and 99; and the VL CDR3 sequence comprises at least an amino acid sequence selected from the group consisting of SEQ ID NO: 72, 83, 84, 91, 110, 100, and 103.

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to an amino acid sequence selected from the group consisting of SEQ ID NO: 67, 73, 78, 88, 95, and 101; a VH CD2 sequence comprises a sequence that is at least 90%, 91%, 92%, 93%, 94%, 95%, 96%, 97%, 98%, 99% or more identical to an amino acid sequence selected from the group consisting of SEQ ID NO: 68, 74, 79, 89, 96, and 102; the VH CDR3 sequence comprises a sequence that is at least 90%, 91%, 92%, 93%, 94%, 95%, 96%, 97%, 98%, 99% or more identical to an amino acid sequence selected from the group consisting of SEQ ID NO: 69, 80, 90, and 97; the VL CDR1 sequence comprises a sequence that is at least 90%, 91%, 92%, 93%, 94%, 95%, 96%, 97%, 98%, 99% or more identical to an amino acid sequence selected from the group consisting of SEQ ID NO: 70, 81, and 98; the VL CDR2 sequence comprises a sequence that is at least 90%, 91%, 92%, 93%, 94%, 95%, 96%, 97%, 98%, 99% or more identical to an amino acid sequence selected from the group consisting of SEQ ID NO: 71, 82, and 99; and the VL CDR3 sequence comprises a sequence that is at least 90%, 91%, 92%, 93%, 94%, 95%, 96%, 97%, 98%, 99% or more identical to an amino acid sequence selected from the group consisting of SEQ ID NO: 72, 83, 84, 91, 110, 100, and 103.

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence NYAVMC (SEQ ID NO: 67), the VH CDR2 sequence comprises the amino acid sequence CIVLGDGGTTYYASWARG (SEQ ID NO: 68), the VH CDR3 sequence comprises the amino acid sequence SFAASSPINYFNL (SEQ ID NO: 69), the VL CDR1 sequence comprises the amino acid sequence QASQRISTYLA (SEQ ID NO: 70), the VL CDR2 sequence comprises the amino acid sequence KASTLAS (SEQ ID NO: 71), and the VL CDR3 sequence comprises the amino acid sequence QSYYFGDTTFA (SEQ ID NO: 72).

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises an amino acid sequence that is at least 90%, 91%, 92%, 93%, 94%, 95%, 96%, 97%, 98%, 99% or more identical to the amino acid sequence NYAVMC (SEQ ID NO: 67), the VH CDR2 sequence comprises an amino acid sequence that is at least 90%, 91%, 92%, 93%, 94%, 95%, 96%, 97%, 98%, 99% or more identical to the amino acid sequence CIVLGDGGTTYYASWARG (SEQ ID NO: 68), the VH CDR3 sequence comprises an amino acid sequence that is at least 90%, 91%, 92%, 93%, 94%, 95%, 96%, 97%, 98%, 99% or more identical to the amino acid sequence SFAASSPINYFNL (SEQ ID NO: 69), the VL CDR1 sequence comprises an amino acid sequence that is at least 90%, 91%, 92%, 93%, 94%, 95%, 96%, 97%, 98%, 99% or more identical to the amino acid sequence QASQRISTYLA (SEQ ID NO: 70), the VL CDR2 sequence comprises an amino acid sequence that is at least 90%, 91%, 92%, 93%, 94%, 95%, 96%, 97%, 98%, 99% or more identical to the amino acid sequence KASTLAS (SEQ ID NO: 71), and the VL CDR3 sequence comprises an amino acid sequence that is at least 90%, 91%, 92%, 93%, 94%, 95%, 96%, 97%, 98%, 99% or more identical to the amino acid sequence QSYYFGDGTTFA (SEQ ID NO: 72).

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence RYGMA (SEQ ID NO: 78), the VH CDR2 sequence comprises the amino acid sequence AISSSGNEDYASWAIG (SEQ ID NO: 79), the VH CDR3 sequence comprises the amino acid sequence GWLSNNAYM (SEQ ID NO: 80), the VL CDR1 sequence comprises the amino acid sequence QASQSIYNKNQLS (SEQ ID NO: 81), the VL CDR2 sequence comprises the amino acid sequence YASTLAS (SEQ ID NO: 82), and the VL CDR3 sequence comprises the amino acid sequence LGDFSCSGVDCLV (SEQ ID NO: 83).

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises an amino acid sequence that is at least 90%, 91%, 92%, 93%, 94%, 95%, 96%, 97%, 98%, 99% or more identical to the amino acid sequence RYGMA (SEQ ID NO: 78), the VH CDR2 sequence comprises an amino acid sequence that is at least 90%, 91%, 92%, 93%, 94%, 95%, 96%, 97%, 98%, 99% or more identical to the amino acid sequence AISSSGNEDYASWAIG (SEQ ID NO: 79), the VH CDR3 sequence comprises an amino acid sequence that is at least 90%, 91%, 92%, 93%, 94%, 95%, 96%, 97%, 98%, 99% or more identical to the amino acid sequence GWLSNNAYM (SEQ ID NO: 80), the VL CDR1 sequence comprises an amino acid sequence that is at least 90%, 91%, 92%, 93%, 94%, 95%, 96%, 97%, 98%, 99% or more identical to the amino acid sequence QASQSIYNKNQLS (SEQ ID NO: 81), the VL CDR2 sequence comprises an amino acid sequence that is at least 90%, 91%, 92%, 93%, 94%, 95%, 96%, 97%, 98%, 99% or more identical to the amino acid sequence YASTLAS (SEQ ID NO: 82), and the VL CDR3 sequence comprises an amino acid sequence that is at least 90%, 91%, 92%, 93%, 94%, 95%, 96%, 97%, 98%, 99% or more identical to the amino acid sequence LGDFSCSGVDCLV (SEQ ID NO: 83).

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence HYGMA (SEQ ID NO: 88), the VH CDR2 sequence comprises the amino acid sequence AISSS-GNEDYASWPKG (SEQ ID NO: 89), the VH CDR3 sequence comprises the amino acid sequence GWLSN-NVYM (SEQ ID NO: 90), the VL CDR1 sequence comprises the amino acid sequence QASQSIYNKNQLS (SEQ ID NO: 81), the VL CDR2 sequence comprises the amino acid sequence YASTLAS (SEQ ID NO: 82), and the VL CDR3 sequence comprises the amino acid sequence LGD-FSCSGVDCLS (SEQ ID NO: 91).

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises an amino acid sequence that is at least 90%, 91%, 92%, 93%, 94%, 95%, 96%, 97%, 98%, 99% or more identical to the amino acid sequence HYGMA (SEQ ID NO: 88), the VH CDR2 sequence comprises an amino acid sequence that is at least 90%, 91%, 92%, 93%, 94%, 95%, 96%, 97%, 98%, 99% or more identical to the amino acid sequence AISSS-GNEDYASWPKG (SEQ ID NO: 89), the VH CDR3 sequence comprises an amino acid sequence that is at least 90%, 91%, 92%, 93%, 94%, 95%, 96%, 97%, 98%, 99% or more identical to the amino acid sequence GWLSNNVYM (SEQ ID NO: 90), the VL CDR1 sequence comprises an amino acid sequence that is at least 90%, 91%, 92%, 93%, 94%, 95%, 96%, 97%, 98%, 99% or more identical to the amino acid sequence QASQSIYNKNQLS (SEQ ID NO: 81), the VL CDR2 sequence comprises an amino acid sequence that is at least 90%, 91%, 92%, 93%, 94%, 95%, 96%, 97%, 98%, 99% or more identical to the amino acid sequence YASTLAS (SEQ ID NO: 82), and the VL CDR3 sequence comprises an amino acid sequence that is at least 90%, 91%, 92%, 93%, 94%, 95%, 96%, 97%, 98%, 99% or more identical to the amino acid sequence LGDFSCSGVD-CLS (SEQ ID NO: 91).

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence SYCMS (SEQ ID NO: 95), the VH CDR2 sequence comprises the amino acid sequence IIG-GICSTYYAAWAKG (SEQ ID NO: 96), the VH CDR3 sequence comprises the amino acid sequence PAYNSDPI (SEQ ID NO: 97), the VL CDR1 sequence comprises the amino acid sequence QASQSVYNNNYLS (SEQ ID NO: 98), the VL CDR2 sequence comprises the amino acid sequence DAATLAS (SEQ ID NO: 99), and the VL CDR3 sequence comprises the amino acid sequence LGEFSCG-SADCNA (SEQ ID NO: 100).

In some embodiments, the antibody or fragment thereof that binds an activatable antibody and/or conjugated activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises an amino acid sequence that is at least 90%, 91%, 92%, 93%, 94%, 95%, 96%, 97%, 98%, 99% or more identical to the amino acid sequence SYCMS (SEQ ID NO: 95), the VH CDR2 sequence comprises an amino acid sequence that is at least 90%, 91%, 92%, 93%, 94%, 95%, 96%, 97%, 98%, 99% or more identical to the amino acid sequence IIGGIC-STYYAAWAKG (SEQ ID NO: 96), the VH CDR3 sequence comprises an amino acid sequence that is at least 90%, 91%, 92%, 93%, 94%, 95%, 96%, 97%, 98%, 99% or more identical to the amino acid sequence PAYNSDPI (SEQ ID NO: 97), the VL CDR1 sequence comprises an amino acid sequence that is at least 90%, 91%, 92%, 93%, 94%, 95%, 96%, 97%, 98%, 99% or more identical to the amino acid sequence QASQSVYNNNYLS (SEQ ID NO: 98), the VL CDR2 sequence comprises an amino acid sequence that is at least 90%, 91%, 92%, 93%, 94%, 95%, 96%, 97%, 98%, 99% or more identical to the amino acid sequence DAAT-LAS (SEQ ID NO: 99), and the VL CDR3 sequence comprises an amino acid sequence that is at least 90%, 91%, 92%, 93%, 94%, 95%, 96%, 97%, 98%, 99% or more identical to the amino acid sequence LGEFSCGSADCNA (SEQ ID NO: 100).

In some embodiments, the antibody or fragment thereof that binds an activatable antibody and/or conjugated activatable antibody is encoded by a nucleic acid sequence that comprises a nucleic acid sequence encoding a heavy chain amino acid sequence comprising an amino acid sequence selected from the group consisting of SEQ ID NO: 2, 6, 10, 14, 76, and 105. In some embodiments, the antibody or fragment thereof that binds an activatable antibody and/or conjugated activatable antibody is encoded by a nucleic acid sequence that comprises a nucleic acid sequence that comprises a nucleic acid sequence encoding a light chain amino acid sequence comprising an amino acid sequence selected from the group consisting of SEQ ID NO: 4, 8, 12, 16, 86, 93, and 108. In some embodiments, the antibody or fragment thereof that binds an activatable antibody and/or conjugated activatable antibody is encoded by a nucleic acid sequence that comprises a nucleic acid sequence encoding a heavy chain amino acid sequence comprising an amino acid sequence selected from the group consisting of SEQ ID NO: 2, 6, 10, 14, 76, and 105, and a nucleic acid sequence that comprises a nucleic acid sequence encoding a light chain amino acid sequence comprising an amino acid sequence selected from the group consisting of SEQ ID NO: 4, 8, 12, 16, 86, 93, and 108.

In some embodiments, the antibody or fragment thereof that binds an activatable antibody and/or conjugated activatable antibody is encoded by a nucleic acid sequence that comprises a nucleic acid sequence encoding a heavy chain amino acid sequence that is at least 90%, 91%, 92%, 93%, 94%, 95%, 96%, 97%, 98% or 99% identical to an amino acid sequence selected from the group consisting of SEQ ID NO: 2, 6, 10, 14, 76, and 105. In some embodiments, the antibody or fragment thereof that binds an activatable antibody and/or conjugated activatable antibody is encoded by a nucleic acid sequence that comprises a nucleic acid sequence that comprises a nucleic acid sequence encoding a light chain amino acid that is at least 90%, 91%, 92%, 93%, 94%, 95%, 96%, 97%, 98% or 99% identical to an amino acid sequence selected from the group consisting of SEQ ID NO: 4, 8, 12, 16, 86, 93, and 108. In some embodiments, the antibody or fragment thereof that binds an activatable antibody and/or conjugated activatable antibody is encoded by a nucleic acid sequence that comprises a nucleic acid sequence encoding a heavy chain amino acid sequence that is at least 90%, 91%, 92%, 93%, 94%, 95%, 96%, 97%, 98% or 99% identical to an amino acid sequence selected from the group consisting of SEQ ID NO: 2, 6, 10, 14, 76, and 105, and a nucleic acid sequence that comprises a nucleic acid sequence encoding a light chain amino acid that is at least 90%, 91%, 92%, 93%, 94%, 95%, 96%, 97%, 98% or 99% identical to an amino acid sequence selected from the group consisting of SEQ ID NO: 4, 8, 12, 16, 86, 93, and 108.

In some embodiments, the antibody or fragment thereof that binds an activatable antibody and/or conjugated activatable antibody is encoded by a nucleic acid sequence that comprises a nucleic acid sequence encoding a combination of a heavy chain and a light chain selected from the group consisting of a heavy chain and a light chain selected from the group consisting of a heavy chain comprising the amino acid sequence of SEQ ID NO: 2 and a light chain comprising the amino acid sequence of SEQ ID NO: 4; a heavy chain comprising the amino acid sequence of SEQ ID NO: 6 and a light chain comprising the amino acid sequence of SEQ ID NO: 8; a heavy chain comprising the amino acid sequence of SEQ ID NO: 10 and a light chain comprising the amino acid sequence of SEQ ID NO: 12; and a heavy chain comprising the amino acid sequence of SEQ ID NO: 14 and a light chain comprising the amino acid sequence of SEQ ID NO: 16.

In some embodiments, the antibody or fragment thereof that binds an activatable antibody and/or conjugated activatable antibody is encoded by a nucleic acid sequence that comprises a nucleic acid sequence encoding a combination of a heavy chain and a light chain selected from the group consisting of a heavy chain comprising the amino acid sequence that is at least 90%, 91%, 92%, 93%, 94%, 95%, 96%, 97%, 98% or 99% identical to the amino acid sequence of SEQ ID NO: 2 and a light chain comprising the amino acid sequence that is at least 90%, 91%, 92%, 93%, 94%, 95%, 96%, 97%, 98% or 99% identical to the amino acid sequence of SEQ ID NO: 4; a heavy chain comprising the amino acid sequence that is at least 90%, 91%, 92%, 93%, 94%, 95%, 96%, 97%, 98% or 99% identical to the amino acid sequence of SEQ ID NO: 6 and a light chain comprising the amino acid sequence that is at least 90%, 91%, 92%, 93%, 94%, 95%, 96%, 97%, 98% or 99% identical to the amino acid sequence of SEQ ID NO: 8; a heavy chain comprising the amino acid sequence that is at least 90%, 91%, 92%, 93%, 94%, 95%, 96%, 97%, 98% or 99% identical to the amino acid sequence of SEQ ID NO: 10 and a light chain comprising the amino acid sequence that is at least 90%, 91%, 92%, 93%, 94%, 95%, 96%, 97%, 98% or 99% identical to the amino acid sequence of SEQ ID NO: 12; and a heavy chain comprising the amino acid sequence that is at least 90%, 91%, 92%, 93%, 94%, 95%, 96%, 97%, 98% or 99% identical to the amino acid sequence of SEQ ID NO: 14 and a light chain comprising the amino acid sequence that is at least 90%, 91%, 92%, 93%, 94%, 95%, 96%, 97%, 98% or 99% identical to the amino acid sequence of SEQ ID NO: 16.

In some embodiments, the antibody or fragment thereof that binds an activatable antibody and/or conjugated activatable antibody is encoded by a nucleic acid sequence that comprises a nucleic acid sequence encoding a variable heavy chain amino acid sequence comprising an amino acid sequence selected from the group consisting of SEQ ID NO: 42, 56, 60, 64, 77, and 106. In some embodiments, the antibody or fragment thereof that binds an activatable antibody and/or conjugated activatable antibody is encoded by a nucleic acid sequence that comprises a nucleic acid sequence encoding a variable light chain amino acid sequence comprising an amino acid sequence selected from the group consisting of SEQ ID NO: 44, 58, 62, 66, 87, 94, and 109. In some embodiments, the antibody or fragment thereof that binds an activatable antibody and/or conjugated activatable antibody is encoded by a nucleic acid sequence that comprises a nucleic acid sequence encoding a variable heavy chain amino acid sequence comprising an amino acid sequence selected from the group consisting of SEQ ID NO: 42, 56, 60, 64, 77, and 106, and a nucleic acid sequence that comprises a nucleic acid sequence encoding a variable light chain amino acid sequence comprising an amino acid sequence selected from the group consisting of SEQ ID NO: 44, 58, 62, 66, 87, 94, and 109.

In some embodiments, the antibody or fragment thereof that binds an activatable antibody and/or conjugated activatable antibody is encoded by a nucleic acid sequence that comprises a nucleic acid sequence encoding a heavy chain amino acid sequence that is at least 90%, 91%, 92%, 93%, 94%, 95%, 96%, 97%, 98% or 99% identical to an amino acid sequence selected from the group consisting of SEQ ID NO: 42, 56, 60, 64, 77, and 106. In some embodiments, the antibody or fragment thereof that binds an activatable antibody and/or conjugated activatable antibody is encoded by a nucleic acid sequence that comprises a nucleic acid sequence encoding a light chain amino acid that is at least 90%, 91%, 92%, 93%, 94%, 95%, 96%, 97%, 98% or 99% identical to an amino acid sequence selected from the group consisting of SEQ ID NO: 44, 58, 62, 66, 87, 94, and 109. In some embodiments, the antibody or fragment thereof that binds an activatable antibody and/or conjugated activatable antibody is encoded by a nucleic acid sequence that comprises a nucleic acid sequence encoding a heavy chain amino acid sequence that is at least 90%, 91%, 92%, 93%, 94%, 95%, 96%, 97%, 98% or 99% identical to an amino acid sequence selected from the group consisting of SEQ ID NO: 42, 56, 60, 64, 77, and 106, and a nucleic acid sequence that comprises a nucleic acid sequence encoding a light chain amino acid that is at least 90%, 91%, 92%, 93%, 94%, 95%, 96%, 97%, 98% or 99% identical to an amino acid sequence selected from the group consisting of SEQ ID NO: 44, 58, 62, 66, 87, 94, and 109.

In some embodiments, the antibody or fragment thereof that binds an activatable antibody and/or conjugated activatable antibody is encoded by a nucleic acid sequence that comprises a nucleic acid sequence encoding a combination of a variable heavy chain and a variable light chain selected from the group consisting of a variable heavy chain comprising the amino acid sequence of SEQ ID NO: 42 and a variable light chain comprising the amino acid sequence of SEQ ID NO: 44; a variable heavy chain comprising the amino acid sequence of SEQ ID NO: 56 and a variable light chain comprising the amino acid sequence of SEQ ID NO: 58; a variable heavy chain comprising the amino acid sequence of SEQ ID NO: 60 and a variable light chain comprising the amino acid sequence of SEQ ID NO: 62; and a variable heavy chain comprising the amino acid sequence of SEQ ID NO: 64 and a variable light chain comprising the amino acid sequence of SEQ ID NO: 66.

In some embodiments, the antibody or fragment thereof that binds an activatable antibody and/or conjugated activatable antibody is encoded by a nucleic acid sequence that comprises a nucleic acid sequence encoding a combination of a variable heavy chain and a variable light chain selected from the group consisting of a variable heavy chain comprising an amino acid sequence that is at least 90%, 91%, 92%, 93%, 94%, 95%, 96%, 97%, 98%, 99% or more identical to the amino acid sequence of SEQ ID NO: 42 and a variable light chain comprising an amino acid sequence that is at least 90%, 91%, 92%, 93%, 94%, 95%, 96%, 97%, 98%, 99% or more identical to the amino acid sequence of SEQ ID NO: 44; a variable heavy chain comprising an amino acid sequence that is at least 90%, 91%, 92%, 93%, 94%, 95%, 96%, 97%, 98%, 99% or more identical to the amino acid sequence of SEQ ID NO: 56 and a variable light chain comprising the amino acid sequence of SEQ ID NO: 58; a variable heavy chain comprising an amino acid sequence that is at least 90%, 91%, 92%, 93%, 94%, 95%, 96%, 97%, 98%, 99% or more identical to the amino acid sequence of SEQ ID NO: 60 and a variable light chain an amino acid sequence that is at least 90%, 91%, 92%, 93%, 94%, 95%, 96%, 97%, 98%, 99% or more identical to the amino acid sequence of SEQ ID NO: 62; and a variable heavy chain comprising an amino acid sequence that is at least 90%, 91%, 92%, 93%, 94%, 95%, 96%, 97%, 98%, 99% or more identical to the amino acid sequence of SEQ ID NO: 64 and a variable light chain comprising an amino acid sequence that is at least 90%, 91%, 92%, 93%, 94%, 95%, 96%, 97%, 98%, 99% or more identical to the amino acid sequence of SEQ ID NO: 66.

In some embodiments, the antibody or fragment thereof that binds an activatable antibody and/or conjugated activatable antibody is encoded by a heavy chain nucleic acid sequence selected from the group consisting of SEQ ID NO: 1, 5, 9, and 13. In some embodiments, the antibody or fragment thereof that binds an activatable antibody and/or conjugated activatable antibody is encoded by a light chain nucleic acid sequence selected from the group consisting of SEQ ID NO: 3, 7, 11, and 15. In some embodiments, the antibody or fragment thereof that binds an activatable antibody and/or conjugated activatable antibody is encoded by a heavy chain nucleic acid sequence selected from the group consisting of SEQ ID NO: 1, 5, 9, and 13, and a light chain nucleic acid sequence selected from the group consisting of SEQ ID NO: 3, 7, 11, and 15.

In some embodiments, the antibody or fragment thereof that binds an activatable antibody and/or conjugated activatable antibody is encoded by a nucleic acid sequence that comprises a heavy chain nucleic acid sequence that is at least 90%, 91%, 92%, 93%, 94%, 95%, 96%, 97%, 98% or 99% identical to a heavy chain nucleic acid sequence selected from the group consisting of SEQ ID NO: 1, 5, 9, and 13. In some embodiments, the antibody or fragment thereof that binds an activatable antibody and/or conjugated activatable antibody is encoded by a light chain nucleic acid sequence that is at least 90%, 91%, 92%, 93%, 94%, 95%, 96%, 97%, 98% or 99% identical to a light chain nucleic acid sequence selected from the group consisting of SEQ ID NO: 3, 7, 11, and 15. In some embodiments, the antibody or fragment thereof that binds an activatable antibody and/or conjugated activatable antibody is encoded by a heavy chain nucleic acid sequence that is at least 90%, 91%, 92%, 93%, 94%, 95%, 96%, 97%, 98% or 99% identical to a heavy chain nucleic acid sequence selected from the group consisting of SEQ ID NO: 1, 5, 9, and 13, and a light chain nucleic acid sequence that is at least 90%, 91%, 92%, 93%, 94%, 95%, 96%, 97%, 98% or 99% identical to a light chain nucleic acid sequence selected from the group consisting of SEQ ID NO: 3, 7, 11, and 15.

In some embodiments, the antibody or fragment thereof that binds an activatable antibody and/or conjugated activatable antibody is encoded by a nucleic acid encoding a heavy chain and a nucleic acid encoding a light chain selected from the group consisting of a heavy chain nucleic acid sequence comprising the nucleic acid sequence of SEQ ID NO: 1 and a light chain nucleic acid sequence comprising the nucleic acid sequence of SEQ ID NO: 3; a heavy chain nucleic acid sequence comprising the nucleic acid sequence of SEQ ID NO: 5 and a light chain nucleic acid sequence comprising the nucleic acid sequence of SEQ ID NO: 7; a heavy chain nucleic acid sequence comprising the nucleic acid sequence of SEQ ID NO: 9 and a light chain nucleic acid sequence comprising the nucleic acid sequence of SEQ ID NO: 11; and a heavy chain nucleic acid sequence comprising the nucleic acid sequence of SEQ ID NO: 13 and a light chain nucleic acid sequence comprising the nucleic acid sequence of SEQ ID NO: 15.

In some embodiments, the antibody or fragment thereof that binds an activatable antibody and/or conjugated activatable antibody is encoded by a nucleic acid encoding a heavy chain and a nucleic acid encoding a light chain selected from the group consisting of a heavy chain nucleic acid sequence that is at least 90%, 91%, 92%, 93%, 94%, 95%, 96%, 97%, 98% or 99% identical to the nucleic acid sequence of SEQ ID NO: 1 and a light chain nucleic acid sequence that is at least 90%, 91%, 92%, 93%, 94%, 95%, 96%, 97%, 98% or 99% identical to the nucleic acid sequence of SEQ ID NO: 3; a heavy chain nucleic acid sequence that is at least 90%, 91%, 92%, 93%, 94%, 95%, 96%, 97%, 98% or 99% identical to the nucleic acid sequence of SEQ ID NO: 5 and a light chain nucleic acid sequence that is at least 90%, 91%, 92%, 93%, 94%, 95%, 96%, 97%, 98% or 99% identical to the nucleic acid sequence of SEQ ID NO: 7; a heavy chain nucleic acid sequence that is at least 90%, 91%, 92%, 93%, 94%, 95%, 96%, 97%, 98% or 99% identical to the nucleic acid sequence of SEQ ID NO: 9 and a light chain nucleic acid sequence that is at least 90%, 91%, 92%, 93%, 94%, 95%, 96%, 97%, 98% or 99% identical to the nucleic acid sequence of SEQ ID NO: 11; and a heavy chain nucleic acid sequence that is at least 90%, 91%, 92%, 93%, 94%, 95%, 96%, 97%, 98% or 99% identical to the nucleic acid sequence of SEQ ID NO: 13 and a light chain nucleic acid sequence that is at least 90%, 91%, 92%, 93%, 94%, 95%, 96%, 97%, 98% or 99% identical to the nucleic acid sequence of SEQ ID NO: 15.

In some embodiments, the antibody or fragment thereof that binds an activatable antibody and/or conjugated activatable antibody is encoded by a heavy chain nucleic acid sequence selected from the group consisting of SEQ ID NO: 41, 55, 59, and 63. In some embodiments, the antibody or fragment thereof that binds an activatable antibody and/or conjugated activatable antibody is encoded by a light chain nucleic acid sequence selected from the group consisting of SEQ ID NO: 43, 57, 61, and 65. In some embodiments, the antibody or fragment thereof that binds an activatable antibody and/or conjugated activatable antibody is encoded by a heavy chain nucleic acid sequence selected from the group consisting of SEQ ID NO: 41, 55, 59, and 63, and a light chain nucleic acid sequence selected from the group consisting of SEQ ID NO: 43, 57, 61, and 65.

In some embodiments, the antibody or fragment thereof that binds an activatable antibody and/or conjugated activatable antibody is encoded by a nucleic acid sequence that comprises a heavy chain nucleic acid sequence that is at least 90%, 91%, 92%, 93%, 94%, 95%, 96%, 97%, 98% or 99% identical to a heavy chain nucleic acid sequence selected from the group consisting of SEQ ID NO: 41, 55, 59, and 63. In some embodiments, the antibody or fragment thereof that binds an activatable antibody and/or conjugated activatable antibody is encoded by a light chain nucleic acid sequence that is at least 90%, 91%, 92%, 93%, 94%, 95%, 96%, 97%, 98% or 99% identical to a light chain nucleic acid sequence selected from the group consisting of SEQ ID NO: 43, 57, 61, and 65. In some embodiments, the antibody or fragment thereof that binds an activatable antibody and/or conjugated activatable antibody is encoded by a heavy chain nucleic acid sequence that is at least 90%, 91%, 92%, 93%, 94%, 95%, 96%, 97%, 98% or 99% identical to a heavy chain nucleic acid sequence selected from the group consisting of SEQ ID NO: 41, 55, 59, and 63, and a light chain nucleic acid sequence that is at least 90%, 91%, 92%, 93%, 94%, 95%, 96%, 97%, 98% or 99% identical to a light chain nucleic acid sequence selected from the group consisting of SEQ ID NO: 43, 57, 61, and 65.

In some embodiments, the antibody or fragment thereof that binds an activatable antibody and/or conjugated activatable antibody is encoded by a nucleic acid encoding a variable heavy chain and a nucleic acid encoding a variable light chain selected from the group consisting of a variable heavy chain nucleic acid sequence comprising the nucleic acid sequence of SEQ ID NO: 41 and a variable light chain nucleic acid sequence comprising the nucleic acid sequence of SEQ ID NO: 43; a variable heavy chain nucleic acid sequence comprising the nucleic acid sequence of SEQ ID NO: 55 and a variable light chain nucleic acid sequence comprising the nucleic acid sequence of SEQ ID NO: 57; a variable heavy chain nucleic acid sequence comprising the nucleic acid sequence of SEQ ID NO: 59 and a variable light chain nucleic acid sequence comprising the nucleic acid sequence of SEQ ID NO: 61; and a variable heavy chain nucleic acid sequence comprising the nucleic acid sequence of SEQ ID NO: 63 and a variable light chain nucleic acid sequence comprising the nucleic acid sequence of SEQ ID NO: 65.

In some embodiments, the antibody or fragment thereof that binds an activatable antibody and/or conjugated activatable antibody is encoded by a nucleic acid encoding a variable heavy chain and a nucleic acid encoding a variable light chain selected from the group consisting of a variable heavy chain nucleic acid sequence that is at least 90%, 91%, 92%, 93%, 94%, 95%, 96%, 97%, 98% or 99% identical to the nucleic acid sequence of SEQ ID NO: 41 and a variable light chain nucleic acid sequence that is at least 90%, 91%, 92%, 93%, 94%, 95%, 96%, 97%, 98% or 99% identical to the nucleic acid sequence of SEQ ID NO: 43; a variable heavy chain nucleic acid sequence that is at least 90%, 91%, 92%, 93%, 94%, 95%, 96%, 97%, 98% or 99% identical to the nucleic acid sequence of SEQ ID NO: 55 and a variable light chain nucleic acid sequence that is at least 90%, 91%, 92%, 93%, 94%, 95%, 96%, 97%, 98% or 99% identical to the nucleic acid sequence of SEQ ID NO: 57; a variable heavy chain nucleic acid sequence that is at least 90%, 91%, 92%, 93%, 94%, 95%, 96%, 97%, 98% or 99% identical to the nucleic acid sequence of SEQ ID NO: 59 and a variable light chain nucleic acid sequence that is at least 90%, 91%, 92%, 93%, 94%, 95%, 96%, 97%, 98% or 99% identical to the nucleic acid sequence of SEQ ID NO: 61; and a variable heavy chain nucleic acid sequence that is at least 90%, 91%, 92%, 93%, 94%, 95%, 96%, 97%, 98% or 99% identical to the nucleic acid sequence of SEQ ID NO: 63 and a variable light chain nucleic acid sequence that is at least 90%, 91%, 92%, 93%, 94%, 95%, 96%, 97%, 98% or 99% identical to the nucleic acid sequence of SEQ ID NO: 65.

In some embodiments, the nucleic acid encoding the isolated antibody comprises a nucleic acid encoding a signal peptide.

In some embodiments, the nucleic acid encoding the signal peptide is operably linked to the nucleic acid encoding the activatable antibody via a nucleic acid encoding a spacer.

In some embodiments, the antibody or fragment thereof that binds an activatable antibody and/or conjugated activatable antibody is an antibody or is derived from an antibody selected from the group consisting of 10 (also referred to herein as 10-10 and/or clone 10), 8 (also referred to herein as 8-8 and/or clone 8), 53 (also referred to herein as 53-1 and/or clone 3), 7 (also referred to herein as 7-11 and/or clone 7), 36 (also referred to herein as 36-3 and/or clone 36), 52 (also referred to herein as 52-10 and/or clone 52), and 27 (also referred to herein as 27-4 and/or clone 27), and antigen-binding fragments thereof.

The disclosure also provides vector(s) that include one or more of a nucleic acid encoding an antibody or fragment thereof that binds an activatable antibody. The disclosure also provides methods producing an isolated antibody or fragment thereof that binds an activatable antibody by culturing a cell under conditions that lead to expression of the isolated antibody, wherein the cell includes a vector of the disclosure.

In some embodiments, the antibody or fragment thereof that binds an activatable antibody and/or conjugated activatable antibody also includes a detectable moiety. In some embodiments, the detectable moiety is a diagnostic agent. In some embodiments, the detectable moiety is a conjugatable detection reagent.

In some embodiments, the detectable moiety includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the detectable moiety is, for example, a fluorescein derivative such as fluorescein isothiocyanate (FITC). In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

The invention provides methods of detecting the presence of activatable antibody and/or conjugated activatable antibody in a sample or a subject using one or more of the antibody or fragment thereof that binds an activatable antibody and/or conjugated activatable antibody described herein.

Compositions according to the invention can include an antibody or fragment thereof that binds an activatable antibody and/or conjugated activatable antibody and a carrier. These compositions can be included in kits, such as, for example, diagnostic kits.

activatable anti-EGFR antibody or intact (non-activated) activatable anti-EGFR antibody.

Figure 1A:
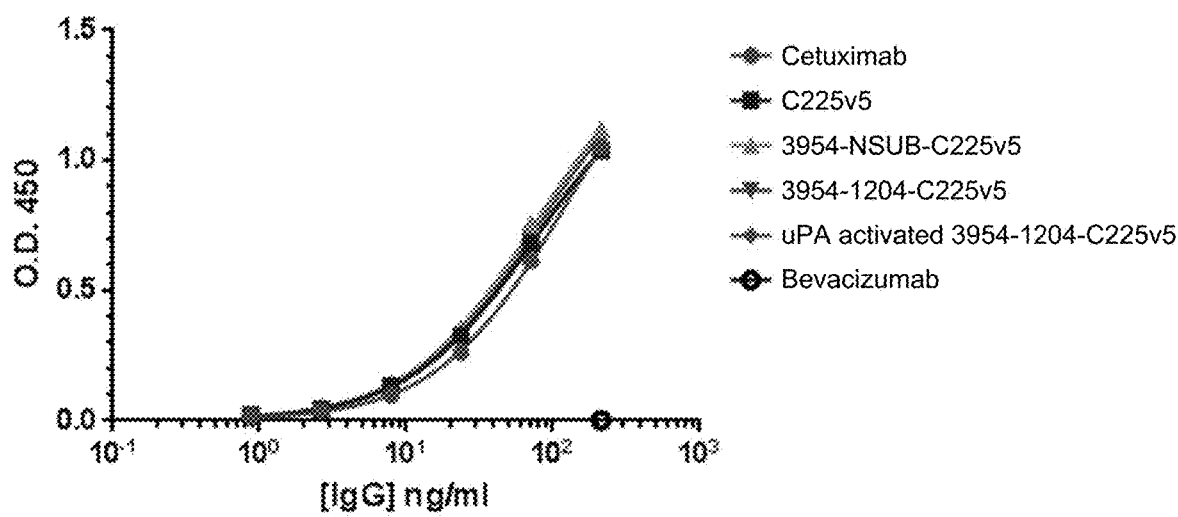
FIGS. 1A-1D are a series of graphs depicting the binding specificity of various antibodies of the disclosure for the activatable anti-EGFR antibody referred to herein as 3954-1204-c225v5.
Figure 1B:
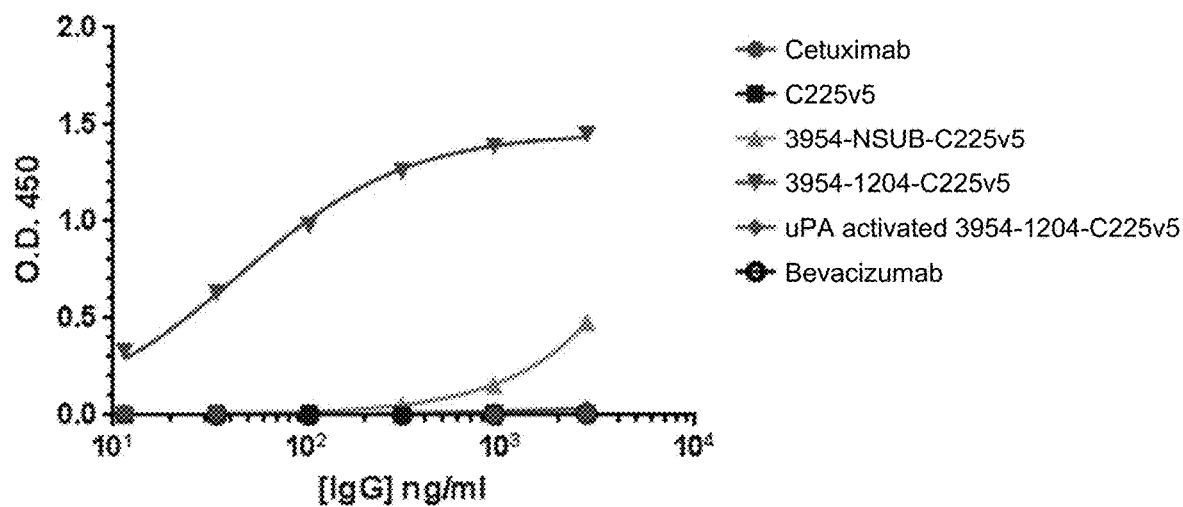
Figure 1C:
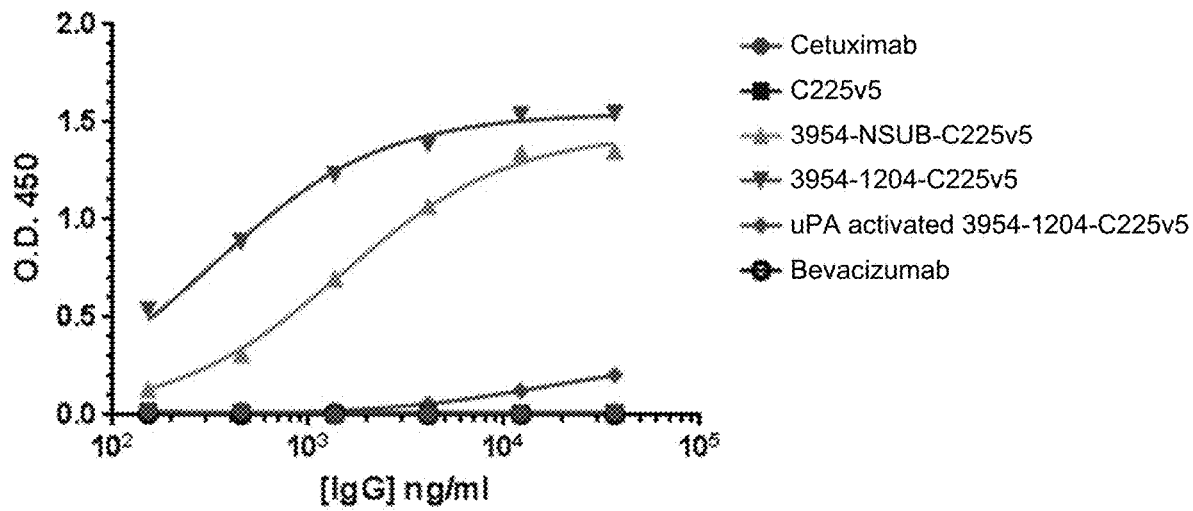
Figure 1D:
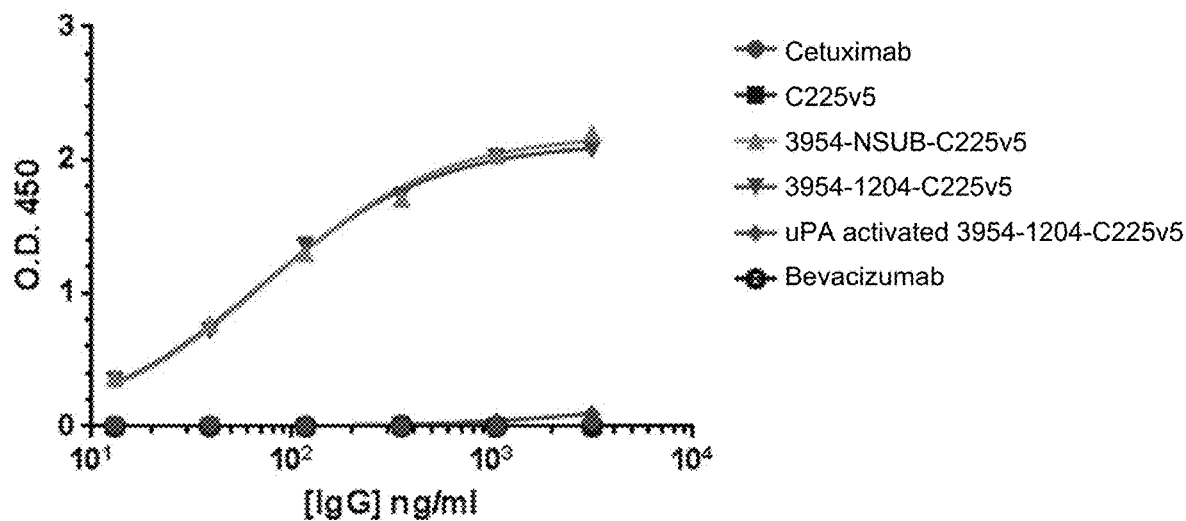
Figure 2A:
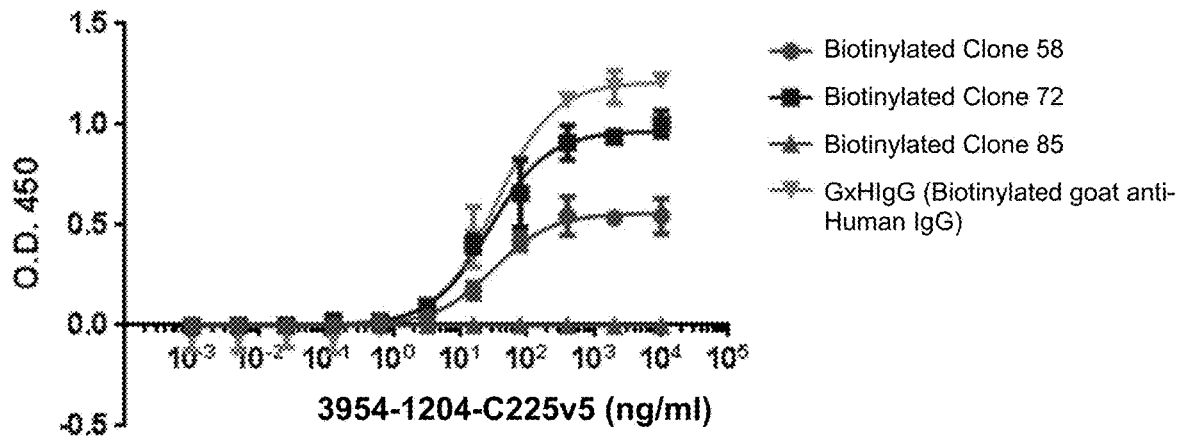
FIGS. 2A and 2B are a series of graphs depicting the results of an ELISA that uses antibodies and antigen-binding fragments thereof of the disclosure that bind activatable antibodies and/or conjugated activatable antibodies to measure the concentration of total (activated and non-activated)
Figure 2B:
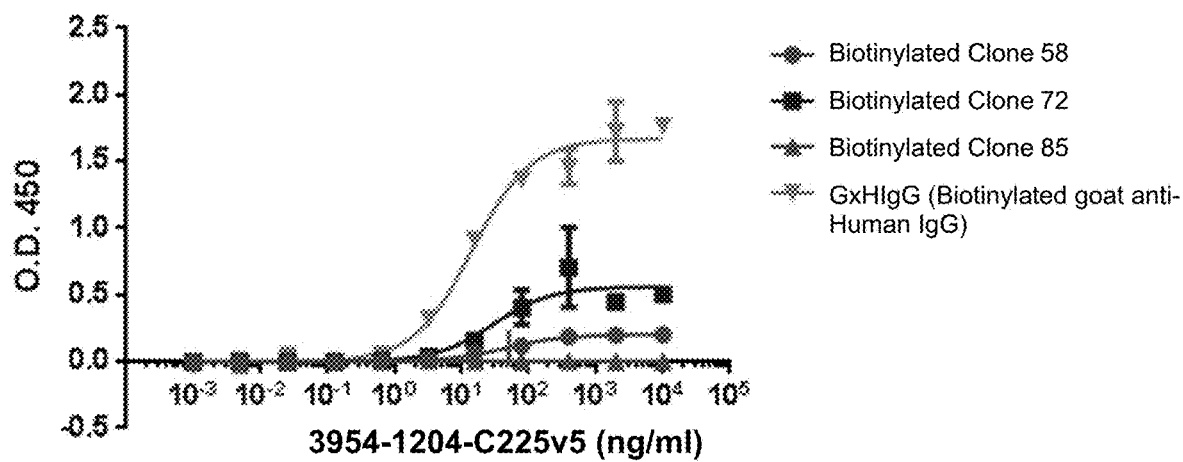
Figure 3:
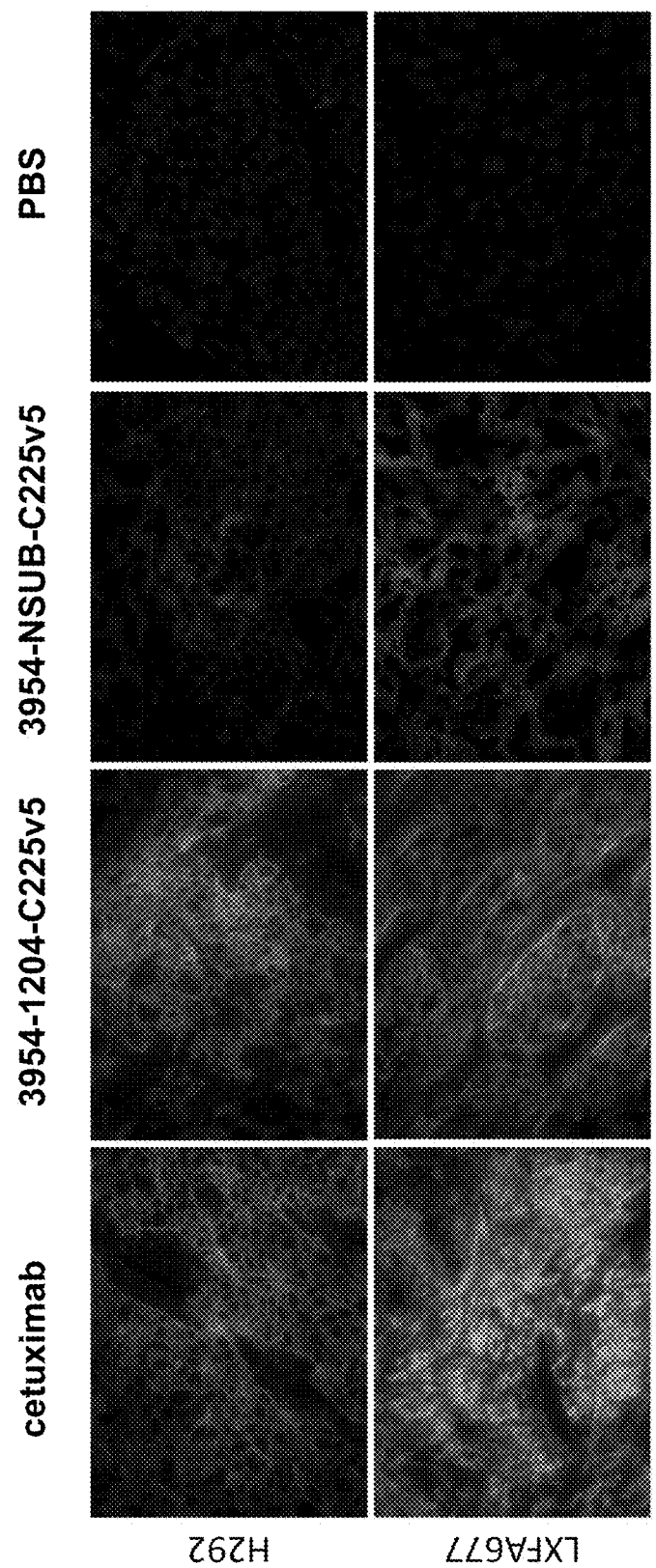

FIG. 3 is a photograph depicting the staining by antibody 41-2 (also referred to herein as antibody 41) observed in H292 and LXFA677 tumors excised from mice treated with (i) anti-EGFR antibody cetuximab (col. 1), (ii) the activatable anti-EGFR antibody 3954-1204-c225v5 (col. 2), (iii) the masked anti-EGFR antibody 3954-NSUB-c225v5 which contains a non-cleavable sequence in lieu of the substrate sequence in 3954-1204-c225v5 (col. 3), or (iv) PBS (col. 4).

Figure 4:
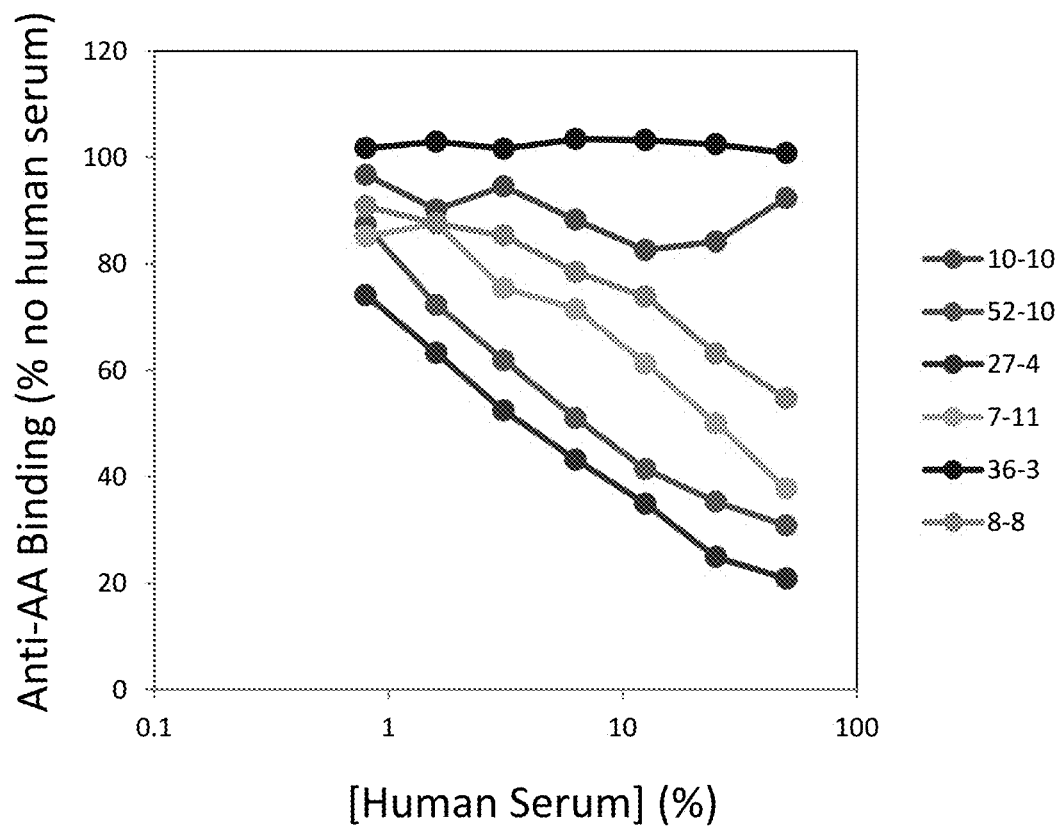

FIG. 4 is a graph depicting the effect of human serum on the binding of antibodies to the anti-Jagged 1/Jagged 2 activatable antibody referred to herein as 5342-1204-4D11 (anti-Jagged AA antibodies).

DETAILED DESCRIPTION OF THE INVENTION

Antibodies and antigen-binding fragments thereof described herein specifically bind an activatable antibody and/or conjugated activatable antibody. Also included in the disclosure are antibodies and antigen-binding fragments thereof that bind to the same epitope as the antibodies and antigen-binding fragments thereof that bind to activatable antibodies and/or conjugated activatable antibodies.

Those skilled in the art will recognize that it is possible to determine, without undue experimentation, if a monoclonal antibody (e.g., a rabbit monoclonal, a mouse monoclonal or humanized antibody) has the same specificity as a monoclonal antibody used in the methods described herein by ascertaining whether the former prevents the latter from binding to an activatable antibody and/or conjugated activatable antibody. If the monoclonal antibody being tested competes with the monoclonal antibody of the invention, as shown by a decrease in binding by the monoclonal antibody of the invention, then the two monoclonal antibodies bind to the same, or a closely related, epitope. An alternative method for determining whether a monoclonal antibody has the specificity of a monoclonal antibody of the invention is to pre-incubate the monoclonal antibody of the invention with an activatable antibody and/or conjugated activatable antibody and then add the monoclonal antibody being tested to determine if the monoclonal antibody being tested is inhibited in its ability to bind the activatable antibody and/or conjugated activatable antibody. If the monoclonal antibody being tested is inhibited then, in all likelihood, it has the same, or functionally equivalent, epitopic specificity as the monoclonal antibody of the invention.

Exemplary antibodies that bind activatable antibodies and/or conjugated activatable antibodies include the antibodies referred to herein as 41 (also referred to as 41-2 and/or clone 41), 58 (also referred to herein as 58-1 and/or clone 58), 72 (also referred to herein as 72-3 and/or clone 72), 85 (also referred to herein as 85-1 and/or clone 85), 10 (also referred to herein as 10-10 and/or clone 10), 8 (also referred to herein as 8-8 and/or clone 8), 53 (also referred to herein as 53-1 and/or clone 3), 7 (also referred to herein as 7-11 and/or clone 7), 36 (also referred to herein as 36-3 and/or clone 36), 52 (also referred to herein as 52-10 and/or clone 52), and 27 (also referred to herein as 27-4 and/or clone 27).

Antibody 41-2 has the amino acid and nucleic acid sequences shown below. The heavy chain complementarity determining regions (CDRs) and light chain CDRs are shown in boxes in the amino acid sequences presented below. In particular, the antibody referred to herein as 41-2 includes a heavy chain CDR1 (CDRH1) sequence that comprises the amino acid sequence NYAVMC (SEQ ID NO: 67), a heavy chain CDR2 (CDRH2) sequence that comprises the amino acid sequence CIVLGDGGTTYYASWARG (SEQ ID NO: 68), a heavy chain CDR3 (CDRH3) sequence that comprises the amino acid sequence SFAASSPINYFNL (SEQ ID NO: 69), a light chain CDR1 (CDRL1) sequence that comprises the amino acid sequence QASQRISTYLA (SEQ ID NO: 70), a light chain CDR2 (CDRL2) sequence that comprises the amino acid sequence KASTLAS (SEQ ID NO: 71), and a light chain CDR3 (CDRL3) sequence that comprises the amino acid sequence QSYYFGDGTTFA (SEQ ID NO: 72). The CDRs of the anti-activatable antibodies of the disclosure are identified according to Kabat, E. A., et al. (1991) Sequences of Protein of Immunological Interest, 5th edition, Public Health Service, National Institutes of Health, Bethesda, Md.

41-2 Heavy Chain (H3) Nucleic Acid Sequence with 5' Sequence
Including HindIII Restriction Site (underlined), Signal Peptide
(bold), and 3' Sequence Including Sequence Including NotI
Restriction Site (underlined):

(SEQ ID NO: 17)

AAGCTTGTACCCTTCACCATGGAGACTGGGCTGCGCTGGCTTC TCCTGGTCGCTGTGCTCAAAG

GTGTCCAGTGTCAGTCGCTGCAGGAGTCCGGGGGAGGCCTGTTCCAGCCTGGGGGATCCCTGAC

ACTCACCTGCACAGCCTCTGGATTCTCCCTCAGTAATTATGCCGTGATGTGCTGGGTCCGCCAG

GCTCCAGGGAAGGGGCTGGAGTGGATCGCATGTATTGTTCTTGGTGATGGTGGTACTACTTATT

ACGCGAGCTGGGCGAGAGGCCGGTTCACCATCTCCAAACCCTCGTCGACCACGGTGACTCTGCA

AATGACCAGTCTGACGGCCGCGGACACGGCCACCTATTTCTGTGCGAGAAGTTTTGCTGCTAGT

AGCCCCATTAACTACTTTAACTTGTGGGGCCCAGGCACCCTGGTCACCGTCTCCTCAGGGCAAC

CTAAGGCTCCATCAGTCTTCCCACTGGCCCCCTGCTGCGGGGACACACCCAGCTCCACGGTGAC

CCTGGGCTGCCTGGTCAAAGGGTACCTCCCGGAGCCAGTGACCGTGACCTGGAACTCGGGCACC

CTCACCAATGGGGTACGCACCTTCCCGTCCGTCCGGCAGTCCTCAGGCCTCTACTCGCTGAGCA

GCGTGGTGAGCGTGACCTCAAGCAGCCAGCCCGTCACCTGCAACGTGGCCCACCCAGCCACCAA

CACCAAAGTGGACAAGACCGTTGCGCCCTCGACATGCAGCAAGCCCACGTGCCCACCCCCTGAA

CTCCTGGGGGACCGTCTGTCTTCATCTTCCCCCCAAAACCCAAGGACACCCTCATGATCTCAC

GCACCCCCGAGGTCACATGCGTGGTGGTGGACGTGAGCCAGGATGACCCCGAGGTGCAGTTCAC

ATGGTACATAAACAACGAGCAGGTGCGCACCGCCCGGCCGCCGCTACGGGAGCAGCAGTTCAAC

AGCACGATCCGCGTGGTCAGCACCCTCCCCATCGCGCACCAGGACTGGCTGAGGGGCAAGGAGT

TCAAGTGCAAAGTCCACAACAAGGCACTCCCGGCCCCCATCGAGAAAACCATCTCCAAAGCCAG

AGGGCAGCCCCTGGAGCCGAAGGTCTACACCATGGGCCCTCCCCGGGAGGAGCTGAGCAGCAGG

TCGGTCAGCCTGACCTGCATGATCAACGGCTTCTACCCTTCCGACATCTCGGTGGAGTGGGAGA

AGAACGGGAAGGCAGAGGACAACTACAAGACCACGCCGGCCGTGCTGGACAGCGACGGCTCCTA

CTTCCTCTACAGCAAGCTCTCAGTGCCCACGAGTGAGTGGCAGCGGGGCGACGTCTTCACCTGC

TCCGTGATGCACGAGGCCTTGCACAACCACTACACGCAGAAGTCCATCTCCCGCTCTCCGGGTA

AATGA<u>GCGCTGTGCCGGCGAGCTGCGGCCGC</u>

41-2 Heavy Chain (H3) Nucleic Acid Sequence with Signal
Peptide (bold):

(SEQ ID NO: 18)

ATGGAGACTGGGCTGCGCTGGCTTCTCCTGGTCGCTGTGCTCAAAGGTGTCCAGTGTCAGTCGC

TGCAGGAGTCCGGGGGAGGCCTGTTCCAGCCTGGGGGATCCCTGACACTCACCTGCACAGCCTC

TGGATTCTCCCTCAGTAATTATGCCGTGATGTGCTGGGTCCGCCAGGCTCCAGGGAAGGGGCTG

GAGTGGATCGCATGTATTGTTCTTGGTGATGGTGGTACTACTTATTACGCGAGCTGGGCGAGAG

GCCGGTTCACCATCTCCAAACCCTCGTCGACCACGGTGACTCTGCAAATGACCAGTCTGACGGC

CGCGGACACGGCCACCTATTTCTGTGCGAGAAGTTTTGCTGCTAGTAGCCCCATTAACTACTTT

AACTTGTGGGGCCCAGGCACCCTGGTCACCGTCTCCTCAGGGCAACCTAAGGCTCCATCAGTCT

TCCCACTGGCCCCCTGCTGCGGGGACACACCCAGCTCCACGGTGACCCTGGGCTGCCTGGTCAA

AGGGTACCTCCCGGAGCCAGTGACCGTGACCTGGAACTCGGGCACCCTCACCAATGGGGTACGC

ACCTTCCCGTCCGTCCGGCAGTCCTCAGGCCTCTACTCGCTGAGCAGCGTGGTGAGCGTGACCT

CAAGCAGCCAGCCCGTCACCTGCAACGTGGCCCACCCAGCCACCAACACCAAAGTGGACAAGAC

CGTTGCGCCCTCGACATGCAGCAAGCCCACGTGCCCACCCCCTGAACTCCTGGGGGGACCGTCT

GTCTTCATCTTCCCCCCAAAACCCAAGGACACCCTCATGATCTCACGCACCCCCGAGGTCACAT

GCGTGGTGGTGGACGTGAGCCAGGATGACCCCGAGGTGCAGTTCACATGGTACATAAACAACGA

GCAGGTGCGCACCGCCCGGCCGCCGCTACGGGAGCAGCAGTTCAACAGCACGATCCGCGTGGTC

AGCACCCTCCCCATCGCGCACCAGGACTGGCTGAGGGGCAAGGAGTTCAAGTGCAAAGTCCACA

ACAAGGCACTCCCGGCCCCCATCGAGAAAACCATCTCCAAAGCCAGAGGGCAGCCCCTGGAGCC

GAAGGTCTACACCATGGGCCCTCCCCGGGAGGAGCTGAGCAGCAGGTCGGTCAGCCTGACCTGC

ATGATCAACGGCTTCTACCCTTCCGACATCTCGGTGGAGTGGGAGAAGAACGGGAAGGCAGAGG

ACAACTACAAGACCACGCCGGCCGTGCTGGACAGCGACGGCTCCTACTTCCTCTACAGCAAGCT

CTCAGTGCCCACGAGTGAGTGGCAGCGGGGCGACGTCTTCACCTGCTCCGTGATGCACGAGGCC

TTGCACAACCACTACACGCAGAAGTCCATCTCCCGCTCTCCGGGTAAATGA 41-2 Heavy Chain (H3) Nucleic Acid Sequence:

(SEQ ID NO: 1)

CAGTCGCTGCAGGAGTCCGGGGGAGGCCTGTTCCAGCCTGGGGGATCCCTGACACTCACCTGCA

CAGCCTCTGGATTCTCCCTCAGTAATTATGCCGTGATGTGCTGGGTCCGCCAGGCTCCAGGGAA

GGGGCTGGAGTGGATCGCATGTATTGTTCTTGGTGATGGTGGTACTACTTATTACGCGAGCTGG

GCGAGAGGCCGGTTCACCATCTCCAAACCCTCGTCGACCACGGTGACTCTGCAAATGACCAGTC

TGACGGCCGCGGACACGGCCACCTATTTCTGTGCGAGAAGTTTTGCTGCTAGTAGCCCCATTAA

-continued

```
CTACTTTAACTTGTGGGGCCCAGGCACCCTGGTCACCGTCTCCTCAGGGCAACCTAAGGCTCCA

TCAGTCTTCCCACTGGCCCCTGCTGCGGGGACACACCCAGCTCCACGGTGACCCTGGGCTGCC

TGGTCAAAGGGTACCTCCCGGAGCCAGTGACCGTGACCTGGAACTCGGGCACCCTCACCAATGG

GGTACGCACCTTCCCGTCCGTCCGGCAGTCCTCAGGCCTCTACTCGCTGAGCAGCGTGGTGAGC

GTGACCTCAAGCAGCCAGCCCGTCACCTGCAACGTGGCCCACCCAGCCACCAACACCAAAGTGG

ACAAGACCGTTGCGCCCTCGACATGCAGCAAGCCCACGTGCCCACCCCCTGAACTCCTGGGGGG

ACCGTCTGTCTTCATCTTCCCCCCAAAACCCAAGGACACCCTCATGATCTCACGCACCCCCGAG

GTCACATGCGTGGTGGTGGACGTGAGCCAGGATGACCCCGAGGTGCAGTTCACATGGTACATAA

ACAACGAGCAGGTGCGCACCGCCCGGCCGCCGCTACGGGAGCAGCAGTTCAACAGCACGATCCG

CGTGGTCAGCACCCTCCCCATCGCGCACCAGGACTGGCTGAGGGGCAAGGAGTTCAAGTGCAAA

GTCCACAACAAGGCACTCCCGGCCCCCATCGAGAAAACCATCTCCAAAGCCAGAGGGCAGCCCC

TGGAGCCGAAGGTCTACACCATGGCCCTCCCCGGGAGGAGCTGAGCAGCAGGTCGGTCAGCCT

GACCTGCATGATCAACGGCTTCTACCCTTCCGACATCTCGGTGGAGTGGGAGAAGAACGGGAAG

GCAGAGGACAACTACAAGACCACGCCGGCCGTGCTGGACAGCGACGGCTCCTACTTCCTCTACA

GCAAGCTCTCAGTGCCCACGAGTGAGTGGCAGCGGGGCGACGTCTTCACCTGCTCCGTGATGCA

CGAGGCCTTGCACAACCACTACACGCAGAAGTCCATCTCCCGCTCTCCGGGTAAATGA
```

41-2 Heavy Chain Variable Region Nucleic Acid Sequence:
(SEQ ID NO: 41)

```
CAGTCGCTGCAGGAGTCCGGGGGAGGCCTGTTCCAGCCTGGGGGATCCCTGACACTCACCTGCA

CAGCCTCTGGATTCTCCCTCAGTAATTATGCCGTGATGTGCTGGGTCCGCCAGGCTCCAGGGAA

GGGGCTGGAGTGGATCGCATGTATTGTTCTTGGTGATGGTGGTACTACTTATTACGCGAGCTGG

GCGAGAGGCCGGTTCACCATCTCCAAACCCTCGTCGACCACGGTGACTCTGCAAATGACCAGTC

TGACGGCCGCGGACACGGCCACCTATTTCTGTGCGAGAAGTTTTGCTGCTAGTAGCCCCATTAA

CTACTTTAACTTGTGGGGCCCAGGCACCCTGGTCACCGTCTCCTCA
```

41-2 Heavy Chain (H3) Amino Acid Sequence with Signal
Peptide (bold):
(SEQ ID NO: 19)

METGLRWLLLVAVLKGVQCQSLQESGGGLFQPGGSLTLTCTASGFSLS NYAVMC WVRQAPGKGL

EWIA CIVLGDGGTTYYASWARG RFTISKPSSTTVTLQMTSLTAADTATYFCAR SFAASSPINYF

NL WGPGTLVTVSSGQPKAPSVFPLAPCCGDTPSSTVTLGCLVKGYLPEPVTVTWNSGTLTNGVR

TFPSVRQSSGLYSLSSVVSVTSSSQPVTCNVAHPATNTKVDKTVAPSTCSKPTCPPPELLGGPS

VFIFPPKPKDTLMISRTPEVTCVVVDVSQDDPEVQFTWYINNEQVRTARPPLREQQFNSTIRVV

STLPIAHQDWLRGKEFKCKVHNKALPAPIEKTISKARGQPLEPKVYTMGPPREELSSRSVSLTC

MINGFYPSDISVEWEKNGKAEDNYKTTPAVLDSDGSYFLYSKLSVPTSEWQRGDVFTCSVMHEA

LHNHYTQKSISRSPGK*

41-2 Heavy Chain (H3) Amino Acid Sequence:
(SEQ ID NO: 2)

QSLQESGGGLFQPGGSLTLTCTASGFSLS NYAVMC WVRQAPGKGLEWIA CIVLGDGGTTYYASW

ARG RFTISKPSSTTVTLQMTSLTAADTATYFCAR SFAASSPINYFNL WGPGTLVTVSSGQPKAP

SVFPLAPCCGDTPSSTVTLGCLVKGYLPEPVTVTWNSGTLTNGVRTFPSVRQSSGLYSLSSVVS

VTSSSQPVTCNVAHPATNTKVDKTVAPSTCSKPTCPPPELLGGPSVFIFPPKPKDTLMISRTPE

-continued

VTCVVVDVSQDDPEVQFTWYINNEQVRTARPPLREQQFNSTIRVVSTLPIAHQDWLRGKEFKCK

VHNKALPAPIEKTISKARGQPLEPKVYTMGPPREELSSRSVSLTCMINGFYPSDISVEWEKNGK

AEDNYKTTPAVLDSDGSYFLYSKLSVPTSEWQRGDVFTCSVMHEALHNHYTQKSISRSPGK*

41-2 Heavy Chain Variable Region Amino Acid Sequence:
(SEQ ID NO: 42)
QSLQESGGGLFQPGGSLTLTCTASGFSLS NYAVMQ WVRQAPGKGLEWIA CIVLGDGGTTYYASW

ARG RFTISKPSSTTVTLQMTSLTAADTATYFCAR SFAASSPINYFNL WGPGTLVTVSS 41-2 Light Chain (L2) Nucleic Acid Sequence with 5' Sequence
Including HindIII Restriction Site (underlined), Signal Peptide
(bold), and 3' Sequence Including NotI Restriction Site
(underlined):
(SEQ ID NO: 20)
<u>AAGCTTGTACCCTTCACC</u>ATGGACACGAGGGCCCCCACTCAGCTGCTGGGGCTCCTGCTGCTCT

GGCTCCCAGGTGCCACATTTGCCCAAGTGCTGACCCAGACTTCATCCCCCGTGTCTGCACCTGT

GGGAGGCACAGTCACCATCAAGTGCCAGGCCAGTCAGCGCATTAGTACCTACCTAGCCTGGTAT

CAACAGAAACCAGGGCAGCCTCCCAAGCTCCTGATCTACAAGGCATCCACTCTGGCATCTGGGG

TCTCATCGCGGTTCAAAGGCAGTGCATCTGGGACAGAGTTCACTCTCACCATCAACGACCTGGA

GTGTGACGATGCTGCCACTTACTACTGTCAGAGCTATTATTTTGGTGATGGTACTACTTTTGCT

TTCGGCGGAGGGACCGAGGTGGTGGTCAAAGGTGATCCAGTTGCACCTACTGTCCTCATCTTCC

CACCAGCTGCTGATCAGGTGGCAACTGGAACAGTCACCATCGTGTGTGTGGCGAATAAATACTT

TCCCGATGTCACCGTCACCTGGGAGGTGGATGGCACCACCCAAACAACTGGCATCGAGAACAGT

AAAACACCGCAGAATTCTGCAGATTGTACCTACAACCTCAGCAGCACTCTGACACTGACCAGCA

CACAGTACAACAGCCACAAAGAGTACACCTGCAAGGTGACCCAGGGCACGACCTCAGTCGTCCA

GAGCTTCAATAGGGGTGACTGTTAG<u>AGCGAGAGCGGCCGC</u>

41-2 Light Chain (L2) Nucleic Acid Sequence with Signal Peptide
(bold):
(SEQ ID NO: 21)
ATGGACACGAGGGCCCCCACTCAGCTGCTGGGGCTCCTGCTGCTCTGGCTCCCAGGTGCCACAT

TTGCCCAAGTGCTGACCCAGACTTCATCCCCCGTGTCTGCACCTGTGGGAGGCACAGTCACCAT

CAAGTGCCAGGCCAGTCAGCGCATTAGTACCTACCTAGCCTGGTATCAACAGAAACCAGGGCAG

CCTCCCAAGCTCCTGATCTACAAGGCATCCACTCTGGCATCTGGGGTCTCATCGCGGTTCAAAG

GCAGTGCATCTGGGACAGAGTTCACTCTCACCATCAACGACCTGGAGTGTGACGATGCTGCCAC

TTACTACTGTCAGAGCTATTATTTTGGTGATGGTACTACTTTTGCTTTCGGCGGAGGGACCGAG

GTGGTGGTCAAAGGTGATCCAGTTGCACCTACTGTCCTCATCTTCCCACCAGCTGCTGATCAGG

TGGCAACTGGAACAGTCACCATCGTGTGTGTGGCGAATAAATACTTTCCCGATGTCACCGTCAC

CTGGGAGGTGGATGGCACCACCCAAACAACTGGCATCGAGAACAGTAAAACACCGCAGAATTCT

GCAGATTGTACCTACAACCTCAGCAGCACTCTGACACTGACCAGCACACAGTACAACAGCCACA

AAGAGTACACCTGCAAGGTGACCCAGGGCACGACCTCAGTCGTCCAGAGCTTCAATAGGGGTGA

CTGTTAG 41-2 Light Chain (L2) Nucleic Acid Sequence:
(SEQ ID NO: 3)
CAAGTGCTGACCCAGACTTCATCCCCCGTGTCTGCACCTGTGGGAGGCACAGTCACCATCAAGT

GCCAGGCCAGTCAGCGCATTAGTACCTACCTAGCCTGGTATCAACAGAAACCAGGGCAGCCTCC

CAAGCTCCTGATCTACAAGGCATCCACTCTGGCATCTGGGGTCTCATCGCGGTTCAAAGGCAGT

GCATCTGGGACAGAGTTCACTCTCACCATCAACGACCTGGAGTGTGACGATGCTGCCACTTACT

ACTGTCAGAGCTATTATTTTGGTGATGGTACTACTTTTGCTTTCGGCGGAGGGACCGAGGTGGT

-continued

```
GGTCAAAGGTGATCCAGTTGCACCTACTGTCCTCATCTTCCCACCAGCTGCTGATCAGGTGGCA

ACTGGAACAGTCACCATCGTGTGTGTGGCGAATAAATACTTTCCCGATGTCACCGTCACCTGGG

AGGTGGATGGCACCACCCAAACAACTGGCATCGAGAACAGTAAAACACCGCAGAATTCTGCAGA

TTGTACCTACAACCTCAGCAGCACTCTGACACTGACCAGCACACAGTACAACAGCCACAAAGAG

TACACCTGCAAGGTGACCCAGGGCACGACCTCAGTCGTCCAGAGCTTCAATAGGGGTGACTGTT

AG
```

41-2 Light Chain Variable Region Nucleic Acid Sequence:
(SEQ ID NO: 43)
```
CAAGTGCTGACCCAGACTTCATCCCCCGTGTCTGCACCTGTGGGAGGCACAGTCACCATCAAGT

GCCAGGCCAGTCAGCGCATTAGTACCTACCTAGCCTGGTATCAACAGAAACCAGGGCAGCCTCC

CAAGCTCCTGATCTACAAGGCATCCACTCTGGCATCTGGGGTCTCATCGCGGTTCAAAGGCAGT

GCATCTGGGACAGAGTTCACTCTCACCATCAACGACCTGGAGTGTGACGATGCTGCCACTTACT

ACTGTCAGAGCTATTATTTTGGTGATGGTACTACTTTTGCTTTCGGCGGAGGGACCGAGGTGGT

GGTCAAA
```

41-2 Light Chain (L2) Amino Acid Sequence with Signal Peptide (bold)
(SEQ ID NO: 22)
MDTRAPTQLLGLLLWLPGATFAQVLTQTSSPVSAPVGGTVTIKCQASQRISTYLAWYQQKPGQ

PPKLLIYKASTLASGVSSRFKGSASGTEFTLTINDLECDDAATYYCQSYYFGDGTTFAFGGGTE

VVVKGDPVAPTVLIFPPAADQVATGTVTIVCVANKYFPDVTVTWEVDGTTQTTGIENSKTPQNS 41-2 Light Chain (L2) Amino Acid Sequence:
(SEQ ID NO: 4)
QVLTQTSSPVSAPVGGTVTIKCQASQRISTYLAWYQQKPGQPPKLLIYKASTLASGVSSRFKGS

ASGTEFTLTINDLECDDAATYYCQSYYFGDGTTFAFGGGTEVVVKGDPVAPTVLIFPPAADQVA

TGTVTIVCVANKYFPDVTVTWEVDGTTQTTGIENSKTPQNSADCTYNLSSTLTLTSTQYNSHKE

YTCKVTQGTTSVVQSFNRGDC*

41-2 Light Chain Variable Region Amino Acid Sequence:
(SEQ ID NO: 44)
QVLTQTSSPVSAPVGGTVTIKCQASQRISTYLAWYQQKPGQPPKLLIYKASTLASGVSSRFKGS

ASGTEFTLTINDLECDDAATYYCQSYYFGDGTTFAFGGGTEVVVK

In some embodiments, antibody 41-2 is modified to remove one or more cysteine residues in one or more CDR sequences. In some embodiments, the antibody includes a CDRH1 sequence that comprises the amino acid sequence NYAVMX (SEQ ID NO: 73), where X is Ala or Ser, a CDRH2 sequence that comprises the amino acid sequence XIVLGDGGTTYYASWARG (SEQ ID NO: 74), where X is Ala or Ser, a CDRH3 sequence that comprises the amino acid sequence SFAASSPINYFNL (SEQ ID NO: 69), a CDRL1 sequence that comprises the amino acid sequence QASQRISTYLA (SEQ ID NO: 70), a CDRL2 sequence that comprises the amino acid sequence KASTLAS (SEQ ID NO: 71), and a CDRL3 sequence that comprises the amino acid sequence QSYYFGDGTTFA (SEQ ID NO: 72). In some embodiments, the antibody includes the following heavy chain amino acid sequences:

41-2 Heavy Chain (H3) Amino Acid Sequence with Signal Peptide (bold):
(SEQ ID NO: 75)
METGLRWLLLLVAVLKGVQCQSLQESGGGLFQPGGSLTLTCTASGFSLSNYAVMXNVRQAPGKGL

EWIAXIVLGDGGTTYYASWARGRFTISKPSSTTVTLQMTSLTAADTATYFCARSFAASSPINYF

-continued

```
NLWGPGTLVTVSSGQPKAPSVFPLAPCCGDTPSSTVTLGCLVKGYLPEPVTVTWNSGTLTNGVR

TFPSVRQSSGLYSLSSVVSVTSSSQPVTCNVAHPATNTKVDKTVAPSTCSKPTCPPPELLGGPS

VFIFPPKPKDTLMISRTPEVTCVVVDVSQDDPEVQFTWYINNEQVRTARPPLREQQFNSTIRVV

STLPIAHQDWLRGKEFKCKVHNKALPAPIEKTISKARGQPLEPKVYTMGPPREELSSRSVSLTC

MINGFYPSDISVEWEKNGKAEDNYKTTPAVLDSDGSYFLYSKLSVPTSEWQRGDVFTCSVMHEA

LHNHYTQKSISRSPGK*
Where X is Ala or Ser
```

41-2 Heavy Chain (H3) Amino Acid Sequence:

(SEQ ID NO: 76)

```
QSLQESGGGLFQPGGSLTLTCTASGFSLSNYAVMXWVRQAPGKGLEWIAKIVLGDGGTTYYASW

ARGRFTISKPSSTTVTLQMTSLTAADTATYFCARSFAASSPINYFNLWGPGTLVTVSSGQPKAP

SVFPLAPCCGDTPSSTVTLGCLVKGYLPEPVTVTWNSGTLTNGVRTFPSVRQSSGLYSLSSVVS

VTSSSQPVTCNVAHPATNTKVDKTVAPSTCSKPTCPPPELLGGPSVFIFPPKPKDTLMISRTPE

VTCVVVDVSQDDPEVQFTWYINNEQVRTARPPLREQQFNSTIRVVSTLPIAHQDWLRGKEFKCK

VHNKALPAPIEKTISKARGPLEPKVYTMGPPREELSSRSVSLTCMINGFYPSDISVEWEKNGK

AEDNYKTTPAVLDSDGSYFLYSKLSVPTSEWQRGDVFTCSVMHEALHNHYTQKSISRSPGK*
Where X is Ala or Ser
```

41-2 Heavy Chain Variable Region Amino Acid Sequence:

(SEQ ID NO: 77)

```
QSLQESGGGLFQPGGSLTLTCTASGFSLSNYAVMXWVRQAPGKGLEWIAKIVLGDGGTTYYASW

ARGRFTISKPSSTTVTLQMTSLTAADTATYFCARSFAASSPINYFNLWGPGTLVTVSS
Where X is Ala or Ser
```

Antibody 58-1 has the amino acid and nucleic acid sequences shown below. The heavy chain complementarity determining regions (CDRs) and light chain CDRs are shown in boxes in the amino acid sequences presented below. In particular, the antibody referred to herein as 58-1 includes a CDRH1 sequence that comprises the amino acid sequence RYGMA (SEQ ID NO: 78), a CDRH2 sequence that comprises the amino acid sequence AISSSGNEDYAS-WAIG (SEQ ID NO: 79), a CDRH3 sequence that comprises the amino acid sequence GWLSNNAYM (SEQ ID NO: 80), a CDRL1 sequence that comprises the amino acid sequence QASQSIYNKNQLS (SEQ ID NO: 81), a CDRL2 sequence that comprises the amino acid sequence YASTLAS (SEQ ID NO: 82), and a CDRL3 sequence that comprises the amino acid sequence LGDFSCSGVDCLV (SEQ ID NO: 83).

58-1 Heavy Chain (H2) Nucleic Acid Sequence 5' Sequence Including HindIII Restriction Site (underlined), Signal Peptide (bold), and 3' Sequence Including NotI Restriction Site (underlined):

(SEQ ID NO: 23)

```
AAGCTTGTACCCTTCACCATGGAGACTGGGCTGCGCTGGCTTCTCCTGGTCGCTGTGCTCAAAG

GTGTCCAGTGTCAGTCGGTGGAGGAGTCCGGGGGTCGTCTGGTCATGCCTGGAGGATCCCTGAC

ACTCACCTGTACAGTCTCTGGAATCGACCTCAGTCGCTATGGAATGGCCTGGTTCCGCCAGGCT

CCAGGGAAGGGGCTGAAATACATCGGAGCCATTAGTAGTAGTGGTAATGAAGACTACGCGAGCT

GGGCGATAGGCCGATTTACCATCTCCAAAACCTCGACCACGGCGGAGCTGAAAATGACCAGTCT

GACAACCGAGGACACGGCCACCTATTTCTGTGGCAGAGGTTGGCTTAGTAATAACGCTTATATG

TGGGGCCCAGGCACCCTGGTCACCGTCTCGTCAGGGCAACCTAAGGCTCCATCAGTCTTCCCAC

TGGCCCCCTGCTGCGGGGACACACCCAGCTCCACGGTGACCCTGGGCTGCCTGGTCAAAGGGTA

CCTCCCGGAGCCAGTGACCGTGACCTGGAACTCGGGCACCCTCACCAATGGGGTACGCACCTTC

CCGTCCGTCCGGCAGTCCTCAGGCCTCTACTCGCTGAGCAGCGTGGTGAGCGTGACCTCAAGCA

GCCAGCCCGTCACCTGCAACGTGGCCCACCCAGCCACCAACACCAAAGTGGACAAGACCGTTGC
```

-continued

GCCCTCGACATGCAGCAAGCCCACGTGCCCACCCCCTGAACTCCTGGGGGGACCGTCTGTCTTC

ATCTTCCCCCCAAAACCCAAGGACACCCTCATGATCTCACGCACCCCCGAGGTCACATGCGTGG

TGGTGGACGTGAGCCAGGATGACCCCGAGGTGCAGTTCACATGGTACATAAACAACGAGCAGGT

GCGCACCGCCCGGCCGCCGCTACGGGAGCAGCAGTTCAACAGCACGATCCGCGTGGTCAGCACC

CTCCCCATCGCGCACCAGGACTGGCTGAGGGGCAAGGAGTTCAAGTGCAAAGTCCACAACAAGG

CACTCCCGGCCCCCATCGAGAAAACCATCTCCAAAGCCAGAGGGCAGCCCCTGGAGCCGAAGGT

CTACACCATGGGCCCTCCCCGGGAGGAGCTGAGCAGCAGGTCGGTCAGCCTGACCTGCATGATC

AACGGCTTCTACCCTTCCGACATCTCGGTGGAGTGGGAGAAGAACGGGAAGGCAGAGGACAACT

ACAAGACCACGCCGGCCGTGCTGGACAGCGACGGCTCCTACTTCCTCTACAGCAAGCTCTCAGT

GCCCACGAGTGAGTGGCAGCGGGGCGACGTCTTCACCTGCTCCGTGATGCACGAGGCCTTGCAC

AACCACTACACGCAGAAGTCCATCTCCCGCTCTCCGGGTAAATGA<u>GCGCTGTGCCGGCGAGCTG</u>

<u>CGGCCGC</u>

58-1 Heavy Chain (H2) Nucleic Acid Sequence with Signal Peptide
(bold):

(SEQ ID NO: 24)

ATGGAGACTGGGCTGCGCTGGCTTCTCCTGGTCGCTGTGCTCAAAGGTGTCCAGTGTCAGTCGG

TGGAGGAGTCCGGGGGTCGTCTGGTCATGCCTGGAGGATCCCTGACACTCACCTGTACAGTCTC

TGGAATCGACCTCAGTCGCTATGGAATGGCCTGGTTCCGCCAGGCTCCAGGGAAGGGGCTGAAA

TACATCGGAGCCATTAGTAGTAGTGGTAATGAAGACTACGCGAGCTGGGCGATAGGCCGATTTA

CCATCTCCAAAACCTCGACCACGGCGGAGCTGAAAATGACCAGTCTGACAACCGAGGACACGGC

CACCTATTTCTGTGGCAGAGGTTGGCTTAGTAATAACGCTTATATGTGGGGCCCAGGCACCCTG

GTCACCGTCTCGTCAGGGCAACCTAAGGCTCCATCAGTCTTCCCACTGGCCCCCTGCTGCGGGG

ACACACCCAGCTCCACGGTGACCCTGGGCTGCCTGGTCAAAGGGTACCTCCCGGAGCCAGTGAC

CGTGACCTGGAACTCGGGCACCCTCACCAATGGGGTACGCACCTTCCCGTCCGTCCGGCAGTCC

TCAGGCCTCTACTCGCTGAGCAGCGTGGTGAGCGTGACCTCAAGCAGCCAGCCCGTCACCTGCA

ACGTGGCCCACCCAGCCACCAACACCAAAGTGGACAAGACCGTTGCGCCCTCGACATGCAGCAA

GCCCACGTGCCCACCCCCTGAACTCCTGGGGGGACCGTCTGTCTTCATCTTCCCCCCAAAACCC

AAGGACACCCTCATGATCTCACGCACCCCCGAGGTCACATGCGTGGTGGTGGACGTGAGCCAGG

ATGACCCCGAGGTGCAGTTCACATGGTACATAAACAACGAGCAGGTGCGCACCGCCCGGCCGCC

GCTACGGGAGCAGCAGTTCAACAGCACGATCCGCGTGGTCAGCACCCTCCCCATCGCGCACCAG

GACTGGCTGAGGGGCAAGGAGTTCAAGTGCAAAGTCCACAACAAGGCACTCCCGGCCCCCATCG

AGAAAACCATCTCCAAAGCCAGAGGGCAGCCCCTGGAGCCGAAGGTCTACACCATGGGCCCTCC

CCGGGAGGAGCTGAGCAGCAGGTCGGTCAGCCTGACCTGCATGATCAACGGCTTCTACCCTTCC

GACATCTCGGTGGAGTGGGAGAAGAACGGGAAGGCAGAGGACAACTACAAGACCACGCCGGCCG

TGCTGGACAGCGACGGCTCCTACTTCCTCTACAGCAAGCTCTCAGTGCCCACGAGTGAGTGGCA

GCGGGGCGACGTCTTCACCTGCTCCGTGATGCACGAGGCCTTGCACAACCACTACACGCAGAAG

TCCATCTCCCGCTCTCCGGGTAAATGA 58-1 Heavy Chain (H2) Nucleic Acid Sequence:

(SEQ ID NO: 5)

CAGTCGGTGGAGGAGTCCGGGGGTCGTCTGGTCATGCCTGGAGGATCCCTGACACTCACCTGTA

CAGTCTCTGGAATCGACCTCAGTCGCTATGGAATGGCCTGGTTCCGCCAGGCTCCAGGGAAGGG

GCTGAAATACATCGGAGCCATTAGTAGTAGTGGTAATGAAGACTACGCGAGCTGGGCGATAGGC

CGATTTACCATCTCCAAAACCTCGACCACGGCGGAGCTGAAAATGACCAGTCTGACAACCGAGG

ACACGGCCACCTATTTCTGTGGCAGAGGTTGGCTTAGTAATAACGCTTATATGTGGGCCCAGG

CACCCTGGTCACCGTCTCGTCAGGGCAACCTAAGGCTCCATCAGTCTTCCCACTGGCCCCCTGC

TGCGGGGACACACCCAGCTCCACGGTGACCCTGGGCTGCCTGGTCAAAGGGTACCTCCCGGAGC

CAGTGACCGTGACCTGGAACTCGGGCACCCTCACCAATGGGGTACGCACCTTCCCGTCCGTCCG

GCAGTCCTCAGGCCTCTACTCGCTGAGCAGCGTGGTGAGCGTGACCTCAAGCAGCCAGCCCGTC

ACCTGCAACGTGGCCCACCCAGCCACCAACACCAAAGTGGACAAGACCGTTGCGCCCTCGACAT

GCAGCAAGCCCACGTGCCCACCCCCTGAACTCCTGGGGGACCGTCTGTCTTCATCTTCCCCCC

AAAACCCAAGGACACCCTCATGATCTCACGCACCCCCGAGGTCACATGCGTGGTGGTGGACGTG

AGCCAGGATGACCCCGAGGTGCAGTTCACATGGTACATAAACAACGAGCAGGTGCGCACCGCCC

GGCCGCCGCTACGGGAGCAGCAGTTCAACAGCACGATCCGCGTGGTCAGCACCCTCCCCATCGC

GCACCAGGACTGGCTGAGGGGCAAGGAGTTCAAGTGCAAAGTCCACAACAAGGCACTCCCGGCC

CCCATCGAGAAAACCATCTCCAAAGCCAGAGGGCAGCCCCTGGAGCCGAAGGTCTACACCATGG

GCCCTCCCCGGGAGGAGCTGAGCAGCAGGTCGGTCAGCCTGACCTGCATGATCAACGGCTTCTA

CCCTTCCGACATCTCGGTGGAGTGGGAGAAGAACGGGAAGGCAGAGGACAACTACAAGACCACG

CCGGCCGTGCTGGACAGCGACGGCTCCTACTTCCTCTACAGCAAGCTCTCAGTGCCCACGAGTG

AGTGGCAGCGGGGCGACGTCTTCACCTGCTCCGTGATGCACGAGGCCTTGCACAACCACTACAC

GCAGAAGTCCATCTCCCGCTCTCCGGGTAAATGA 58-1 Heavy Chain Variable Region Nucleic Acid Sequence:
(SEQ ID NO: 55)
CAGTCGGTGGAGGAGTCCGGGGGTCGTCTGGTCATGCCTGGAGGATCCCTGACACTCACCTGTA

CAGTCTCTGGAATCGACCTCAGTCGCTATGGAATGGCCTGGTTCCGCCAGGCTCCAGGGAAGGG

GCTGAAATACATCGGAGCCATTAGTAGTAGTGGTAATGAAGACTACGCGAGCTGGGCGATAGGC

CGATTTACCATCTCCAAAACCTCGACCACGGCGGAGCTGAAAATGACCAGTCTGACAACCGAGG

ACACGGCCACCTATTTCTGTGGCAGAGGTTGGCTTAGTAATAACGCTTATATGTGGGGCCCAGG

CACCCTGGTCACCGTCTCGTCA 58-1 Heavy Chain (H2) Amino Acid Sequence with Signal Peptide
(bold):
(SEQ ID NO: 25)
METGLRWLLLVAVLKGVQCQSVEESGGRLVMPGGSLTLTCTVSGIDLSRYGMAWFRQAPGKGLK

YIGAISSSGNEDYASWAIGRFTISKTSTTAELKMTSLTTEDTATYFCGRGWLSNNAYMWGPGTL

VTVSSGQPKAPSVFPLAPCCGDTPSSTVTLGCLVKGYLPEPVTVTWNSGTLTNGVRTFPSVRQS

SGLYSLSSVVSVTSSSQPVTCNVAHPATNTKVDKTVAPSTCSKPTCPPPELLGGPSVFIFPPKP

KDTLMISRTPEVTCVVVDVSQDDPEVQFTWYINNEQVRTARPPLREQQFNSTIRVVSTLPIAHQ

DWLRGKEFKCKVHNKALPAPIEKTISKARGQPLEPKVYTMGPPREELSSRSVSLTCMINGFYPS

DISVEWEKNGKAEDNYKTTPAVLDSDGSYFLYSKLSVPTSEWQRGDVFTCSVMHEALHNHYTQK

SISRSPGK*

58-1 Heavy Chain (H2) Amino Acid Sequence:
(SEQ ID NO: 6)
QSVEESGGRLVMPGGSLTLTCTVSGIDLSRYGMAWFRQAPGKGLKYIGAISSSGNEDYASWAIG

RFTISKTSTTAELKMTSLTTEDTATYFCGRGWLSNNAYMWGPGTLVTVSSGQPKAPSVFPLAPC

CGDTPSSTVTLGCLVKGYLPEPVTVTWNSGTLTNGVRTFPSVRQSSGLYSLSSVVSVTSSSQPV

TCNVAHPATNTKVDKTVAPSTCSKPTCPPPELLGGPSVFIFPPKPKDTLMISRTPEVTCVVVDV

SQDDPEVQFTWYINNEQVRTARPPLREQQFNSTIRVVSTLPIAHQDWLRGKEFKCKVHNKALPA

PIEKTISKARGQPLEPKVYTMGPPREELSSRSVSLTCMINGFYPSDISVEWEKNGKAEDNYKTT

PAVLDSDGSYFLYSKLSVPTSEWQRGDVFTCSVMHEALHNHYTQKSISRSPGK*

58-1 Heavy Chain Variable Region Amino Acid Sequence:

(SEQ ID NO: 56)

QSVEESGGRLVMPGGSLTLTCTVSGIDLSRYGMAWFRQAPGKGLKYIGAISSSGNEDYASWAIG

RFTISKTSTTAELKMTSLTTEDTATYFCGRGWLSNNAYMWGPGTLVTVSS 58-1 Light Chain (L2) Nucleic Acid Sequence with 5' Sequence
Including HindIII Restriction Site (underlined), Signal Peptide
(bold), and 3' Sequence Including NotI Restriction Site
(underlined):

(SEQ ID NO: 26)

AAGCTTGTACCCTTCACCATGGACACGAGGGCCCCCACTCAGCTGCTGGGGCTCCTGCTGCTCT

GGCTCCCAGGTGCCACATTTGCCCCGGTGCTGACCCAGACTCCAACGCCCGTGTCTGCAGCTGT

GGGAGGCACAGTCACCATCAATTGCCAGGCCAGTCAAAGTATTTATAATAAAAATCAATTATCC

TGGTTTCAGCAGAAACCAGGGCAGCCTCCCAAGCTCCTGATCCATTATGCATCCACTCTGGCAT

CTGGGGTCTCATCGCGGTTCAAAGGCAGTGGATCTGGGACACAGTTCACTCTCACCATCAGCGA

CGTGCAGTGTGACGATGCTGCCACTTACTATTGTCTAGGCGATTTTAGTTGTAGTGGTGTTGAT

TGTCTTGTTGTCGGCGGAGGACCGAGGTGGTCGTCGAAGGTGATCCAGTTGCACCTACTGTCC

TCATCTTCCCACCATCTGCTGATCTTGTGGCAACTGGAACAGTCACCATCGTGTGTGTGGCGAA

TAAATACTTTCCCGATGTCACCGTCACCTGGGAGGTGGATGGCACCACCCAAACAACTGGCATC

GAGAACAGTAAAACACCGCAGAATTCTGCAGATTGTACCTACAACCTCAGCAGCACTCTGACAC

TGACCAGCACACAATACAACAGCCACAAAGAGTACACCTGCAAGGTGACCCAGGGCACGACCTC

AGTCGTCCAGAGCTTCAATAGGGGTGACTGTTAGAGCGAGAGCGGCCGC 58-1 Light Chain (L2) Nucleic Acid Sequence Signal Peptide
(bold):

(SEQ ID NO: 27)

ATGGACACGAGGGCCCCCACTCAGCTGCTGGGGCTCCTGCTGCTCTGGCTCCCAGGTGCCACAT

TTGCCCCGGTGCTGACCCAGACTCCAACGCCCGTGTCTGCAGCTGTGGGAGGCACAGTCACCAT

CAATTGCCAGGCCAGTCAAAGTATTTATAATAAAAATCAATTATCCTGGTTTCAGCAGAAACCA

GGGCAGCCTCCCAAGCTCCTGATCCATTATGCATCCACTCTGGCATCTGGGGTCTCATCGCGGT

TCAAAGGCAGTGGATCTGGGACACAGTTCACTCTCACCATCAGCGACGTGCAGTGTGACGATGC

TGCCACTTACTATTGTCTAGGCGATTTTAGTTGTAGTGGTGTTGATTGTCTTGTTGTCGGCGGA

GGGACCGAGGTGGTCGTCGAAGGTGATCCAGTTGCACCTACTGTCCTCATCTTCCCACCATCTG

CTGATCTTGTGGCAACTGGAACAGTCACCATCGTGTGTGTGGCGAATAAATACTTTCCCGATGT

CACCGTCACCTGGGAGGTGGATGGCACCACCCAAACAACTGGCATCGAGAACAGTAAAACACCG

CAGAATTCTGCAGATTGTACCTACAACCTCAGCAGCACTCTGACACTGACCAGCACACAATACA

ACAGCCACAAAGAGTACACCTGCAAGGTGACCCAGGGCACGACCTCAGTCGTCCAGAGCTTCAA

TAGGGGTGACTGTTAG 58-1 Light Chain (L2) Nucleic Acid Sequence:

(SEQ ID NO: 7)

CCGGTGCTGACCCAGACTCCAACGCCCGTGTCTGCAGCTGTGGGAGGCACAGTCACCATCAATT

GCCAGGCCAGTCAAAGTATTTATAATAAAAATCAATTATCCTGGTTTCAGCAGAAACCAGGGCA

GCCTCCCAAGCTCCTGATCCATTATGCATCCACTCTGGCATCTGGGGTCTCATCGCGGTTCAAA

GGCAGTGGATCTGGGACACAGTTCACTCTCACCATCAGCGACGTGCAGTGTGACGATGCTGCCA

CTTACTATTGTCTAGGCGATTTTAGTTGTAGTGGTGTTGATTGTCTTGTTGTCGGCGGAGGGAC

```
CGAGGTGGTCGTCGAAGGTGATCCAGTTGCACCTACTGTCCTCATCTTCCCACCATCTGCTGAT

CTTGTGGCAACTGGAACAGTCACCATCGTGTGTGTGGCGAATAAATACTTTCCCGATGTCACCG

TCACCTGGGAGGTGGATGGCACCACCCAAACAACTGGCATCGAGAACAGTAAAACACCGCAGAA

TTCTGCAGATTGTACCTACAACCTCAGCAGCACTCTGACACTGACCAGCACACAATACAACAGC

CACAAAGAGTACACCTGCAAGGTGACCCAGGGCACGACCTCAGTCGTCCAGAGCTTCAATAGGG

GTGACTGTTAG
```

58-1 Light Chain Variable Region Nucleic Acid Sequence:
(SEQ ID NO: 57)
```
CCGGTGCTGACCCAGACTCCAACGCCCGTGTCTGCAGCTGTGGGAGGCACAGTCACCATCAATT

GCCAGGCCAGTCAAAGTATTTATAATAAAAATCAATTATCCTGGTTTCAGCAGAAACCAGGGCA

GCCTCCCAAGCTCCTGATCCATTATGCATCCACTCTGGCATCTGGGGTCTCATCGCGGTTCAAA

GGCAGTGGATCTGGGACACAGTTCACTCTCACCATCAGCGACGTGCAGTGTGACGATGCTGCCA

CTTACTATTGTCTAGGCGATTTTAGTTGTAGTGGTGTTGATTGTCTTGTTGTCGGCGGAGGGAC

CGAGGTGGTCGTCGAA
```

58-1 Light Chain (L2) Amino Acid Sequence with Signal Peptide (bold):
(SEQ ID NO: 28)
MDTRAPTQLLGLLLLWLPGATFAPVLTQTPTPVSAAVGGTVTINC QASQSIYNKNQLS WFQQKP

GQPPKLLIH YASTLAS GVSSRFKGSGSGTQFTLTISDVQCDDAATYYC LGDFSCSGVDCLV VGG

GTEVVVEGDPVAPTVLIFPPSADLVATGTVTIVCVANKYFPDVTVTWEVDGTTQTTGIENSKTP

QNSADCTYNLSSTLTLTSTQYNSHKEYTCKVTQGTTSVVQSFNRGDC*

58-1 Light Chain (L2) Amino Acid Sequence:
(SEQ ID NO: 8)
PVLTQTPTPVSAAVGGTVTINC QASQSIYNKNQLS WFQQKPGQPPKLLIH YASTLAS GVSSRFK

GSGSGTQFTLTISDVQCDDAATYYC LGDFSCSGVDCLV VGGGTEVVVEGDPVAPTVLIFPPSAD

LVATGTVTIVCVANKYFPDVTVTWEVDGTTQTTGIENSKTPQNSADCTYNLSSTLTLTSTQYNS

HKEYTCKVTQGTTSVVQSFNRGDC*

58-1 Light Chain Variable Region Amino Acid Sequence:
(SEQ ID NO: 58)
PVLTQTPTPVSAAVGGTVTINC QASQSIYNKNQLS WFQQKPGQPPKLLIH YASTLAS GVSSRFK

GSGSGTQFTLTISDVQCDDAATYYC LGDFSCSGVDCLV VGGGTEVVVE

In some embodiments, antibody 58-1 is modified to remove one or more cysteine residues in one or more CDR sequences. In some embodiments, the antibody includes a CDRH1 sequence that comprises the amino acid sequence RYGMA (SEQ ID NO: 78), a CDRH2 sequence that comprises the amino acid sequence AISSSGNEDYASWAIG (SEQ ID NO: 79), a CDRH3 sequence that comprises the amino acid sequence GWLSNNAYM (SEQ ID NO: 80), a CDRL1 sequence that comprises the amino acid sequence QASQSIYNKNQLS (SEQ ID NO: 81), a CDRL2 sequence that comprises the amino acid sequence YASTLAS (SEQ ID NO: 82), and a CDRL3 sequence that comprises the amino acid sequence LGDFSXSGVDXLV (SEQ ID NO: 84), where X is Ala or Ser. In some embodiments, the antibody includes the following light chain amino acid sequences:

58-1 Light Chain (L2) Amino Acid Sequence with Signal Peptide (bold):
(SEQ ID NO: 85)
MDTRAPTQLLGLLLLWLPGATFAPVLTQTPTPVSAAVGGTVTINC QASQSIYNKNQLS WFQQKP

GQPPKLLIH YASTLAS GVSSRFKGSGSGTQFTLTISDVQCDDAATYYC LGDFSXSGVDXLV VGG

-continued

```
GTEVVVEGDPVAPTVLIFPPSADLVATGTVTIVCVANKYFPDVTVTWEVDGTTQTTGIENSKTP

QNSADCTYNLSSTLTLTSTQYNSHKEYTCKVTQGTTSVVQSFNRGDC*
Where X is Ala or Ser 58-1 Light Chain (L2) Amino Acid Sequence:
                                                    (SEQ ID NO: 86)
PVLTQTPTPVSAAVGGTVTINCQASQSIYNKNQLSWFQQKPGQPPKLLIHYASTLASGVSSRFK

GSGSGTQFTLTISDVQCDDAATYYCLGDFSXSGVDXLVVGGGTEVVVEGDPVAPTVLIFPPSAD

LVATGTVTIVCVANKYFPDVTVTWEVDGTTQTTGIENSKTPQNSADCTYNLSSTLTLTSTQYNS

HKEYTCKVTQGTTSVVQSFNRGDC*
Where X is Ala or Ser 58-1 Light Chain Variable Region Amino Acid Sequence:
                                                    (SEQ ID NO: 87)
PVLTQTPTPVSAAVGGTVTINCQASQSIYNKNQLSWFQQKPGQPPKLLIHYASTLASGVSSRFK GSGSGTQFTLTISDVQCDDAATYYCLGDFSXSGVDXLVVGGGTEVVVE
Where X is Ala or Ser
```

Antibody 72-3 has the amino acid and nucleic acid sequences shown below. The heavy chain complementarity determining regions (CDRs) and light chain CDRs are shown in boxes in the amino acid sequences presented below. In particular, the antibody referred to herein as 72-3 includes a CDRH1 sequence that comprises the amino acid sequence HYGMA (SEQ ID NO: 88), a CDRH2 sequence that comprises the amino acid sequence AISSSGNEDYAS- WPKG (SEQ ID NO: 89), a CDRH3 sequence that comprises the amino acid sequence GWLSNNVYM (SEQ ID NO: 90), a CDRL1 sequence that comprises the amino acid sequence QASQSIYNKNQLS (SEQ ID NO: 81), a CDRL2 sequence that comprises the amino acid sequence YASTLAS (SEQ ID NO: 82), and a CDRL3 sequence that comprises the amino acid sequence LGDFSCSGVDCLS (SEQ ID NO: 91).

```
72-3 Heavy Chain (H1) Nucleic Acid Sequence with 5' Sequence
Including HindIII Restriction Site (underlined), Signal Peptide
(bold), and 3' Sequence Including NotI Restriction Site
(underlined):
                                                    (SEQ ID NO: 29)
AAGCTTGTACCCTTCACCATGGAGACTGGGCTGCGCTGGCTTCTCCTGGTCGCTGTGCTCAAAG

GTGTCCAGTGTCAGTCGGTGGAGGAGTCCGGGGGTCGTCTGGTCATGCCTGGAGGATCCCTGAC

ACTCACCTGCACAGTCTCTGGAATCGACCTCAGTCACTATGGAATGGCCTGGTTCCGCCAGGCT

CCAGGGAAGGGGCTGGAATACATCGGAGCCATTAGTAGTAGTGGTAATGAAGACTACGCGAGCT

GGCCGAAAGGCCGATTCACCATCTCCAAAACCTCGACCACGGTGACTCTGAAAATGACCAGTCT

GACAACCGAGGACACGGCCACCTATTTCTGTGGCAGAGGTTGGCTTAGTAATAATGTTTATATG

TGGGGCCCAGGCACCCTGGTCACCGTCTCGTCAGGGCAACCTAAGGCTCCATCAGTCTTCCCAC

TGGCCCCCTGCTGCGGGGACACACCCAGCTCCACGGTGACCCTGGGCTGCCTGGTCAAAGGGTA

CCTCCCGGAGCCAGTGACCGTGACCTGGAACTCGGGCACCCTCACCAATGGGGTACGCACCTTC

CCGTCCGTCCGGCAGTCCTCAGGCCTCTACTCGCTGAGCAGCGTGGTGAGCGTGACCTCAAGCA

GCCAGCCCGTCACCTGCAACGTGGCCCACCCAGCCACCAACACCAAAGTGGACAAGACCGTTGC

GCCCTCGACATGCAGCAAGCCCACGTGCCCACCCCCTGAACTCCTGGGGGGACCGTCTGTCTTC

ATCTTCCCCCCAAAACCCAAGGACACCCTCATGATCTCACGCACCCCCGAGGTCACATGCGTGG

TGGTGGACGTGAGCCAGGATGACCCCGAGGTGCAGTTCACATGGTACATAAACAACGAGCAGGT

GCGCACCGCCCGGCCGCCGCTACGGGAGCAGCAGTTCAACAGCACGATCCGCGTGGTCAGCACC

CTCCCCATCGCGCACCAGGACTGGCTGAGGGGCAAGGAGTTCAAGTGCAAAGTCCACAACAAGG

CACTCCCGGCCCCCATCGAGAAAACCATCTCCAAAGCCAGAGGGCAGCCCCTGGAGCCGAAGGT

CTACACCATGGGCCCTCCCCGGGAGGAGCTGAGCAGCAGGTCGGTCAGCCTGACCTGCATGATC

AACGGCTTCTACCCTTCCGACATCTCGGTGGAGTGGGAGAAGAACGGGAAGGCAGAGGACAACT
```

-continued

ACAAGACCACGCCGGCCGTGCTGGACAGCGACGGCTCCTACTTCCTCTACAGCAAGCTCTCAGT

GCCCACGAGTGAGTGGCAGCGGGGCGACGTCTTCACCTGCTCCGTGATGCACGAGGCCTTGCAC

AACCACTACACGCAGAAGTCCATCTCCCGCTCTCCGGGTAAATGA<u>GCGCTGTGCCGGCGAGCTG</u>

<u>CGGCCGC</u>

72-3 Heavy Chain (H1) Nucleic Acid Sequence with Signal Peptide
(bold):
(SEQ ID NO: 30)
ATGGAGACTGGGCTGCGCTGGCTTCTCCTGGTCGCTGTGCTCAAAGGTGTCCAGTGTCAGTCGG

TGGAGGAGTCCGGGGGTCGTCTGGTCATGCCTGGAGGATCCCTGACACTCACCTGCACAGTCTC

TGGAATCGACCTCAGTCACTATGGAATGGCCTGGTTCCGCCAGGCTCCAGGGAAGGGGCTGGAA

TACATCGGAGCCATTAGTAGTAGTGGTAATGAAGACTACGCGAGCTGGCCGAAAGGCCGATTCA

CCATCTCCAAAACCTCGACCACGGTGACTCTGAAAATGACCAGTCTGACAACCGAGGACACGGC

CACCTATTTCTGTGGCAGAGGTTGGCTTAGTAATAATGTTTATATGTGGGGCCCAGGCACCCTG

GTCACCGTCTCGTCAGGGCAACCTAAGGCTCCATCAGTCTTCCCACTGGCCCCTGCTGCGGGG

ACACACCCAGCTCCACGGTGACCCTGGGCTGCCTGGTCAAAGGGTACCTCCCGGAGCCAGTGAC

CGTGACCTGGAACTCGGGCACCCTCACCAATGGGGTACGCACCTTCCCGTCCGTCCGGCAGTCC

TCAGGCCTCTACTCGCTGAGCAGCGTGGTGAGCGTGACCTCAAGCAGCCAGCCCGTCACCTGCA

ACGTGGCCCACCCAGCCACCAACACCAAAGTGGACAAGACCGTTGCGCCCTCGACATGCAGCAA

GCCCACGTGCCCACCCCCTGAACTCCTGGGGGGACCGTCTGTCTTCATCTTCCCCCCAAAACCC

AAGGACACCCTCATGATCTCACGCACCCCCGAGGTCACATGCGTGGTGGTGGACGTGAGCCAGG

ATGACCCCGAGGTGCAGTTCACATGGTACATAAACAACGAGCAGGTGCGCACCGCCCGGCCGCC

GCTACGGGAGCAGCAGTTCAACAGCACGATCCGCGTGGTCAGCACCCTCCCCATCGCGCACCAG

GACTGGCTGAGGGGCAAGGAGTTCAAGTGCAAAGTCCACAACAAGGCACTCCCGGCCCCCATCG

AGAAAACCATCTCCAAAGCCAGAGGGCAGCCCCTGGAGCCGAAGGTCTACACCATGGGCCCTCC

CCGGGAGGAGCTGAGCAGCAGGTCGGTCAGCCTGACCTGCATGATCAACGGCTTCTACCCTTCC

GACATCTCGGTGGAGTGGGAGAAGAACGGGAAGGCAGAGGACAACTACAAGACCACGCCGGCCG

TGCTGGACAGCGACGGCTCCTACTTCCTCTACAGCAAGCTCTCAGTGCCCACGAGTGAGTGGCA

GCGGGGCGACGTCTTCACCTGCTCCGTGATGCACGAGGCCTTGCACAACCACTACACGCAGAAG

TCCATCTCCCGCTCTCCGGGTAAATGA 72-3 Heavy Chain (H1) Nucleic Acid Sequence:
(SEQ ID NO: 9)
CAGTCGGTGGAGGAGTCCGGGGGTCGTCTGGTCATGCCTGGAGGATCCCTGACACTCACCTGCA

CAGTCTCTGGAATCGACCTCAGTCACTATGGAATGGCCTGGTTCCGCCAGGCTCCAGGGAAGGG

GCTGGAATACATCGGAGCCATTAGTAGTAGTGGTAATGAAGACTACGCGAGCTGGCCGAAAGGC

CGATTCACCATCTCCAAAACCTCGACCACGGTGACTCTGAAAATGACCAGTCTGACAACCGAGG

ACACGGCCACCTATTTCTGTGGCAGAGGTTGGCTTAGTAATAATGTTTATATGTGGGGCCCAGG

CACCCTGGTCACCGTCTCGTCAGGGCAACCTAAGGCTCCATCAGTCTTCCCACTGGCCCCTGC

TGCGGGGACACACCCAGCTCCACGGTGACCCTGGGCTGCCTGGTCAAAGGGTACCTCCCGGAGC

CAGTGACCGTGACCTGGAACTCGGGCACCCTCACCAATGGGGTACGCACCTTCCCGTCCGTCCG

GCAGTCCTCAGGCCTCTACTCGCTGAGCAGCGTGGTGAGCGTGACCTCAAGCAGCCAGCCCGTC

ACCTGCAACGTGGCCCACCCAGCCACCAACACCAAAGTGGACAAGACCGTTGCGCCCTCGACAT

GCAGCAAGCCCACGTGCCCACCCCCTGAACTCCTGGGGGGACCGTCTGTCTTCATCTTCCCCCC

AAAACCCAAGGACACCCTCATGATCTCACGCACCCCCGAGGTCACATGCGTGGTGGTGGACGTG

-continued

AGCCAGGATGACCCCGAGGTGCAGTTCACATGGTACATAAACAACGAGCAGGTGCGCACCGCCC

GGCCGCCGCTACGGGAGCAGCAGTTCAACAGCACGATCCGCGTGGTCAGCACCCTCCCCATCGC

GCACCAGGACTGGCTGAGGGGCAAGGAGTTCAAGTGCAAAGTCCACAACAAGGCACTCCCGGCC

CCCATCGAGAAAACCATCTCCAAAGCCAGAGGGCAGCCCCTGGAGCCGAAGGTCTACACCATGG

GCCCTCCCCGGGAGGAGCTGAGCAGCAGGTCGGTCAGCCTGACCTGCATGATCAACGGCTTCTA

CCCTTCCGACATCTCGGTGGAGTGGGAGAAGAACGGGAAGGCAGAGGACAACTACAAGACCACG

CCGGCCGTGCTGGACAGCGACGGCTCCTACTTCCTCTACAGCAAGCTCTCAGTGCCCACGAGTG

AGTGGCAGCGGGGCGACGTCTTCACCTGCTCCGTGATGCACGAGGCCTTGCACAACCACTACAC

GCAGAAGTCCATCTCCCGCTCTCCGGGTAAATGA 72-3 Heavy Chain Variable Region Nucleic Acid Sequence:
(SEQ ID NO: 59)
CAGTCGGTGGAGGAGTCCGGGGGTCGTCTGGTCATGCCTGGAGGATCCCTGACACTCACCTGCA

CAGTCTCTGGAATCGACCTCAGTCACTATGGAATGGCCTGGTTCCGCCAGGCTCCAGGGAAGGG

GCTGGAATACATCGGAGCCATTAGTAGTAGTGGTAATGAAGACTACGCGAGCTGGCCGAAAGGC

CGATTCACCATCTCCAAAACCTCGACCACGGTGACTCTGAAAATGACCAGTCTGACAACCGAGG

ACACGGCCACCTATTTCTGTGGCAGAGGTTGGCTTAGTAATAATGTTTATATGTGGGGCCCAGG

CACCCTGGTCACCGTCTCGTCA 72-3 Heavy Chain (H1) Amino Acid Sequence with Signal Peptide
(bold):
(SEQ ID NO: 31)
METGLRWLLLVAVLKGVQCQSVEESGGRLVMPGGSLTLTCTVSGIDLSHYGMAWFRQAPGKGLE

YIGAISSSGNEDYASWPKGRFTISKTSTTVTLKMTSLTTEDTATYFCGRGWLSNNVYMWGPGTL

VTVSSGQPKAPSVFPLAPCCGDTPSSTVTLGCLVKGYLPEPVTVTWNSGTLTNGVRTFPSVRQS

SGLYSLSSVVSVTSSSQPVTCNVAHPATNTKVDKTVAPSTCSKPTCPPPELLGGPSVFIFPPKP

KDTLMISRTPEVTCVVVDVSQDDPEVQFTWYINNEQVRTARPPLREQQFNSTIRVVSTLPIAHQ

DWLRGKEFKCKVHNKALPAPIEKTISKARGQPLEPKVYTMGPPREELSSRSVSLTCMINGFYPS

DISVEWEKNGKAEDNYKTTPAVLDSDGSYFLYSKLSVPTSEWQRGDVFTCSVMHEALHNHYTQK

SISRSPGK*

72-3 Heavy Chain (H1) Amino Acid Sequence:
(SEQ ID NO: 10)
QSVEESGGRLVMPGGSLTLTCTVSGIDLSHYGMAWFRQAPGKGLEYIGAISSSGNEDYASWPKG

RFTISKTSTTVTLKMTSLTTEDTATYFCGRGWLSNNVYMWGPGTLVTVSSGQPKAPSVFPLAPC

CGDTPSSTVTLGCLVKGYLPEPVTVTWNSGTLTNGVRTFPSVRQSSGLYSLSSVVSVTSSSQPV

TCNVAHPATNTKVDKTVAPSTCSKPTCPPPELLGGPSVFIFPPKPKDTLMISRTPEVTCVVVDV

SQDDPEVQFTWYINNEQVRTARPPLREQQFNSTIRVVSTLPIAHQDWLRGKEFKCKVHNKALPA

PIEKTISKARGQPLEPKVYTMGPPREELSSRSVSLTCMINGFYPSDISVEWEKNGKAEDNYKTT

PAVLDSDGSYFLYSKLSVPTSEWQRGDVFTCSVMHEALHNHYTQKSISRSPGK*

72-3 Heavy Chain Variable Region Amino Acid Sequence:
(SEQ ID NO: 60)
QSVEESGGRLVMPGGSLTLTCTVSGIDLSHYGMAWFRQAPGKGLEYIGAISSSGNEDYASWPKG

RFTISKTSTTVTLKMTSLTTEDTATYFCGRGWLSNNVYMWGPGTLVTVSS 72-3 Light Chain (L1) Nucleic Acid Sequence with 5' Sequence Including HindIII Restriction Site (underlined), Signal Peptide (bold), and 3' Sequence Including NotI Restriction Site (underlined):

(SEQ ID NO: 32)

<u>AAGCTTGTACCCTTCACC</u>ATGGACACGAGGGCCCCCACTCAGCTGCTGGGGCTCCTGCTGCTCT GGCTCCCAGGTGCCACATTTGCCCAAGTGCTGACCCAGACTCCACCCTCCGTGTCTGCAGCTGT GGGAGGCACAGTCACCATCAATTGCCAGGCCAGTCAAAGTATTTATAATAAAAATCAATTATCC TGGCTTCAGCAGAAACCAGGGCAGCCTCCCAAGGTCCTGATCCATTATGCATCCACTCTGGCAT CTGGGGTCTCATCGCGGTTCAAAGGCAGTGGATCTGGGACACAGTTCACTCTCACCATCAGCGA CGTGCAGTGTGACGATGCTGCCACTTACTACTGTCTAGGCGATTTTAGTTGTAGTGGTGTTGAT TGTCTTTCTGTCGGCGGAGGGACCGAGGTGGTCGTCGAAGGTGATCCAGTTGCACCTACTGTCC TCATCTTCCCACCATCTGCTGATCTTGTGGCAACTGGAACAGTCACCATCGTGTGTGTGGCGAA TAAATACTTTCCCGATGTCACCGTCACCTGGGAGGTGGATGGCACCACCCAAACAACTGGCATC GAGAACAGTAAAACACCGCAGAATTCTGCAGATTGTACCTACAACCTCAGCAGCACTCTGACAC TGACCAGCACACAGTACAACAGCCACAAAGAGTACACCTGCAAGGTGACCCAGGGCACGACCTC AGTCGTCCAGAGCTTCAATAGGGGTGACTGTTAG<u>AGCGAGAGCGGCCGC</u>

72-3 Light Chain (L1) Nucleic Acid Sequence with Signal Peptide (bold):

(SEQ ID NO: 33)

ATGGACACGAGGGCCCCCACTCAGCTGCTGGGGCTCCTGCTGCTCTGGCTCCCAGGTGCCACAT TTGCCCAAGTGCTGACCCAGACTCCACCCTCCGTGTCTGCAGCTGTGGGAGGCACAGTCACCAT CAATTGCCAGGCCAGTCAAAGTATTTATAATAAAAATCAATTATCCTGGCTTCAGCAGAAACCA GGGCAGCCTCCCAAGGTCCTGATCCATTATGCATCCACTCTGGCATCTGGGGTCTCATCGCGGT TCAAAGGCAGTGGATCTGGGACACAGTTCACTCTCACCATCAGCGACGTGCAGTGTGACGATGC TGCCACTTACTACTGTCTAGGCGATTTTAGTTGTAGTGGTGTTGATTGTCTTTCTGTCGGCGGA GGGACCGAGGTGGTCGTCGAAGGTGATCCAGTTGCACCTACTGTCCTCATCTTCCCACCATCTG CTGATCTTGTGGCAACTGGAACAGTCACCATCGTGTGTGTGGCGAATAAATACTTTCCCGATGT CACCGTCACCTGGGAGGTGGATGGCACCACCCAAACAACTGGCATCGAGAACAGTAAAACACCG CAGAATTCTGCAGATTGTACCTACAACCTCAGCAGCACTCTGACACTGACCAGCACACAGTACA ACAGCCACAAAGAGTACACCTGCAAGGTGACCCAGGGCACGACCTCAGTCGTCCAGAGCTTCAA TAGGGGTGACTGTTAG 72-3 Light Chain (L1) Nucleic Acid Sequence:

(SEQ ID NO: 11)

CAAGTGCTGACCCAGACTCCACCCTCCGTGTCTGCAGCTGTGGGAGGCACAGTCACCATCAATT GCCAGGCCAGTCAAAGTATTTATAATAAAAATCAATTATCCTGGCTTCAGCAGAAACCAGGGCA GCCTCCCAAGGTCCTGATCCATTATGCATCCACTCTGGCATCTGGGGTCTCATCGCGGTTCAAA GGCAGTGGATCTGGGACACAGTTCACTCTCACCATCAGCGACGTGCAGTGTGACGATGCTGCCA CTTACTACTGTCTAGGCGATTTTAGTTGTAGTGGTGTTGATTGTCTTTCTGTCGGCGGAGGGAC CGAGGTGGTCGTCGAAGGTGATCCAGTTGCACCTACTGTCCTCATCTTCCCACCATCTGCTGAT CTTGTGGCAACTGGAACAGTCACCATCGTGTGTGTGGCGAATAAATACTTTCCCGATGTCACCG TCACCTGGGAGGTGGATGGCACCACCCAAACAACTGGCATCGAGAACAGTAAAACACCGCAGAA TTCTGCAGATTGTACCTACAACCTCAGCAGCACTCTGACACTGACCAGCACACAGTACAACAGC CACAAAGAGTACACCTGCAAGGTGACCCAGGGCACGACCTCAGTCGTCCAGAGCTTCAATAGGG

```
GTGACTGTTAG 72-3 Light Chain Variable Region Nucleic Acid Sequence:
                                                    (SEQ ID NO: 61)
CAAGTGCTGACCCAGACTCCACCCTCCGTGTCTGCAGCTGTGGGAGGCACAGTCACCATCAATT

GCCAGGCCAGTCAAAGTATTTATAATAAAAATCAATTATCCTGGCTTCAGCAGAAACCAGGGCA

GCCTCCCAAGGTCCTGATCCATTATGCATCCACTCTGGCATCTGGGGTCTCATCGCGGTTCAAA

GGCAGTGGATCTGGGACACAGTTCACTCTCACCATCAGCGACGTGCAGTGTGACGATGCTGCCA

CTTACTACTGTCTAGGCGATTTTAGTTGTAGTGGTGTTGATTGTCTTTCTGTCGGCGGAGGGAC

CGAGGTGGTCGTCGAA 72-3 Light Chain (L1) Amino Acid Sequence with Signal Peptide
(bold):
                                                    (SEQ ID NO: 34)
MDTRAPTQLLGLLLLWLPGATFAQVLTQTPPSVSAAVGGTVTINCQASQSIYNKNQLSWLQQKP

GQPPKVLIHYASTLASGVSSRFKGSGSGTQFTLTISDVQCDDAATYYCLGDFSCSGVDCLSVGG

GTEVVVEGDPVAPTVLIFPPSADLVATGTVTIVCVANKYFPDVTVTWEVDGTTQTTGIENSKTP

QNSADCTYNLSSTLTLTSTQYNSHKEYTCKVTQGTTSVVQSFNRGDC*

72-3 Light Chain (L1) Amino Acid Sequence:
                                                    (SEQ ID NO: 12)
QVLTQTPPSVSAAVGGTVTINCQASQSIYNKNQLSWLQQKPGQPPKVLIHYASTLASGVSSRFK

GSGSGTQFTLTISDVQCDDAATYYCLGDFSCSGVDCLSVGGGTEVVVEGDPVAPTVLIFPPSAD

LVATGTVTIVCVANKYFPDVTVTWEVDGTTQTTGIENSKTPQNSADCTYNLSSTLTLTSTQYNS

HKEYTCKVTQGTTSVVQSFNRGDC*

72-3 Light Chain Variable Region Amino Acid Sequence:
                                                    (SEQ ID NO: 62)
QVLTQTPPSVSAAVGGTVTINCQASQSIYNKNQLSWLQQKPGQPPKVLIHYASTLASGVSSRFK

GSGSGTQFTLTISDVQCDDAATYYCLGDFSCSGVDCLSVGGGTEVVVE
```

In some embodiments, antibody 72-3 is modified to remove one or more cysteine residues in one or more CDR sequences. In some embodiments, the antibody includes a CDRH1 sequence that comprises the amino acid sequence HYGMA (SEQ ID NO: 88), a CDRH2 sequence that comprises the amino acid sequence AISSSGNEDYASWPKG (SEQ ID NO: 89), a CDRH3 sequence that comprises the amino acid sequence GWLSNNVYM (SEQ ID NO: 90), a CDRL1 sequence that comprises the amino acid sequence QASQSIYNKNQLS (SEQ ID NO: 81), a CDRL2 sequence that comprises the amino acid sequence YASTLAS (SEQ ID NO: 82), and a CDRL3 sequence that comprises the amino acid sequence LGDFSXSGVDXLS (SEQ ID NO: 110), where X is Ala or Ser. In some embodiments, the antibody includes the following light chain amino acid sequences:

```
72-3 Light Chain (L1) Amino Acid Sequence with Signal Peptide
(bold):
                                                    (SEQ ID NO: 92)
MDTRAPTQLLGLLLLWLPGATFAQVLTQTPPSVSAAVGGTVTINCQASQSIYNKNQLSWLQQKP

GQPPKVLIHYASTLASGVSSRFKGSGSGTQFTLTISDVQCDDAATYYCLGDFSXSGVDXLSVGG

GTEVVVEGDPVAPTVLIFPPSADLVATGTVTIVCVANKYFPDVTVTWEVDGTTQTTGIENSKTP

QNSADCTYNLSSTLTLTSTQYNSHKEYTCKVTQGTTSVVQSFNRGDC*
Where X is Ala or Ser 72-3 Light Chain (L1) Amino Acid Sequence:
                                                    (SEQ ID NO: 93)
QVLTQTPPSVSAAVGGTVTINCQASQSIYNKNQLSWLQQKPGQPPKVLIHYASTLASGVSSRFK

GSGSGTQFTLTISDVQCDDAATYYCLGDFSXSGVDXLSVGGGTEVVVEGDPVAPTVLIFPPSAD

LVATGTVTIVCVANKYFPDVTVTWEVDGTTQTTGIENSKTPQNSADCTYNLSSTLTLTSTQYNS
```

HKEYTCKVTQGTTSVVQSFNRGDC*
Where X is Ala or Ser 72-3 Light Chain Variable Region Amino Acid Sequence:
(SEQ ID NO: 94)
QVLTQTPPSVSAAVGGTVTINC QASQSIYNKNQLS WLQQKPGQPPKVLIH YASTLAS GVSSRFK GSGSGTQFTLTISDVQCDDAATYYC LGDFSXSGVDXLS VGGGTEVVVE
Where X is Ala or Ser Antibody 85-1 has the amino acid and nucleic acid sequences shown below. The heavy chain complementarity determining regions (CDRs) and light chain CDRs are shown in boxes in the amino acid sequences presented below. In particular, the antibody referred to herein as 85-1 includes a CDRH1 sequence that comprises the amino acid sequence SYCMS (SEQ ID NO: 95), a CDRH2 sequence that comprises the amino acid sequence IIGGICSTYYA-AWAKG (SEQ ID NO: 96), a CDRH3 sequence that comprises the amino acid sequence PAYNSDPI (SEQ ID NO: 97), a CDRL1 sequence that comprises the amino acid sequence QASQSVYNNNYLS (SEQ ID NO: 98), a CDRL2 sequence that comprises the amino acid sequence DAATLAS (SEQ ID NO: 99), and a CDRL3 sequence that comprises the amino acid sequence LGEFSCGSADCNA (SEQ ID NO: 100).

85-1 Heavy Chain (H1) Nucleic Acid Sequence with 5' Sequence Including HindIII Restriction Site (underlined), Signal Peptide (bold), and 3' Sequence Including NotI Restriction Site (underlined):
(SEQ ID NO: 35)
<u>AAGCTTGTACCCTTCACC</u>ATGGAGACTGGGCTGCGCTGGCTTCTCCTGGTCGCTGTGCTCAAAG

GTGTCCAGTGTCAGTCGCTGGAGGAGTCCGGGGGTCACCTGGTCACGCCTGGGACACCCCTGAC

ACTCACCTGCAAAGCCTCTGGATTCTCCCTCAGTAGCTACTGCATGAGCTGGGTCCGCCAGGCT

CCAGGGAAGGGGCTGGAATGGATCGGAATCATTGGTGGTATCTGTAGCACATACTACGCAGCCT

GGGCGAAAGGCCGATTCACCATCTCCAAAACCTCGACCACGGTGGATCTGAAAATCGCCAGTCC

GACAACCGAGGACACGGCCACCTATTTCTGTGCCAGACCTGCTTATAATAGTGACCCAATCTGG

GGCCCAGGCACCCTGGTCACCGTCTCCTCAGGGCAACCTAAGGCTCCATCAGTCTTCCCACTGG

CCCCCTGCTGCGGGGACACACCCAGCTCCACGGTGACCCTGGGCTGCCTGGTCAAAGGGTACCT

CCCGGAGCCAGTGACCGTGACCTGGAACTCGGGCACCCTCACCAATGGGGTACGCACCTTCCCG

TCCGTCCGGCAGTCCTCAGGCCTCTACTCGCTGAGCAGCGTGGTGAGCGTGACCTCAAGCAGCC

AGCCCGTCACCTGCAACGTGGCCCACCCAGCCACCAACACCAAAGTGGACAAGACCGTTGCGCC

CTCGACATGCAGCAAGCCCACGTGCCCACCCCCTGAACTCCTGGGGGGACCGTCTGTCTTCATC

TTCCCCCCAAAACCCAAGGACACCCTCATGATCTCACGCACCCCCGAGGTCACATGCGTGGTGG

TGGACGTGAGCCAGGATGACCCCGAGGTGCAGTTCACATGGTACATAAACAACGAGCAGGTGCG

CACCGCCCGGCCGCCGCTACGGGAGCAGCAGTTCAACAGCACGATCCGCGTGGTCAGCACCCTC

CCCATCGCGCACCAGGACTGGCTGAGGGGCAAGGAGTTCAAGTGCAAAGTCCACAACAAGGCAC

TCCCGGCCCCCATCGAGAAAACCATCTCCAAAGCCAGAGGGCAGCCCCTGGAGCCGAAGGTCTA

CACCATGGGCCCTCCCCGGGAGGAGCTGAGCAGCAGGTCGGTCAGCCTGACCTGCATGATCAAC

GGCTTCTACCCTTCCGACATCTCGGTGGAGTGGGAGAAGAACGGGAAGGCAGAGGACAACTACA

AGACCACGCCGGCCGTGCTGGACAGCGACGGCTCCTACTTCCTCTACAGCAAGCTCTCAGTGCC

CACGAGTGAGTGGCAGCGGGGCGACGTCTTCACCTGCTCCGTGATGCACGAGGCCTTGCACAAC

CACTACACGCAGAAGTCCATCTCCCGCTCTCCGGGTAAATGA<u>GCGCTGTGCCGGCGAGCTGCGG</u>

<u>CCGC</u>

85-1 Heavy Chain (H1) Nucleic Acid Sequence with Signal Peptide (bold):

(SEQ ID NO: 36)
ATGGAGACTGGGCTGCGCTGGCTTCTCCTGGTCGCTGTGCTCAAAGGTGTCCAGTGTCAGTCGC
TGGAGGAGTCCGGGGGTCACCTGGTCACGCCTGGGACACCCCTGACACTCACCTGCAAAGCCTC
TGGATTCTCCCTCAGTAGCTACTGCATGAGCTGGGTCCGCCAGGCTCCAGGGAAGGGGCTGGAA
TGGATCGGAATCATTGGTGGTATCTGTAGCACATACTACGCAGCCTGGGCGAAAGGCCGATTCA
CCATCTCCAAAACCTCGACCACGGTGGATCTGAAAATCGCCAGTCCGACAACCGAGGACACGGC
CACCTATTTCTGTGCCAGACCTGCTTATAATAGTGACCCAATCTGGGGCCCAGGCACCCTGGTC
ACCGTCTCCTCAGGGCAACCTAAGGCTCCATCAGTCTTCCCACTGGCCCCCTGCTGCGGGGACA
CACCCAGCTCCACGGTGACCCTGGGCTGCCTGGTCAAAGGGTACCTCCCGGAGCCAGTGACCGT
GACCTGGAACTCGGGCACCCTCACCAATGGGGTACGCACCTTCCCGTCCGTCCGGCAGTCCTCA
GGCCTCTACTCGCTGAGCAGCGTGGTGAGCGTGACCTCAAGCAGCCAGCCCGTCACCTGCAACG
TGGCCCACCCAGCCACCAACACCAAAGTGGACAAGACCGTTGCGCCCTCGACATGCAGCAAGCC
CACGTGCCCACCCCCTGAACTCCTGGGGGACCGTCTGTCTTCATCTTCCCCCCAAAACCCAAG
GACACCCTCATGATCTCACGCACCCCCGAGGTCACATGCGTGGTGGTGGACGTGAGCCAGGATG
ACCCCGAGGTGCAGTTCACATGGTACATAAACAACGAGCAGGTGCGCACCGCCCGGCCGCCGCT
ACGGGAGCAGCAGTTCAACAGCACGATCCGCGTGGTCAGCACCCTCCCCATCGCGCACCAGGAC
TGGCTGAGGGGCAAGGAGTTCAAGTGCAAAGTCCACAACAAGGCACTCCCGGCCCCCATCGAGA
AAACCATCTCCAAAGCCAGAGGGCAGCCCCTGGAGCCGAAGGTCTACACCATGGGCCCTCCCCG
GGAGGAGCTGAGCAGCAGGTCGGTCAGCCTGACCTGCATGATCAACGGCTTCTACCCTTCCGAC
ATCTCGGTGGAGTGGGAGAAGAACGGGAAGGCAGAGGACAACTACAAGACCACGCCGGCCGTGC
TGGACAGCGACGGCTCCTACTTCCTCTACAGCAAGCTCTCAGTGCCCACGAGTGAGTGGCAGCG
GGGCGACGTCTTCACCTGCTCCGTGATGCACGAGGCCTTGCACAACCACTACACGCAGAAGTCC
ATCTCCCGCTCTCCGGGTAAATGA 85-1 Heavy Chain (H1) Nucleic Acid Sequence:
(SEQ ID NO: 13)
CAGTCGCTGGAGGAGTCCGGGGGTCACCTGGTCACGCCTGGGACACCCCTGACACTCACCTGCA
AAGCCTCTGGATTCTCCCTCAGTAGCTACTGCATGAGCTGGGTCCGCCAGGCTCCAGGGAAGGG
GCTGGAATGGATCGGAATCATTGGTGGTATCTGTAGCACATACTACGCAGCCTGGGCGAAAGGC
CGATTCACCATCTCCAAAACCTCGACCACGGTGGATCTGAAAATCGCCAGTCCGACAACCGAGG
ACACGGCCACCTATTTCTGTGCCAGACCTGCTTATAATAGTGACCCAATCTGGGGCCCAGGCAC
CCTGGTCACCGTCTCCTCAGGGCAACCTAAGGCTCCATCAGTCTTCCCACTGGCCCCCTGCTGC
GGGGACACACCCAGCTCCACGGTGACCCTGGGCTGCCTGGTCAAAGGGTACCTCCCGGAGCCAG
TGACCGTGACCTGGAACTCGGGCACCCTCACCAATGGGGTACGCACCTTCCCGTCCGTCCGGCA
GTCCTCAGGCCTCTACTCGCTGAGCAGCGTGGTGAGCGTGACCTCAAGCAGCCAGCCCGTCACC
TGCAACGTGGCCCACCCAGCCACCAACACCAAAGTGGACAAGACCGTTGCGCCCTCGACATGCA
GCAAGCCCACGTGCCCACCCCCTGAACTCCTGGGGGACCGTCTGTCTTCATCTTCCCCCCAAA
ACCCAAGGACACCCTCATGATCTCACGCACCCCCGAGGTCACATGCGTGGTGGTGGACGTGAGC
CAGGATGACCCCGAGGTGCAGTTCACATGGTACATAAACAACGAGCAGGTGCGCACCGCCCGGC
CGCCGCTACGGGAGCAGCAGTTCAACAGCACGATCCGCGTGGTCAGCACCCTCCCCATCGCGCA
CCAGGACTGGCTGAGGGGCAAGGAGTTCAAGTGCAAAGTCCACAACAAGGCACTCCCGGCCCCC
ATCGAGAAAACCATCTCCAAAGCCAGAGGGCAGCCCCTGGAGCCGAAGGTCTACACCATGGGCC
CTCCCCGGGAGGAGCTGAGCAGCAGGTCGGTCAGCCTGACCTGCATGATCAACGGCTTCTACCC -continued

TTCCGACATCTCGGTGGAGTGGGAGAAGAACGGGAAGGCAGAGGACAACTACAAGACCACGCCG

GCCGTGCTGGACAGCGACGGCTCCTACTTCCTCTACAGCAAGCTCTCAGTGCCCACGAGTGAGT

GGCAGCGGGGCGACGTCTTCACCTGCTCCGTGATGCACGAGGCCTTGCACAACCACTACACGCA

GAAGTCCATCTCCCGCTCTCCGGGTAAATGA 85-1 Heavy Chain Variable Region Nucleic Acid Sequence:
(SEQ ID NO: 63)
CAGTCGCTGGAGGAGTCCGGGGGTCACCTGGTCACGCCTGGGACACCCCTGACACTCACCTGCA

AAGCCTCTGGATTCTCCCTCAGTAGCTACTGCATGAGCTGGGTCCGCCAGGCTCCAGGGAAGGG

GCTGGAATGGATCGGAATCATTGGTGGTATCTGTAGCACATACTACGCAGCCTGGGCGAAAGGC

CGATTCACCATCTCCAAAACCTCGACCACGGTGGATCTGAAAATCGCCAGTCCGACAACCGAGG

ACACGGCCACCTATTTCTGTGCCAGACCTGCTTATAATAGTGACCCAATCTGGGGCCCAGGCAC

CCTGGTCACCGTCTCCTCA 85-1 Heavy Chain (H1) Amino Acid Sequence with Signal Peptide
(bold):
(SEQ ID NO: 37)
TVSSGQPKAPSVFPLAPCCGDTPSSTVTLGCLVKGYLPEPVTVTWNSGTLTNGVRTFPSVRQSS

GLYSLSSVVSVTSSSQPVTCNVAHPATNTKVDKTVAPSTCSKPTCPPPELLGGPSVFIFPPKPK

DTLMISRTPEVTCVVVDVSQDDPEVQFTWYINNEQVRTARPPLREQQFNSTIRVVSTLPIAHQD

WLRGKEFKCKVHNKALPAPIEKTISKARGQPLEPKVYTMGPPREELSSRSVSLTCMINGFYPSD

ISVEWEKNGKAEDNYKTTPAVLDSDGSYFLYSKLSVPTSEWQRGDVFTCSVMHEALHNHYTQKS

ISRSPGK*

85-1 Heavy Chain (H1) Amino Acid Sequence:
(SEQ ID NO: 14)
QSLEESGGHLVTPGTPLTLTCKASGFSLS[SYCMS]WVRQAPGKGLEWIG[IIGGICSTYYAAWAKG]

RFTISKTSTTVDLKIASPTTEDTATYFCAR[PAYNSDPI]WGPGTLVTVSSGQPKAPSVFPLAPCC

GDTPSSTVTLGCLVKGYLPEPVTVTWNSGTLTNGVRTFPSVRQSSGLYSLSSVVSVTSSSQPVT

CNVAHPATNTKVDKTVAPSTCSKPTCPPPELLGGPSVFIFPPKPKDTLMI SRTPEVTCVVVDVS

QDDPEVQFTWYINNEQVRTARPPLREQQFNSTIRVVSTLPIAHQDWLRGKEFKCKVHNKALPAP

IEKTISKARGQPLEPKVYTMGPPREELSSRSVSLTCMINGFYPSDISVEWEKNGKAEDNYKTTP

AVLDSDGSYFLYSKLSVPTSEWQRGDVFTCSVMHEALHNHYTQKSISRSPGK*

85-1 Heavy Chain Variable Region Amino Acid Sequence:
(SEQ ID NO: 64)
QSLEESGGHLVTPGTPLTLTCKASGFSLS[SYCMS]WVRQAPGKGLEWIG[IIGGICSTYYAAWAKG]

RFTISKTSTTVDLKIASPTTEDTATYFCAR[PAYNSDPI]WGPGTLVTVSS

Clone 85-1 Light Chain (L3) Nucleic Acid Sequence with 5'
Sequence Including HindIII Restriction Site (underlined) and
Signal Peptide (bold:
(SEQ ID NO: 38)
<u>AAGCTTGTACCCTTCACC</u>ATGGACACGAGGGCCCCCACTCAGCTGCTGGGGCTCCTGCTGCTCT

GGCTCCCAGGTGCCACATTTGCCCAAGTGCTGACCCAGACTCCATCCCCTGTGTCTGTAGCTGT

GGGAGGCACAGTCACCATCAATTGCCAGGCCAGTCAGAGTGTTTATAATAACAACTACTTATCC

TGGTATCAGCAGAAACCAGGGCAGCCTCCCAAAGTCCTGATCTATGATGCTGCCACTCTGGCAT

CTGGGGTCTCATCGCGGTTCAGAGGCAGTGGATCTGGGACACAGTTCACTCTCACCATCAGCGA

CGTGCAGTGTGACGATGCTGCCACTTACTACTGTCTAGGCGAATTTAGTTGTGGTAGTGCTGAT

TGTAATGCTTTCGGCGGAGGGACCGAGGTGGTCGTCAAAGGTGATCCAGTTGCACCTACTGTCC

TCATCTTCCCACCAGCTGCTGATCAGGTGGCAACTGGAACAGTCACCATCGTGTGTGTGGCGAA

-continued

```
TAAATACTTTCCCGATGTCACCGTCACCTGGGAGGTGGATGGCACCACCCAAACAACTGGCATC

GAGAACAGTAAAACACCGCAGAATTCTGCAGATTGTACCTACAACCTCAGCAGCACTCTGACAC

TGACCAGCACACAGTACAACAGCCACAAAGAGTACACCTGCAAGGTGACCCAGGGCACGACCTC

AGTCGTCCAGAGCTTCAATAGGGGTGACTGTTAGAGTGAGAGCGGCCGC
```

Clone 85-1 Light Chain (L3) Nucleic Acid Sequence with Signal Peptide (bold):

(SEQ ID NO: 39)

ATGGACACGAGGGCCCCCACTCAGCTGCTGGGGCTCCTGCTGCTCTGGCTCCCAGGTGCCACAT

TTGCCCAAGTGCTGACCCAGACTCCATCCCCTGTGTCTGTAGCTGTGGGAGGCACAGTCACCAT

CAATTGCCAGGCCAGTCAGAGTGTTTATAATAACAACTACTTATCCTGGTATCAGCAGAAACCA

GGGCAGCCTCCCAAAGTCCTGATCTATGATGCTGCCACTCTGGCATCTGGGGTCTCATCGCGGT

TCAGAGGCAGTGGATCTGGGACACAGTTCACTCTCACCATCAGCGACGTGCAGTGTGACGATGC

TGCCACTTACTACTGTCTAGGCGAATTTAGTTGTGGTAGTGCTGATTGTAATGCTTTCGGCGGA

GGGACCGAGGTGGTCGTCAAAGGTGATCCAGTTGCACCTACTGTCCTCATCTTCCCACCAGCTG

CTGATCAGGTGGCAACTGGAACAGTCACCATCGTGTGTGGCGAATAAATACTTTCCCGATGT

CACCGTCACCTGGGAGGTGGATGGCACCACCCAAACAACTGGCATCGAGAACAGTAAAACACCG

CAGAATTCTGCAGATTGTACCTACAACCTCAGCAGCACTCTGACACTGACCAGCACACAGTACA

ACAGCCACAAAGAGTACACCTGCAAGGTGACCCAGGGCACGACCTCAGTCGTCCAGAGCTTCAA

TAGGGGTGACTGTTAGAGTGAGAGCGGCCGC

Clone 85-1 Light Chain (L3) Nucleic Acid Sequence:

(SEQ ID NO: 15)

CAAGTGCTGACCCAGACTCCATCCCCTGTGTCTGTAGCTGTGGGAGGCACAGTCACCATCAATT

GCCAGGCCAGTCAGAGTGTTTATAATAACAACTACTTATCCTGGTATCAGCAGAAACCAGGGCA

GCCTCCCAAAGTCCTGATCTATGATGCTGCCACTCTGGCATCTGGGGTCTCATCGCGGTTCAGA

GGCAGTGGATCTGGGACACAGTTCACTCTCACCATCAGCGACGTGCAGTGTGACGATGCTGCCA

CTTACTACTGTCTAGGCGAATTTAGTTGTGGTAGTGCTGATTGTAATGCTTTCGGCGGAGGGAC

CGAGGTGGTCGTCAAAGGTGATCCAGTTGCACCTACTGTCCTCATCTTCCCACCAGCTGCTGAT

CAGGTGGCAACTGGAACAGTCACCATCGTGTGTGGCGAATAAATACTTTCCCGATGTCACCG

TCACCTGGGAGGTGGATGGCACCACCCAAACAACTGGCATCGAGAACAGTAAAACACCGCAGAA

TTCTGCAGATTGTACCTACAACCTCAGCAGCACTCTGACACTGACCAGCACACAGTACAACAGC

CACAAAGAGTACACCTGCAAGGTGACCCAGGGCACGACCTCAGTCGTCCAGAGCTTCAATAGGG

GTGACTGTTAGAGTGAGAGCGGCCGC

Clone 85-1 Light Chain Variable Region Nucleic Acid Sequence:

(SEQ ID NO: 65)

CAAGTGCTGACCCAGACTCCATCCCCTGTGTCTGTAGCTGTGGGAGGCACAGTCACCATCAATT

GCCAGGCCAGTCAGAGTGTTTATAATAACAACTACTTATCCTGGTATCAGCAGAAACCAGGGCA

GCCTCCCAAAGTCCTGATCTATGATGCTGCCACTCTGGCATCTGGGGTCTCATCGCGGTTCAGA

GGCAGTGGATCTGGGACACAGTTCACTCTCACCATCAGCGACGTGCAGTGTGACGATGCTGCCA

CTTACTACTGTCTAGGCGAATTTAGTTGTGGTAGTGCTGATTGTAATGCTTTCGGCGGAGGGAC

CGAGGTGGTCGTCAAA 85-1 Light Chain (L3) Amino Acid Sequence with Signal Peptide (bold):

(SEQ ID NO: 40)

MDTRAPTQLLGLLLLWLPGATFAQVLTQTPSPVSVAVGGTVTINC[QASQSVYNNNYLS]WLQQKP

GQPPKVLIY[DAATLAS]GVSSRFRGSGSGTQFTLTISDVQCDDAATYYC[LGEFSCGSADCNA]FGG

```
GTEVVVKGDPVAPTVLIFPPAADQVATGTVTIVCVANKYFPDVTVTWEVDGTTQTTGIENSKTP

QNSADCTYNLSSTLTLTSTQYNSHKEYTCKVTQGTTSVVQSFNRGDC*

85-1 Light Chain (L3) Amino Acid Sequence:
                                                    (SEQ ID NO: 16)
QVLTQTPSPVSVAVGGTVTINC QASQSVYNNNYLS WYQQKPGQPPKVLIY DAATLAS GVSSRFR

GSGSGTQFTLTISDVQCDDAATYYC LGEFSCGSADCNA FGGGTEVVVKGDPVAPTVLIFPPAAD

QVATGTVTIVCVANKYFPDVTVTWEVDGTTQTTGIENSKTPQNSADCTYNLSSTLTLTSTQYNS

HKEYTCKVTQGTTSVVQSFNRGDC*

85-1 Light Chain Variable Region Amino Acid Sequence:
                                                    (SEQ ID NO: 66)
QVLTQTPSPVSVAVGGTVTINC QASQSVYNNNYLS WYQQKPGQPPKVLIY DAATLAS GVSSRFR

GSGSGTQFTLTISDVQCDDAATYYC LGEFSCGSADCNA FGGGTEVVVK
```

In some embodiments, antibody 85-1 is modified to remove one or more cysteine residues in one or more CDR sequences. In some embodiments, the antibody includes a CDRH1 sequence that comprises the amino acid sequence SYXMS (SEQ ID NO: 101), where X is Ala or Ser, a CDRH2 sequence that comprises the amino acid sequence IIGGIXSTYYAAWAKG (SEQ ID NO: 102), where X is Ala or Ser, a CDRH3 sequence that comprises the amino acid sequence PAYNSDPI (SEQ ID NO: 97), a CDRL1 sequence that comprises the amino acid sequence QASQSVYNN-NYLS (SEQ ID NO: 98), a CDRL2 sequence that comprises the amino acid sequence DAATLAS (SEQ ID NO: 99), and a CDRL3 sequence that comprises the amino acid sequence LGEFSXGSADXNA (SEQ ID NO: 103), where X is Ala or Ser. In some embodiments, the antibody includes the following heavy and light chain amino acid sequences:

```
85-1 Heavy Chain (H1) Amino Acid Sequence with Signal Peptide
(bold):
                                                    (SEQ ID NO: 104)
METGLRWLLLVAVLKGVQC QSLEESGGHLVTPGTPLTLTCKASGFSLS SYXMS WVRQAPGKGLE

WIG IIGGIXSTYYAAWAKG RFTISKTSTTVDLKIASPTTEDTATYFCAR PAYNSDPI WGPGTLV

TVSSGQPKAPSVFPLAPCCGDTPSSTVTLGCLVKGYLPEPVTVTWNSGTLTNGVRTFPSVRQSS

GLYSLSSVVSVTSSSQPVTCNVAHPATNTKVDKTVAPSTCSKPTCPPPELLGGPSVFIFPPKPK

DTLMISRTPEVTCVVVDVSQDDPEVQFTWYINNEQVRTARPPLREQQFNSTIRVVSTLPIAHQD

WLRGKEFKCKVHNKALPAPIEKTISKARGQPLEPKVYTMGPPREELSSRSVSLTCMINGFYPSD

ISVEWEKNGKAEDNYKTTPAVLDSDGSYFLYSKLSVPTSEWQRGDVFTCSVMHEALHNHYTQKS

ISRSPGK*
Where X is Ala or Ser 85-1 Heavy Chain (H1) Amino Acid Sequence:
                                                    (SEQ ID NO: 105)
QSLEESGGHLVTPGTPLTLTCKASGFSLS SYXMS WVRQAPGKGLEWIG IIGGIXSTYYAAWAKG

RFTISKTSTTVDLKIASPTTEDTATYFCAR PAYNSDPI WGPGTLVTVSSGQPKAPSVFPLAPCC

GDTPSSTVTLGCLVKGYLPEPVTVTWNSGTLTNGVRTFPSVRQSSGLYSLSSVVSVTSSSQPVT

CNVAHPATNTKVDKTVAPSTCSKPTCPPPELLGGPSVFIFPPKPKDTLMISRTPEVTCVVVDVS

QDDPEVQFTWYINNEQVRTARPPLREQQFNSTIRVVSTLPIAHQDWLRGKEFKCKVHNKALPAP

IEKTISKARGQPLEPKVYTMGPPREELSSRSVSLTCMINGFYPSDISVEWEKNGKAEDNYKTTP

AVLDSDGSYFLYSKLSVPTSEWQRGDVFTCSVMHEALHNHYTQKSISRSPGK*
Where X is Ala or Ser 85-1 Heavy Chain Variable Region Amino Acid Sequence:
                                                    (SEQ ID NO: 106)
QSLEESGGHLVTPGTPLTLTCKASGFSLS SYXMS WVRQAPGKGLEWIG IIGGIXSTYYAAWAKG RFTISKTSTTVDLKIASPTTEDTATYFCAR PAYNSDPI WGPGTLVTVSS
Where X is Ala or Ser
```

```
85-1 Light Chain (L3) Amino Acid Sequence with Signal Peptide
(bold):
                                                 (SEQ ID NO: 107)
MDTRAPTQLLGLLLLWLPGATFAQVLTQTPSPVSVAVGGTVTINCQASQSVYNNNYLSWYQQKP

GQPPKVLIYDAATLASGVSSRFRGSGSGTQFTLTISDVQCDDAATYYCLGEFSXGSADXNAFGG

GTEVVVKGDPVAPTVLIFPPAADQVATGTVTIVCVANKYFPDVTVTWEVDGTTQTTGIENSKTP

QNSADCTYNLSSTLTLTSTQYNSHKEYTCKVTQGTTSVVQSFNRGDC*
Where X is Ala or Ser 85-1 Light Chain (L3) Amino Acid Sequence:
                                                 (SEQ ID NO: 108)
QVLTQTPSPVSVAVGGTVTINCQASQSVYNNNYLSWYQQKPGQPPKVLIYDAATLASGVSSRFR

GSGSGTQFTLTISDVQCDDAATYYCLGEFSXGSADXNAFGGGTEVVVKGDPVAPTVLIFPPAAD

QVATGTVTIVCVANKYFPDVTVTWEVDGTTQTTGIENSKTPQNSADCTYNLSSTLTLTSTQYNS

HKEYTCKVTQGTTSVVQSFNRGDC*
Where X is Ala or Ser 85-1 Light Chain Variable Region Amino Acid Sequence:
                                                 (SEQ ID NO: 109)
QVLTQTPSPVSVAVGGTVTINCQASQSVYNNNYLSWYQQKPGQPPKVLIYDAATLASGVSSRFR GSGSGTQFTLTISDVQCDDAATYYCLGEFSXGSADXNAFGGGTEVVVK
Where X is Ala or Ser
```

Activatable Antibodies

The antibodies and antigen-binding fragments thereof of the disclosure bind an activatable antibody and/or a conjugated activatable antibody that binds a target. The activatable antibodies include an antibody or antigen-binding fragment thereof (AB) that specifically binds a target coupled to a masking moiety (MM), such that coupling of the MM reduces the ability of the antibody or antigen-binding fragment thereof to bind the target. In some embodiments, the MM is coupled to the AB via a sequence that includes a substrate for a protease, for example, a protease that is co-localized with the target at a treatment site in a subject.

The conjugated activatable antibodies include an antibody or antigen-binding fragment thereof (AB) that specifically binds a target coupled to a masking moiety (MM), such that coupling of the MM reduces the ability of the antibody or antigen-binding fragment thereof to bind the target, and an agent conjugated or otherwise coupled to the activatable antibody. In some embodiments, the MM is coupled to the AB via a sequence that includes a substrate for a protease, for example, a protease that is co-localized with the target at a treatment site in a subject.

The conjugated antibodies and/or activatable antibodies include an antibody or antigen-binding fragment thereof (AB) that specifically binds a target. Exemplary classes of targets of an AB include, but are not necessarily limited to, cell surface receptors and secreted binding proteins (e.g., growth factors), soluble enzymes, structural proteins (e.g. collagen, fibronectin) and the like. In some embodiments, conjugated antibodies and/or activatable antibodies have an AB that binds an extracellular target, usually an extracellular protein target. In other embodiments, conjugated antibodies and/or activatable antibodies are designed for cellular uptake such that the conjugated antibodies and/or activatable antibodies are activated inside a cell.

As a non-limiting example, the AB is a binding partner for any target listed in Table 1.

TABLE 1

| Exemplary Targets |
|---|
| 1-92-LFA-3 |
| Alpha-4 integrin |
| Alpha-V integrin |
| alpha4beta1 integrin |
| alpha4beta7 integrin |
| AGR2 |
| Anti-Lewis-Y |
| Apelin J receptor |
| APRIL |
| B7-H4 |
| BAFF |
| BTLA |
| C5 complement |
| C-242 |
| CA9 |
| CA19-9 (Lewis a) |
| Carbonic anhydrase 9 |
| CD2 |
| CD3 |
| CD6 |
| CD9 |
| CD11a |
| CD19 |
| CD20 |
| CD22 |
| CD24 |
| CD25 |
| CD27 |
| CD28 |
| CD30 |
| CD33 |
| CD38 |
| CD40 |

TABLE 1-continued

Exemplary Targets

CD40L
CD41
CD44
CD44v6
CD47
CD51
CD52
CD56
CD64
CD70
CD71
CD74
CD80
CD81
CD86
CD95
CD117
CD125
CD132
(IL-2RG)
CD133
CD137
CD138
CD166
CD172A
CD248
CDH6
CEACAM5
(CEA)
CEACAM6
(NCA-90)
CLAUDIN-3
CLAUDIN-4
cMet
Collagen
Cripto
CSFR
CSFR-1
CTLA-4
CTGF
CXCL10
CXCL13
CXCR1
CXCR2
CXCR4
CYR61
DL44
DLK1
DLL4
DPP-4
DSG1
EGFR
EGFRviii
Endothelin B
receptor
(ETBR)
ENPP3
EpCAM
EPHA2
EPHB2
ERBB3
F protein of
RSV
FAP
FGF-2
FGF8
FGFR1
FGFR2
FGFR3
FGFR4
Folate
receptor
GAL3ST1
G-CSF
G-CSFR
GD2
GITR
GLUT1

TABLE 1-continued

Exemplary Targets

GLUT4
GM-CSF
GM-CSFR
GP IIb/IIIa
receptors
Gp130
GPIIB/IIIA
GPNMB
GRP78
HER2/neu
HGF
hGH
HVEM
Hyaluronidase
ICOS
IFNalpha
IFNbeta
IFNgamma
IgE
IgE Receptor
(FceRI)
IGF
IGF1R
IL1B
IL1R
IL2
IL11
IL12
IL12p40
IL-12R,
IL-12Rbeta1
IL13
IL13R
IL15
IL17
IL18
IL21
IL23
IL23R
IL27/IL27R
(wsx1)
IL29
IL-31R
IL31/IL31R
IL2R
IL4
IL4R
IL6, IL6R
Insulin
Receptor
Jagged
Ligands
Jagged 1
Jagged 2
LAG-3
LIF-R
Lewis X
LIGHT
LRP4
LRRC26
MCSP
Mesothelin
MRP4
MUC1
Mucin-16
(MUC16,
CA-125)
Na/K ATPase
Neutrophil
elastase
NGF
Nicastrin
Notch
Receptors
Notch 1
Notch 2
Notch 3
Notch 4

TABLE 1-continued

| Exemplary Targets |
| --- |
| NOV |
| OSM-R |
| OX-40 |
| PAR2 |
| PDGF-AA |
| PDGF-BB |
| PDGFRalpha |
| PDGFRbeta |
| PD-1 |
| PD-L1 |
| PD-L2 |
| Phosphatidyl-serine |
| P1GF |
| PSCA |
| PSMA |
| RAAG12 |
| RAGE |
| SLC44A4 |
| Sphingosine 1 Phosphate |
| STEAP1 |
| STEAP2 |
| TAG-72 |
| TAPA1 |
| TGFbeta |
| TIGIT |
| TIM-3 |
| TLR2 |
| TLR4 |
| TLR6 |
| TLR7 |
| TLR8 |
| TLR9 |
| TMEM31 |
| TNFalpha |
| TNFR |
| TNFRS12A |
| TRAIL-R1 |
| TRAIL-R2 |
| Transferrin |
| Transferrin receptor |
| TRK-A |
| TRK-B |
| uPAR |
| VAP1 |
| VCAM-1 |
| VEGF |
| VEGF-A |
| VEGF-B |
| VEGF-C |
| VEGF-D |
| VEGFR1 |
| VEGFR2 |
| VEGFR3 |
| VISTA |
| WISP-1 |
| WISP-2 |
| WISP-3 |

As a non-limiting example, the AB is or is derived from an antibody listed in Table 2.

TABLE 2

Exemplary sources for ABs

| Antibody Trade Name (antibody name) | Target |
| --- | --- |
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |
| Obinutuzumab | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
|  | Notch, e.g., Notch 1 |
|  | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

In some embodiments, the activatable antibody includes an antibody or antigen-binding fragment thereof that specifically binds the target. In some embodiments, the antibody or immunologically active fragment thereof is a monoclonal antibody, domain antibody, single chain, Fab fragment, a F(ab')2 fragment, a scFv, a scAb, a dAb, a single domain heavy chain antibody, and a single domain light chain antibody. In some embodiments, such an antibody or immunologically active fragment thereof is a rabbit, mouse, chimeric, humanized or fully human monoclonal antibody.

The activatable antibodies and activatable antibody compositions provided herein contain at least an antibody or antibody fragment thereof (collectively referred to as AB throughout the disclosure) that specifically binds a target, e.g., a human target, wherein the AB is modified by a masking moiety (MM).

In some embodiments, the MM has an equilibrium dissociation constant for binding to the AB that is greater than the equilibrium dissociation constant of the AB to the target.

In some embodiments, the MM has an equilibrium dissociation constant for binding to the AB that is no more than the equilibrium dissociation constant of the AB to the target.

In some embodiments, the MM does not interfere or compete with the AB of the activatable antibody in a cleaved state for binding to the target.

In some embodiments, the masking moiety is selected for use with a specific antibody or antibody fragment. For example, suitable masking moieties for use with antibodies that bind EGFR include MMs that include the sequence CISPRG (SEQ ID NO: 111). By way of non-limiting examples, the MM can include a sequence such as CISPRGCG (SEQ ID NO: 112); CISPRGCPDGPYVMY (SEQ ID NO: 113); CISPRGCPDGPYVM (SEQ ID NO: 114), CISPRGCEPGTYVPT (SEQ ID NO: 115) and CISPRGCPGQIWHPP (SEQ ID NO: 116). Other suitable masking moieties include any of the EGFR-specific masks disclosed in PCT Publication No. WO 2010/081173, such as, by way of non-limiting example, GSHCLIPINMGAPSC (SEQ ID NO: 117); CISPRGCGGSSASQSGQGSHCLIPINMGAPSC (SEQ ID NO: 118); CNHHYFYTCGCISPRGCPG (SEQ ID NO: 119); ADHVFWGSYGCISPRGCPG (SEQ ID NO: 120); CHHVYWGHCGCISPRGCPG (SEQ ID NO: 121); CPHFTTTSCGCISPRGCPG (SEQ ID NO: 122); CNHHYHYYCGCISPRGCPG (SEQ ID NO: 123); CPHVSFGSCGCISPRGCPG (SEQ ID NO: 124); CPYYTLSYCGCISPRGCPG (SEQ ID NO: 125); CNHVYFGTCGCISPRGCPG (SEQ ID NO: 126); CNHFTLTTCGCISPRGCPG (SEQ ID NO: 127); CHHFTLTTCGCISPRGCPG (SEQ ID NO: 128); YNPCATPMCCISPRGCPG (SEQ ID NO: 129); CNHHYFYTCGCISPRGCG (SEQ ID NO: 130); CNHHYHYYCGCISPRGCG (SEQ ID NO: 131); CNHVYFGTCGCISPRGCG (SEQ ID NO: 132); CHHVYWGHCGCISPRGCG (SEQ ID NO: 133); CPHFTTTSCGCISPRGCG (SEQ ID NO: 134); CNHFTLTTCGCISPRGCG (SEQ ID NO: 135); CHHFTLTTCGCISPRGCG (SEQ ID NO: 136); CPYYTLSYCGCISPRGCG (SEQ ID NO: 137); CPHVSFGSCGCISPRGCG (SEQ ID NO: 138); ADHVFWGSYGCISPRGCG (SEQ ID NO: 139); YNPCATPMCCISPRGCG (SEQ ID NO: 140); CHHVYWGHCGCISPRGCG (SEQ ID NO: 141); C(N/P)H(H/V/F)(Y/T)(F/W/T/L)(Y/G/T/S)(T/S/Y/H)CGCISPRGCG (SEQ ID NO: 142); CISPRGCGQPIPSVK (SEQ ID NO: 143); CISPRGCTQPYHVSR (SEQ ID NO: 144); and/or CISPRGCNAVSGLGS (SEQ ID NO: 145).

Suitable masking moieties for use with antibodies that bind a Jagged target, e.g., Jagged 1 and/or Jagged 2, include, by way of non-limiting example, masking moieties that include a sequence such as QGQSGQGQQQWCNIWINGGDCRGWNG (SEQ ID NO: 146); PWCMQRQDFLRCPQP (SEQ ID NO: 147); QLGLPAYMCTFECLR (SEQ ID NO: 148); CNLWVSGGDCGGLQG (SEQ ID NO: 149); SCSLWTSGSCLPHSP (SEQ ID NO: 150); YCLQLPHYMQAMCGR (SEQ ID NO: 151); CFLYSCTDVSYWNNT (SEQ ID NO: 152); PWCMQRQDYLRCPQP (SEQ ID NO: 153); CNLWISGGDCRGLAG (SEQ ID NO: 154); CNLWVSGGDCRGVQG (SEQ ID NO: 155); CNLWVSGGDCRGLRG (SEQ ID NO: 156); CNLWISGGDCRGLPG (SEQ ID NO: 157); CNLWVSGGDCRDAPW (SEQ ID NO: 158); CNLWVSGGDCRDLLG (SEQ ID NO: 159); CNLWVSGGDCRGLQG (SEQ ID NO: 160); CNLWLHGGDCRGWQG (SEQ ID NO: 161); CNIWLVGGDCRGWQG (SEQ ID NO: 162); CTTWFCGGDCGVMRG (SEQ ID NO: 163); CNIWGPSVDCGALLG (SEQ ID NO: 164); CNIWVNGGDCRSFEG (SEQ ID NO: 165); YCLNLPRYMQDMCWA (SEQ ID NO: 166); YCLALPHYMQADCAR (SEQ ID NO: 167); CFLYSCGDVSYWGSA (SEQ ID NO: 168); CYLYSCTDSAFWNNR (SEQ ID NO: 169); CYLYSCNDVSYWSNT (SEQ ID NO: 170); CFLYSCTDVSYW (SEQ ID NO: 171); CFLYSCTDVAYWNSA (SEQ ID NO: 172); CFLYSCTDVSYWGDT (SEQ ID NO: 173); CFLYSCTDVSYWGNS (SEQ ID NO: 174); CFLYSCTDVAYWNNT (SEQ ID NO: 175); CFLYSCGDVSYWGNPGLS (SEQ ID NO: 176); CFLYSCTDVAYWSGL (SEQ ID NO: 177); CYLYSCTDGSYWNST (SEQ ID NO: 178); CFLYSCSDVSYWGNI (SEQ ID NO: 179); CFLYSCTDVAYW (SEQ ID NO: 180); CFLYSCTDVSYWGST (SEQ ID NO: 181); CFLYSCTDVAYWGDT (SEQ ID NO: 182); GCNIWLNGGDCRGWVDPLQG (SEQ ID NO: 183); GCNIWLVGGDCRGWIGDTNG (SEQ ID NO: 184); GCNIWLVGGDCRGWIEDSNG (SEQ ID NO: 185); GCNIWANGGDCRGWIDNIDG (SEQ ID NO: 186); GCNIWLVGGDCRGWLGEAVG (SEQ ID NO: 187); GCNIWLVGGDCRGWLEEAVG (SEQ ID NO: 188); GGPALCNIWLNGGDCRGWSG (SEQ ID NO: 189); GAPVFCNIWLNGGDCRGWMG (SEQ ID NO: 190); GQQQWCNIWINGGDCRGWNG (SEQ ID NO: 191); GKSEFCNIWLNGGDCRGWIG (SEQ ID NO: 192); GTPGGCNIWANGGDCRGWEG (SEQ ID NO: 193); GASQYCNLWINGGDCRGWRG (SEQ ID NO: 194); GCNIWLVGGDCRPWVEGG (SEQ ID NO: 195); GCNIWAVGGDCRPFVDGG (SEQ ID NO: 196); GCNIWLNGGDCRAWVDTG (SEQ ID NO: 197); GCNIWIVGGDCRPFINDG (SEQ ID NO: 198); GCNIWLNGGDCRPVVFGG (SEQ ID NO: 199); GCNIWLSGGDCRMFMNEG (SEQ ID NO: 200); GCNIWVNGGDCRSFVYSG (SEQ ID NO: 201); GCNIWLNGGDCRGWEASG (SEQ ID NO: 202); GCNIWAHGGDCRGFIEPG (SEQ ID NO: 203); GCNIWLNGGDCRTFVASG (SEQ ID NO: 204); GCNIWAHGGDCRGFIEPG (SEQ ID NO: 205); GFLENCNIWLNGGDCRTG (SEQ ID NO: 206); GIYENCNIWLNGGDCRMG (SEQ ID NO: 207); and/or GIPDNCNIWINGGDCRYG (SEQ ID NO: 208).

Suitable masking moieties for use with antibodies that bind an interleukin 6 target, e.g., interleukin 6 receptor (IL-6R), include, by way of non-limiting example, masking moieties that include a sequence such as QGQSGQYGSCSWNYVHIFMDC (SEQ ID NO: 209); QGQSGQGDFDIPFPAHWVPIT (SEQ ID NO: 210); QGQSGQMGVPAGCVWNYAHIFMDC (SEQ ID NO: 211); YRSCNWNYVSIFLDC (SEQ ID NO: 212); PGAFDIPFPAHWVPNT (SEQ ID NO: 213); ESSCVWNYVHIYMDC (SEQ ID NO: 214); YPGCKWNYDRIFLDC (SEQ ID NO: 215); YRTCSWNYVGIFLDC (SEQ ID NO: 216); YGSCSWNYVHIFMDC (SEQ ID NO: 217); YGSCSWNYVHIFLDC (SEQ ID NO: 218); YGSCNWNYVHIFLDC (SEQ ID NO: 219); YTSCNWNYVHIFMDC (SEQ ID NO: 220); YPGCKWNYDRIFLDC (SEQ ID NO: 221); WRSCNWNYAHIFLDC (SEQ ID NO: 222); WSNCHWNYVHIFLDC (SEQ ID NO: 223); DRSCTWNYVRISYDC (SEQ ID NO: 224); SGSCKWDYVHIFLDC (SEQ ID NO: 225); SRSCIWNYAHIHLDC (SEQ ID NO: 226); SMSCYWQYERIFLDC (SEQ ID NO: 227); YRSCNWNYVSIFLDC (SEQ ID NO: 228); SGSCKWDYVHIFLDC (SEQ ID NO: 229); YKSCHWDYVHIFLDC (SEQ ID NO: 230); YGSCTWNYVHIFMEC (SEQ ID NO: 231); FSSCNWNYVHIFLDC (SEQ ID NO: 232); WRSCNWNYAHIFLDC (SEQ ID NO: 233); YGSCQWNYVHIFLDC (SEQ ID NO: 234); YRSCNWNYVHIFLDC (SEQ ID NO: 235); NMSCHWDYVHIFLDC (SEQ ID NO: 236); FGPCTWNYARISWDC (SEQ ID NO: 237); XXsCXWXYvhIfXdC (SEQ ID NO: 238); MGVPAGCVWNYAHIFMDC (SEQ ID NO: 239); RDTGGQCRWDYVHIFMDC (SEQ ID NO: 240); AGVPAGCTWNYVHIFMEC (SEQ ID NO: 241); VGVPNGCVWNYAHIFMEC (SEQ ID NO: 242); DGGPAGCSWNYVHIFMEC (SEQ ID NO: 243); AVGPAGCWWNYVHIFMEC (SEQ ID NO: 244); CTWNYVHIFMDCGEGEGP (SEQ ID NO: 245); GGVPEGCTWNYAHIFMEC (SEQ ID NO: 246); AEVPAGCWWNYVHIFMEC (SEQ ID NO: 247); AGVPAGCTWNYVHIFMEC (SEQ ID NO: 248); SGASGGCKWNYVHIFMDC (SEQ ID NO: 249); TPGCRWNYVHIFMECEAL (SEQ ID NO: 250); VGVPNGCVWNYAHIFMEC (SEQ ID NO: 251); PGAFDIPFPAHWVPNT (SEQ ID NO: 252); RGACDIPFPAHWIPNT (SEQ ID NO: 253); QGDFDIPFPAHWVPIT (SEQ ID NO: 254); XGafDIPFPAHWvPnT (SEQ ID NO: 255); RGDGNDSDIPFPAHWVPRT (SEQ ID NO: 256); SGVGRDRDIPFPAHWVPRT (SEQ ID NO: 257); WAGGNDCDIPFPAHWIPNT (SEQ ID NO: 258); WGDGMDVDIPFPAHWVPVT (SEQ ID NO: 259); AGSGNDSDIPFPAHWVPRT (SEQ ID NO: 260); ESRSGYADIPFPAHWVPRT (SEQ ID NO: 261); and/or RECGRCGDIPFPAHWVPRT (SEQ ID NO: 262).

In some embodiments, the activatable antibody in the uncleaved state has the structural arrangement from N-terminus to C-terminus as follows: MM-CM-AB or AB-CM-MM.

In some embodiments, the activatable antibody includes a linking peptide between the MM and the CM, i.e., the substrate sequence.

In some embodiments, the activatable antibody includes a linking peptide between the CM and the AB.

In some embodiments, the activatable antibody includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, the two linking peptides need not be identical to each other.

In some embodiments, the MM is a polypeptide of about 2 to 40 amino acids in length, for example, no more than 40 amino acids long.

In some embodiments, the MM polypeptide sequence is different from that of the target, and the MM polypeptide sequence is no more than 50% identical to any natural binding partner of the AB. In some embodiments, the MM does not include more than 25% amino acid sequence identity to the target. In some embodiments, the MM does not include more than 10% amino acid sequence identity to the target.

In some embodiments, the CM is positioned in the activatable antibody such that in the uncleaved state, binding of the activatable antibody to the target is reduced to occur with an equilibrium dissociation constant that is at least twofold greater than the equilibrium dissociation constant of an unmodified AB binding to the target, and whereas the AB of the activatable antibody in the cleaved state binds the target.

In some embodiments, the CM is positioned in the activatable antibody such that in the uncleaved state, binding of the activatable antibody to the target is reduced to occur with an equilibrium dissociation constant that is at least five-fold greater than the equilibrium dissociation constant of an unmodified AB binding to the target, and whereas the AB of the activatable antibody in the cleaved state binds the target.

In some embodiments, the CM is positioned in the activatable antibody such that in the uncleaved state, binding of the activatable antibody to the target is reduced to occur with an equilibrium dissociation constant that is at least ten-fold greater than the equilibrium dissociation constant of an unmodified AB binding to the target, and whereas the AB of the activatable antibody in the cleaved state binds the target.

In some embodiments, the CM is positioned in the activatable antibody such that in the uncleaved state, binding of the activatable antibody to the target is reduced to occur with an equilibrium dissociation constant that is at least 20-fold greater than the equilibrium dissociation constant of an unmodified AB binding to the target, and whereas the AB of the activatable antibody in the cleaved state binds the target.

In some embodiments, the CM is positioned in the activatable antibody such that in the uncleaved state, binding of the activatable antibody to the target is reduced to occur with an equilibrium dissociation constant that is at least 40-fold greater than the equilibrium dissociation constant of an unmodified AB binding to the target, and whereas the AB of the activatable antibody in the cleaved state binds the target.

In some embodiments, the CM is positioned in the activatable antibody such that in the uncleaved state, binding of the activatable antibody to the target is reduced to occur with an equilibrium dissociation constant that is at least 100-fold greater than the equilibrium dissociation constant of an unmodified AB binding to the target, and whereas the AB of the activatable antibody in the cleaved state binds the target.

In some embodiments, the CM is positioned in the activatable antibody such that in the uncleaved state, binding of the activatable antibody to the target is reduced to occur with an equilibrium dissociation constant that is at least 200-fold greater than the equilibrium dissociation constant of an unmodified AB binding to the target, and whereas the AB of the activatable antibody in the cleaved state binds the target.

In some embodiments, the coupling of the MM reduces the ability of the AB to bind the target such that the dissociation constant ($K_d$) of the AB when coupled to the MM towards the target is at least two times greater than the $K_d$ of the AB when not coupled to the MM towards the target. In some embodiments, the coupling of the MM reduces the ability of the AB to bind the target such that the dissociation constant ($K_d$) of the AB when coupled to the MM towards the target is at least four times greater than the $K_d$ of the AB when not coupled to the MM towards the target. In some embodiments, the coupling of the MM reduces the ability of the AB to bind the target such that the dissociation constant ($K_d$) of the AB when coupled to the MM towards the target is at least five times greater than the $K_d$ of the AB when not coupled to the MM towards the target. In some embodiments, the coupling of the MM reduces the ability of the AB to bind the target such that the dissociation constant ($K_d$) of the AB when coupled to the MM towards the target is at least 10 times greater than the $K_d$ of the AB when not coupled to the MM towards the target. In some embodiments, the coupling of the MM reduces the ability of the AB to bind the target such that the dissociation constant ($K_d$) of the AB when coupled to the MM towards the target is at least 20 times greater than the $K_d$ of the AB when not coupled to the MM towards the target. In some embodiments, the coupling of the MM reduces the ability of the AB to bind the target such that the $K_d$ of the AB when coupled to the MM towards the target is at least 40 times greater than the $K_d$ of the AB when not coupled to the MM towards the target. In some embodiments, the coupling of the MM reduces the ability of the AB to bind the target such that the $K_d$ of the AB when coupled to the MM towards the target is at least 100 times greater than the $K_d$ of the AB when not coupled to the MM towards the target. In some embodiments, the coupling of the MM reduces the ability of the AB to bind the target such that the $K_d$ of the AB when coupled to the MM towards the target is at least 1000 times greater than the $K_d$ of the AB when not coupled to the MM towards the target. In some embodiments, the coupling of the MM reduces the ability of the AB to bind the target such that the $K_d$ of the AB when coupled to the MM towards the target is at least 10,000 times greater than the $K_d$ of the AB when not coupled to the MM towards the target.

In some embodiments, the CM is a polypeptide of up to 15 amino acids in length. The CM is cleaved by a protease. In some embodiments, the protease is co-localized with the target in a tissue, and the protease cleaves the CM in the activatable antibody when the activatable antibody is exposed to the protease. In some embodiments, the protease is not active or is significantly less active in tissues that do not significantly express the target. In some embodiments, the protease is not active or is significantly less active in healthy, e.g., non-diseased tissues.

In some embodiments, the CM is cleaved by a protease shown in Table 3.

TABLE 3

| Exemplary proteases |
| --- |
| ADAMS, ADAMTS, e.g. |
| ADAM8 |
| ADAM9 |
| ADAM10 |
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |

TABLE 3-continued

| Exemplary proteases |
| --- |
| Neprilysin |
| PSMA |
| BMP-1 |
| MMPs, e.g., |
| MMP1 |
| MMP2 |
| MMP3 |
| MMP7 |
| MMP8 |
| MMP9 |
| MMP10 |
| MMP11 |
| MMP12 |
| MMP13 |
| MMP14 |
| MMP15 |
| MMP16 |
| MMP17 |
| MMP19 |
| MMP20 |
| MMP23 |
| MMP24 |
| MMP26 |
| MMP27 |
| Serine proteases, e.g., |
| activated protein C |
| Cathepsin A |
| Cathepsin G |
| Chymase |
| coagulation factor proteases |
| (e.g., FVIIa, FIXa, FXa, FXIa, FXIIa) |
| Elastase |
| Granzyme B |
| Guanidinobenzoatase |
| HtrA1 |
| Human Neutrophil Elastase |
| Lactoferrin |
| Marapsin |
| NS3/4A |
| PACE4 |
| Plasmin |
| PSA |
| tPA |
| Thrombin |
| Tryptase |
| uPA |
| Type II Transmembrane Serine Proteases (TTSPs), e.g., |
| DESC1 |
| DPP-4 |
| FAP |
| Hepsin |
| Matriptase-2 |
| MT-SP1/Matriptase |
| TMPRSS2 |
| TMPRSS3 |
| TMPRSS4 |

In some embodiments, the CM is selected for use with a specific protease. In some embodiments, the CM is a substrate for at least one protease selected from the group consisting of an ADAM 17, a BMP-1, a cysteine protease such as a cathepsin, a HtrA1, a legumain, a matriptase (MT-SP1), a matrix metalloprotease (MMP), a neutrophil elastase, a TMPRSS, such as TMPRSS3 or TMPRSS4, a thrombin, and a u-type plasminogen activator (uPA, also referred to as urokinase), In some embodiments, the CM is a substrate for an ADAM17. In some embodiments, the CM is a substrate for a BMP-1. In some embodiments, the CM is a substrate for a cathepsin. In some embodiments, the CM is a substrate for a cysteine protease. In some embodiments, the CM is a substrate for a HtrA1. In some embodiments, the CM is a substrate for a legumain. In some embodiments, the CM is a substrate for a matriptase. In some embodiments, the CM is a substrate for a MMP. In some embodiments, the CM is a substrate for a neutrophil elastase. In some embodiments, the CM is a substrate for a thrombin. In some embodiments, the CM is a substrate for a TMPRSS. In some embodiments, the CM is a substrate for TMPRSS3. In some embodiments, the CM is a substrate for TMPRSS4. In some embodiments, the CM is a substrate for uPA.

For example, suitable CM are cleaved by at least one protease and include the sequence TGRGPSWV (SEQ ID NO: 263); SARGPSRW (SEQ ID NO: 264); TARGPSFK (SEQ ID NO: 265); LSGRSDNH (SEQ ID NO: 266); GGWHTGRN (SEQ ID NO: 267); HTGRSGAL (SEQ ID NO: 268); PLTGRSGG (SEQ ID NO: 269); AARGPAIH (SEQ ID NO: 270); RGPAFNPM (SEQ ID NO: 271); SSRGPAYL (SEQ ID NO: 272); RGPATPIM (SEQ ID NO: 273); RGPA (SEQ ID NO: 274); GGQPSGMWGW (SEQ ID NO: 275); FPRPLGITGL (SEQ ID NO: 276); VHMPLGFLGP (SEQ ID NO: 277); SPLTGRSG (SEQ ID NO: 278); SAGFSLPA (SEQ ID NO: 279); LAPLGLQRR (SEQ ID NO: 280); SGGPLGVR (SEQ ID NO: 281); PLGL (SEQ ID NO: 282); GPRSFGL (SEQ ID NO: 283) and/or GPRSFG (SEQ ID NO: 284).

In some embodiments, the CM comprises the amino acid sequence TGRGPSWV (SEQ ID NO: 263). In some embodiments, the CM comprises the amino acid sequence SARGPSRW (SEQ ID NO: 264). In some embodiments, the CM comprises the amino acid sequence TARGPSFK (SEQ ID NO: 265). In some embodiments, the CM comprises the amino acid sequence LSGRSDNH (SEQ ID NO: 266). In some embodiments, the CM comprises the amino acid sequence GGWHTGRN (SEQ ID NO: 267). In some embodiments, the CM comprises the amino acid sequence HTGRSGAL (SEQ ID NO: 268). In some embodiments, the CM comprises the amino acid sequence PLTGRSGG (SEQ ID NO: 269). In some embodiments, the CM comprises the amino acid sequence AARGPAIH (SEQ ID NO: 270). In some embodiments, the CM comprises the amino acid sequence RGPAFNPM (SEQ ID NO: 271). In some embodiments, the CM comprises the amino acid sequence SSRGPAYL (SEQ ID NO: 272). In some embodiments, the CM comprises the amino acid sequence RGPATPIM (SEQ ID NO: 273). In some embodiments, the CM comprises the amino acid sequence RGPA (SEQ ID NO: 274). In some embodiments, the CM comprises the amino acid sequence GGQPSGMWGW (SEQ ID NO: 275). In some embodiments, the CM comprises the amino acid sequence FPRPLGITGL (SEQ ID NO: 276). In some embodiments, the CM comprises the amino acid sequence VHMPLGFLGP (SEQ ID NO: 277). In some embodiments, the CM comprises the amino acid sequence SPLTGRSG (SEQ ID NO: 278). In some embodiments, the CM comprises the amino acid sequence SAGFSLPA (SEQ ID NO: 279). In some embodiments, the CM comprises the amino acid sequence LAPLGLQRR (SEQ ID NO: 280). In some embodiments, the CM comprises the amino acid sequence SGGPLGVR (SEQ ID NO: 281). In some embodiments, the CM comprises the amino acid sequence PLGL (SEQ ID NO: 282). In some embodiments, the CM comprises the amino acid sequence GPRSFGL (SEQ ID NO: 283). In some embodiments, the CM comprises the amino acid sequence GPRSFG (SEQ ID NO: 284).

In some embodiments, the CM is a substrate for at least one MMP. In some embodiments, the CM is a substrate for at least one MMP listed in the Table 3. In some embodiments the CM1 is a substrate for MMP9. In some embodiments, the CM1 is a substrate for MMP14. In some embodiments, the CM is a substrate for two or more MMPs. In some embodiments, the CM is a substrate for at least MMP9 or MMP14. In some embodiments, the CM is a substrate for two or more MMPs.

In some embodiments, the CM is a substrate for an MMP and includes the sequence ISSGLLSS (SEQ ID NO: 45); QNQALRMA (SEQ ID NO: 46); AQNLLGMV (SEQ ID NO: 47); STFPFGMF (SEQ ID NO: 48); PVGYTSSL (SEQ ID NO: 49); DWLYWPGI (SEQ ID NO: 50) MIAPVAYR (SEQ ID NO: 51); RPSPMWAY (SEQ ID NO: 52); WATPRPMR (SEQ ID NO: 53); FRLLDWQW (SEQ ID NO: 54); LKAAPRWA (SEQ ID NO: 398); GPSHLVLT (SEQ ID NO: 399); LPGGLSPW (SEQ ID NO: 400); MGLFSEAG (SEQ ID NO: 401); SPLPLRVP (SEQ ID NO: 402); RMHLRSLG (SEQ ID NO: 403); LAAPLGLL (SEQ ID NO: 404); AVGLLAPP (SEQ ID NO: 405); LLAPSHRA (SEQ ID NO: 406), PAGLWLDP (SEQ ID NO: 407); and/or ISSGLSS (SEQ ID NO: 408).

In some embodiments, at least one of LP1 or LP2 includes an amino acid sequence selected from the group consisting of $(GS)_n$, $(GGS)_n$, $(GSGGS)_n$ (SEQ ID NO: 285) and $(GGGS)_n$ (SEQ ID NO: 286), where n is an integer of at least one. In some embodiments, at least one of LP1 or LP2 includes an amino acid sequence selected from the group consisting of GGSG (SEQ ID NO: 287), GGSGG (SEQ ID NO: 288), GSGSG (SEQ ID NO: 289), GSGGG (SEQ ID NO: 290), GGGSG (SEQ ID NO: 291), and GSSSG (SEQ ID NO: 292).

In some embodiments, LP1 includes the amino acid sequence GSSGGSGGSGGSG (SEQ ID NO: 293).

In some embodiments, LP2 includes the amino acid sequence GSSGT (SEQ ID NO: 294) or GSSG (SEQ ID NO: 295).

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one MMP-cleavable substrate sequence. In some embodiments, the agent is conjugated to the AB via a linker that includes at least one cathepsin-cleavable substrate sequence. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine (PBD).

In some embodiments, the agent is conjugated to the AB via a linker. In some embodiments, the linker is a cleavable linker.

In some embodiments, the activatable antibody also includes a detectable moiety. In some embodiments, the detectable moiety is a diagnostic agent. In some embodiments, the detectable moiety is a conjugatable detection reagent. In some embodiments, the detectable moiety is, for example, a fluorescein derivative such as fluorescein isothiocyanate (FITC).

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer includes at least the amino acid sequence QGQSGQ (SEQ ID NO: 296). In some embodiments, an activatable antibody includes a spacer of sequence QGQSGQ (SEQ ID NO: 296) joined directly to a MM sequence in the structural arrangement from N-terminus to C-terminus of spacer-MM-CM-AB.

In some embodiments, the serum half-life of the activatable antibody and/or conjugated activatable antibody is longer than that of the corresponding antibody; e.g., the pK of the activatable antibody and/or conjugated activatable antibody is longer than that of the corresponding antibody. In some embodiments, the serum half-life of the activatable antibody and/or conjugated activatable antibody is similar to that of the corresponding antibody. In some embodiments, the serum half-life of the activatable antibody and/or conjugated activatable antibody is at least 15 days when administered to an organism. In some embodiments, the serum half-life of the activatable antibody and/or conjugated activatable antibody is at least 12 days when administered to an organism. In some embodiments, the serum half-life of the activatable antibody and/or conjugated activatable antibody is at least 11 days when administered to an organism. In some embodiments, the serum half-life of the activatable antibody and/or conjugated activatable antibody is at least 10 days when administered to an organism. In some embodiments, the serum half-life of the activatable antibody and/or conjugated activatable antibody is at least 9 days when administered to an organism. In some embodiments, the serum half-life of the activatable antibody and/or conjugated activatable antibody is at least 8 days when administered to an organism. In some embodiments, the serum half-life of the activatable antibody and/or conjugated activatable antibody is at least 7 days when administered to an organism. In some embodiments, the serum half-life of the activatable antibody and/or conjugated activatable antibody is at least 6 days when administered to an organism. In some embodiments, the serum half-life of the activatable antibody and/or conjugated activatable antibody is at least 5 days when administered to an organism. In some embodiments, the serum half-life of the activatable antibody and/or conjugated activatable antibody is at least 4 days when administered to an organism. In some embodiments, the serum half-life of the activatable antibody and/or conjugated activatable antibody is at least 3 days when administered to an organism. In some embodiments, the serum half-life of the activatable antibody and/or conjugated activatable antibody is at least 2 days when administered to an organism. In some embodiments, the serum half-life of the activatable antibody and/or conjugated activatable antibody is at least 24 hours when administered to an organism. In some embodiments, the serum half-life of the activatable antibody and/or conjugated activatable antibody is at least 20 hours when administered to an organism. In some embodiments, the serum half-life of the activatable antibody and/or conjugated activatable antibody is at least 18 hours when administered to an organism. In some embodiments, the serum half-life of the activatable antibody and/or conjugated activatable antibody is at least 16 hours when administered to an organism. In some embodiments, the serum half-life of the activatable antibody and/or conjugated activatable antibody is at least 14 hours when administered to an organism. In some embodiments, the serum half-life of the activatable antibody and/or conjugated activatable antibody is at least 12 hours when administered to an organism. In some embodiments, the serum half-life of the activatable antibody and/or conjugated activatable antibody is at least 10 hours when administered to an organism. In some embodiments, the serum half-life of the activatable antibody and/or conjugated activatable antibody is at least 8 hours when administered to an organism. In some embodiments, the serum half-life of the activatable antibody and/or conjugated activatable antibody is at least 6 hours when administered to an organism. In some embodiments, the serum half-life of the activatable antibody and/or conjugated activatable antibody is at least 4 hours when administered to an organism. In some embodiments, the serum half-life of the activatable antibody and/or conjugated activatable antibody is at least 3 hours when administered to an organism.

In some embodiments, the activatable antibody is monospecific. In some embodiments, the activatable antibody is multispecific, e.g., by way of non-limiting example, bispecific or trifunctional. In some embodiments, the activatable antibody is formulated as part of a pro-Bispecific T Cell Engager (BITE) molecule. In some embodiments, the activatable antibody is formulated as part of a pro-Chimeric Antigen Receptor (CAR) modified T cell or other engineered receptor.

Exemplary activatable anti-EGFR antibodies of the invention include, for example, the activatable antibody referred to herein as the 3954-1204-C225v5 activatable antibody, which binds epidermal growth factor receptor (EGFR) when the activatable antibody is in an activated, i.e., cleaved, state. Three sequences of the 3954-1204-C225v5 activatable anti-EGFR antibody are shown below, Sequence 1 is the sequence of a version of the 3954-1204-C225v5 activatable anti-EGFR antibody that includes a signal peptide, Sequence 2 is the sequence of the 3954-1204-C225v5 activatable anti-EGFR antibody without the signal peptide, and Sequence 3 is the sequence of the 3954-1204-C225v5 activatable anti-EGFR antibody without the signal peptide and without the spacer sequence:

```
3954-1204-C225v5 Activatable Antibody Heavy Chain Nucleotide Sequence 1:
[Signal peptide (SEQ ID NO: 297)][C225v5 (SEQ ID NO: 298)]
                                                           (SEQ ID NO: 299)
[atgtacaggatgcaactcctgtcttgcattgcactaagtcttgcacttgtcacgaattcg]

[caggtgcagctgaaacagagcggcccgggcctggtgcagccgagccagagcctgagcattacctg caccgtgagcggctttagcctgaccaactatggcgtgcattgggtgcgccagagcccgggcaaa
```

```
ggcctggaatggctgggcgtgatttggagcggcggcaacaccgattataacaccccgtttacca gccgcctgagcattaacaaagataacagcaaaagccaggtgtttttttaaaatgaacagcctgca aagccaggataccgcgatttattattgcgcgcgcgcgctgacctattatgattatgaatttgcg tattggggccagggcacccctggtgaccgtgagcgcggctagcaccaagggcccatcggtcttcc ccctggcaccctcctccaagagcacctctgggggcacagcggccctgggctgcctggtcaagga ctacttccccgaaccggtgacggtgtcgtggaactcaggcgccctgaccagcggcgtgcacacc ttcccggctgtcctacagtcctcaggactctactccctcagcagcgtggtgaccgtgccctcca gcagcttgggcacccagacctacatctgcaacgtgaatcacaagcccagcaacaccaaggtgga caagaaagttgagcccaaatcttgtgacaaaactcacacatgcccaccgtgcccagcacctgaa ctcctggggggaccgtcagtcttcctcttccccccaaaacccaaggacaccctcatgatctccc ggacccctgaggtcacatgcgtggtggtggacgtgagccacgaagaccctgaggtcaagttcaa ctggtacgtggacggcgtggaggtgcataatgccaagacaaagccgcgggaggagcagtacaac agcacgtaccgtgtggtcagcgtcctcaccgtcctgcaccaggactggctgaatggcaaggagt acaagtgcaaggtctccaacaaagccctcccagcccccatcgagaaaaccatctccaaagccaa agggcagccccgagaaccacaggtgtacaccctgcccccatcccgggatgaactgaccaagaac caggtcagcctgacctgcctggtcaaaggcttctatcccagcgacatcgccgtggagtgggaga gcaatgggcagccggagaacaactacaagaccacgcctcccgtgctggactccgacggctcctt cttcctctacagcaagctcaccgtggacaagagcaggtggcagcaggggaacgtcttctcatgc tccgtgatgcatgaggctctgcacaaccactacacgcagaagagcctctccctgtctccgggta aatga]
Italics: Signal peptide
Normal text: anti-EGFR antibody derived sequence 3954-1204-C225v5 Activatable Antibody Heavy Chain Amino Acid Sequence 1:
[Signal peptide (SEQ ID NO: 300)][C225v5 (SEQ ID NO: 301)]
                                                          (SEQ ID NO: 302)
[MYRMQLLSCIALSLALVTNS][QVQLKQSGPGLVQPSQSLSITCTVSGFSLTNYGVHWVRQSP

GKGLEWLGVIWSGGNTDYNTPFTSRLSINKDNSKSQVFFKMNSLQSQDTAIYYCARALTYYDYE

FAYWGQGTLVTVSAASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQGNVF

SCSVMHEALHNHYTQKSLSLSPGK*]
Italics: Signal peptide
Normal text: anti-EGFR antibody derived sequence 3954-1204-C225v5 Activatable Antibody Light Chain Nucleotide Sequence 1:
[Signal peptide (SEQ ID NO: 297)][Spacer (SEQ ID NO: 303)][Mask
(SEQ ID NO: 304)][Linker 1 (SEQ ID NO: 305)][1204 Substrate (SEQ
ID NO: 306)][Linker 2 (SEQ ID NO: 307)][C225 (SEQ ID NO: 308)]
                                                          (SEQ ID NO: 309)
[atgtacaggatgcaactcctgtcttgcattgcactaagtcttgcacttgtcacgaattcg]

[caaggccagtctggccag][tgcatctcacctcgtggttgtccggacggcccatacgtcatgtac]

[ggctcgagcggtggcagcggtggctctggtggatccggt][ctgagcggccgttccgataatcat]

[ggcagtagcggtacc][cagatcttgctgacccagagcccggtgattctgagcgtgagc ccgggcgaacgtgtgagctttagctgccgcgcgagccagagcattggcaccaacattcattggt atcagcagcgcaccaacggcagcccgcgcctgctgattaaatatgcgagcgaaagcattagcgg
```

-continued cattccgagccgctttagcggcagcggcagcggcaccgattttaccctgagcattaacagcgtg gaaagcgaagatattgcggattattattgccagcagaacaacaactggccgaccaccttggcg cgggcaccaaactggaactgaaacgtacggtggctgcaccatctgtcttcatcttcccgccatc tgatgagcagttgaaatctggaactgcctctgttgtgtgcctgctgaataacttctatcccaga gaggccaaagtacagtggaaggtggataacgcccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgttag]
Italics: Signal peptide
Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v5 Activatable Antibody Light Chain Amino Acid Sequence 1:
[Signal peptide (SEQ ID NO: 300)][Spacer (SEQ ID NO: 296)][Mask
(SEQ ID NO: 113)][Linker 1 (SEQ ID NO: 293)][1204 Substrate (SEQ
ID NO: 266)][Linker 2 (SEQ ID NO: 294)][C225 (SEQ ID NO: 310)]

(SEQ ID NO: 311)

[*MYRMQLLSCIALSLALVTNS*][QGQSGQ][CISPRGCPDGPYVMY][*GSSGGSGGSGGSG*]

[LSGRSDNH][*GSSGT*][QILLTQSPVILSVSPGERVSFSCRASQSIGTNIHWYQQRTNGSPRLLI

KYASESISGIPSRFSGSGSGTDFTLSINSVESEDIADYYCQQNNNWPTTFGAGTKLELKRTVAA

PSVFIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC*]
Italics: Signal peptide
Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v5 Activatable Antibody Heavy Chain Nucleotide Sequence 2:
[C225v5 (SEQ ID NO: 298)]

(SEQ ID NO: 298)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacacccccgtttac cagccgcctgagcattaacaaagataacagcaaaagccaggtgttttttaaaatgaacagcctg caaagccaggataccgcgatttattattgcgcgcgcgcgctgacctattatgattatgaatttg cgtattgggcccagggcaccctggtgaccgtgagcgcggctagcaccaagggcccatcggtctt cccccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagcccccagccccccatcgagaaaaccatctccaaagcc aaagggcagccccgagaaccacaggtgtacaccctgcccccatcccgggatgaactgaccaaga

```
accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctcccctgtctccggg taaatga]
```

3954-1204-C225v5 Activatable Antibody Heavy Chain Amino Acid Sequence 2:
[C225v5 (SEQ ID NO: 301)]

(SEQ ID NO: 301)

[QVQLKQSGPGLVQPSQSLSITCTVSGFSLTNYGVHWVRQSPGKGLEWLGVIWSGGNTDYNTPF

TSRLSINKDNSKSQVFFKMNSLQSQDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

3954-1204-C225v5 Activatable Antibody Light Chain Nucleotide Sequence 2:
[Spacer (SEQ ID NO: 303)][Mask (SEQ ID NO: 304)][Linker 1 (SEQ
ID NO: 305)][1204 Substrate (SEQ ID NO: 306)][Linker 2 (SEQ ID
NO: 307)][C225 (SEQ ID NO: 308)]

(SEQ ID NO: 312)

[caaggccagtctggccag][tgcatctcacctcgtggttgtccggacggcccatacgtcatgt

*acggctcgagcggtggcagcggtggctctggtggatccggt*][ctgagcggccgttccgataat cat][*ggcatagcggtacc*][cagatcttgctgacccagagcccggtgattctgagcgtgagc ccgggcgaacgtgtgagctttagctgccgcgcgagccagagcattggcaccaacattcattggt atcagcagcgcaccaacggcagcccgcgcctgctgattaaatatgcgagcgaaagcattagcgg cattccgagccgctttagcggcagcggcagcggcaccgattttaccctgagcattaacagcgtg gaaagcgaagatattgcggattattattgccagcagaacaacaactggccgaccacctttggcg cgggcaccaaactggaactgaaacgtacggtggctgcaccatctgtcttcatcttcccgccatc tgatgagcagttgaaatctggaactgcctctgttgtgtgcctgctgaataacttctatcccaga gaggccaaagtacagtggaaggtggataacgccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgttag]
Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v5 Activatable Antibody Light Chain Amino Acid Sequence 2:
[Spacer (SEQ ID NO: 296)][Mask (SEQ ID NO: 113)][Linker 1 (SEQ
ID NO: 293)][1204Substrate (SEQ ID NO: 266)][Linker 2 (SEQ ID
NO: 294)][C225 (SEQ ID NO: 310)]

(SEQ ID NO: 313)

[QGQSGQ][CISPRGCPDGPYVMY][*GSSGGSGGSGGSG*][LSGRSDNH][*GSSGT*][QILLTQ

SPVILSVSPGERVSFSCRASQSIGTNIHWYQQRTNGSPRLLIKYASESISGIPSRFSGSGSGTD

FTLSINSVESEDIADYYCQQNNNWPTTFGAGTKLELKRTVAAPSVFIFPPSDEQLKSGTASVVC

LLNNFYPREAKVQWKVDNALQSGNSQESVTEQDSKDSTYSLSSTLTLSKADYEKHKVYACEVTH

QGLSSPVTKSFNRGEC*]

-continued

Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v5 Activatable Antibody Heavy Chain Nucleotide Sequence 3:
[C225v5 (SEQ ID NO: 298)]

(SEQ ID NO: 298)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgttttttaaaatgaacagcctg caaagccaggataccgcgatttattattgcgcgcgcgcgctgacctattatgattatgaatttg cgtattggggccagggcaccctggtgaccgtgagcgcggctagcaccaagggcccatcggtctt ccccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagccctcccagccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

3954-1204-C225v5 Activatable Antibody Heavy Chain Amino Acid Sequence 3:
[C225v5 (SEQ ID NO: 301)]

(SEQ ID NO: 301)

[QVQLKQSGPGLVQPSQSLSITCTVSGFSLTNYGVHWVRQSPGKGLEWLGVIWSGGNTDYNTPF

TSRLSINKDNSKSQVFFKMNSLQSQDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

3954-1204-C225v5 Activatable Antibody Light Chain Nucleotide Sequence 3:
[Mask (SEQ ID NO: 304)][Linker 1 (SEQ ID NO: 305)][1204 Substrate
(SEQ ID NO: 306)][Linker 2 (SEQ ID NO: 307)][C225 (SEQ ID NO: 308)]

(SEQ ID NO: 409)

[<u>tgcatctcacctcgtggttgtccggacggcccatacgtcatgtac</u><u>*ggctcgagcggtggcagc*</u>

<u>*ggtggctctggtggatccggt*</u>][<u>ctgagcggccgttccgataatcat</u>][**<u>*ggcagtagcggtacc*</u>**]

-continued

```
[cagatcttgctgacccagagcccggtgattctgagcgtgagcccgggcgaacgtgtgagctt tagctgccgcgcgagccagagcattggcaccaacattcattggtatcagcagcgcaccaacggc agcccgcgcctgctgattaaatatgcgagcgaaagcattagcggcattccgagccgctttagcg gcagcggcagcggcaccgattttaccctgagcattaacagcgtggaaagcgaagatattgcgga ttattattgccagcagaacaacaactggccgaccacctttggcgcgggcaccaaactggaactg aaacgtacggtggctgcaccatctgtcttcatcttcccgccatctgatgagcagttgaaatctg gaactgcctctgttgtgtgcctgctgaataacttctatcccagagaggccaaagtacagtggaa ggtggataacgccctccaatcgggtaactcccaggagagtgtcacagagcaggacagcaaggac agcacctacagcctcagcagcaccctgacgctgagcaaagcagactacgagaacacaaagtct acgcctgcgaagtcacccatcagggcctgagctcgcccgtcacaaagagcttcaacaggggaga gtgttag]
```

Underline: Mask
Italics and Underline: Linker 1
Bold and Underline: 1204 Substrate
Bold, Italics and Underline: Linker 2
Normal text: anti-EGFR antibody derived sequence 3954-1204-C225v5 Activatable Antibody Light Chain Amino Acid Sequence 3:
[Mask (SEQ ID NO: 113)][Linker 1 (SEQ ID NO: 293)][1204 Substrate
(SEQ ID NO: 266)][Linker 2 (SEQ ID NO: 294)][C225 (SEQ ID NO: 310)]

(SEQ ID NO: 410)

[CISPRGCPDGPYVMY][*GSSGGSGGSGGSG*][LSGRSDNH][*GSSGT*][QILLTQSPVILSVS

PGERVSFSCRASQSIGTNIHWYQQRTNGSPRLLIKYASESISGIPSRFSGSGSGTDFTLSINSV

ESEDIADYYCQQNNNWPTTFGAGTKLELKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVT

KSFNRGEC*]

Underline: Mask
Italics and Underline: Linker 1
Bold and Underline: 1204 Substrate
Bold, Italics and Underline: Linker 2
Normal text: anti-EGFR antibody derived sequence Another exemplary activatable anti-EGFR antibody of the invention is the activatable antibody referred to herein as the 3954-1204-C225v4 activatable antibody, which binds epidermal growth factor receptor (EGFR) when the activatable antibody is in an activated state. Three sequences of the 3954-1204-C225v4 activatable anti-EGFR antibody are shown below, Sequence 1 is the sequence of a version of the 3954-1204-C225v4 activatable anti-EGFR antibody that includes a signal peptide, Sequence 2 is the sequence of the 3954-1204-C225v4 activatable anti-EGFR antibody without the signal peptide, and Sequence 3 is the sequence of the 3954-1204-C225v4 activatable anti-EGFR antibody without the signal peptide and without the spacer sequence:

3954-1204-C225v4 Activatable Antibody Heavy Chain Nucleotide
Sequence 1:
[Signal Peptide (SEQ ID NO: 297)] [C225v4 (SEQ ID NO: 314)]

(SEQ ID NO: 315)

```
[atgtacaggatgcaactcctgtcttgcattgcactaagtcttgcacttgtcacgaattcg][c aggtgcagctgaaacagagcggcccgggcctggtgcagccgagccagagcctgagcattacctg caccgtgagcggctttagcctgaccaactatggcgtgcattgggtgcgccagagcccgggcaaa ggcctggaatggctgggcgtgatttggagcggcggcaacaccgattataacacccccgtttacca gccgcctgagcattaacaaagataacagcaaaagccaggtgttttttaaaatgaacagcctgca aagcaacgataccgcgatttattattgcgcgcgcgcgctgacctattatgattatgaatttgcg tattggggccagggcaccctggtgaccgtgagcgcggctagcaccaagggcccatcggtcttcc ccctggcaccctcctccaagagcacctctggggggcacagcggccctgggctgcctggtcaagga ctacttccccgaaccggtgacggtgtcgtggaactcaggcgccctgaccagcggcgtgcacacc ttcccggctgtcctacagtcctcaggactctactccctcagcagcgtggtgaccgtgccctcca
```

-continued

```
gcagcttgggcacccagacctacatctgcaacgtgaatcacaagcccagcaacaccaaggtgga caagaaagttgagcccaaatcttgtgacaaaactcacacatgcccaccgtgcccagcacctgaa ctcctggggggaccgtcagtcttcctcttccccccaaaacccaaggacaccctcatgatctccc ggacccctgaggtcacatgcgtggtggtggacgtgagccacgaagaccctgaggtcaagttcaa ctggtacgtggacggcgtggaggtgcataatgccaagacaaagccgcgggaggagcagtacaac agcacgtaccgtgtggtcagcgtcctcaccgtcctgcaccaggactggctgaatggcaaggagt acaagtgcaaggtctccaacaaagcccctcccagcccccatcgagaaaaccatctccaaagcca agggcagccccgagaaccacaggtgtacaccctgcccccatcccgggatgaactgaccaagaac caggtcagcctgacctgcctggtcaaaggcttctatcccagcgacatcgccgtggagtgggaga gcaatgggcagccggagaacaactacaagaccacgcctcccgtgctggactccgacggctcctt cttcctctacagcaagctcaccgtggacaagagcaggtggcagcaggggaacgtcttctcatgc tccgtgatgcatgaggctctgcacaaccactacacgcagaagagcctctccctgtctccgggta aatga]
```

Italics: Signal peptide

Normal text: anti-EGFR antibody derived sequence 3954-1204-C225v4 Activatable Antibody Heavy Chain Amino Acid Sequence 1:
[Signal Peptide (SEQ ID NO: 300)] [C225v4 (SEQ ID NO: 316)]

(SEQ ID NO: 317)

[*MYRMQLLSCIALSLALVTNS*][QVQLKQSGPGLVQPSQSLSITCTVSGFSLTNYGVHWVRQSP

GKGLEWLGVIWSGGNTDYNTPFTSRLSINKDNSKSQVFFKMNSLQSNDTAIYYCARALTYYDYE

FAYWGQGTLVTVSAASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQGNVF

SCSVMHEALHNHYTQKSLSLSPGK*]

Italics: Signal peptide

Normal text: anti-EGFR antibody derived sequence 3954-1204-C225v4 Activatable Antibody Light Chain Nucleotide Sequence 1:
[Signal peptide (SEQ ID NO: 297)] [Spacer (SEQ ID NO: 303)]
[Mask (SEQ ID NO: 304)] [Linker 1 (SEQ ID NO: 305)] [1204 Substrate (SEQ ID NO: 306)] [Linker 2 (SEQ ID NO: 307)] [C225 (SEQ ID NO: 308)]

(SEQ ID NO: 318)

[*atgtacaggatgcaactcctgtcttgcattgcactaagtcttgcacttgtcacgaattcg*][**c
aaggccagtctggccag**][<u>tgcatctcacctcgtggttgtccggacggcccatacgtcatgtac</u>]

[*ggctcgagcggtggcagcggtggctctggtggatccggt*][**ctgagcggccgttccgataat
cat**][<u>*ggcagtagcggtacc*</u>][cagatcttgctgacccagagcccggtgattctgagcgtgagc ccgggcgaacgtgtgagctttagctgccgcgcgagccagagcattggcaccaacattcattggt atcagcagcgcaccaacggcagcccgcgcctgctgattaaatatgcgagcgaaagcattagcgg cattccgagccgctttagcggcagcggcagcggcaccgattttaccctgagcattaacagcgtg gaaagcgaagatattgcggattattattgccagcagaacaacaactggccgaccacctttggcg cgggcaccaaactggaactgaaacgtacggtggctgcaccatctgtcttcatcttcccgccatc tgatgagcagttgaaatctggaactgcctctgttgtgtgcctgctgaataacttctatcccaga
```

-continued

```
gaggccaaagtacagtggaaggtggataacgccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgttag]
```

Italics: Signal peptide

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v4 Activatable Antibody Light Chain Amino Acid Sequence 1:
[Signal peptide (SEQ ID NO: 300)] [Spacer (SEQ ID NO: 296)]
[Mask (SEQ ID NO: 113)] [Linker 1 (SEQ ID NO: 293)] [1204
Substrate (SEQ ID NO: 266)] [Linker 2 (SEQ ID NO: 294)]
[C225 (SEQ ID NO: 310)]

(SEQ ID NO: 319)

[*MYRMQLLSCIALSLALVTNS*][QGQSGQ][CISPRGCPDGPYVMY][*GSSGGSGGSGGSG*][LSGRSDNH][*GSSGT*][QILLTQSPVILSVSPGERVSFSCRASQSIGTNIHWYQQRTNGSPRLLI KYASESISGIPSRFSGSGSGTDFTLSINSVESEDIADYYCQQNNNWPTTFGAGTKLELKRTVAA PSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC*]

Italics: Signal peptide

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v4 Activatable Antibody Heavy Chain Nucleotide Sequence 2:
[C225v4 (SEQ ID NO: 314)]

(SEQ ID NO: 314)

```
[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacacccgtttac cagccgcctgagcattaacaaagataacagcaaaagccaggtgttttttaaaatgaacagcctg caaagcaacgataccgcgatttattattgcgcgcgcgcgctgacctattatgattatgaatttg cgtattggggccagggcaccctggtgaccgtgagcgcggctagcaccaagggcccatcggtctt ccccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc
```

-continued

```
ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagcccccagccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]
```

3954-1204-C225v4 Activatable Antibody Heavy Chain Amino Acid Sequence 2:
[C225v4 (SEQ ID NO: 316)]

(SEQ ID NO: 316)

[QVQLKQSGPGLVQPSQSLSITCTVSGFSLTNYGVHWVRQSPGKGLEWLGVIWSGGNTDYNTPF

TSRLSINKDNSKSQVFFKMNSLQSNDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

3954-1204-C225v4 Activatable Antibody Light Chain Nucleotide Sequence 2:
[Spacer (SEQ ID NO: 303)] [Mask (SEQ ID NO: 304)] [Linker 1 (SEQ ID NO: 305)] [1204 Substrate (SEQ ID NO: 306)] [Linker 2 (SEQ ID NO: 307)] [C225 (SEQ ID NO: 308)]

(SEQ ID NO: 320)

[caaggccagtctggccag][tgcatctcacctcgtggttgtccggacggcccatacgtcatgt ac][*ggctcgagcggtggcagcggtggctctggtggatccggt*][ctgagcggccgttccgata atcat][*ggcagtagcggtacc*][cagatcttgctgacccagagcccggtgattctgagcgtga gcccgggcgaacgtgtgagctttagctgccgcgcgagccagagcattggcaccaacattcattg gtatcagcagcgcaccaacggcagcccgcgcctgctgattaaatatgcgagcgaaagcattagc ggcattccgagccgctttagcggcagcggcagcggcaccgatttacccctgagcattaacagcg tggaaagcgaagatattgcggattattattgccagcagaacaacaactggccgaccacctttgg cgcgggcaccaaactggaactgaaacgtacggtggctgcaccatctgtcttcatcttcccgcca tctgatgagcagttgaaatctggaactgcctctgttgtgtgcctgctgaataacttctatccca gagaggccaaagtacagtggaaggtggataacgccctccaatcgggtaactcccaggagagtgt cacagagcaggacagcaaggacagcacctacagcctcagcagcaccctgacgctgagcaaagca gactacgagaaacacaaagtctacgcctgcgaagtcacccatcagggcctgagctcgcccgtca caaagagcttcaacaggggagagtgttag]

Bold: Spacer

Underline: Mask

Italics and Underline: Linker 1

Bold and Underline: 1204 Substrate

-continued

Bold, Italics and Underline: Linker 2

Normal text: anti-EGFR antibody derived sequence 3954-1204-C225v4 Activatable Antibody Light Chain Amino Acid Sequence 2:
[Spacer (SEQ ID NO: 296)] [Mask (SEQ ID NO: 113)] [Linker 1 (SEQ ID NO: 293)] [1204 Substrate (SEQ ID NO: 266)] [Linker 2 (SEQ ID NO: 294)] [C225 (SEQ ID NO: 310)]

(SEQ ID NO: 321)

[QGQSGQ][CISPRGCPDGPYVMY][*GSSGGSGGSGGSG*][LSGRSDNH][*GSSGT*][QILLTQ

SPVILSVSPGERVSFSCRASQSIGTNIHWYQQRTNGSPRLLIKYASESISGIPSRFSGSGSGTD

FTLSINSVESEDIADYYCQQNNNWPTTFGAGTKLELKRTVAAPSVFIFPPSDEQLKSGTASVVC

LLNNFYPREAKVQWKVDNALQSGNSQESVTEQDSKDSTYSLSSTLTLSKADYEKHKVYACEVTH

QGLSSPVTKSFNRGEC*]

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v4 Activatable Antibody Heavy Chain Nucleotide Sequence 3:
[C225v4 (SEQ ID NO: 314)]

(SEQ ID NO: 314)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgttttttaaaatgaacagcctg caaagcaacgataccgcgatttattattgcgcgcgcgcgctgacctattatgattatgaatttg cgtattggggccagggcaccctggtgaccgtgagcgcggctagcaccaagggcccatcggtctt ccccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagcccctcccagcccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

3954-1204-C225v4 Activatable Antibody Heavy Chain Amino Acid

-continued

Sequence 3:
[C225v4 (SEQ ID NO: 316)]

(SEQ ID NO: 316)
[QVQLKQSGPGLVQPSQSLSITCTVSGFSLTNYGVHWVRQSPGKGLEWLGVIWSGGNTDYNTPF

TSRLSINKDNSKSQVFFKMNSLQSNDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

3954-1204-C225v4 Activatable Antibody Light Chain Nucleotide
Sequence 3:
[Mask (SEQ ID NO: 304)] [Linker 1 (SEQ ID NO: 305)] [1204
Substrate (SEQ ID NO: 306)] [Linker 2 (SEQ ID NO: 307)] [C225
(SEQ ID NO: 308)]

(SEQ ID NO: 411)
[tgcatctcacctcgtggttgtccggacggcccatacgtcatgtac][*ggctcgagcggtggca*

*gcggtggctctggtggatccggt*][ctgagcggccgttccgataatcat][*ggcagtagcggta*

*cc*][cagatcttgctgacccagagcccggtgattctgagcgtgagcccgggcgaacgtgtgagc tttagctgccgcgcgagccagagcattggcaccaacattcattggtatcagcagcgcaccaacg gcagcccgcgcctgctgattaaatatgcgagcgaaagcattagcggcattccgagccgctttag cggcagcggcagcggcaccgattttaccctgagcattaacagcgtggaaagcgaagatattgcg gattattattgccagcagaacaacaactggccgaccacctttggcgcgggcaccaaactggaac tgaaacgtacggtggctgcaccatctgtcttcatcttcccgccatctgatgagcagttgaaatc tggaactgcctctgttgtgtgcctgctgaataacttctatcccagagaggccaaagtacagtgg aaggtggataacgccctccaatcgggtaactcccaggagagtgtcacagagcaggacagcaagg acagcacctacagcctcagcagcaccctgacgctgagcaaagcagactacgagaaacacaaagt ctacgcctgcgaagtcacccatcagggcctgagctcgcccgtcacaaagagcttcaacagggga gagtgttag]

Underline: Mask

Italics and Underline: Linker 1

Bold and Underline: 1204 Substrate

Bold, Italics and Underline: Linker 2

Normal text: anti-EGFR antibody derived sequence 3954-1204-C225v4 Activatable Antibody Light Chain Amino Acid
Sequence3:
[Mask (SEQ ID NO: 113)] [Linker 1 (SEQ ID NO: 293)] [1204
Substrate (SEQ ID NO: 266)] [Linker 2 (SEQ ID NO: 294)] [C225
(SEQ ID NO: 310)]

(SEQ ID NO: 412)
[CISPRGCPDGPYVMY][*GSSGGSGGSGGSG*][LSGRSDNH][*GSSGT*][QILLTQSPVILSVS

PGERVSFSCRASQSIGTNIHWYQQRTNGSPRLLIKYASESISGIPSRFSGSGSGTDFTLSINSV

ESEDIADYYCQQNNNWPTTFGAGTKLELKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVT

KSFNRGEC*]

Underline: Mask

Italics and Underline: Linker 1

-continued

Bold and Underline: 1204 Substrate

Bold, Italics and Underline: Linker 2

Normal text: anti-EGFR antibody derived sequence

Another exemplary activatable anti-EGFR antibody of the invention is the activatable antibody referred to herein as the 3954-1204-C225v6 activatable antibody, which binds epidermal growth factor receptor (EGFR) when the activatable antibody is in an activated state. Three sequences of the 3954-1204-C225v6 activatable anti-EGFR antibody are shown below, Sequence 1 is the sequence of a version of the 3954-1204-C225v6 activatable anti-EGFR antibody that includes a signal peptide, Sequence 2 is the sequence of the 3954-1204-C225v6 activatable anti-EGFR antibody without the signal peptide, and Sequence 3 is the sequence of the 3954-1204-C225v6 activatable anti-EGFR antibody without the signal peptide and without the spacer sequence:

```
3954-1204-C225v6 Activatable Antibody Heavy Chain Nucleotide
Sequence 1:
[Signal peptide (SEQ ID NO: 297)] [C225v6 (SEQ ID NO: 322)]
                                                      (SEQ ID NO: 323)
[atgtacaggatgcaactcctgtcttgcattgcactaagtcttgcacttgtcacgaattcg][c aggtgcagctgaaacagagcggcccgggcctggtgcagccgagccagagcctgagcattacctg caccgtgagcggctttagcctgaccaactatggcgtgcattgggtgcgccagagcccgggcaaa ggcctggaatggctgggcgtgatttggagcggcggcaacaccgattataacaccccgtttacca gccgcctgagcattaacaaagataacagcaaaagccaggtgttttttaaaatgaacagcctgca aagccaggataccgcgatttattattgcgcgcgcgcgctgacctattatgattatgaatttgcg tattggggccagggcaccctggtgaccgtgagcgcggctagcaccaagggcccatcggtcttcc ccctggcaccctcctccaagagcacctctggggcacagcggccctgggctgcctggtcaagga ctacttccccgaaccggtgacggtgtcgtggaactcaggcgccctgaccagcggcgtgcacacc ttcccggctgtcctacagtcctcaggactctactccctcagcagcgtggtgaccgtgccctcca gcagcttgggcacccagacctacatctgcaacgtgaatcacaagcccagcaacaccaaggtgga caagaaagttgagcccaaatcttgtgacaaaactcacacatgcccaccgtgcccagcacctgaa ctcctggggggaccgtcagtcttcctcttccccccaaaacccaaggacaccctcatgatctccc ggacccctgaggtcacatgcgtggtggtggacgtgagccacgaagaccctgaggtcaagttcaa ctggtacgtggacggcgtggaggtgcataatgccaagacaaagccgcgggaggagcagtacgcc agcacgtaccgtgtggtcagcgtcctcaccgtcctgcaccaggactggctgaatggcaaggagt acaagtgcaaggtctccaacaaagccctcccagccccatcgagaaaaccatctccaaagccaa agggcagccccgagaaccacaggtgtacaccctgcccccatcccgggatgaactgaccaagaac caggtcagcctgacctgcctggtcaaaggcttctatcccagcgacatcgccgtggagtgggaga gcaatgggcagccggagaacaactacaagaccacgcctcccgtgctggactccgacggctcctt cttcctctacagcaagctcaccgtggacaagagcaggtggcagcaggggaacgtcttctcatgc tccgtgatgcatgaggctctgcacaaccactacacgcagaagagcctctccctgtctccgggta aatga]

Italics: Signal peptide

Normal text: anti-EGFR antibody derived sequence 3954-1204-C225v6 Activatable Antibody Heavy Chain Amino Acid
Sequence 1:
[Signal peptide (SEQ ID NO: 300)] [C225v6 (SEQ ID NO: 324)]
                                                      (SEQ ID NO: 325)
[MYRMQLLSCIALSLALVTNS][QVQLKQSGPGLVQPSQSLSITCTVSGFSLTNYGVHWVRQSP

GKGLEWLGVIWSGGNTDYNTPFTSRLSINKDNSKSQVFFKMNSLQSQDTAIYYCARALTYYDYE

FAYWGQGTLVTVSAASTKGPSVFPLAPSSKSTSGGTAALGCLVKDYFPEPVTVSWNSGALTSGV
```

HTFPAVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTKPREEQ

Y*A*STYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQGNVF

SCSVMHEALHNHYTQKSLSLSPGK*]

Italics: Signal peptide

Normal text: anti-EGFR antibody derived sequence 3954-1204-C225v6 Activatable Antibody Light Chain Nucleotide Sequence 1:
[Signal peptide (SEQ ID NO: 297)] [Spacer (SEQ ID NO: 303)]
[Mask (SEQ ID NO: 304)] [Linker 1 (SEQ ID NO: 305)] [1204
Substrate (SEQ ID NO: 306)] [Linker 2 (SEQ ID NO: 307)] [C225
(SEQ ID NO: 308)]

(SEQ ID NO: 326)

[*atgtacaggatgcaactcctgtcttgcattgcactaagtcttgcacttgtcacgaattcg*][**c
aaggccagtctggccag**][tgcatctcacctcgtggttgtccggacggcccatacgtcatgtac]

[*ggctcgagcggtggcagcggtggctctggtggatccggt*][**ctgagcggccgttccgataat
cat][*ggcagtagcggtacc***][cagatcttgctgacccagagcccggtgattctgagcgtgagc ccgggcgaacgtgtgagctttagctgccgcgcgagccagagcattggcaccaacattcattggt atcagcagcgcaccaacggcagcccgcgcctgctgattaaatatgcgagcgaaagcattagcgg cattccgagccgctttagcggcagcggcagcggcaccgattttaccctgagcattaacagcgtg gaaagcgaagatattgcggattattattgccagcagaacaacaactggccgaccacctttggcg cgggcaccaaactggaactgaaacgtacggtggctgcaccatctgtcttcatcttcccgccatc tgatgagcagttgaaatctggaactgcctctgttgtgtgcctgctgaataacttctatcccaga gaggccaaagtacagtggaaggtggataacgccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgttag]

Italics: Signal peptide

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v6 Activatable Antibody Light Chain Amino Acid Sequence 1:
[Signal peptide (SEQ ID NO: 300)] [Spacer (SEQ ID NO: 296)]
[Mask (SEQ ID NO: 113)] [Linker 1 (SEQ ID NO: 293)] [1204
Substrate (SEQ ID NO: 266)] [Linker 2 (SEQ ID NO: 294)] [C225
(SEQ ID NO: 310)]

(SEQ ID NO: 327)

[*MYRMQLLSCIALSLALVTNS*][QGQSGQ][CISPRGCPDGPYVMY][*GSSGGSGGSGGSG*][**L
SGRSDNH][*GSSGT***][QILLTQSPVILSVSPGERVSFSCRASQSIGTNIHWYQQRTNGSPRLLI

KYASESISGIPSRFSGSGSGTDFTLSINSVESEDIADYYCQQNNNWPTTFGAGTKLELKRTVAA

PSVFIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC*]

-continued

Italics: Signal peptide

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v6 Activatable Antibody Heavy Chain Nucleotide Sequence 2:
[C225v6 (SEQ ID NO: 322)]

(SEQ ID NO: 322)
[caggtgcagctgaaacagagcggcccgggcctggtgcagccgagccagagcctgagcattacc tgcaccgtgagcggctttagcctgaccaactatggcgtgcattgggcgccagagcccgggca aaggcctggaatggctgggcgtgatttggagcggcggcaacaccgattataacacccccgtttac cagccgcctgagcattaacaaagataacagcaaaagccaggtgtttttaaaatgaacagcctg caaagccaggataccgcgatttattattgcgcgcgcgcgctgacctattatgattatgaatttg cgtattggggccagggcacccctggtgaccgtgagcgcggctagcaccaagggcccatcggtctt cccctggcaccctcctccaagagcacctctggggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtacg ccagcacgtaccgtgtggtcagcgtcctcaccgtcctgcaccaggactggctgaatggcaagga gtacaagtgcaaggtctccaacaaagcccctcccagccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

3954-1204-C225v6 Activatable Antibody Heavy Chain Amino Acid Sequence 2:
[C225v6 (SEQ ID NO: 324)]

(SEQ ID NO: 324)
[QVQLKQSGPGLVQPSQSLSITCTVSGFSLTNYGVHWVRQSPGKGLEWLGVIWSGGNTDYNTPF

TSRLSINKDNSKSQVFFKMNSLQSQDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

-continued 3954-1204-C225v6 Activatable Antibody Light Chain Nucleotide Sequence 2:
[Spacer (SEQ ID NO: 303)] [Mask (SEQ ID NO: 304)] [Linker 1 (SEQ ID NO: 305)] [1204 Substrate (SEQ ID NO: 306)] [Linker 2 (SEQ ID NO: 307)] [C225 (SEQ ID NO: 308)]

(SEQ ID NO: 328)

[caaggccagtctggccag][tgcatctcacctcgtggttgtccggacggcccatacgtcatgt ac][*ggctcgagcggtggcagcggtggctctggtggatccggt*][ctgagcggccgttccgata atcat][*ggcagtagggcagtag*][cagatcttgctgacccagagcccggtgattctgagcgtga gcccgggcgaacgtgtgagctttagctgccgcgcgagccagagcattggcaccaacattcattg gtatcagcagcgcaccaacggcagcccgcgcctgctgattaaatatgcgagcgaaagcattagc ggcattccgagccgctttagcggcagcggcagcggcaccgattttaccctgagcattaacagcg tggaaagcgaagatattgcggattattattgccagcagaacaacaactggccgaccacctttgg cgcgggcaccaaactggaactgaaacgtacggtggctgcaccatctgtcttcatcttcccgcca tctgatgagcagttgaaatctggaactgcctctgttgtgtgcctgctgaataacttctatccca gagaggccaaagtacagtggaaggtggataacgccctccaatcgggtaactcccaggagagtgt cacagagcaggacagcaaggacagcacctacagcctcagcagcaccctgacgctgagcaaagca gactacgagaaacacaaagtctacgcctgcgaagtcacccatcagggcctgagctcgcccgtca caaagagcttcaacaggggagagtgttag]

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v6 Activatable Antibody Light Chain Amino Acid Sequence 2:
[Spacer (SEQ ID NO: 296)] [Mask (SEQ ID NO: 113)] [Linker 1 (SEQ ID NO: 293)] [1204 Substrate (SEQ ID NO: 266)] [Linker 2 (SEQ ID NO: 294)] [C225 (SEQ ID NO: 310)]

(SEQ ID NO: 329)

[QGQSGQ][CISPRGCPDGPYVMY][*GSSGGSGGSGGSG*][LSGRSDNH][*GSSGT*][QILLTQ

SPVILSVSPGERVSFSCRASQSIGTNIHWYQQRTNGSPRLLIKYASESISGIPSRFSGSGSGTD

FTLSINSVESEDIADYYCQQNNNWPTTFGAGTKLELKRTVAAPSVFIFPPSDEQLKSGTASVVC

LLNNFYPREAKVQWKVDNALQSGNSQESVTEQDSKDSTYSLSSTLTLSKADYEKHKVYACEVTH

QGLSSPVTKSFNRGEC*]

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v6 Activatable Antibody Heavy Chain Nucleotide Sequence 3:
[C225v6 (SEQ ID NO: 322)]

(SEQ ID NO: 322)

[caggtgcagctgaaacagagcggcccgggcctggtgcagccgagccagagcctgagcattacc tgcaccgtgagcggctttagcctgaccaactatggcgtgcattgggtgcgccagagcccgggca -continued

```
aaggcctggaatggctgggcgtgatttggagcggcggcaacaccgattataacaccccgtttac cagccgcctgagcattaacaaagataacagcaaaagccaggtgttttttaaaatgaacagcctg caaagccaggataccgcgatttattattgcgcgcgcgcgctgacctattatgattatgaatttg cgtattggggccagggcaccctggtgaccgtgagcgcggctagcaccaagggcccatcggtctt cccccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtacg ccagcacgtaccgtgtggtcagcgtcctcaccgtcctgcaccaggactggctgaatggcaagga gtacaagtgcaaggtctccaacaaagcccctcccagccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]
```

3954-1204-C225v6 Activatable Antibody Heavy Chain Amino Acid
Sequence 3:
[C225v6 (SEQ ID NO: 324)]

(SEQ ID NO: 324)

[QVQLKQSGPGLVQPSQSLSITCTVSGFSLTNYGVHWVRQSPGKGLEWLGVIWSGGNTDYNTPF

TSRLSINKDNSKSQVFFKMNSLQSQDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

3954-1204-C225v6 Activatable Antibody Light Chain Nucleotide
Sequence 3:
[Mask (SEQ ID NO: 304)] [Linker 1 (SEQ ID NO: 305)] [1204
Substrate (SEQ ID NO: 306)] [Linker 2 (SEQ ID NO: 307)] [C225
(SEQ ID NO: 308)]

(SEQ ID NO: 413)

[tgcatctcacctcgtggttgtccggacggcccatacgtcatgtac][*ggctcgagcggtggca*

*gcggtggctctggtggatccggt*][ctgagcggccgttccgataatcat][*ggcagtagcggta*

*cc*][cagatcttgctgacccagagcccggtgattctgagcgtgagcccgggcgaacgtgtgagc tttagctgccgcgcgagccagagcattggcaccaacattcattggtatcagcagcgcaccaacg gcagcccgcgcctgctgattaaatatgcgagcgaaagcattagcggcattccgagccgctttag cggcagcggcagcggcaccgattttaccctgagcattaacagcgtggaaagcgaagatattgcg gattattattgccagcagaacaacaactggccgaccacctttggcgcgggcaccaaactggaac tgaaacgtacggtggctgcaccatctgtcttcatcttcccgccatctgatgagcagttgaaatc
```

```
tggaactgcctctgttgtgtgcctgctgaataacttctatcccagagaggccaaagtacagtgg aaggtggataacgccctccaatcgggtaactcccaggagagtgtcacagagcaggacagcaagg acagcacctacagcctcagcagcaccctgacgctgagcaaagcagactacgagaaacacaaagt ctacgcctgcgaagtcacccatcagggcctgagctcgcccgtcacaaagagcttcaacagggga gagtgttag]
```

Underline: Mask

Italics and Underline: Linker 1

Bold and Underline: 1204 Substrate

Bold, Italics and Underline: Linker 2

Normal text: anti-EGFR antibody derived sequence

```
3954-1204-C225v6 Activatable Antibody Light Chain Amino Acid
Sequence 3:
[Mask (SEQ ID NO: 113)] [Linker 1 (SEQ ID NO: 293)] [1204
Substrate (SEQ ID NO: 266)] [Linker 2 (SEQ ID NO: 294)] [C225
(SEQ ID NO: 310)]
                                                 (SEQ ID NO: 414)
[CISPRGCPDGPYVMY][GSSGGSGGSGGSG][LSGRSDNH][GSSGT][QILLTQSPVILSVS

PGERVSFSCRASQSIGTNIHWYQQRTNGSPRLLIKYASESISGIPSRFSGSGSGTDFTLSINSV

ESEDIADYYCQQNNNWPTTFGAGTKLELKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVT

KSFNRGEC*]
```

Underline: Mask

Italics and Underline: Linker 1

Bold and Underline: 1204 Substrate

Bold, Italics and Underline: Linker 2

Normal text: anti-EGFR antibody derived sequence

Another exemplary activatable anti-EGFR antibody of the invention is the activatable antibody referred to herein as the 3954-1204-C225v7 activatable antibody, which binds epidermal growth factor receptor (EGFR) when the activatable antibody is in an activated state. Three sequences of the 3954-1204-C225v7 activatable anti-EGFR antibody are shown below, Sequence 1 is the sequence of a version of the 3954-1204-C225v7 activatable anti-EGFR antibody that includes a signal peptide, Sequence 2 is the sequence of the 3954-1204-C225v7 activatable anti-EGFR antibody without the signal peptide, and Sequence 3 is the sequence of the 3954-1204-C225v7 activatable anti-EGFR antibody without the signal peptide and without the spacer sequence:

```
3954-1204-C225v7 Activatable Antibody Heavy Chain Nucleotide
Sequence 1:
[Signal peptide (SEQ ID NO: 297)] [C225v7 (SEQ ID NO: 425)]
                                                 (SEQ ID NO: 426)
[atgtacaggatgcaactcctgtcttgcattgcactaagtcttgcacttgtcacgaattcg][c aggtgcagctgaaacagagcggcccgggcctggtgcagccgagccagagcctgagcattacctg caccgtgagcggctttagcctgaccaactatggcgtgcattgggtgcgccagagcccgggcaaa ggcctggaatggctgggcgtgatttggagcggcggcaacaccgattataacaccccgtttacca gccgcctgagcattaacaaagataacagcaaaagccaggtgttttttaaaatgaacagcctgca aagccaggataccgcgatttattattgcgcgcgcgcgctgacctattatgattatgaatttgcg tattggggccagggcaccctggtgaccgtgagcgcggctagcaccaagggcccatcggtcttcc ccctggcaccctcctccaagagcacctctgggggcacagcggccctgggctgcctggtcaagga ctacttccccgaaccggtgacggtgtcgtggaactcaggcgccctgaccagcggcgtgcacacc
```

-continued

```
ttcccggctgtcctacagtcctcaggactctactccctcagcagcgtggtgaccgtgccctca gcagcttgggcaccagacctacatctgcaacgtgaatcacaagcccagcaacaccaaggtgga caagaaagttgagcccaaatcttgtgacaaaactcacacatgcccaccgtgcccagcacctgaa ctcctggggggaccgtcagtcttcctcttccccccaaaacccaaggacaccctcatgatctccc ggacccctgaggtcacatgcgtggtggtggacgtgagccacgaagaccctgaggtcaagttcaa ctggtacgtggacggcgtggaggtgcataatgccaagacaaagccgcgggaggagcagtaccar agcacgtaccgtgtggtcagcgtcctcaccgtcctgcaccaggactggctgaatggcaaggagt acaagtgcaaggtctccaacaaagccctcccagcccccatcgagaaaaccatctccaaagccaa agggcagccccgagaaccacaggtgtacaccctgcccccatcccgggatgaactgaccaagaac caggtcagcctgacctgcctggtcaaaggcttctatcccagcgacatcgccgtggagtgggaga gcaatgggcagccggagaacaactacaagaccacgcctcccgtgctggactccgacggctcctt cttcctctacagcaagctcaccgtggacaagagcaggtggcagcaggggaacgtcttctcatgc tccgtgatgcatgaggctctgcacaaccactacacgcagaagagcctctccctgtctccgggta aatga]
```

Italics: Signal peptide

Normal text: anti-EGFR antibody derived sequence 3954-1204-C225v7 Activatable Antibody Heavy Chain Amino Acid Sequence 1:
[Signal peptide (SEQ ID NO: 300)] [C225v7 (SEQ ID NO: 427)]

(SEQ ID NO: 428)

[*MYRMQLLSCIALSLALVTNS*][QVQLKQSGPGLVQPSQSLSITCTVSGFSLTNYGVHWVRQSP

GKGLEWLGVIWSGGNTDYNTPFTSRLSINKDNSKSQVFFKMNSLQSQDTAIYYCARALTYYDYE

FAYWGQGTLVTVSAASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTKPREEQ

YQSTYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQGNVF

SCSVMHEALHNHYTQKSLSLSPGK*]

Italics: Signal peptide

Normal text: anti-EGFR antibody derived sequence 3954-1204-C225v7 Activatable Antibody Light Chain Nucleotide Sequence 1:
[Signal peptide (SEQ ID NO: 297)] [Spacer (SEQ ID NO: 303)]
[Mask (SEQ ID NO: 304)] [Linker 1 (SEQ ID NO: 305)] [1204 Substrate (SEQ ID NO: 306)] [Linker 2 (SEQ ID NO: 307)] [C225 (SEQ ID NO: 308)]

(SEQ ID NO: 326)

[atgtacaggatgcaactcctgtcttgcattgcactaagtcttgcacttgtcacgaattcg][c aaggccagtctggccag][tgcatctcacctcgtggttgtccggacggcccatacgtcatgtac]

[*ggctcgagcggtggcagcggtggctctggtggatccggt*][ctgagcggccgttccgataat cat][*ggcagtagcggtacc*][cagatcttgctgacccagagcccggtgattctgagcgtgagc ccgggcgaacgtgtgagctttagctgccgcgcgagccagagcattggcaccaacattcattggt atcagcagcgcaccaacggcagcccgcgcctgctgattaaatatgcgagcgaaagcattagcgg cattccgagccgctttagcggcagcggcagcggcaccgatttacccctgagcattaacagcgtg gaaagcgaagatattgcggattattattgccagcagaacaacaactggccgaccaccttggcg cgggcaccaaactggaactgaaacgtacggtggctgcaccatctgtcttcatcttcccgccatc
```

-continued

```
tgatgagcagttgaaatctggaactgcctctgttgtgtgcctgctgaataacttctatcccaga gaggccaaagtacagtggaaggtggataacgccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgttag]
```

Italics: Signal peptide

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v7 Activatable Antibody Light Chain Amino Acid Sequence 1:
[Signal peptide (SEQ ID NO: 300)] [Spacer (SEQ ID NO: 296)]
[Mask (SEQ ID NO: 113)] [Linker 1 (SEQ ID NO: 293)] [1204
Substrate (SEQ ID NO: 266)] [Linker 2 (SEQ ID NO: 294)] [C225
(SEQ ID NO: 310)]

(SEQ ID NO: 327)

[*MYRMQLLSCIALSLALVTNS*][QGQSGQ][CISPRGCPDGPYVMY][*GSSGGSGGSGGSG*][LSGRSDNH][*GSSGT*][QILLTQSPVILSVSPGERVSFSCRASQSIGTNIHWYQQRTNGSPRLLI

KYASESISGIPSRFSGSGSGTDFTLSINSVESEDIADYYCQQNNNWPTTFGAGTKLELKRTVAA

PSVFIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC*]

Italics: Signal peptide

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v7 Activatable Antibody Heavy Chain Nucleotide Sequence 2:
[C225v7 (SEQ ID NO: 425)]

(SEQ ID NO: 425)

```
[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgttttttaaaatgaacagcctg caaagccaggataccgcgatttattattgcgcgcgcgcgctgacctattatgattatgaatttg cgtattggggccagggcacccctggtgaccgtgagcgcggctagcaccaagggcccatcggtctt ccccctggcaccctcctccaagagcacctctggggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg
```

-continued
aactcctgggggaccgtcagtcttcctcttcccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtacc aragcacgtaccgtgtggtcagcgtcctcaccgtcctgcaccaggactggctgaatggcaagga gtacaagtgcaaggtctccaacaaagcccctcccagcccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

3954-1204-C225v7 Activatable Antibody Heavy Chain Amino Acid
Sequence 2:
[C225v7 (SEQ ID NO: 427)]

(SEQ ID NO: 427)
[QVQLKQSGPGLVQPSQSLSITCTVSGFSLTNYGVHWVRQSPGKGLEWLGVIWSGGNTDYNTPF

TSRLSINKDNSKSQVFFKMNSLQSQDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYQSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

3954-1204-C225v7 Activatable Antibody Light Chain Nucleotide
Sequence 2:
[Spacer (SEQ ID NO: 303)] [Mask (SEQ ID NO: 304)] [Linker 1
(SEQ ID NO: 305)] [1204 Substrate (SEQ ID NO: 306)] [Linker 2
(SEQ ID NO: 307)] [C225 (SEQ ID NO: 308)]

(SEQ ID NO: 328)
[caaggccagtctggccag][tgcatctcacctcgtggttgtccggacggcccatacgtcatgt ac][*ggctcgagcggtggcagcggtggctctggtggatccggt*][ctgagcggccgttccgata atcat][*ggcagtagcggtacc*][cagatcttgctgacccagagcccggtgattctgagcgtga gcccgggcgaacgtgtgagctttagctgccgcgcgagccagagcattggcaccaacattcattg gtatcagcagcgcaccaacggcagcccgcgcctgctgattaaatatgcgagcgaaagcattagc ggcattccgagccgctttagcggcagcggcagcggcaccgattttaccctgagcattaacagcg tggaaagcgaagatattgcggattattattgccagcagaacaacaactggccgaccacctttgg cgcgggcaccaaactggaactgaaacgtacggtggctgcaccatctgtcttcatcttcccgcca tctgatgagcagttgaaatctggaactgcctctgttgtgtgcctgctgaataacttctatccca gagaggccaaagtacagtggaaggtggataacgccctccaatcgggtaactcccaggagagtgt cacagagcaggacagcaaggacagcacctacagcctcagcagcaccctgacgctgagcaaagca gactacgagaaacacaaagtctacgcctgcgaagtcacccatcagggcctgagctcgcccgtca caaagagcttcaacaggggagagtgttag]

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v7 Activatable Antibody Light Chain Amino Acid Sequence 2:
[Spacer (SEQ ID NO: 296)] [Mask (SEQ ID NO: 113)] [Linker 1 (SEQ ID NO: 293)] [1204 Substrate (SEQ ID NO: 266)] [Linker 2 (SEQ ID NO: 294)] [C225 (SEQ ID NO: 310)]

(SEQ ID NO: 329)

[QGQSGQ][CISPRGCPDGPYVMY][*GSSGGSGGSGGSG*][LSGRSDNH][*GSSGT*][QILLTQ

SPVILSVSPGERVSFSCRASQSIGTNIHWYQQRTNGSPRLLIKYASESISGIPSRFSGSGSGTD

FTLSINSVESEDIADYYCQQNNNWPTTFGAGTKLELKRTVAAPSVFIFPPSDEQLKSGTASVVC

LLNNFYPREAKVQWKVDNALQSGNSQESVTEQDSKDSTYSLSSTLTLSKADYEKHKVYACEVTH

QGLSSPVTKSFNRGEC*]

Bold: Spacer

Underline: Mask

Italics and Underline: Linker 1

Bold and Underline: 1204 Substrate

Bold, Italics and Underline: Linker 2

Normal text: anti-EGFR antibody derived sequence 3954-1204-C225v7 Activatable Antibody Heavy Chain Nucleotide Sequence 3:
[C225v7 (SEQ ID NO: 425)]

(SEQ ID NO: 425)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgttttttaaaatgaacagcctg caaagccaggataccgcgatttattattgcgcgcgcgcgctgacctattatgattatgaatttg cgtattggggccagggcacccctggtgaccgtgagcgcggctagcaccaagggcccatcggtctt ccccctggcaccctcctccaagagcacctctggggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtacc aragcacgtaccgtgtggtcagcgtcctcaccgtcctgcaccaggactggctgaatggcaagga gtacaagtgcaaggtctccaacaaagcccctcccagccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

-continued 3954-1204-C225v7 Activatable Antibody Heavy Chain Amino Acid Sequence 3:
[C225v7 (SEQ ID NO: 427)]

(SEQ ID NO: 427)
[QVQLKQSGPGLVQPSQSLSITCTVSGFSLTNYGVHWVRQSPGKGLEWLGVIWSGGNTDYNTPF

TSRLSINKDNSKSQVFFKMNSLQSQDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYQSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

3954-1204-C225v7 Activatable Antibody Light Chain Nucleotide Sequence 3:
[Mask (SEQ ID NO: 304)] [Linker 1 (SEQ ID NO: 305)] [1204 Substrate (SEQ ID NO: 306)] [Linker 2 (SEQ ID NO: 307)] [C225 (SEQ ID NO: 308)]

(SEQ ID NO: 413)
[tgcatctcacctcgtggttgtccggacggcccatacgtcatgtac][*ggctcgagcggtggca*

*gcggtggctctggtggatccggt*][ctgagcggccgttccgataatcat][*__ggcagtagcggta__*

*__cc__*][cagatcttgctgacccagagcccggtgattctgagcgtgagcccgggcgaacgtgtgagc tttagctgccgcgcgagccagagcattggcaccaacattcattggtatcagcagcgcaccaacg gcagcccgcgcctgctgattaaatatgcgagcgaaagcattagcggcattccgagccgctttag cggcagcggcagcggcaccgatttttaccctgagcattaacagcgtggaaagcgaagatattgcg gattattattgccagcagaacaacaactggccgaccacctttggcgcgggcaccaaactggaac tgaaacgtacggtggctgcaccatctgtcttcatcttcccgccatctgatgagcagttgaaatc tggaactgcctctgttgtgtgcctgctgaataacttctatcccagagaggccaaagtacagtgg aaggtggataacgcccctccaatcgggtaactcccaggagagtgtcacagagcaggacagcaagg acagcacctacagcctcagcagcaccctgacgctgagcaaagcagactacgagaaacacaaagt ctacgcctgcgaagtcacccatcagggcctgagctcgcccgtcacaaagagcttcaacagggga gagtgttag]

Underline: Mask

Italics and Underline: Linker 1

Bold and Underline: 1204 Substrate

Bold, Italics and Underline: Linker 2

Normal text: anti-EGFR antibody derived sequence 3954-1204-C225v7 Activatable Antibody Light Chain Amino Acid Sequence 3:
[Mask (SEQ ID NO: 113)] [Linker 1 (SEQ ID NO: 293)] [1204 Substrate (SEQ ID NO: 266)] [Linker 2 (SEQ ID NO: 294)] [C225 (SEQ ID NO: 310)]

(SEQ ID NO: 414)
[CISPRGCPDGPYVMY][*GSSGGSGGSGGSG*][LSGRSDNH][*__GSSGT__*][QILLTQSPVILSVS

PGERVSFSCRASQSIGTNIHWYQQRTNGSPRLLIKYASESISGIPSRFSGSGSGTDFTLSINSV

ESEDIADYYCQQNNNWPTTFGAGTKLELKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVT

KSFNRGEC*]

Underline: Mask

Italics and Underline: Linker 1

Bold and Underline: 1204 Substrate

Bold, Italics and Underline: Linker 2

Normal text: anti-EGFR antibody derived sequence

Exemplary conjugated antibodies and/or activatable antibodies of the invention include, for example, antibodies that bind interleukin 6 receptor (IL-6R) and that include a heavy chain and a light chain that are, or are derived from, the antibody referred to herein as the "AV1" antibody, which binds interleukin-6 receptor (IL-6R). The amino acid sequences for the Av1 heavy chain and the Av1 light chain are shown below in SEQ ID NO: 330 and SEQ ID NO: 331, respectively.

```
Av1 Antibody Heavy Chain Amino Acid Sequence:
                                          (SEQ ID NO: 330)
QVQLQESGPGLVRPSQTLSLTCTVSGYSITSDHAWSWVRQPPGRGLEWIG

YISYSGITTYNPSLKSRVTISRDNSKNTLYLQMNSLRAEDTAVYYCARSL

ARTTAMDYWGQGSLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

Av1 Antibody Light Chain Amino Acid Sequence:
                                          (SEQ ID NO: 331)
DIQMTQSPSSLSASVGDRVTITCRASQDISSYLNWYQQKPGKAPKLLIYY

TSRLHSGVPSRFSGSGSGTDFTFTISSLQPEDIATYYCQQGNTLPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Exemplary conjugated antibodies and/or activatable antibodies of the invention include, for example, antibodies that bind interleukin 6 receptor (IL-6R) and that include a heavy chain and a light chain that are, or are derived from, the Av1 antibody and a masking moiety. Exemplary conjugated antibodies and/or activatable antibodies of the invention include an amino acid sequence attached to the N-terminus of the AV1 light chain. These N-terminal masking moiety amino acid sequences include, for example, YGSCSWNYVHIFMDC (SEQ ID NO: 332); QGDFDIPFPAHWVPIT (SEQ ID NO: 333); MGVPAGCVWNYAHIFMDC (SEQ ID NO: 334); QGQSGQYGSCSWNYVHIFMDC (SEQ ID NO: 335); QGQSGQGDFDIPFPAHWVPIT (SEQ ID NO: 336); or QGQSGQMGVPAGCVWNYAHIFMDC (SEQ ID NO: 337). It is also to be appreciated that such amino acid sequences can be attached to the N-terminus of the AV1 heavy chain or to the C-terminus of the AV1 heavy or light chain.

Exemplary activatable antibodies of the invention include, for example, antibodies that bind a Jagged target, e.g., Jagged-1, Jagged-2 and/or both Jagged-1 and Jagged-2, and that include a combination of a variable heavy chain region and a variable light chain region that are, or are derived from, the variable heavy chain and variable light chain sequences shown below.

```
Variable Light Chain Amino Sequence Lc4
                                          (SEQ ID NO: 338)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc4
                                          (SEQ ID NO: 339)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc5
                                          (SEQ ID NO: 340)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc5
                                          (SEQ ID NO: 341)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYHGQFDYWGQGTLVTVSS

Variable Light Chain Amino Sequence Lc7
                                          (SEQ ID NO: 342)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc7
                                          (SEQ ID NO: 343)
```

-continued

```
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPFFGQFDYWGQGTLVTVSS

Variable Light Chain Amino Sequence Lc8
                                                       (SEQ ID NO: 344)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc8
                                                       (SEQ ID NO: 345)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKHIGRTNPFDYWGQGTLVTVSS Variable Light Chain Amino Sequence Lc13
                                                       (SEQ ID NO: 346)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc13
                                                       (SEQ ID NO: 347)
EVQLLESGGGLVQPGGSLRLSCAASGFTFSSYAMSWVRQAPGKGLEWVSSIEQMGWQTEYADSV
KGRFTISRDNSKNTLYLQMNSLRAEDTAVYYCAKSAAAFDYWGQGTLVTVSS Variable Light Chain Amino Sequence Lc16
                                                       (SEQ ID NO: 348)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc16
                                                       (SEQ ID NO: 349)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPYYGQFDYWGQGTLVTVSS Variable Light Chain Amino Sequence Lc19
                                                       (SEQ ID NO: 350)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc19
                                                       (SEQ ID NO: 351)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPFFGQFDYWGQGTLVTVSS Variable Light Chain Amino Sequence Lc21
                                                       (SEQ ID NO: 352)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc21
                                                       (SEQ ID NO: 353)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKDIGGRSAFDYWGQGTLVTVSS Variable Light Chain Amino Sequence Lc24
                                                       (SEQ ID NO: 354)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc24
                                                       (SEQ ID NO: 355)
EVQLLESGGGLVQPGGSLRLSCAASGFTFSSYAMSWVRQAPGKGLEWVSSIEEMGWQTLYADSV
KGRFTISRDNSKNTLYLQMNSLRAEDTAVYYCAKSAAAFDYWGQGTLVTVSS Variable Light Chain Amino Sequence Lc26
                                                       (SEQ ID NO: 356)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR
```

Variable Heavy Chain Amino Sequence Hc26
(SEQ ID NO: 357)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKDIGGRSAFDYWGQGTLVTVSS Variable Light Chain Amino Sequence Lc27
(SEQ ID NO: 358)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc27
(SEQ ID NO: 359)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPFYGQFDYWGQGTLVTVSS Variable Light Chain Amino Sequence Lc28
(SEQ ID NO: 360)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc28
(SEQ ID NO: 361)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPFFGQFDYWGQGTLVTVSS Variable Light Chain Amino Sequence Lc30
(SEQ ID NO: 362)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc30
(SEQ ID NO: 363)
EVQLLESGGGLVQPGGSLRLSCAASGFTFSSYAMSWVRQAPGKGLEWVSSIEEMGWQTLYADSV
KGRFTISRDNSKNTLYLQMNSLRAEDTAVYYAKSAAAFDYWGQGTLVTVSS Variable Light Chain Amino Sequence Lc31
(SEQ ID NO: 364)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc31
(SEQ ID NO: 365)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKDIGGRSAFDYWGQGTLVTVSS Variable Light Chain Amino Sequence Lc32
(SEQ ID NO: 366)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc32
(SEQ ID NO: 367)
EVQLLESGGGLVQPGGSLRLSCAASGFTFSSYAMSWVRQAPGKGLEWVSSIDPEGWQTYYADSV
KGRFTISRDNSKNTLYLQMNSLRAEDTAVYYCAKSAAAFDYWGQGTLVTVSS Variable Light Chain Amino Sequence Lc37
(SEQ ID NO: 368)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc37
(SEQ ID NO: 369)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPHNGQFDYWGQGTLVTVSS Variable Light Chain Amino Sequence Lc39
(SEQ ID NO: 370)

-continued

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc39
(SEQ ID NO: 371)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc40
(SEQ ID NO: 372)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Heavy Chain Amino Sequence Hc40
(SEQ ID NO: 373)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc47
(SEQ ID NO: 374)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc47
(SEQ ID NO: 375)
EVQLLESGGGLVQPGGSLRLSCAASGFTFSSYAMSWVRQAPGKGLEWVSSIDEMGWQTEYADSV

KGRFTISRDNSKNTLYLQMNSLRAEDTAVYYCAKSAAAFDYWGQGTLVTVSS

Variable 4B2 Light Chain
(SEQ ID NO: 376)
DIQMTQSPSSLSASVGDRVTITCRASQSISSYLNWYQQKPGKAPKLLIYAASSLQSGVPSRFSG

SGSGTDFTLTISSLQPEDFATYYCQQTLDAPPQFGQGTKVEIKR

Variable 4B2 Heavy Chain
(SEQ ID NO: 377)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable 4D11 Light Chain
(SEQ ID NO: 378)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKR

Variable 4D11 Heavy Chain
(SEQ ID NO: 379)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSS

Variable 4E7 Light Chain
(SEQ ID NO: 380)
DIQMTQSPSSLSASVGDRVTITCRASQSISSYLNWYQQKPGKAPKLLIYAASSLQSGVPSRFSG

SGSGTDFTLTISSLQPEDFATYYCQQSLVAPLTFGQGTKVEIKR

Variable 4E7 Heavy Chain
(SEQ ID NO: 381)
EVQLLESGGGLVQPGGSLRLSCAASGFTFSSYAMSWVRQAPGKGLEWVSSIEEMGWQTKYADSV

KGRFTISRDNSKNTLYLQMNSLRAEDTAVYYCAKSAAAFDYWGQGTLVTVSS

Variable 4E11 Light Chain
(SEQ ID NO: 382)
DIQMTQSPSSLSASVGDRVTITCRASQSISSYLNWYQQKPGKAPKLLIYAASSLQSGVPSRFSG

SGSGTDFTLTISSLQPEDFATYYCQQALDAPLMFGQGTKVEIKR

Variable 4E11 Heavy Chain
(SEQ ID NO: 383)

EVQLLESGGGLVQPGGSLRLSCAASGFTFSSYAMSWVRQAPGKGLEWVSSIEPMGQLTEYADSV

KGRFTISRDNSKNTLYLQMNSLRAEDTAVYYCAKDIGGRSAFDYWGQGTLVTVSS

Variable 6B7 Light Chain
(SEQ ID NO: 384)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6B7 Heavy Chain
(SEQ ID NO: 385)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Variable 6F8 Light Chain
(SEQ ID NO: 386)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6F8 Heavy Chain
(SEQ ID NO: 387)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Exemplary activatable antibodies of the invention include, for example, antibodies that bind a Jagged target, e.g., Jagged-1, Jagged-2 and/or both Jagged-1 and Jagged-2, and that include a combination of a heavy chain region and a light chain region that are, or are derived from, the heavy chain and light chain sequences shown below.

4D11 Light Chain sequence:
(SEQ ID NO: 388)
DIQMTQSPSSLSASVGDRVTITCRASQSISSYLNWYQQKPGKAPKLLIYA

ASSLQSGVPSRFSGSGSGTDFTLTISSLQPEDFATYYCQQTVVAPPLFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

4D11 Heavy Chain sequence:
(SEQ ID NO: 389)
EVQLLESGGGLVQPGGSLRLSCAASGFTFSSYAMSWVRQAPGKGLEWVSS

IDPEGRQTYYADSVKGRFTISRDNSKNTLYLQMNSLRAEDTAVYYCAKDI

GGRSAFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

4D11v2 Heavy Chain sequence
(SEQ ID NO: 390)
EVHLLESGGGLVQPGGSLRLSCAASGFTFSSYAMSWVRQAPGKGLEWVSS

IDPEGRQTYYADSVKGRFTISRDNSKNTLYLQMNSLRAEDTAVYYCAKDI

GGRSAFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

4D11v2 Light Chain Sequence
(SEQ ID NO: 391)
DIQMTQSPSSLSASVGDRVTITCRASQSISSYLNWYQQKPGKAPKLLIYA

ASSLQSGVPSRFSGSGSGTDFTLTISSLQPEDFATYYCQQTVVAPPLFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

An exemplary activatable anti-Jagged antibody of the invention is the activatable antibody referred to herein as the 5342-1204-4D11 activatable antibody, which binds human Jagged 1 and human Jagged 2 when the activatable antibody is in an activated state. Two sequences of the 5342-1204-4D11 activatable anti-Jagged antibody are shown below, Sequence 1 is the sequence of a version of the 5342-1204-4D11 activatable anti-Jagged antibody that includes a spacer peptide, and Sequence 2 is the sequence of the 5342-1204-4D11 activatable anti-Jagged antibody without the spacer sequence:

5342-1204-4D11 Activatable Antibody Heavy Chain Nucleotide Sequence 1:
(SEQ ID NO: 415)
GAGGTGCAGCTGTTGGAGTCTGGGGGAGGCTTGGTACAGCCTGGGGGGTCCCTGAGACTCTCCT

GTGCAGCCTCTGGATTCACCTTTAGCAGCTATGCCATGAGCTGGGTCCGCCAGGCTCCAGGGAA

```
GGGGCTGGAGTGGGTGTCAAGTATTGACCCGGAAGGTCGGCAGACATATTACGCAGACTCCGTG

AAGGGCCGGTTCACCATCTCCAGAGACAATTCCAAGAACACGCTGTATCTGCAAATGAACAGCC

TGAGAGCCGAGGACACGGCCGTATATTACTGTGCGAAAGACATCGGCGGCAGGTCGGCCTTTGA

CTACTGGGGCCAGGGAACCCTGGTCACCGTCTCCTCAGCTAGCACCAAGGGCCCATCGGTCTTC

CCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACAC

CTTCCCGGCTGTCCTACAGTCCTCAGGACTCTACTCCCTCAGCAGCGTGGTGACCGTGCCCTCC

AGCAGCTTGGGCACCCAGACCTACATCTGCAACGTGAATCACAAGCCCAGCAACACCAAGGTGG

ACAAGAAAGTTGAGCCCAAATCTTGTGACAAAACTCACACATGCCCACCGTGCCCAGCACCTGA

ACTCCTGGGGGGACCGTCAGTCTTCCTCTTCCCCCCAAAACCCAAGGACACCCTCATGATCTCC

CGGACCCCTGAGGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAGGAGATGACCAAGAA

CCAGGTCAGCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGACGGCTCCT

TCTTCCTCTACAGCAAGCTCACCGTGGACAAGAGCAGGTGGCAGCAGGGGAACGTCTTCTCATG

CTCCGTGATGCATGAGGCTCTGCACAACCACTACACGCAGAAGAGCCTCTCCCTGTCTCCGGGT

AAA 5342-1204-4D11 Activatable Antibody Heavy Chain Amino Acid Sequence 1:
                                               (SEQ ID NO: 416)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K]

5342-1204-4D11 Activatable Antibody Light Chain Nucleotide Sequence 1:
                                              (SEQ ID NO: 417)
CAAGGCCAGTCTGGCCAGTGCAATATTTGGCTCGTAGGTGGTGATTGCAGGGGCTGGCAGGGGG

GCTCGAGCGGTGGCAGCGGTGGCTCTGGTGGTCTGAGCGGCCGTTCCGATAATCATGGCGGCGG

TTCTGACATCCAGATGACCCAGTCTCCATCCTCCCTGTCTGCATCTGTAGGAGACAGAGTCACC

ATCACTTGCCGGGCAAGTCAGAGCATTAGCAGCTATTTAAATTGGTATCAGCAGAAACCAGGGA

AAGCCCCTAAGCTCCTGATCTATGCGGCATCCAGTTTGCAAAGTGGGGTCCCATCAAGGTTCAG

TGGCAGTGGATCTGGGACAGATTTCACTCTCACCATCAGCAGTCTGCAACCTGAAGATTTTGCA

ACTTACTACTGTCAACAGACGGTTGTGGCGCCTCCGTTATTCGGCCAAGGGACCAAGGTGGAAA

TCAAACGTACGGTGGCTGCACCATCTGTCTTCATCTTCCCGCCATCTGATGAGCAGTTGAAATC

TGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGG
```

```
ACAGCACCTACAGCCTCAGCAGCACCCTGACGCTGAGCAAAGCAGACTACGAGAAACACAAAGT

CTACGCCTGCGAAGTCACCCATCAGGGCCTGAGCTCGCCCGTCACAAAGAGCTTCAACAGGGGA

GAGTGT
```

5342-1204-4D11 Activatable Antibody Light Chain Amino Acid Sequence 1:
(SEQ ID NO: 418)
```
QGQSGQCNIWLVGGDCRGWQGSSGGSGGSGGLSGRSDNHGGGSDIQMTQSPSSLSASVGDRVT

ITCRASQSISSYLNWYQQKPGKAPKLLIYAASSLQSGVPSRFSGSGSGTDFTLTISSLQPEDFA

TYYCQQTVVAPPLFGQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPVTKSFNRG

EC
```

5342-1204-4D11 Activatable Antibody Heavy Chain Nucleotide Sequence 2:
(SEQ ID NO: 415)
```
GAGGTGCAGCTGTTGGAGTCTGGGGGAGGCTTGGTACAGCCTGGGGGGTCCCTGAGACTCTCCT

GTGCAGCCTCTGGATTCACCTTTAGCAGCTATGCCATGAGCTGGGTCCGCCAGGCTCCAGGGAA

GGGGCTGGAGTGGGTGTCAAGTATTGACCCGGAAGGTCGGCAGACATATTACGCAGACTCCGTG

AAGGGCCGGTTCACCATCTCCAGAGACAATTCCAAGAACACGCTGTATCTGCAAATGAACAGCC

TGAGAGCCGAGGACACGGCCGTATATTACTGTGCGAAAGACATCGGCGGCAGGTCGGCCTTTGA

CTACTGGGGCCAGGGAACCCTGGTCACCGTCTCCTCAGCTAGCACCAAGGGCCCATCGGTCTTC

CCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACAC

CTTCCCGGCTGTCCTACAGTCCTCAGGACTCTACTCCCTCAGCAGCGTGGTGACCGTGCCCTCC

AGCAGCTTGGGCACCCAGACCTACATCTGCAACGTGAATCACAAGCCCAGCAACACCAAGGTGG

ACAAGAAAGTTGAGCCCAAATCTTGTGACAAAACTCACACATGCCCACCGTGCCCAGCACCTGA

ACTCCTGGGGGGACCGTCAGTCTTCCTCTTCCCCCCAAAACCCAAGGACACCCTCATGATCTCC

CGGACCCCTGAGGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAGGAGATGACCAAGAA

CCAGGTCAGCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGACGGCTCCT

TCTTCCTCTACAGCAAGCTCACCGTGGACAAGAGCAGGTGGCAGCAGGGGAACGTCTTCTCATG

CTCCGTGATGCATGAGGCTCTGCACAACCACTACACGCAGAAGAGCCTCTCCCTGTCTCCGGGT

AAA
```

5342-1204-4D11 Activatable Antibody Heavy Chain Amino Acid Sequence 2:
(SEQ ID NO: 416)
```
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K]
```

```
5342-1204-4D11 Activatable Antibody Light Chain Nucleotide Sequence 2:
                                                       (SEQ ID NO: 419)
TGCAATATTTGGCTCGTAGGTGGTGATTGCAGGGGCTGGCAGGGGGGCTCGAGCGGTGGCAGCG

GTGGCTCTGGTGGTCTGAGCGGCCGTTCCGATAATCATGGCGGCGGTTCTGACATCCAGATGAC

CCAGTCTCCATCCTCCCTGTCTGCATCTGTAGGAGACAGAGTCACCATCACTTGCCGGGCAAGT

CAGAGCATTAGCAGCTATTTAAATTGGTATCAGCAGAAACCAGGGAAAGCCCCTAAGCTCCTGA

TCTATGCGGCATCCAGTTTGCAAAGTGGGGTCCCATCAAGGTTCAGTGGCAGTGGATCTGGGAC

AGATTTCACTCTCACCATCAGCAGTCTGCAACCTGAAGATTTTGCAACTTACTACTGTCAACAG

ACGGTTGTGGCGCCTCCGTTATTCGGCCAAGGGACCAAGGTGGAAATCAAACGTACGGTGGCTG

CACCATCTGTCTTCATCTTCCCGCCATCTGATGAGCAGTTGAAATCTGGAACTGCCTCTGTTGT

GTGCCTGCTGAATAACTTCTATCCCAGAGAGGCCAAAGTACAGTGGAAGGTGGATAACGCCCTC

CAATCGGGTAACTCCCAGGAGAGTGTCACAGAGCAGGACAGCAAGGACAGCACCTACAGCCTCA

GCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT 5342-1204-4D11 Activatable Antibody Light Chain Amino Acid Sequence 2:
                                                       (SEQ ID NO: 420)
CNIWLVGGDCRGWQGGSSGGSGGSGGLSGRSDNHGGGSDIQMTQSPSSLSASVGDRVTITCRAS

QSISSYLNWYQQKPGKAPKLLIYAASSLQSGVPSRFSGSGSGTDFTLTISSLQPEDFATYYCQQ

TVVAPPLFGQGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC
```

When an activatable antibody is cleaved by a protease, i.e., when the activatable antibody is in an active or cleaved state, the activated antibody will retain only a portion of the amino acid sequence of the activatable antibody in an inactive or uncleaved state. The sequence of the activatable antibody in an active or cleaved state will vary depending on which protease cleaves the substrate (CM), as different proteases can have different recognition sites.

For example, when an activatable anti-EGFR antibody is cleaved by a protease, i.e., when the activatable anti-EGFR antibody is in an active or cleaved state, the activated anti-EGFR antibody will retain only a portion of the amino acid sequence of the activatable antibody in an inactive or uncleaved state. The sequence of the activatable anti-EGFR antibody in an active or cleaved state will vary depending on which protease cleaves the substrate (CM), as different proteases can have different recognition sites.

Examples of various N-terminal sequences of the light chain of activated versions 3954-1204-C225v5 anti-EGFR activatable antibody, where the activatable antibody has been activated by various proteases is shown below in Table 5, where the N-terminal portion of the uncleaved sequence (–) is SEQ ID NO: 392, the N-terminal portion of the matriptase-activated sequence is SEQ ID NO: 393, the N-terminal portion of the uPA activated sequence is SEQ ID NO: 393, and the N-terminal portion of the legumain activated sequence is SEQ ID NO: 394. The annotated sequences show the residues that compose the masking moiety (MM), the first linker peptide (LP1), the substrate (CM), the second linker peptide (LP2), and the N-terminal residue of the C225v5 antibody (i.e., the N-terminal Q residue of the C225v5 AB).

TABLE 5

| Enzyme | SFI site - mask - linker - substrate - linker - Lc | SEQ ID NO: |
|---|---|---|
| – | QGQSGQCISPRGCPDGPYVMY*GSSGGSGGSGGSG*LSGRSDNH*GSSGTQ* | 392 |
| Matriptase | SDNH*GSSGTQ* | 393 |
| uPA | SDNH*GSSGTQ* | 393 |
| Legumain | H*GSSGTQ* | 394 |

In some embodiments, the activatable antibodies described herein also include an agent conjugated to the activatable antibody. In some embodiments, the conjugated agent is a therapeutic agent, such as an antineoplastic agent. In such embodiments, the agent is conjugated to a carbohydrate moiety of the activatable antibody, for example, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody. In some embodiments, the agent is conjugated to an amino group of the antibody or antigen-binding fragment of the activatable antibody. In some embodiments the agent is conjugated to a carboxylic acid group of the antibody or antigen-binding fragment of the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, any of the cytotoxic agents listed in Table 4. In some embodiments, the cytotoxic agent is a dolastatin or a derivative thereof (e.g. auristatin E, AFP, MMAF, MMAE, MMAD, DMAF, DMAE). For example, the cytotoxic agent is monomethyl auristatin E (MMAE) or monomethyl auristatin D (MMAD). In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the conjugated activatable antibody can be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

Enzymatically active toxins and antigen-binding fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Table 4 lists some of the exemplary pharmaceutical agents but in no way is meant to be an exhaustive list.

TABLE 4

Exemplary Pharmaceutical Agents for Conjugation

CYTOTOXIC AGENTS

Auristatins
Auristatin E
Monomethyl auristatin E (MMAE)
Monomethyl auristatin D (MMAD)
Desmethyl auristatin E (DMAE)
Auristatin F
Monomethyl auristatin F (MMAF)
Desmethyl auristatin F (DMAF)
Auristatin derivatives, e.g., amides thereof
Auristatin tyramine
Auristatin quinoline
Dolastatins
Dolostatin 10
Dolastatin derivatives
Dolastatin 16 DmJ
Dolastatin 16 Dpv
Maytansinoids, e.g. DM-1; DM-4
Maytansinoid derivatives
Duocarmycin
Duocarmycin derivatives
Alpha-amanitin
Anthracyclines
Doxorubicin
Daunorubicin
Bryostatins
Camptothecin
Camptothecin derivatives
7-substituted Camptothecin
10,11-Difluoromethylenedioxycamptothecin
Combretastatins
Debromoaplysiatoxin
Kahalalide-F
Discodermolide
Ecteinascidins

ANTIVIRALS

Acyclovir
Vira A
Symmetrel

ANTIFUNGALS

Nystatin

ADDITIONAL ANTI-NEOPLASTICS

Adriamycin
Cerubidine
Bleomycin
Alkeran
Velban
Oncovin
Fluorouracil
Methotrexate
Thiotepa
Bisantrene
Novantrone
Thioguanine
Procarabizine
Cytarabine

ANTI-BACTERIALS

Aminoglycosides
Streptomycin
Neomycin
Kanamycin

TABLE 4-continued

Exemplary Pharmaceutical Agents for Conjugation

Amikacin
Gentamicin
Tobramycin
Streptomycin B
Spectinomycin
Ampicillin
Sulfanilamide
Polymyxin
Chloramphenicol
Turbostatin
Phenstatins
Hydroxyphenstatin
Spongistatin 5
Spongistatin 7
Halistatin 1
Halistatin 2
Halistatin 3
Modified Bryostatins
Halocomstatins
Pyrrolobenzimidazoles (PBI)
Cibrostatin6
Doxaliform
Anthracyclins analogues
Cemadotin analogue (CemCH2-SH)
*Pseudomonas* toxin A (PE38) variant
*Pseudomonas* toxin A (ZZ-PE38) variant
ZJ-101
OSW-1
4-Nitrobenzyloxycarbonyl Derivatives of
O6-Benzylguanine
Topoisomerase inhibitors
Hemiasterlin
Cephalotaxine
Homoharringtonine
Pyrrolobenzodiazepine dimers (PBDs)
Functionalized pyrrolobenzodiazepenes
Calicheamicins
Podophyllotoxins
Taxanes
Vinca alkaloids
CONJUGATABLE DETECTION
REAGENTS Fluorescein and derivatives thereof
Fluorescein isothiocyanate (FITC)
RADIOPHARMACEUTICALS $^{125}$I
$^{131}$I
$^{89}$Zr
$^{111}$In
$^{123}$I
$^{131}$I
$^{99m}$Tc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99m}$Tc (Technetium)
HEAVY METALS Barium
Gold
Platinum
ANTI-MYCOPLASMALS Tylosine
Spectinomycin Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The binding is, in some embodiments, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Suitable linkers include: (i) SMPT (4-succinimidyloxycarbonyl-alpha-methyl-alpha-(2-pridyl-dithio)-toluene (Pierce Chem. Co., Cat. (21558G); (ii) SPDP (succinimidyl-6 [3-(2-pyridyldithio) propionamido]hexanoate (Pierce Chem. Co., Cat #21651G); and (iii) Sulfo-LC-SPDP (sulfosuccinimidyl 6 [3-(2-pyridyldithio)-propianamide] hexanoate (Pierce Chem. Co. Cat. #2165-G.

In some embodiments, the linkers are cleavable. In some embodiments, the linkers are non-cleavable. In some embodiments, two or more linkers are present. The two or more linkers are all the same, e.g., cleavable or non-cleavable, or the two or more linkers are different, e.g., at least one cleavable and at least one non-cleavable.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')$_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; in some embodiments ≤100 nM and in some embodiments ≤10 nM.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to EGFR, when the equilibrium binding constant ($K_d$) is ≤1 µM, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of rabbit or murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. For example, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland? Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present invention, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Suitable amino acid substitutions are those that: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (e.g., conservative amino acid substitutions) may be made in the naturally-occurring sequence (e.g., in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to EGFR, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects. The terms patient and subject are used interchangeably herein. In some embodiments, the subject is a mammal, such as a human, non-human primate, companion animal (e.g., cat, dog, horse), farm animal, work animal, or zoo animal. In some embodiments, the subject is a human. In some embodiments, the subject is a companion animal. In some embodiments, the subject is an animal in the care of a veterinarian.

Use of Antibodies that Bind Activatable Antibodies

It will be appreciated that administration of antibodies and antigen-binding fragments thereof in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Antibodies and antigen-binding fragments thereof can be administered in the form of compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest fragment that specifically binds to the target activatable antibody and/or conjugated activatable antibody is used in some embodiments. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

In some embodiments, the antibody contains a detectable label. An intact antibody, or a fragment thereof (e.g., Fab, scFv, or $F(ab)_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Diagnostic Formulations

Antibodies and/or fragments of the disclosure are also useful in the detection of activatable antibodies and/or conjugated activatable antibodies in patient samples and accordingly are useful as diagnostics. For example, the antibodies and antigen-binding fragments thereof that bind activatable antibodies and/or conjugated activatable antibodies are used in in vitro assays, e.g., ELISA, to detect activatable antibodies and/or conjugated activated antibodies levels in a patient sample. In some embodiments, the antibodies and antigen-binding fragments thereof that bind activatable antibodies and/or conjugated activatable antibodies are used in in vitro assays, e.g., ELISA, to detect the total level (activated and non-activated) of activatable antibodies and/or conjugated activated antibodies and/or the intact level (non-activated) activatable antibodies and/or conjugated activated antibodies as shown in the Examples provided herein.

In one embodiment, an antibody or fragment of the disclosure is immobilized on a solid support (e.g., the well(s) of a microtiter plate). The immobilized antibody and/or fragment serves as a capture antibody for any activatable antibody and/or conjugated activatable antibody that may be present in a test sample. Prior to contacting the immobilized antibody with a sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of activatable antibody and/or conjugated activatable antibody in the test sample is determined by comparison with a standard curve developed from the standard samples.

An antibody and/or fragment of the disclosure can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods.

The invention will be further described in the following examples, which do not limit the scope of the invention described in the claims.

EXAMPLES

Example 1. Generation of Antibodies that Bind Activatable Antibodies

Exemplary antibodies that bind activatable antibodies and/or conjugated activatable antibodies include the antibodies referred to herein as 41 (also referred to herein as 41-2 and/or clone 41), 58 (also referred to herein as 58-1 and/or clone 58), 72 (also referred to herein as 72-3 and/or clone 72), and 85 (also referred to herein as 85-1 and/or clone 85) and antigen-binding fragments thereof. These antibodies were generated using the following peptide antigen (SEQ ID NO: 395): QGQSGQCISPRGCPDG-PYVMYGSSGGSGGSK; which includes a disulfide bridge between C7 and C16. This 33 amino acid peptide represents the sequence of the masking moiety (MM) and the first linker peptide (LP1) of the activatable anti-EGFR antibody referred to herein as 3954-1204-c225v5. This peptide antigen was conjugated to two different carrier proteins for immunization: immunization: (i) 5 mg to Keyhole Limpet Hemocyanin (KLH) or (ii) 3 mg to ovalbumin (OVA). Selected rabbits were also immunized with the full length version of the 3954-1204-c225v5 anti-EGFR activatable antibody.

The rabbits were immunized using the following procedure. Four three month old New Zealand white rabbits were immunized using a customized protocol of 5 or 6 injections. At the time of each injection, the antigen aliquot was thawed and combined with Complete Freund's Adjuvant (CFA) (for the first injection) or with incomplete Freund's Adjuvant (IFA) for the subsequent injections. The injection route was subcutaneous (SC).

Two rabbits were immunized with the conjugated peptide and two other rabbits were immunized with the conjugated peptide and the full length version of the 3954-1204-c225v5 anti-EGFR activatable antibody.

Serum titer against the free peptide or the activatable anti-EGFR antibody as well as counter screen antigen (human IgG) was evaluated using test bleeds using a standard ELISA procedure. The results indicated that all 4 rabbits had comparable titers against the respective immunogen and were ready for splenectomy.

Splenocytes from the immunized rabbits were isolated using the following method. Three rabbits were selected for final intravenous boost and splenectomy. Splenocytes from a rabbit immunized with the 3954-1204-c225v5 and the peptide antigen and a rabbit immunized with the peptide only were used for monoclonal development. The final intravenous boost was performed with OVA-conjugated peptide (2 rabbits immunized with peptide only) or a mixture of OVA conjugated peptide and 3954-1204-c225v5 (one rabbit immunized with peptide and 3954-1204-c225v5).

Rabbit monoclonal antibodies were generated as follows: Lymphocytes from rabbits E5251 and E5253 were used for hybridoma fusion with partner cells 240E-W2 and plated on forty 96-wells plates (400 million lymphocytes per rabbit). The plates were kept in tissue culture incubators under standard conditions.

Clones 41, 58, 72, 85 were selected for subcloning and characterization.

Molecular cloning was performed using the following method. mRNA from hybridoma cells was isolated using a TuboCapture Kit (Qiagen: Catalog #72232) following the manufacturer's instruction and reverse transcribed into cDNA using oligo-dT primer. The variable region of heavy chain (VH) was PCR amplified using primers OYZ64-2 and OYZvh3. The entire light chain (LC) was PCR amplified using primers OYZ62 and OYZ71. The VH region of PCR fragments was digested using restriction enzyme HindIII and KpnI. The LC PCR fragments were digested using HindIII and NotI. All digested products were purified using Qiagen QIAquick PCR Purification Kit (catalog #28014). After purification, the VH or LC fragment, respectively, was ligated into the corresponding heavy or light chain proprietary expression vectors and transformed into competent cells DH5α (MC Lab, catalog #DA-100). The transformed colonies were picked and inserts were confirmed (by expected size: approximately 440 bp for VH and 740 bp for LC) using the corresponding restriction enzymes. Plasmids with inserts of the expected sizes were sequenced using the TT5 primer. The sequences for VH or LC regions are provided herein. The light chain and heavy chain encoding nucleic acid molecules were co-transfected into 293 cells in 6-well plates. The supernatants were collected five days post transfection and tested against corresponding antigen. In addition, the IgG concentration was measured by ELISA.

In addition, the entire light chain and heavy chain fragments were excised from the corresponding vector with HindIII and NotI and subsequently purified using Qiagen QIAquick PCR Purification Kit (catalog #28014).

Example 2. Binding Specificity of Antibodies that Bind Anti-EGFR Activatable Antibodies Microsorp (Nunc) 96-well plate(s) were coated with 50 µl/well of 1 µg/ml (i) cetuximab, (ii) parental antibody C225v5 (a variant of cetuximab, the sequence of which is provided herein), (iii) a masked anti-EGFR antibody, referred to herein as 3954-NSUB-c225v5, which contains the noncleavable sequence GSSGGSGGSGGSGGGSGGGSGGS (SEQ ID NO: 396) between the mask and the light chain of the anti-EGFR antibody c225v5; (iv) an activatable anti-EGFR antibody referred to herein as 3954-1204-c225v5; (v) the 3954-1204-c225v5 activatable anti-EGFR antibody activated with uPA, or (vi) the anti-VEGF-A antibody bevacizumab; each of the antibodies in PBS overnight at 4° C. The plates were washed with PBS/0.05% Tween 20 (wash butter) and then blocked with PBS/1% BSA for 1 hour at room temperature. The blocking buffer was removed, and the anti-AA antibodies 41, 58, 72 or 85, i.e., antibodies that bind activatable antibodies and/or conjugated activatable antibodies, were added and incubated for 1 hour. The plates were washed with wash buffer and incubated with 50 µl of 1 µg/ml of horseradish peroxidase conjugated donkey anti-rabbit IgG antibody for 1 hour. The plates were washed with wash buffer and 100 µl/well of TMB substrate was added. The reaction was stopped by the addition of 100 µl 1M HCl and the OD 450 nm was measured.

As shown in FIG. 1, each anti-AA antibody demonstrated a different but overlapping specificity. Clone 41 bound to all antibodies tested (cetuximab, C225v5, intact 3954-1204-c225v5, 3954-NSUB-c225v5), with the exception of bevacizumab. Clone 58 bound with greater specificity to the intact 3954-1204-c225v5 but also bound weakly to 3954-NSUB-c225v5. Clone 72 bound with greater specificity to 3954-1204-c225v5 but also recognized 3954-NSUB-c225v5 well. Clone 72 also demonstrated a very weak binding to the uPA activated 3954-1204-c225v5. Clone 85 bound equally well to 3954-1204-c225v5 and 3954-NSUB-c225v5 but did not bind to any other antibody tested.

Example 3. Quantification of Total (Activated and Non-Activated) Activatable Antibodies and Intact (Non-Activated) Activatable Antibodies The antibodies and antigen-binding fragments thereof that bind activatable antibody and/or conjugated activatable antibodies, i.e., anti-AA antibodies of the disclosure, were used to develop assays to measure the concentration of total (activated and non-activated) and intact (non-activated) activatable antibodies, using the 3954-1204-c225v5 anti-EGFR activatable antibody as an example.

Microsorp (Nunc) 96-well plate(s) were coated with 50 µl/well, 1 µg/ml anti-AA clone 41 in PBS overnight at 4 C. The plates were washed with PBS/0.05% Tween 20 (wash buffer) and blocked with PBS/1% BSA for 1 hour at room temperature. The blocking buffer was removed and 50 µl/well of sample were added and incubated for 1 hour. Intact or partially (~50%) activated 3954-1204-c225v5 in human plasma was used as each sample. The plates were washed with wash buffer and incubated with 50 µl (e.g., at 2 µg/ml) biotinylated anti-AA antibodies (clones 58 or 72) or biotinylated goat anti-human IgG for 1 hour at room temperature. The plates were washed with wash buffer and incubated for 30 min with 1 µg/ml horse radish peroxidase conjugated streptavidin. The plates were washed with wash buffer and the binding was measured using a colorimetric substrate by incubating 100 µl/well of TMB substrate. The reaction was stopped by the addition of 100 µl 1M HCl and the OD 450 nm was measured.

When the biotinylated goat anti-human IgG was used, the detection of 3954-1204-c225v5 gave a high signal for the intact 3954-1204-c225v5 and the partially activated 3954-1204-c225v5. However, when the biotinylated clones 58 or the clone 72 were used, the detection of the partially activated 3954-1204-c225v5 gave a signal approximately 50% lower relative to the signal given by the detection of the intact 3954-1204-c225v5. These data showed that a combination of these antibodies can be used to develop an assay to measure the concentration of total and intact 3954-1204-c225v5 in human plasma. These assays are, therefore, useful in methods to measure concentrations of total and intact 3954-1204-c225v5, for example in treated subjects.

Example 4. Use of Antibodies that Bind Activatable Antibodies to Detect Activatable Antibodies in Tumor Samples The example provided herein demonstrates the detection of cetuximab, activatable anti-EGFR antibody (3954-1204-c225v5), and masked anti-EGFR antibody (3954-NSUB-c225v5) by immunofluorescence using the anti-AA antibody clone 41. Nude mice bearing a subcutaneous cell line xenograft tumor (H292 non-small cell lung cancer; NSCLC) or patient derived tumor (LXFA NSCLC) were injected intraperitoneally with cetuximab, 3954-1204-c225v5, 3954-NSUB-c225v5, or PBS. After the injection (72 h) the tumors were excised and embedded in OCT and frozen. The tumors were cryosectioned and immunofluorescence was performed using clone 41 and a FITC-conjugated anti-rabbit IgG.

FIG. 3 demonstrates that immunofluorescent detection with clone 41 revealed a strong signal for tumors from mice treated with cetuximab and 3954-1204-c225v5 but a lower signal for tumors from mice injected with 3954-NSUB-c225v5. No fluorescent signal was detected in the tumors resected from mice injected with PBS. These results suggest that the anti-AA antibody clone 41 is useful in methods to detect cetuximab, 3954-1204-c225v5, or 3954-NSUB-c225v5, for example in tissues from treated animal or human subjects.

Example 5. Generation of Additional Antibodies that Bind Activatable Antibodies

In addition to the antibodies descried in Example 1, exemplary antibodies that bind activatable antibodies and/or conjugated activatable antibodies include the antibodies referred to herein as 10 (also referred to herein as 10-10 and/or clone 10), 8 (also referred to herein as 8-8 and/or clone 8), 53 (also referred to herein as 53-1 and/or clone 3), 7 (also referred to herein as 7-11 and/or clone 7), 36 (also referred to herein as 36-3 and/or clone 36), 52 (also referred to herein as 52-10 and/or clone 52), and 27 (also referred to herein as 27-4 and/or clone 27), and antigen-binding fragments thereof. These antibodies were generated using the following peptide antigen (SEQ ID NO: 397): QGQSGQC-NIWLVGGDCRGWQGGSSGGSGGSGGLSGRSDN-HGGGSK, which includes a disulfide bridge between C7 and C16. This 45 amino acid peptide represents the sequence of the masking moiety (MM) and the first linker peptide (LP1) of the activatable anti-Jagged-1/-2 antibody referred to herein as 5342-1204-4D11, which comprises the heavy chain sequence of SEQ ID NO: 416 and the light chain sequence of SEQ ID NO: 420. This peptide antigen was conjugated to two different carrier proteins for immunization: immunization: (i) 2 mg to Keyhole Limpet Hemocyanin (KLH) or (ii) 2 mg to ovalbumin (OVA). Selected rabbits were also immunized with the full length version of the 5342-1204-4D11 anti-Jagged-1/-2 activatable antibody.

The rabbits were immunized using the following procedure. Two three month old New Zealand white rabbits were immunized using a customized protocol of 6 injections. The rabbits were alternatively injected with the conjugated peptide and the full length version of the 5342-1204-4D11 anti-Jagged-1/-2 activatable antibody at a two weeks interval schedule. At the time of each injection, the antigen aliquot was thawed and combined with Complete Freund's Adjuvant (CFA) (for the first injection) or with incomplete Freund's Adjuvant (IFA) for the subsequent injections. The injection route was subcutaneous (SC).

Serum titer against the free peptide or the activatable anti-Jagged-1/-2 antibody as well as counter screen antigen (human IgG) was evaluated using test bleeds using a standard ELISA procedure. The results indicated that both rabbits had comparable titers against the respective immunogen and were ready for splenectomy.

Splenocytes from the immunized rabbits were isolated using the following method. The selected rabbit received a final intravenous boost and splenectomy. The final intravenous boost was performed with OVA-conjugated peptide.

Rabbit monoclonal antibodies were generated as follows: Lymphocytes from rabbits #359 were used for hybridoma fusion with partner cells 240E-W2 and plated on forty 96-wells plates (400 million lymphocytes per rabbit). The plates were kept in tissue culture incubators under standard conditions.

Clones 10, 8, 53, 7, 36, 52, and 27 were selected for subcloning and characterization. The following final subclones were selected, 10-10, 8-8, 53-1, 7-11, 36-3, 52-10, and 27-4.

Example 6. Binding Specificity of Antibodies that Bind Anti-Jagged-1/-2 Activatable Antibodies Microsorp (Nunc) 96-well plate(s) were coated with 50 µl/well of 1 µg/ml (i) parental antibody 4D11, (ii) an activatable anti-Jagged-1/-2 antibody referred to herein as 5342-1204-4D11, which comprises the heavy chain sequence of SEQ ID NO: 416 and the light chain sequence of SEQ ID NO: 420; (iii) a masked anti-Jagged-1/-2 antibody, referred to herein as 5342-NSUB-4D11, which comprises the heavy chain sequence of SEQ ID NO: 416 and contains the noncleavable sequence GSSGGSGGSGGSGGGSGGGSGGS (SEQ ID NO: 396) between the mask and the light chain of the anti-Jagged-1/-2 antibody 4D11 as shown below in SEQ ID NO: 421; (iv) the 5342-1203-4D11 activatable anti-Jagged-1/-2 antibody, which comprises the heavy chain sequence of SEQ ID NO: 416 and the light chain sequence of SEQ ID NO: 422 shown below; (v) an activatable anti-Jagged-1/-2 antibody referred to herein as 5342-PLGL-4D11, which comprises the heavy chain sequence of SEQ ID NO: 416 and the light chain sequence of SEQ ID NO: 423 shown below; (vi) an activatable anti-EGFR antibody referred to herein as 3954-1204-C225v5, which comprises the heavy chain sequence of SEQ ID NO: 301 and the light chain sequence of SEQ ID NO: 410; (vii) an activatable anti-Jagged-1/-2 antibody referred to herein as 5872-1204-4D11, which comprises the heavy chain sequence of SEQ ID NO: 416 and the light chain sequence of SEQ ID NO: 424 shown below, (viii) pooled human IgG (Gammaguard); or (ix) the 5342-1204-4D11 activatable anti-Jagged-1/-2 antibody activated with uPA. Each of the antibodies was incubated in PBS overnight at 4° C.

5342-NSUB-4D11 Activatable Antibody Light Chain Amino Acid Sequence:
(SEQ ID NO: 421)
CNIWLVGGDCRGWQGGSSGGSGGSGGGSSGGSGGSGGSGGGSGGSGGSG

GGSDIQMTQSPSSLSASVGDRVTITCRASQSISSYLNWYQQKPGKAPKLL

IYAASSLQSGVPSRFSGSGSGTDFTLTISSLQPEDFATYYCQQTVVAPPL

FGQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC 5342-1203-4D11 Activatable Antibody Light Chain Amino Acid Sequence:
(SEQ ID NO: 422)
CNIWLVGGDCRGWQGGSSGGSGGSGGTGRGPSWVGGGSDIQMTQSPSSLS

ASVGDRVTITCRASQSISSYLNWYQQKPGKAPKLLIYAASSLQSGVPSRF

SGSGSGTDFTLTISSLQPEDFATYYCQQTVVAPPLFGQGTKVEIKRTVAA

PSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRG

EC

5342-PLGL-4D11 Activatable Antibody Light Chain Amino Acid Sequence:
(SEQ ID NO: 423)
CNIWLVGGDCRGWQGGSSGGSGGSGGSGGGSPLGLGGSDIQMTQSPSSLS

ASVGDRVTITCRASQSISSYLNWYQQKPGKAPKLLIYAASSLQSGVPSRF

SGSGSGTDFTLTISSLQPEDFATYYCQQTVVAPPLFGQGTKVEIKRTVAA

PSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRG

EC 5872-1204-4D11 Activatable Antibody Light Chain Amino Acid Sequence:
(SEQ ID NO: 424)
GCNIWLNGGDCRGWVDPLQGGSSGGSGGSGGLSGRSDNHGGGSDIQMTQS

PSSLSASVGDRVTITCRASQSISSYLNWYQQKPGKAPKLLIYAASSLQSG

VPSRFSGSGSGTDFTLTISSLQPEDFATYYCQQTVVAPPLFGQGTKVEIK

RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

The plates were washed with PBS/0.05% Tween 20 (wash buffer) and then blocked with PBS/1% BSA for 1 hour at room temperature. The blocking buffer was removed, and the anti-AA antibodies 10, 8, 53, 7, 36, 52, and 27, i.e., antibodies that bind activatable antibodies and/or conjugated activatable antibodies, were added and incubated for 1 hour. The plates were washed with wash buffer and incubated with 50 µl of 1 µg/ml of horseradish peroxidase conjugated donkey anti-rabbit IgG antibody for 1 hour. The plates were washed with wash buffer and 100 µl/well of TMB substrate was added. The reaction was stopped by the addition of 100 µl 1M HCl and the OD 450 nm was measured.

As shown in Table 6, each anti-AA antibody demonstrated a different but overlapping specificity:

TABLE 6

Specificity of Anti-Activatable Anti-Jagged-1/-2 Antibodies

|  | 10-10 | 8-8 | 53-1 | 7-11 | 36-3 | 52-10 | 27-4 |
| --- | --- | --- | --- | --- | --- | --- | --- |
| 4D11 | − | − | − | − | + | ++ | +++ |
| 5342-1204-4D11 | +++ | ++ | ++ | +++ | +++ | ++ | +++ |
| 5342-NSUB-4D11 | +++ | ++ | ++ | +++ | + | ++ | +++ |
| 5342-1203-4D11 | +++ | ++ | ++ | +++ | + | ++ | +++ |
| 5342-PLGL-4D11 | +++ | ++ | ++ | +++ | + | ++ | +++ |
| 3954-1204-C225v5 | − | − | − | +++ | +++ | − | − |
| 5872-1204-4D11 | − | ++ | ++ | +++ | +++ | ++ | +++ |
| IvIg | − | − | − | − | − | − | − |
| active 5342-1204-4D11 | − | − | ++ | + | ++ | N/A | N/A |

Clone 10 bound only to the activatable anti-Jagged-1/-2 antibodies bearing the 5342 mask tested (5342-1204-4D11, 5342-NSUB-4D11, 5342-1203-4D11, 5342-PLGL-4D11). Clone 8 bound only to the intact activatable anti-Jagged-1/-2 antibodies tested (5342-1204-4D11, 5342-NSUB-4D11, 5342-1203-4D11, 5342-PLGL-4D11, 5872-1204-4D11). Clone 53 bound to all the activatable anti-Jagged-1/-2 antibodies tested (5342-1204-4D11, 5342-NSUB-4D11, 5342-1203-4D11, 5342-PLGL-4D11, 5872-1204-4D11, activated 5342-1204-4D11). Clone 7 bound to all the activatable antibodies tested (5342-1204-4D11, 5342-NSUB-4D11, 5342-1203-4D11, 5342-PLGL-4D11, 3954-1204-C225v5, 5872-1204-4D11, activated 5342-1204-4D11) with a greater binding to the intact activatable antibodies compared to the activated one. Clone 36 bound to all the antibodies tested at the exception of MG and demonstrated a greater binding to the activatable antibodies bearing the 1204 substrate. Clone 52 and 27 showed a similar specificity and bound to the anti-Jagged-1/-2 antibody and all the activatable anti-Jagged-1/-2 antibodies tested (5342-1204-4D11, 5342-NSUB-4D11, 5342-1203-4D11, 5342-PLGL-4D11, 5872-1204-4D11).

Example 7. Effect of Human Serum on the Binding of Anti-AA to the Activatable Anti-Jagged-1/-2 Antibody 5342-1204-4D11

The effect of the presence of human serum on the binding of antibodies to the activatable anti-Jagged-1/-2 5342-1204-4D11 was tested by ELISA.

Microsorp (Nunc) 96-well plate(s) were coated with 50 µl/well, 1 µg/ml 5342-1204-4D11 in PBS overnight at 4° C. The plates were washed with PBS/0.05% Tween 20 (wash buffer) and blocked with PBS/1% BSA for 1 hour at room temperature. The blocking buffer was removed and the anti-AA antibodies 10, 8, 53, 7, 36, 52, and 27, i.e., antibodies that bind activatable antibodies and/or conjugated activatable antibodies, were added and incubated for 1 hour in the presence of human serum (0%-50%). The plates were washed with wash buffer and incubated with 50 µl of 1 µg/ml of horseradish peroxidase conjugated donkey anti-rabbit IgG antibody for 1 hour. The plates were washed with wash buffer and 100 µl/well of TMB substrate was added. The reaction was stopped by the addition of 100 µl 1M HCl and the OD 450 nm was measured.

As shown in FIG. 4, the binding of the anti-AA 10 and 36 was not altered by the presence of human serum. However in the presence of increasing concentrations of human serum the binding of the anti-AA 8, 7, 27 and 52 to 5342-1204-4D11 gradually decreased (FIG. 4).

These data showed that a combination of these antibodies can be used to develop an assay to measure the concentration of 5342-1204-4D11 in human plasma. Such an assay would be useful in methods to measure concentrations of 5342-1204-4D11, for example, in treated subjects.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

SEQUENCE LISTING

```
<160> NUMBER OF SEQ ID NOS: 428

<210> SEQ ID NO 1
<211> LENGTH: 1338
<212> TYPE: DNA
<213> ORGANISM: Artificial Sequence
<220> FEATURE:
<223> OTHER INFORMATION: chemically synthesized

<400> SEQUENCE: 1
cagtcgctgc aggagtccgg gggaggcctg ttccagcctg ggggatccct gacactcacc      60
tgcacagcct ctggattctc cctcagtaat tatgccgtga tgtgctgggt ccgccaggct     120
ccagggaagg ggctggagtg gatcgcatgt attgttcttg gtgatggtgg tactacttat     180
tacgcgagct gggcgagagg ccggttcacc atctccaaac cctcgtcgac cacggtgact     240
ctgcaaatga ccagtctgac ggccgcggac acggccacct atttctgtgc gagaagtttt     300
gctgctagta gccccattaa ctactttaac ttgtggggcc caggcaccct ggtcaccgtc     360
tcctcagggc aacctaaggc tccatcagtc ttcccactgg cccctgctg cggggacaca     420 cccagctcca cggtgaccct gggctgcctg gtcaaagggt acctcccgga gccagtgacc     480
gtgacctgga actcgggcac cctcaccaat ggggtacgca ccttcccgtc cgtccggcag     540
tcctcaggcc tctactcgct gagcagcgtg gtgagcgtga cctcaagcag ccagcccgtc     600
acctgcaacg tggcccaccc agccaccaac accaaagtgg acaagaccgt tgcgccctcg     660
acatgcagca gcccacgtg cccacccct gaactcctgg ggggaccgtc tgtcttcatc      720
ttccccccaa aacccaagga caccctcatg atctcacgca cccccgaggt cacatgcgtg     780
gtggtggacg tgagccagga tgaccccgag gtgcagttca catggtacat aaacaacgag     840
caggtgcgca ccgcccgcc gccgctacgg gagcagcagt tcaacagcac gatccgcgtg     900
gtcagcaccc tccccatcgc gcaccaggac tggctgaggg gcaaggagtt caagtgcaaa     960
```

```
gtccacaaca aggcactccc ggcccccatc gagaaaacca tctccaaagc cagagggcag    1020
cccctggagc cgaaggtcta caccatgggc cctccccggg aggagctgag cagcaggtcg    1080
gtcagcctga cctgcatgat caacggcttc tacccttccg acatctcggt ggagtgggag    1140
aagaacggga aggcagagga caactacaag accacgccgg ccgtgctgga cagcgacggc    1200
tcctacttcc tctacagcaa gctctcagtg cccacgagtg agtggcagcg gggcgacgtc    1260
ttcacctgct ccgtgatgca cgaggccttg cacaaccact acacgcagaa gtccatctcc    1320
cgctctccgg gtaaatga                                                  1338
```

<210> SEQ ID NO 2
<211> LENGTH: 445
<212> TYPE: PRT
<213> ORGANISM: Artificial Sequence
<220> FEATURE:
<223> OTHER INFORMATION: chemically synthesized

<400> SEQUENCE: 2

```
Gln Ser Leu Gln Glu Ser Gly Gly Gly Leu Phe Gln Pro Gly Gly Ser
1               5                   10                  15

Leu Thr Leu Thr Cys Thr Ala Ser Gly Phe Ser Leu Ser Asn Tyr Ala
            20                  25                  30

Val Met Cys Trp Val Arg Gln Ala Pro Gly Lys Gly Leu Glu Trp Ile
        35                  40                  45

Ala Cys Ile Val Leu Gly Asp Gly Gly Thr Thr Tyr Tyr Ala Ser Trp
    50                  55                  60

Ala Arg Gly Arg Phe Thr Ile Ser Lys Pro Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Phe Ala Ala Ser Ser Pro Ile Asn Tyr Phe Asn Leu Trp
            100                 105                 110

Gly Pro Gly Thr Leu Val Thr Val Ser Ser Gly Gln Pro Lys Ala Pro
        115                 120                 125

Ser Val Phe Pro Leu Ala Pro Cys Cys Gly Asp Thr Pro Ser Ser Thr
    130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                165                 170                 175

Ser Val Arg Gln Ser Ser Gly Leu Tyr Ser Leu Ser Ser Val Val Ser
            180                 185                 190

Val Thr Ser Ser Ser Gln Pro Val Thr Cys Asn Val Ala His Pro Ala
        195                 200                 205

Thr Asn Thr Lys Val Asp Lys Thr Val Ala Pro Ser Thr Cys Ser Lys
    210                 215                 220

Pro Thr Cys Pro Pro Pro Glu Leu Leu Gly Gly Pro Ser Val Phe Ile
225                 230                 235                 240

Phe Pro Pro Lys Pro Lys Asp Thr Leu Met Ile Ser Arg Thr Pro Glu
                245                 250                 255

Val Thr Cys Val Val Asp Val Ser Gln Asp Pro Glu Val Gln
            260                 265                 270

Phe Thr Trp Tyr Ile Asn Asn Glu Gln Val Arg Thr Ala Arg Pro Pro
        275                 280                 285

Leu Arg Glu Gln Gln Phe Asn Ser Thr Ile Arg Val Val Ser Thr Leu
```

```
Pro Ile Ala His Gln Asp Trp Leu Arg Gly Lys Glu Phe Lys Cys Lys
305                 310                 315                 320

Val His Asn Lys Ala Leu Pro Ala Pro Ile Glu Lys Thr Ile Ser Lys
                325                 330                 335

Ala Arg Gly Gln Pro Leu Glu Pro Lys Val Tyr Thr Met Gly Pro Pro
            340                 345                 350

Arg Glu Glu Leu Ser Ser Arg Ser Val Ser Leu Thr Cys Met Ile Asn
        355                 360                 365

Gly Phe Tyr Pro Ser Asp Ile Ser Val Glu Trp Glu Lys Asn Gly Lys
    370                 375                 380

Ala Glu Asp Asn Tyr Lys Thr Thr Pro Ala Val Leu Asp Ser Asp Gly
385                 390                 395                 400

Ser Tyr Phe Leu Tyr Ser Lys Leu Ser Val Pro Thr Ser Glu Trp Gln
                405                 410                 415

Arg Gly Asp Val Phe Thr Cys Ser Val Met His Glu Ala Leu His Asn
            420                 425                 430

His Tyr Thr Gln Lys Ser Ile Ser Arg Ser Pro Gly Lys
        435                 440                 445

<210> SEQ ID NO 3
<211> LENGTH: 642
<212> TYPE: DNA
<213> ORGANISM: Artificial Sequence
<220> FEATURE:
<223> OTHER INFORMATION: chemically synthesized

<400> SEQUENCE: 3
caagtgctga cccagacttc atcccccgtg tctgcacctg tgggaggcac agtcaccatc    60
aagtgccagg ccagtcagcg cattagtacc tacctagcct ggtatcaaca gaaaccaggg   120
cagcctccca agctcctgat ctacaaggca tccactctgg catctggggt ctcatcgcgg   180
ttcaaaggca gtgcatctgg gacagagttc actctcacca tcaacgacct ggagtgtgac   240
gatgctgcca cttactactg tcagagctat tattttggtg atggtactac ttttgctttc   300
ggcggaggga ccgaggtggt ggtcaaaggt gatccagttg cacctactgt cctcatcttc   360
ccaccagctg ctgatcaggt ggcaactgga acagtcacca tcgtgtgtgt ggcgaataaa   420
tactttcccg atgtcaccgt cacctgggag gtggatggcc cacccaaac aactggcatc   480 gagaacagta aaacaccgca gaattctgca gattgtacct acaacctcag cagcactctg   540
acactgacca gcacacagta caacagccac aaagagtaca cctgcaaggt gacccagggc   600
acgacctcag tcgtccagag cttcaatagg ggtgactgtt ag                      642

<210> SEQ ID NO 4
<211> LENGTH: 213
<212> TYPE: PRT
<213> ORGANISM: Artificial Sequence
<220> FEATURE:
<223> OTHER INFORMATION: chemically synthesized

<400> SEQUENCE: 4

Gln Val Leu Thr Gln Thr Ser Pro Val Ser Ala Pro Val Gly Gly
1               5                   10                  15

Thr Val Thr Ile Lys Cys Gln Ala Ser Gln Arg Ile Ser Thr Tyr Leu
                20                  25                  30

Ala Trp Tyr Gln Gln Lys Pro Gly Gln Pro Pro Lys Leu Leu Ile Tyr
            35                  40                  45
```

Lys Ala Ser Thr Leu Ala Ser Gly Val Ser Arg Phe Lys Gly Ser
    50                  55                  60

Ala Ser Gly Thr Glu Phe Thr Leu Thr Ile Asn Asp Leu Glu Cys Asp
65                  70                  75                  80

Asp Ala Ala Thr Tyr Tyr Cys Gln Ser Tyr Tyr Phe Gly Asp Gly Thr
                85                  90                  95

Thr Phe Ala Phe Gly Gly Gly Thr Glu Val Val Lys Gly Asp Pro
                100                 105                 110

Val Ala Pro Thr Val Leu Ile Phe Pro Pro Ala Ala Asp Gln Val Ala
            115                 120                 125

Thr Gly Thr Val Thr Ile Val Cys Val Ala Asn Lys Tyr Phe Pro Asp
        130                 135                 140

Val Thr Val Thr Trp Glu Val Asp Gly Thr Thr Gln Thr Thr Gly Ile
145                 150                 155                 160

Glu Asn Ser Lys Thr Pro Gln Asn Ser Ala Asp Cys Thr Tyr Asn Leu
                165                 170                 175

Ser Ser Thr Leu Thr Leu Thr Ser Thr Gln Tyr Asn Ser His Lys Glu
            180                 185                 190

Tyr Thr Cys Lys Val Thr Gln Gly Thr Thr Ser Val Val Gln Ser Phe
        195                 200                 205

Asn Arg Gly Asp Cys
    210

<210> SEQ ID NO 5
<211> LENGTH: 1314
<212> TYPE: DNA
<213> ORGANISM: Artificial Sequence
<220> FEATURE:
<223> OTHER INFORMATION: chemically synthesized

<400> SEQUENCE: 5
cagtcggtgg aggagtccgg gggtcgtctg gtcatgcctg gaggatccct gacactcacc      60
tgtacagtct ctggaatcga cctcagtcgc tatggaatgg cctggttccg ccaggctcca     120
gggaaggggc tgaaatacat cggagccatt agtagtagtg gtaatgaaga ctacgcgagc     180
tgggcgatag ccgatttac catctccaaa acctcgacca cggcggagct gaaaatgacc     240
agtctgacaa ccgaggacac ggccacctat ttctgtggca gaggttggct tagtaataac     300
gcttatatgt ggggcccagg caccctggtc accgtctcgt cagggcaacc taaggctcca     360
tcagtcttcc cactggcccc ctgctgcggg gacacaccca gctccacggt gaccctgggc     420
tgcctggtca aagggtacct cccggagcca gtgaccgtga cctggaactc gggcacccct     480
accaatgggg tacgcacctt cccgtccgtc ggcagtcct caggcctcta ctcgctgagc     540
agcgtggtga gcgtgacctc aagcagccag cccgtcacct gcaacgtggc ccacccagcc     600
accaacacca aagtggacaa gaccgttgcg ccctcgacat gcagcaagcc cacgtgccca     660
ccccctgaac tcctgggggg accgtctgtc ttcatcttcc ccccaaaacc caaggacacc     720
ctcatgatct cacgcacccc cgaggtcaca tgcgtggtgg tggacgtgag ccaggatgac     780
cccgaggtgc agttcacatg gtacataaac aacgagcagg tgcgcaccgc ccggccgccg     840
ctacgggagc agcagttcaa cagcacgatc cgcgtggtca gcaccctccc catcgcgcac     900
caggactggc tgaggggcaa ggagttcaag tgcaaagtcc acaacaaggc actcccggcc     960
cccatcgaga aaaccatctc caaagccaga gggcagcccc tggagccgaa ggtctacacc    1020
atgggccctc cccgggagga gctgagcagc aggtcggtca gcctgacctg catgatcaac    1080

```
ggcttctacc cttccgacat ctcggtggag tgggagaaga acgggaaggc agaggacaac    1140
tacaagacca cgccggccgt gctggacagc gacggctcct acttcctcta cagcaagctc    1200
tcagtgccca cgagtgagtg gcagcggggc gacgtcttca cctgctccgt gatgcacgag    1260
gccttgcaca accactacac gcagaagtcc atctcccgct ctccgggtaa atga          1314
```

<210> SEQ ID NO 6
<211> LENGTH: 437
<212> TYPE: PRT
<213> ORGANISM: Artificial Sequence
<220> FEATURE:
<223> OTHER INFORMATION: chemically synthesized

<400> SEQUENCE: 6

```
Gln Ser Val Glu Glu Ser Gly Gly Arg Leu Val Met Pro Gly Gly Ser
1               5                   10                  15

Leu Thr Leu Thr Cys Thr Val Ser Gly Ile Asp Leu Ser Arg Tyr Gly
            20                  25                  30

Met Ala Trp Phe Arg Gln Ala Pro Gly Lys Gly Leu Lys Tyr Ile Gly
        35                  40                  45

Ala Ile Ser Ser Ser Gly Asn Glu Asp Tyr Ala Ser Trp Ala Ile Gly
    50                  55                  60

Arg Phe Thr Ile Ser Lys Thr Ser Thr Ala Glu Leu Lys Met Thr
65                  70                  75                  80

Ser Leu Thr Thr Glu Asp Thr Ala Thr Tyr Phe Cys Gly Arg Gly Trp
                85                  90                  95

Leu Ser Asn Asn Ala Tyr Met Trp Gly Pro Gly Thr Leu Val Thr Val
            100                 105                 110

Ser Ser Gly Gln Pro Lys Ala Pro Ser Val Phe Pro Leu Ala Pro Cys
        115                 120                 125

Cys Gly Asp Thr Pro Ser Ser Thr Val Thr Leu Gly Cys Leu Val Lys
    130                 135                 140

Gly Tyr Leu Pro Glu Pro Val Thr Val Thr Trp Asn Ser Gly Thr Leu
145                 150                 155                 160

Thr Asn Gly Val Arg Thr Phe Pro Ser Val Arg Gln Ser Ser Gly Leu
                165                 170                 175

Tyr Ser Leu Ser Ser Val Val Ser Val Thr Ser Ser Gln Pro Val
            180                 185                 190

Thr Cys Asn Val Ala His Pro Ala Thr Asn Thr Lys Val Asp Lys Thr
        195                 200                 205

Val Ala Pro Ser Thr Cys Ser Lys Pro Thr Cys Pro Pro Pro Glu Leu
    210                 215                 220

Leu Gly Gly Pro Ser Val Phe Ile Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser Gln Asp Asp Pro Glu Val Gln Phe Thr Trp Tyr Ile Asn Asn Glu
            260                 265                 270

Gln Val Arg Thr Ala Arg Pro Pro Leu Arg Glu Gln Gln Phe Asn Ser
        275                 280                 285

Thr Ile Arg Val Val Ser Thr Leu Pro Ile Ala His Gln Asp Trp Leu
    290                 295                 300

Arg Gly Lys Glu Phe Lys Cys Lys Val His Asn Lys Ala Leu Pro Ala
305                 310                 315                 320
```

```
Pro Ile Glu Lys Thr Ile Ser Lys Ala Arg Gly Gln Pro Leu Glu Pro
            325                 330                 335

Lys Val Tyr Thr Met Gly Pro Pro Arg Glu Glu Leu Ser Ser Arg Ser
            340                 345                 350

Val Ser Leu Thr Cys Met Ile Asn Gly Phe Tyr Pro Ser Asp Ile Ser
            355                 360                 365

Val Glu Trp Glu Lys Asn Gly Lys Ala Glu Asp Asn Tyr Lys Thr Thr
        370                 375                 380

Pro Ala Val Leu Asp Ser Asp Gly Ser Tyr Phe Leu Tyr Ser Lys Leu
385                 390                 395                 400

Ser Val Pro Thr Ser Glu Trp Gln Arg Gly Asp Val Phe Thr Cys Ser
            405                 410                 415

Val Met His Glu Ala Leu His Asn His Tyr Thr Gln Lys Ser Ile Ser
            420                 425                 430

Arg Ser Pro Gly Lys
            435

<210> SEQ ID NO 7
<211> LENGTH: 651
<212> TYPE: DNA
<213> ORGANISM: Artificial Sequence
<220> FEATURE:
<223> OTHER INFORMATION: chemically synthesized

<400> SEQUENCE: 7
ccggtgctga cccagactcc aacgcccgtg tctgcagctg tgggaggcac agtcaccatc    60
aattgccagg ccagtcaaag tatttataat aaaaatcaat tatcctggtt tcagcagaaa   120
ccagggcagc ctcccaagct cctgatccat atgcatcca ctctggcatc tggggtctca    180
tcgcggttca aaggcagtgg atctgggaca cagttcactc tcaccatcag cgacgtgcag   240
tgtgacgatg ctgccactta ctattgtcta ggcgatttta gttgtagtgg tgttgattgt   300
cttgttgtcg gcggagggac cgaggtggtc gtcgaaggtg atccagttgc acctactgtc   360
ctcatcttcc caccatctgc tgatcttgtg caactggaa cagtcaccat cgtgtgtgtg    420
gcgaataaat actttcccga tgtcaccgtc acctgggagg tggatggcac acccaaaca   480 actggcatcg agaacagtaa acaccgcag aattctgcag attgtaccta caacctcagc    540
agcactctga cactgaccag cacacaatac aacagccaca agagtacac ctgcaaggtg    600 acccagggca cgacctcagt cgtccagagc ttcaataggg gtgactgtta g            651

<210> SEQ ID NO 8
<211> LENGTH: 216
<212> TYPE: PRT
<213> ORGANISM: Artificial Sequence
<220> FEATURE:
<223> OTHER INFORMATION: chemically synthesized

<400> SEQUENCE: 8

Pro Val Leu Thr Gln Thr Pro Thr Pro Val Ser Ala Ala Val Gly Gly
1               5                  10                  15

Thr Val Thr Ile Asn Cys Gln Ala Ser Gln Ser Ile Tyr Asn Lys Asn
            20                  25                  30

Gln Leu Ser Trp Phe Gln Gln Lys Pro Gly Gln Pro Pro Lys Leu Leu
        35                  40                  45

Ile His Tyr Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
```

```
            65                  70                  75                  80
Cys Asp Asp Ala Ala Thr Tyr Tyr Cys Leu Gly Asp Phe Ser Cys Ser
                85                  90                  95

Gly Val Asp Cys Leu Val Val Gly Gly Thr Glu Val Val Glu
            100                 105                 110

Gly Asp Pro Val Ala Pro Thr Val Leu Ile Phe Pro Ser Ala Asp
        115                 120                 125

Leu Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
210                 215

<210> SEQ ID NO 9
<211> LENGTH: 1314
<212> TYPE: DNA
<213> ORGANISM: Artificial Sequence
<220> FEATURE:
<223> OTHER INFORMATION: chemically synthesized

<400> SEQUENCE: 9
cagtcggtgg aggagtccgg gggtcgtctg gtcatgcctg gaggatccct gacactcacc      60
tgcacagtct ctggaatcga cctcagtcac tatggaatgg cctggttccg ccaggctcca     120
gggaaggggc tggaatacat cggagccatt agtagtagtg gtaatgaaga ctacgcgagc     180
tggccgaaag gccgattcac catctcccaaa acctcgacca cggtgactct gaaaatgacc     240
agtctgacaa ccgaggacac ggccacctat ttctgtggca gaggttggct tagtaataat     300
gtttatatgt ggggcccagg caccctggtc accgtctcgt cagggcaacc taaggctcca     360
tcagtcttcc cactggcccc ctgctgcggg gacacaccca gctccacggt gaccctgggc     420
tgcctggtca agggtaccct cccggagcca gtgaccgtga cctggaactc gggcaccctc     480
accaatgggg tacgcacctt cccgtccgtc ggcagtcct caggcctcta ctcgctgagc     540
agcgtggtga gcgtgacctc aagcagccag cccgtcacct gcaacgtggc cacccagcc     600 accaacacca agtggacaa gaccgttgcg ccctcgacat gcagcaagcc cacgtgccca     660 cccctgaac tcctgggggg accgtctgtc ttcatcttcc ccccaaaacc caaggacacc     720
ctcatgatct cacgcacccc cgaggtcaca tgcgtggtgg tggacgtgag ccaggatgac     780
cccgaggtgc agttcacatg gtacataaac aacgagcagg tcgcaccgc ccggccgccg     840 ctacgggagc agcagttcaa cagcacgatc cgcgtggtca gcaccctccc catcgcgcac     900
caggactggc tgagggggcaa ggagttcaag tgcaaagtcc acaacaaggc actcccggcc     960
cccatcgaga aaaccatctc caaagccaga gggcagcccc tggagccgaa ggtctacacc    1020
atgggccctc ccgggagga gctgagcagc aggtcggtca gcctgacctg catgatcaac    1080
ggcttctacc cttccgacat ctcggtggag tgggagaaga cgggaaggc agaggacaac    1140 tacaagacca cgccggccgt gctggacagc gacggctcct acttcctcta cagcaagctc    1200
```

```
tcagtgccca cgagtgagtg gcagcggggc gacgtcttca cctgctccgt gatgcacgag    1260
gccttgcaca accactacac gcagaagtcc atctcccgct ctccgggtaa atga          1314
```

<210> SEQ ID NO 10
<211> LENGTH: 437
<212> TYPE: PRT
<213> ORGANISM: Artificial Sequence
<220> FEATURE:
<223> OTHER INFORMATION: chemically synthesized

<400> SEQUENCE: 10

```
Gln Ser Val Glu Glu Ser Gly Gly Arg Leu Val Met Pro Gly Gly Ser
1               5                   10                  15

Leu Thr Leu Thr Cys Thr Val Ser Gly Ile Asp Leu Ser His Tyr Gly
            20                  25                  30

Met Ala Trp Phe Arg Gln Ala Pro Gly Lys Gly Leu Glu Tyr Ile Gly
        35                  40                  45

Ala Ile Ser Ser Ser Gly Asn Glu Asp Tyr Ala Ser Trp Pro Lys Gly
    50                  55                  60

Arg Phe Thr Ile Ser Lys Thr Ser Thr Val Thr Leu Lys Met Thr
65                  70                  75                  80

Ser Leu Thr Thr Glu Asp Thr Ala Thr Tyr Phe Cys Gly Arg Gly Trp
                85                  90                  95

Leu Ser Asn Asn Val Tyr Met Trp Gly Pro Gly Thr Leu Val Thr Val
            100                 105                 110

Ser Ser Gly Gln Pro Lys Ala Pro Ser Val Phe Pro Leu Ala Pro Cys
        115                 120                 125

Cys Gly Asp Thr Pro Ser Ser Thr Val Thr Leu Gly Cys Leu Val Lys
    130                 135                 140

Gly Tyr Leu Pro Glu Pro Val Thr Val Thr Trp Asn Ser Gly Thr Leu
145                 150                 155                 160

Thr Asn Gly Val Arg Thr Phe Pro Ser Val Arg Gln Ser Ser Gly Leu
                165                 170                 175

Tyr Ser Leu Ser Ser Val Val Ser Val Thr Ser Ser Ser Gln Pro Val
            180                 185                 190

Thr Cys Asn Val Ala His Pro Ala Thr Asn Thr Lys Val Asp Lys Thr
        195                 200                 205

Val Ala Pro Ser Thr Cys Ser Lys Pro Thr Cys Pro Pro Pro Glu Leu
    210                 215                 220

Leu Gly Gly Pro Ser Val Phe Ile Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser Gln Asp Asp Pro Glu Val Gln Phe Thr Trp Tyr Ile Asn Asn Glu
            260                 265                 270

Gln Val Arg Thr Ala Arg Pro Pro Leu Arg Glu Gln Gln Phe Asn Ser
        275                 280                 285

Thr Ile Arg Val Val Ser Thr Leu Pro Ile Ala His Gln Asp Trp Leu
    290                 295                 300

Arg Gly Lys Glu Phe Lys Cys Lys Val His Asn Lys Ala Leu Pro Ala
305                 310                 315                 320

Pro Ile Glu Lys Thr Ile Ser Lys Ala Arg Gly Gln Pro Leu Glu Pro
                325                 330                 335

Lys Val Tyr Thr Met Gly Pro Pro Arg Glu Glu Leu Ser Ser Arg Ser
            340                 345                 350
```

```
Val Ser Leu Thr Cys Met Ile Asn Gly Phe Tyr Pro Ser Asp Ile Ser
        355                 360                 365

Val Glu Trp Glu Lys Asn Gly Lys Ala Glu Asp Asn Tyr Lys Thr Thr
        370                 375                 380

Pro Ala Val Leu Asp Ser Asp Gly Ser Tyr Phe Leu Tyr Ser Lys Leu
385                 390                 395                 400

Ser Val Pro Thr Ser Glu Trp Gln Arg Gly Asp Val Phe Thr Cys Ser
                405                 410                 415

Val Met His Glu Ala Leu His Asn His Tyr Thr Gln Lys Ser Ile Ser
            420                 425                 430

Arg Ser Pro Gly Lys
            435

<210> SEQ ID NO 11
<211> LENGTH: 651
<212> TYPE: DNA
<213> ORGANISM: Artificial Sequence
<220> FEATURE:
<223> OTHER INFORMATION: chemically synthesized

<400> SEQUENCE: 11
caagtgctga cccagactcc accctccgtg tctgcagctg tgggaggcac agtcaccatc      60
aattgccagg ccagtcaaag tatttataat aaaaatcaat tatcctggct tcagcagaaa     120
ccagggcagc ctcccaaggt cctgatccat tatgcatcca ctctggcatc tggggtctca     180
tcgcggttca aaggcagtgg atctgggaca cagttcactc tcaccatcag cgacgtgcag     240
tgtgacgatg ctgccactta ctactgtcta ggcgatttta gttgtagtgg tgttgattgt     300
ctttctgtcg gcggagggac cgaggtggtc gtcgaaggtg atccagttgc acctactgtc     360
ctcatcttcc caccatctgc tgatcttgtg caactggaa cagtcaccat cgtgtgtgtg     420
gcgaataaat actttcccga tgtcaccgtc acctgggagg tggatggcac acccaaaca     480 actggcatcg agaacagtaa acaccgcag aattctgcag attgtaccta caacctcagc     540
agcactctga cactgaccag cacacagtac aacagccaca agagtacac ctgcaaggtg     600 acccagggca cgacctcagt cgtccagagc ttcaataggg gtgactgtta g             651

<210> SEQ ID NO 12
<211> LENGTH: 216
<212> TYPE: PRT
<213> ORGANISM: Artificial Sequence
<220> FEATURE:
<223> OTHER INFORMATION: chemically synthesized

<400> SEQUENCE: 12

Gln Val Leu Thr Gln Thr Pro Pro Ser Val Ser Ala Ala Val Gly Gly
1               5                   10                  15

Thr Val Thr Ile Asn Cys Gln Ala Ser Gln Ser Ile Tyr Asn Lys Asn
            20                  25                  30

Gln Leu Ser Trp Leu Gln Gln Lys Pro Gly Gln Pro Pro Lys Val Leu
        35                  40                  45

Ile His Tyr Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Asp Phe Ser Cys Ser
                85                  90                  95
```

```
Gly Val Asp Cys Leu Ser Val Gly Gly Thr Glu Val Val Glu
            100                 105                 110

Gly Asp Pro Val Ala Pro Thr Val Leu Ile Phe Pro Ser Ala Asp
        115                 120                 125

Leu Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215

<210> SEQ ID NO 13
<211> LENGTH: 1311
<212> TYPE: DNA
<213> ORGANISM: Artificial Sequence
<220> FEATURE:
<223> OTHER INFORMATION: chemically synthesized

<400> SEQUENCE: 13
cagtcgctgg aggagtccgg gggtcacctg gtcacgcctg ggacacccct gacactcacc      60
tgcaaagcct ctggattctc cctcagtagc tactgcatga gctgggtccg ccaggctcca     120
gggaaggggc tggaatggat cggaatcatt ggtggtatct gtagcacata ctacgcagcc     180
tgggcgaaag gccgattcac catctccaaa acctcgacca cggtggatct gaaaatcgcc     240
agtccgacaa ccgaggacac ggccacctat ttctgtgcca gacctgctta taatagtgac     300
ccaatctggg gccaggcac cctggtcacc gtctcctcag gcaacctaa ggctccatca      360
gtcttcccac tggccccctg ctgcggggac acacccagct ccacggtgac cctgggctgc     420
ctggtcaaag gtaccctccc ggagccagtg accgtgacct ggaactcggg caccctcacc     480
aatggggtac gcaccttccc gtccgtccgg cagtcctcag gcctctactc gctgagcagc     540
gtggtgagcg tgacctcaag cagccagccc gtcacctgca acgtggccca cccagccacc     600
aacaccaaag tggacaagac cgttgcgccc tcgacatgca gcaagcccac gtgcccaccc     660
cctgaactcc tggggggacc gtctgtcttc atcttccccc caaaacccaa ggacacccte     720
atgatctcac gcaccccga ggtcacatgc gtggtggtgg acgtgagcca ggatgacccc     780
gaggtgcagt tcacatggta cataaacaac gagcaggtgc gcaccgcccg ccgccgccta     840
cgggagcagc agttcaacag cacgatccgc gtggtcagca ccctccccat cgcgcaccag     900
gactggctga gggcaagga gttcaagtgc aaagtccaca caaggcact cccggccccc     960
atcgagaaaa ccatctccaa agccagaggg cagcccctgg agccgaaggt ctacaccatg    1020
ggccctcccc gggaggagct gagcagcagg tcggtcagcc tgacctgcat gatcaacggc    1080
ttctacccct tccgacatctc ggtggagtgg gagaagaacg gaaggcaga ggacaactac    1140
aagaccacgc cggccgtgct ggacagcgac ggctcctact cctctacag caagctctca    1200
gtgcccacga gtgagtggca gcgggcgac gtcttcacct gctccgtgat gcacgaggcc    1260
ttgcacaacc actacacgca gaagtccatc tcccgctctc cgggtaaatg a              1311
```

<210> SEQ ID NO 14
<211> LENGTH: 436
<212> TYPE: PRT
<213> ORGANISM: Artificial Sequence
<220> FEATURE:
<223> OTHER INFORMATION: chemically synthesized

<400> SEQUENCE: 14

```
Gln Ser Leu Glu Glu Ser Gly Gly His Leu Val Thr Pro Gly Thr Pro
1               5                   10                  15

Leu Thr Leu Thr Cys Lys Ala Ser Gly Phe Ser Leu Ser Ser Tyr Cys
            20                  25                  30

Met Ser Trp Val Arg Gln Ala Pro Gly Lys Gly Leu Glu Trp Ile Gly
        35                  40                  45

Ile Ile Gly Gly Ile Cys Ser Thr Tyr Tyr Ala Ala Trp Ala Lys Gly
    50                  55                  60

Arg Phe Thr Ile Ser Lys Thr Ser Thr Val Asp Leu Lys Ile Ala
65                  70                  75                  80

Ser Pro Thr Thr Glu Asp Thr Ala Thr Tyr Phe Cys Ala Arg Pro Ala
                85                  90                  95

Tyr Asn Ser Asp Pro Ile Trp Gly Pro Gly Thr Leu Val Thr Val Ser
            100                 105                 110

Ser Gly Gln Pro Lys Ala Pro Ser Val Phe Pro Leu Ala Pro Cys Cys
        115                 120                 125

Gly Asp Thr Pro Ser Ser Thr Val Thr Leu Gly Cys Leu Val Lys Gly
    130                 135                 140

Tyr Leu Pro Glu Pro Val Thr Val Thr Trp Asn Ser Gly Thr Leu Thr
145                 150                 155                 160

Asn Gly Val Arg Thr Phe Pro Ser Val Arg Gln Ser Ser Gly Leu Tyr
                165                 170                 175

Ser Leu Ser Ser Val Val Ser Val Thr Ser Ser Gln Pro Val Thr
            180                 185                 190

Cys Asn Val Ala His Pro Ala Thr Asn Thr Lys Val Asp Lys Thr Val
        195                 200                 205

Ala Pro Ser Thr Cys Ser Lys Pro Thr Cys Pro Pro Pro Glu Leu Leu
    210                 215                 220

Gly Gly Pro Ser Val Phe Ile Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

Gln Asp Asp Pro Glu Val Gln Phe Thr Trp Tyr Ile Asn Asn Glu Gln
            260                 265                 270

Val Arg Thr Ala Arg Pro Pro Leu Arg Glu Gln Gln Phe Asn Ser Thr
        275                 280                 285

Ile Arg Val Val Ser Thr Leu Pro Ile Ala His Gln Asp Trp Leu Arg
    290                 295                 300

Gly Lys Glu Phe Lys Cys Lys Val His Asn Lys Ala Leu Pro Ala Pro
305                 310                 315                 320

Ile Glu Lys Thr Ile Ser Lys Ala Arg Gly Gln Pro Leu Glu Pro Lys
                325                 330                 335

Val Tyr Thr Met Gly Pro Pro Arg Glu Glu Leu Ser Ser Arg Ser Val
            340                 345                 350

Ser Leu Thr Cys Met Ile Asn Gly Phe Tyr Pro Ser Asp Ile Ser Val
        355                 360                 365

Glu Trp Glu Lys Asn Gly Lys Ala Glu Asp Asn Tyr Lys Thr Thr Pro
```

-continued

```
                    370                 375                 380
Ala Val Leu Asp Ser Asp Gly Ser Tyr Phe Leu Tyr Ser Lys Leu Ser
385                 390                 395                 400

Val Pro Thr Ser Glu Trp Gln Arg Gly Asp Val Phe Thr Cys Ser Val
                405                 410                 415

Met His Glu Ala Leu His Asn His Tyr Thr Gln Lys Ser Ile Ser Arg
                420                 425                 430

Ser Pro Gly Lys
            435
```

```
<210> SEQ ID NO 15
<211> LENGTH: 666
<212> TYPE: DNA
<213> ORGANISM: Artificial Sequence
<220> FEATURE:
<223> OTHER INFORMATION: chemically synthesized

<400> SEQUENCE: 15
caagtgctga cccagactcc atccctgtg tctgtagctg tgggaggcac agtcaccatc      60
aattgccagg ccagtcagag tgtttataat aacaactact tatcctggta tcagcagaaa    120
ccagggcagc ctcccaaagt cctgatctat gatgctgcca ctctggcatc tggggtctca    180
tcgcggttca gaggcagtgg atctgggaca cagttcactc tcaccatcag cgacgtgcag    240
tgtgacgatg ctgccactta ctactgtcta ggcgaattta gttgtggtag tgctgattgt    300
aatgctttcg gcggagggac cgaggtggtc gtcaaaggtg atccagttgc acctactgtc    360
ctcatcttcc caccagctgc tgatcaggtg gcaactggaa cagtcaccat cgtgtgtgtg    420
gcgaataaat actttcccga tgtcaccgtc acctgggagg tggatggcac cacccaaaca    480
actggcatcg agaacagtaa aaacaccgca gaattctgcag attgtaccta caacctcagc    540
agcactctga cactgaccag cacacagtac aacagccaca agagtacac ctgcaaggtg      600 acccagggca cgacctcagt cgtccagagc ttcaataggg gtgactgtta gagtgagagc    660
ggccgc                                                                666
```

```
<210> SEQ ID NO 16
<211> LENGTH: 216
<212> TYPE: PRT
<213> ORGANISM: Artificial Sequence
<220> FEATURE:
<223> OTHER INFORMATION: chemically synthesized

<400> SEQUENCE: 16

Gln Val Leu Thr Gln Thr Pro Ser Pro Val Ser Val Ala Val Gly Gly
1               5                   10                  15

Thr Val Thr Ile Asn Cys Gln Ala Ser Gln Ser Val Tyr Asn Asn Asn
            20                  25                  30

Tyr Leu Ser Trp Tyr Gln Gln Lys Pro Gly Gln Pro Pro Lys Val Leu
        35                  40                  45

Ile Tyr Asp Ala Ala Thr Leu Ala Ser Gly Val Ser Ser Arg Phe Arg
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Glu Phe Ser Cys Gly
                85                  90                  95

Ser Ala Asp Cys Asn Ala Phe Gly Gly Gly Thr Glu Val Val Val Lys
            100                 105                 110
```

```
Gly Asp Pro Val Ala Pro Thr Val Leu Ile Phe Pro Pro Ala Ala Asp
            115                 120                 125

Gln Val Ala Thr Gly Thr Val Thr Ile Val Cys Val Ala Asn Lys Tyr
        130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215

<210> SEQ ID NO 17
<211> LENGTH: 1439
<212> TYPE: DNA
<213> ORGANISM: Artificial Sequence
<220> FEATURE:
<223> OTHER INFORMATION: chemically synthesized

<400> SEQUENCE: 17
```

| | | | | | |
|---|---|---|---|---|---|
| aagcttgtac | ccttcaccat | ggagactggg | ctgcgctggc | ttctcctggt | cgctgtgctc | 60 |
| aaaggtgtcc | agtgtcagtc | gctgcaggag | tccggggggag | gcctgttcca | gcctggggga | 120 |
| tccctgacac | tcacctgcac | agcctctgga | ttctccctca | gtaattatgc | cgtgatgtgc | 180 |
| tgggtccgcc | aggctccagg | gaaggggctg | gagtggatcg | catgtattgt | tcttggtgat | 240 |
| ggtggtacta | cttattacgc | gagctgggcg | agaggccggt | tcaccatctc | caaaccctcg | 300 |
| tcgaccacgg | tgactctgca | aatgaccagt | ctgacggccg | cggacacggc | cacctatttc | 360 |
| tgtgcgagaa | gtttttgctgc | tagtagcccc | attaactact | ttaacttgtg | ggcccaggc | 420 |
| accctggtca | ccgtctcctc | agggcaacct | aaggctccat | cagtcttccc | actggccccc | 480 |
| tgctgcgggg | acacacccag | ctccacggtg | accctgggct | gcctggtcaa | agggtacctc | 540 |
| ccggagccag | tgaccgtgac | ctggaactcg | ggcaccctca | ccaatgggt | acgcaccttc | 600 |
| ccgtccgtcc | ggcagtcctc | aggcctctac | tcgctgagca | gcgtggtgag | cgtgacctca | 660 |
| agcagccagc | ccgtcacctg | caacgtggcc | cacccagcca | ccaacaccaa | agtggacaag | 720 |
| accgttgcgc | cctcgacatg | cagcaagccc | acgtgcccac | ccctgaact | cctgggggga | 780 |
| ccgtctgtct | tcatcttccc | cccaaaaccc | aaggacaccc | tcatgatctc | acgcaccccc | 840 |
| gaggtcacat | gcgtggtggt | ggacgtgagc | caggatgacc | ccgaggtgca | gttcacatgg | 900 |
| tacataaaca | acgagcaggt | gcgcaccgcc | cggccgccgc | tacgggagca | gcagttcaac | 960 |
| agcacgatcc | gcgtggtcag | caccctcccc | atcgcgcacc | aggactggct | gaggggcaag | 1020 |
| gagttcaagt | gcaaagtcca | caacaaggca | ctcccggccc | catcgagaa | aaccatctcc | 1080 |
| aaagccagag | ggcagcccct | ggagccgaag | gtctacacca | tgggccctcc | ccgggaggag | 1140 |
| ctgagcagca | ggtcggtcag | cctgacctgc | atgatcaacg | gcttctaccc | ttccgacatc | 1200 |
| tcggtggagt | gggagaagaa | cgggaaggca | gaggacaact | acaagaccac | gccgccgtg | 1260 |
| ctggacagcg | acggctccta | cttcctctac | agcaagctct | cagtgcccac | gagtgagtgg | 1320 |
| cagcggggcg | acgtcttcac | ctgctccgtg | atgcacgagg | ccttgcacaa | ccactacacg | 1380 |
| cagaagtcca | tctcccgctc | tccgggtaaa | tgagcgctgt | gccggcgagc | tgcggccgc | 1439 |

<210> SEQ ID NO 18
<211> LENGTH: 1395
<212> TYPE: DNA
<213> ORGANISM: Artificial Sequence
<220> FEATURE:
<223> OTHER INFORMATION: chemically synthesized

<400> SEQUENCE: 18

```
atggagactg ggctgcgctg gcttctcctg gtcgctgtgc tcaaaggtgt ccagtgtcag    60
tcgctgcagg agtccggggg aggcctgttc agcctggggg atccctgac actcacctgc    120
acagcctctg gattctccct cagtaattat gccgtgatgt gctgggtccg ccaggctcca    180
gggaagggc tggagtggat cgcatgtatt gttcttggtg atggtggtac tacttattac    240
gcgagctggg cgagaggccg gttcaccatc tccaaaccct cgtcgaccac ggtgactctg    300
caaatgacca gtctgacggc cgcggacacg gccacctatt tctgtgcgag aagttttgct    360
gctagtagcc ccattaacta ctttaacttg tggggcccag gcaccctggt caccgtctcc    420
tcagggcaac ctaaggctcc atcagtcttc ccactggccc cctgctgcgg ggacacaccc    480
agctccacgg tgaccctggg ctgcctggtc aaagggtacc tcccggagcc agtgaccgtg    540
acctggaact cgggcaccct caccaatggg gtacgcacct cccgtccgt ccggcagtcc    600
tcaggcctct actcgctgag cagcgtggtg agcgtgacct caagcagcca gcccgtcacc    660
tgcaacgtgg cccacccagc caccaacacc aaagtggaca gaccgttgc gccctcgaca    720
tgcagcaagc ccacgtgccc acccctgaa ctcctggggg gaccgtctgt cttcatcttc    780
cccccaaaac ccaaggacac cctcatgatc tcacgcaccc ccgaggtcac atgcgtggtg    840
gtggacgtga gccaggatga ccccgaggtg cagttcacat ggtacataaa caacgagcag    900
gtgcgcaccg cccggccgcc gctacgggag cagcagttca acagcacgat ccgcgtggtc    960
agcaccctcc ccatcgcgca ccaggactgg ctgagggca aggagttcaa gtgcaaagtc   1020
cacaacaagg cactccccgg ccccatcgag aaaaccatct ccaaagccag agggcagccc   1080
ctggagccga aggtctacac catgggccct ccccgggagg agctgagcag caggtcggtc   1140
agcctgacct gcatgatcaa cggcttctac ccttccgaca tctcggtgga gtgggagaag   1200
aacgggaagg cagaggacaa ctacaagacc acgccggccg tgctggacag cgacggctcc   1260
tacttcctct acagcaagct ctcagtgccc acgagtgagt ggcagcgggg cgacgtcttc   1320
acctgctccg tgatgcacga ggccttgcac aaccactaca cgcagaagtc catctcccgc   1380
tctccgggta atga                                                      1395
```

<210> SEQ ID NO 19
<211> LENGTH: 464
<212> TYPE: PRT
<213> ORGANISM: Artificial Sequence
<220> FEATURE:
<223> OTHER INFORMATION: chemically synthesized

<400> SEQUENCE: 19

```
Met Glu Thr Gly Leu Arg Trp Leu Leu Leu Val Ala Val Leu Lys Gly
1               5                   10                  15

Val Gln Cys Gln Ser Leu Gln Glu Ser Gly Gly Gly Leu Phe Gln Pro
            20                  25                  30

Gly Gly Ser Leu Thr Leu Thr Cys Thr Ala Ser Gly Phe Ser Leu Ser
        35                  40                  45

Asn Tyr Ala Val Met Cys Trp Val Arg Gln Ala Pro Gly Lys Gly Leu
    50                  55                  60
```

```
Glu Trp Ile Ala Cys Ile Val Leu Gly Asp Gly Thr Thr Tyr Tyr
 65                  70                  75                  80

Ala Ser Trp Ala Arg Gly Arg Phe Thr Ile Ser Lys Pro Ser Ser Thr
                 85                  90                  95

Thr Val Thr Leu Gln Met Thr Ser Leu Thr Ala Ala Asp Thr Ala Thr
            100                 105                 110

Tyr Phe Cys Ala Arg Ser Phe Ala Ala Ser Pro Ile Asn Tyr Phe
        115                 120                 125

Asn Leu Trp Gly Pro Gly Thr Leu Val Thr Val Ser Ser Gly Gln Pro
130                 135                 140

Lys Ala Pro Ser Val Phe Pro Leu Ala Pro Cys Cys Gly Asp Thr Pro
145                 150                 155                 160

Ser Ser Thr Val Thr Leu Gly Cys Leu Val Lys Gly Tyr Leu Pro Glu
                165                 170                 175

Pro Val Thr Val Thr Trp Asn Ser Gly Thr Leu Thr Asn Gly Val Arg
                180                 185                 190

Thr Phe Pro Ser Val Arg Gln Ser Ser Gly Leu Tyr Ser Leu Ser Ser
        195                 200                 205

Val Val Ser Val Thr Ser Ser Ser Gln Pro Val Thr Cys Asn Val Ala
210                 215                 220

His Pro Ala Thr Asn Thr Lys Val Asp Lys Thr Val Ala Pro Ser Thr
225                 230                 235                 240

Cys Ser Lys Pro Thr Cys Pro Pro Glu Leu Leu Gly Gly Pro Ser
                245                 250                 255

Val Phe Ile Phe Pro Pro Lys Pro Lys Asp Thr Leu Met Ile Ser Arg
                260                 265                 270

Thr Pro Glu Val Thr Cys Val Val Val Asp Val Ser Gln Asp Asp Pro
        275                 280                 285

Glu Val Gln Phe Thr Trp Tyr Ile Asn Asn Glu Gln Val Arg Thr Ala
        290                 295                 300

Arg Pro Pro Leu Arg Glu Gln Gln Phe Asn Ser Thr Ile Arg Val Val
305                 310                 315                 320

Ser Thr Leu Pro Ile Ala His Gln Asp Trp Leu Arg Gly Lys Glu Phe
                325                 330                 335

Lys Cys Lys Val His Asn Lys Ala Leu Pro Ala Pro Ile Glu Lys Thr
                340                 345                 350

Ile Ser Lys Ala Arg Gly Gln Pro Leu Glu Pro Lys Val Tyr Thr Met
        355                 360                 365

Gly Pro Pro Arg Glu Glu Leu Ser Ser Arg Ser Val Ser Leu Thr Cys
        370                 375                 380

Met Ile Asn Gly Phe Tyr Pro Ser Asp Ile Ser Val Glu Trp Glu Lys
385                 390                 395                 400

Asn Gly Lys Ala Glu Asp Asn Tyr Lys Thr Thr Pro Ala Val Leu Asp
                405                 410                 415

Ser Asp Gly Ser Tyr Phe Leu Tyr Ser Lys Leu Ser Val Pro Thr Ser
                420                 425                 430

Glu Trp Gln Arg Gly Asp Val Phe Thr Cys Ser Val Met His Glu Ala
        435                 440                 445

Leu His Asn His Tyr Thr Gln Lys Ser Ile Ser Arg Ser Pro Gly Lys
        450                 455                 460

<210> SEQ ID NO 20
<211> LENGTH: 744
```

<212> TYPE: DNA
<213> ORGANISM: Artificial Sequence
<220> FEATURE:
<223> OTHER INFORMATION: chemically synthesized

<400> SEQUENCE: 20

```
aagcttgtac ccttcaccat ggacacgagg gcccccactc agctgctggg gctcctgctg      60
ctctggctcc caggtgccac atttgcccaa gtgctgaccc agacttcatc ccccgtgtct     120
gcacctgtgg gaggcacagt caccatcaag tgccaggcca gtcagcgcat tagtacctac     180
ctagcctggt atcaacagaa accagggcag cctcccaagc tcctgatcta caaggcatcc     240
actctggcat ctggggtctc atcgcggttc aaaggcagtg catctgggac agagttcact     300
ctcaccatca acgacctgga gtgtgacgat gctgccactt actactgtca gagctattat     360
tttggtgatg gtactacttt tgctttcggc ggagggaccg aggtggtggt caaaggtgat     420
ccagttgcac ctactgtcct catcttccca ccagctgctg atcaggtggc aactggaaca     480
gtcaccatcg tgtgtgtggc gaataaatac tttcccgatg tcaccgtcac ctgggaggtg     540
gatggcacca cccaaacaac tggcatcgag aacagtaaaa caccgcagaa ttctgcagat     600
tgtacctaca acctcagcag cactctgaca ctgaccagca cacagtacaa cagccacaaa     660
gagtacacct gcaaggtgac ccagggcacg acctcagtcg tccagagctt caataggggt     720
gactgttaga gcgagagcgg ccgc                                            744
```

<210> SEQ ID NO 21
<211> LENGTH: 711
<212> TYPE: DNA
<213> ORGANISM: Artificial Sequence
<220> FEATURE:
<223> OTHER INFORMATION: chemically synthesized

<400> SEQUENCE: 21

```
atggacacga gggcccccac tcagctgctg gggctcctgc tgctctggct cccaggtgcc      60
acatttgccc aagtgctgac ccagacttca tccccgtgt ctgcacctgt gggaggcaca     120
gtcaccatca gtgccaggc cagtcagcgc attagtacct acctagcctg gtatcaacag     180
aaaccagggc agcctcccaa gctcctgatc tacaaggcat ccactctggc atctggggtc     240
tcatcgcggt tcaaaggcag tgcatctggg acagagttca ctctcaccat caacgacctg     300
gagtgtgacg atgctgccac ttactactgt cagagctatt attttggtga tggtactact     360
tttgctttcg gcggagggac cgaggtggtg gtcaaaggtg atccagttgc acctactgtc     420
ctcatcttcc caccagctgc tgatcaggtg gcaactggaa cagtcaccat cgtgtgtgtg     480
gcgaataaat actttcccga tgtcaccgtc acctgggagg tggatggcac acccaaaca     540
actggcatcg agaacagtaa aacaccgcag aattctgcag attgtaccta caacctcagc     600
agcactctga cactgaccag cacacagtac aacagccaca agagtacac ctgcaaggtg     660
acccagggca cgacctcagt cgtccagagc ttcaataggg gtgactgtta g              711
```

<210> SEQ ID NO 22
<211> LENGTH: 236
<212> TYPE: PRT
<213> ORGANISM: Artificial Sequence
<220> FEATURE:
<223> OTHER INFORMATION: chemically synthesized

<400> SEQUENCE: 22

```
Met Asp Thr Arg Ala Pro Thr Gln Leu Leu Gly Leu Leu Leu Leu Trp
1               5                   10                  15
```

Leu Pro Gly Ala Thr Phe Ala Gln Val Leu Thr Gln Thr Ser Ser Pro
            20                  25                  30

Val Ser Ala Pro Val Gly Gly Thr Val Thr Ile Lys Cys Gln Ala Ser
        35                  40                  45

Gln Arg Ile Ser Thr Tyr Leu Ala Trp Tyr Gln Lys Pro Gly Gln
 50                  55                  60

Pro Pro Lys Leu Leu Ile Tyr Lys Ala Ser Thr Leu Ala Ser Gly Val
65                  70                  75                  80

Ser Ser Arg Phe Lys Gly Ser Ala Ser Gly Thr Glu Phe Thr Leu Thr
                85                  90                  95

Ile Asn Asp Leu Glu Cys Asp Asp Ala Ala Thr Tyr Tyr Cys Gln Ser
            100                 105                 110

Tyr Tyr Phe Gly Asp Gly Thr Thr Phe Ala Phe Gly Gly Gly Thr Glu
        115                 120                 125

Val Val Val Lys Gly Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235

<210> SEQ ID NO 23
<211> LENGTH: 1415
<212> TYPE: DNA
<213> ORGANISM: Artificial Sequence
<220> FEATURE:
<223> OTHER INFORMATION: chemically synthesized

<400> SEQUENCE: 23
aagcttgtac ccttcaccat ggagactggg ctgcgctggc ttctcctggt cgctgtgctc      60
aaaggtgtcc agtgtcagtc ggtggaggag tccgggggtc gtctggtcat gcctggagga     120
tccctgacac tcacctgtac agtctctgga atcgacctca gtcgctatgg aatgccctgg     180
ttccgccagg ctccagggaa ggggctgaaa tacatcggag ccattagtag tagtggtaat     240
gaagactacg cgagctgggc gataggccga tttaccatct ccaaaacctc gaccacggcg     300
gagctgaaaa tgaccagtct gacaaccgag gacacggcca cctatttctg tggcagaggt     360
tggcttagta taacgcttat tgtgggggc caggcaccc tggtcaccgt ctcgtcaggg       420
caacctaagg ctccatcagt cttcccactg gcccctgct gcgggacac acccagctcc      480 acggtgaccc tgggctgcct ggtcaaaggg tacctcccgg agccagtgac cgtgacctgg     540
aactcgggca cctcaccaa tggggtacgc accttcccgt ccgtcggca gtcctcaggc      600 ctctactcgc tgagcagcgt ggtgagcgtg acctcaagca gccagcccgt cacctgcaac     660
gtggcccacc cagccaccaa caccaaagtg gacaagaccg ttgcgccctc gacatgcagc     720
aagcccacgt gcccaccccc tgaactcctg gggggaccgt ctgtcttcat cttcccccca     780

```
aaacccaagg acaccctcat gatctcacgc accccgagg tcacatgcgt ggtggtggac    840
gtgagccagg atgaccccga ggtgcagttc acatggtaca taaacaacga gcaggtgcgc    900
accgcccggc cgccgctacg ggagcagcag ttcaacagca cgatccgcgt ggtcagcacc    960
ctccccatcg cgcaccagga ctggctgagg ggcaaggagt tcaagtgcaa agtccacaac   1020
aaggcactcc cggcccccat cgagaaaacc atctccaaag ccagagggca gcccctggag   1080
ccgaaggtct acaccatggg ccctcccgg gaggagctga gcagcaggtc ggtcagcctg   1140
acctgcatga tcaacggctt ctacccttcc gacatctcgg tggagtggga agaacgggg   1200 aaggcagagg acaactacaa gaccacgccg ccgtgctgg acagcgacgg ctcctacttc   1260
ctctacagca agctctcagt gcccacgagt gagtggcagc ggggcgacgt cttcacctgc   1320
tccgtgatgc acgaggcctt gcacaaccac tacacgcaga agtccatctc ccgctctccg   1380
ggtaaatgag cgctgtgccg gcgagctgcg gccgc                               1415
```

<210> SEQ ID NO 24
<211> LENGTH: 1371
<212> TYPE: DNA
<213> ORGANISM: Artificial Sequence
<220> FEATURE:
<223> OTHER INFORMATION: chemically synthesized

<400> SEQUENCE: 24

```
atggagactg ggctgcgctg gcttctcctg gtcgctgtgc tcaaaggtgt ccagtgtcag     60
tcggtggagg agtccggggg tcgtctggtc atgcctggag atccctgac actcacctgt    120 acagtctctg gaatcgacct cagtcgctat ggaatggcct ggttccgcca ggctccaggg    180
aaggggctga atacatcgg agccattagt agtagtggta atgaagacta cgcgagctgg    240
gcgataggcc gatttaccat ctccaaaacc tcgaccacgg cggagctgaa aatgaccagt    300
ctgacaaccg aggacacggc cacctatttc tgtggcagag gttggcttag taataacgct    360
tatatgtggg gccaggcac cctggtcacc gtctcgtcag gcaacctaa ggctccatca    420 gtcttcccac tggccccctg ctgcggggac acacccagct ccacggtgac cctgggctgc    480
ctggtcaaag ggtacctccc ggagccagtg accgtgacct ggaactcggg caccctcacc    540 aatgggtac gcaccttccc gtccgtccgg cagtcctcag gcctctactc gctgagcagc    600
gtggtgagcg tgacctcaag cagccagccc gtcacctgca acgtggccca cccagccacc    660
aacaccaaag tggacaagac cgttgcgccc tcgacatgca gcaagcccac gtgcccaccc    720
cctgaactcc tgggggggacc gtctgtcttc atcttcccc caaaacccaa ggacaccctc    780
atgatctcac gcacccccga ggtcacatgc gtggtggtgg acgtgagcca ggatgacccc    840
gaggtgcagt tcacatggta cataaacaac gagcaggtgc gcaccgcccg gccgccgcta    900
cgggagcagc agttcaacag cacgatccgc gtggtcagca ccctcccat cgcgcaccag    960 gactggctga gggcaagga gttcaagtgc aaagtccaca acaaggcact cccggccccc   1020
atcgagaaaa ccatctccaa agccagaggg cagcccctgg agccgaaggt ctacaccatg   1080
ggccctcccc gggaggagct gagcagcagg tcggtcagcc tgacctgcat gatcaacggc   1140
ttctaccctt ccgacatctc ggtggagtgg gagaagaacg ggaaggcaga ggacaactac   1200
aagaccacgc cggccgtgct ggacagcgac ggctcctact cctctacag caagctctca   1260 gtgcccacga gtgagtggca gcggggcgac gtcttcacct gctccgtgat gcacgaggcc   1320
ttgcacaacc actacacgca gaagtccatc tcccgctctc cgggtaaatg a            1371
```

-continued

```
<210> SEQ ID NO 25
<211> LENGTH: 456
<212> TYPE: PRT
<213> ORGANISM: Artificial Sequence
<220> FEATURE:
<223> OTHER INFORMATION: chemically synthesized

<400> SEQUENCE: 25

Met Glu Thr Gly Leu Arg Trp Leu Leu Leu Val Ala Val Leu Lys Gly
1               5                   10                  15

Val Gln Cys Gln Ser Val Glu Ser Gly Gly Arg Leu Val Met Pro
            20                  25                  30

Gly Gly Ser Leu Thr Leu Thr Cys Thr Val Ser Gly Ile Asp Leu Ser
                35                  40                  45

Arg Tyr Gly Met Ala Trp Phe Arg Gln Ala Pro Gly Lys Gly Leu Lys
    50                  55                  60

Tyr Ile Gly Ala Ile Ser Ser Gly Asn Glu Asp Tyr Ala Ser Trp
65                  70                  75                  80

Ala Ile Gly Arg Phe Thr Ile Ser Lys Thr Ser Thr Ala Glu Leu
                85                  90                  95

Lys Met Thr Ser Leu Thr Thr Glu Asp Thr Ala Thr Tyr Phe Cys Gly
            100                 105                 110

Arg Gly Trp Leu Ser Asn Asn Ala Tyr Met Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
```

```
                  370              375              380
Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455

<210> SEQ ID NO 26
<211> LENGTH: 753
<212> TYPE: DNA
<213> ORGANISM: Artificial Sequence
<220> FEATURE:
<223> OTHER INFORMATION: chemically synthesized

<400> SEQUENCE: 26
aagcttgtac ccttcaccat ggacacgagg gcccccactc agctgctggg gctcctgctg      60
ctctggctcc caggtgccac atttgccccg gtgctgaccc agactccaac gcccgtgtct     120
gcagctgtgg gaggcacagt caccatcaat tgccaggcca gtcaaagtat ttataataaa     180
aatcaattat cctggtttca gcagaaacca gggcagcctc caagctcct gatccattat      240 gcatccactc tggcatctgg ggtctcatcg cggttcaaag gcagtggatc tgggacacag     300
ttcactctca ccatcagcga cgtgcagtgt gacgatgctg ccacttacta ttgtctaggc     360
gattttagtt gtagtggtgt tgattgtctt gttgtcggcg gagggaccga ggtggtcgtc     420
gaaggtgatc cagttgcacc tactgtcctc atcttcccac catctgctga tcttgtggca     480
actggaacag tcaccatcgt gtgtgtggcg aataaatact ttcccgatgt caccgtcacc     540
tgggaggtgg atggcaccac ccaaacaact ggcatcgaga cagtaaaaac accgcagaat     600
tctgcagatt gtacctacaa cctcagcagc actctgacac tgaccagcac acaatacaac     660
agccacaaag agtacacctg caaggtgacc cagggcacga cctcagtcgt ccagagcttc     720 aatagggtg actgttagag cgagagcggc cgc                                   753

<210> SEQ ID NO 27
<211> LENGTH: 720
<212> TYPE: DNA
<213> ORGANISM: Artificial Sequence
<220> FEATURE:
<223> OTHER INFORMATION: chemically synthesized

<400> SEQUENCE: 27
atggacacga gggcccccac tcagctgctg ggctcctgc tgctctggct cccaggtgcc      60
acatttgccc cggtgctgac ccagactcca cgcccgtgt ctgcagctgt ggaggcaca     120 gtcaccatca attgccaggc cagtcaaagt atttataata aaaatcaatt atcctggttt     180
cagcagaaac cagggcagcc tcccaagctc ctgatccatt atgcatccac tctggcatct     240
ggggtctcat cgcggttcaa aggcagtgga tctgggacac agttcactct caccatcagc     300
gacgtgcagt gtgacgatgc tgccacttac tattgtctag gcgattttag ttgtagtggt     360
gttgattgtc ttgttgtcgg cggagggacc gaggtggtcg tcgaaggtga tccagttgca     420
cctactgtcc tcatcttccc accatctgct gatcttgtgg caactggaac agtcaccatc     480
```

```
gtgtgtgtgg cgaataaata ctttcccgat gtcaccgtca cctgggaggt ggatggcacc      540
acccaaacaa ctggcatcga gaacagtaaa acaccgcaga attctgcaga ttgtacctac      600
aacctcagca gcactctgac actgaccagc acacaataca acagccacaa agagtacacc      660
tgcaaggtga cccagggcac gacctcagtc gtccagagct tcaatagggg tgactgttag      720
```

<210> SEQ ID NO 28
<211> LENGTH: 239
<212> TYPE: PRT
<213> ORGANISM: Artificial Sequence
<220> FEATURE:
<223> OTHER INFORMATION: chemically synthesized

<400> SEQUENCE: 28

```
Met Asp Thr Arg Ala Pro Thr Gln Leu Leu Gly Leu Leu Leu Leu Trp
1               5                   10                  15

Leu Pro Gly Ala Thr Phe Ala Pro Val Leu Thr Gln Thr Pro Thr Pro
            20                  25                  30

Val Ser Ala Ala Val Gly Gly Thr Val Thr Ile Asn Cys Gln Ala Ser
        35                  40                  45

Gln Ser Ile Tyr Asn Lys Asn Gln Leu Ser Trp Phe Gln Gln Lys Pro
    50                  55                  60

Gly Gln Pro Pro Lys Leu Leu Ile His Tyr Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Asp Phe Ser Cys Ser Gly Val Asp Cys Leu Val Val Gly Gly
        115                 120                 125

Gly Thr Glu Val Val Val Glu Gly Asp Pro Val Ala Pro Thr Val Leu
130                 135                 140

Ile Phe Pro Pro Ser Ala Asp Leu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 29
<211> LENGTH: 1415
<212> TYPE: DNA
<213> ORGANISM: Artificial Sequence
<220> FEATURE:
<223> OTHER INFORMATION: chemically synthesized

<400> SEQUENCE: 29

```
aagcttgtac ccttcaccat ggagactggg ctgcgctggc ttctcctggt cgctgtgctc      60
aaaggtgtcc agtgtcagtc ggtggaggag tccggggggtc gtctggtcat gcctggagga     120
tccctgacac tcacctgcac agtctctgga atcgacctca gtcactatgg aatggcctgg     180
```

```
ttccgccagg ctccagggaa ggggctggaa tacatcggag ccattagtag tagtggtaat    240
gaagactacg cgagctggcc gaaaggccga ttcaccatct ccaaaacctc gaccacggtg    300
actctgaaaa tgaccagtct gacaaccgag gacacggcca cctatttctg tggcagaggt    360
tggcttagta ataatgttta tatgtggggc ccaggcaccc tggtcaccgt ctcgtcaggg    420
caacctaagg ctccatcagt cttcccactg gcccctgct gcggggacac acccagctcc    480
acggtgaccc tgggctgcct ggtcaaaggg tacctcccgg agccagtgac cgtgacctgg    540
aactcgggca ccctcaccaa tggggtacgc accttcccgt ccgtccggca gtcctcaggc    600
ctctactcgc tgagcagcgt ggtgagcgtg acctcaagca gccagcccgt cacctgcaac    660
gtggcccacc cagccaccaa caccaaagtg gacaagaccg ttgcgccctc gacatgcagc    720
aagcccacgt gcccaccccc tgaactcctg ggggaccgt ctgtcttcat cttccccca    780 aaacccaagg acaccctcat gatctcacgc acccccgagg tcacatgcgt ggtggtggac    840
gtgagccagg atgaccccga ggtgcagttc acatggtaca aaacaacga gcaggtgcgc    900 accgcccggc cgccgctacg ggagcagcag ttcaacagca cgatccgcgt ggtcagcacc    960
ctccccatcg cgcaccagga ctggctgagg ggcaaggagt tcaagtgcaa agtccacaac   1020
aaggcactcc cggcccccat cgagaaaacc atctccaaag ccagagggca gcccctggag   1080
ccgaaggtct acaccatggg ccctccccgg gaggagctga gcagcaggtc ggtcagcctg   1140
acctgcatga tcaacggctt ctaccttcc gacatctcgg tggagtggga agaacggg    1200 aaggcagagg acaactacaa gaccacgccg gccgtgctgg acagcgacgg ctcctacttc   1260
ctctacagca agctctcagt gcccacgagt gagtggcagc ggggcgacgt cttcacctgc   1320
tccgtgatgc acgaggcctt gcacaaccac tacacgcaga agtccatctc ccgctctccg   1380
ggtaaatgag cgctgtgccg gcgagctgcg gccgc                              1415

<210> SEQ ID NO 30
<211> LENGTH: 1371
<212> TYPE: DNA
<213> ORGANISM: Artificial Sequence
<220> FEATURE:
<223> OTHER INFORMATION: chemically synthesized

<400> SEQUENCE: 30
atggagactg gctgcgctg gcttctcctg gtcgctgtgc tcaaaggtgt ccagtgtcag     60
tcggtggagg agtccggggg tcgtctggtc atgcctggag gatccctgac actcacctgc    120
acagtctctg gaatcgacct cagtcactat ggaatggcct ggttccgcca ggctccaggg    180
aaggggctgg aatacatcgg agccattagt agtagtggta tgaagactga cgcgagctgg    240
ccgaaaggcc gattcaccat ctccaaaacc tcgaccacgg tgactctgaa atgaccagt    300 ctgacaaccg aggacacggc cacctatttc tgtggcagag gttggcttag taataatgtt    360
tatatgtggg gcccaggcac cctggtcacc gtctcgtcag gcaacctaa ggctccatca    420 gtcttcccac tggcccctg ctgcggggac acacccagct ccacggtgac cctgggctgc    480
ctggtcaaag ggtacctccc ggagccagtg accgtgacct ggaactcggg caccctcacc    540
aatggggtac gcaccttccc gtccgtccgg cagtcctcag gcctctactc gctgagcagc    600
gtggtgagcg tgacctcaag cagccagccc gtcacctgca acgtggccca cccagccacc    660
aacaccaaag tggacaagac cgttgcgccc tcgacatgca gcaagcccac gtgcccaccc    720
cctgaactcc tgggggacc gtctgtcttc atcttccccc caaaacccaa ggacaccctc    780
atgatctcac gcaccccga ggtcacatgc gtggtggtgg acgtgagcca ggatgacccc    840
```

-continued

```
gaggtgcagt tcacatggta cataaacaac gagcaggtgc gcaccgcccg gccgccgcta      900
cgggagcagc agttcaacag cacgatccgc gtggtcagca ccctccccat cgcgcaccag      960
gactggctga ggggcaagga gttcaagtgc aaagtccaca acaaggcact cccggccccc     1020
atcgagaaaa ccatctccaa agccagaggg cagcccctgg agccgaaggt ctacaccatg     1080
ggccctcccc gggaggagct gagcagcagg tcggtcagcc tgacctgcat gatcaacggc     1140
ttctacccct tccgacatct cggtggagtgg gagaagaacg ggaaggcaga ggacaactac     1200
aagaccacgc cggccgtgct ggacagcgac ggctcctact tcctctacag caagctctca     1260
gtgcccacga gtgagtggca gcggggcgac gtcttcacct gctccgtgat gcacgaggcc     1320
ttgcacaacc actacacgca gaagtccatc tcccgctctc cgggtaaatg a              1371
```

<210> SEQ ID NO 31
<211> LENGTH: 456
<212> TYPE: PRT
<213> ORGANISM: Artificial Sequence
<220> FEATURE:
<223> OTHER INFORMATION: chemically synthesized

<400> SEQUENCE: 31

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Met Pro
            20                  25                  30

Gly Gly Ser Leu Thr Leu Thr Cys Thr Val Ser Gly Ile Asp Leu Ser
        35                  40                  45

His Tyr Gly Met Ala Trp Phe Arg Gln Ala Pro Gly Lys Gly Leu Glu
    50                  55                  60

Tyr Ile Gly Ala Ile Ser Ser Ser Gly Asn Glu Asp Tyr Ala Ser Trp
65                  70                  75                  80

Pro Lys Gly Arg Phe Thr Ile Ser Lys Thr Ser Thr Thr Val Thr Leu
                85                  90                  95

Lys Met Thr Ser Leu Thr Thr Glu Asp Thr Ala Thr Tyr Phe Cys Gly
            100                 105                 110

Arg Gly Trp Leu Ser Asn Asn Val Tyr Met Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270
```

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455

<210> SEQ ID NO 32
<211> LENGTH: 753
<212> TYPE: DNA
<213> ORGANISM: Artificial Sequence
<220> FEATURE:
<223> OTHER INFORMATION: chemically synthesized

<400> SEQUENCE: 32
aagcttgtac ccttcaccat ggacacgagg gcccccactc agctgctggg gctcctgctg    60
ctctggctcc caggtgccac atttgccaa gtgctgaccc agactccacc ctccgtgtct   120
gcagctgtgg gaggcacagt caccatcaat tgccaggcca gtcaaagtat ttataataaa   180
aatcaattat cctggcttca gcagaaacca gggcagcctc ccaaggtcct gatccattat   240
gcatccactc tggcatctgg ggtctcatcg cggttcaaag gcagtggatc tgggacacag   300
ttcactctca ccatcagcga cgtgcagtgt gacgatgctg ccacttacta ctgtctaggc   360
gattttagtt gtagtggtgt tgattgtctt tctgtcggcg agggaccga ggtggtcgtc   420 gaaggtgatc cagttgcacc tactgtcctc atcttcccac catctgctga tcttgtggca   480
actggaacag tcaccatcgt gtgtgtggcg aataaatact ttcccgatgt caccgtcacc   540
tgggaggtgg atggcaccac ccaaacaact ggcatcgaga acagtaaaac accgcagaat   600
tctgcagatt gtacctacaa cctcagcagc actctgacac tgaccagcac acagtacaac   660
agccacaaag agtacacctg caaggtgacc cagggcacga cctcagtcgt ccagagcttc   720 aatagggtg actgttagag cgagagcggc cgc   753

<210> SEQ ID NO 33
<211> LENGTH: 720
<212> TYPE: DNA
<213> ORGANISM: Artificial Sequence
<220> FEATURE:

<223> OTHER INFORMATION: chemically synthesized

<400> SEQUENCE: 33

```
atggacacga gggcccccac tcagctgctg gggctcctgc tgctctggct cccaggtgcc    60
acatttgccc aagtgctgac ccagactcca ccctccgtgt ctgcagctgt gggaggcaca   120
gtcaccatca attgccaggc cagtcaaagt atttataata aaatcaatt atcctggctt   180
cagcagaaac cagggcagcc tcccaaggtc ctgatccatt atgcatccac tctggcatct   240
ggggtctcat cgcggttcaa aggcagtgga tctgggacac agttcactct caccatcagc   300
gacgtgcagt gtgacgatgc tgccacttac tactgtctag cgattttag ttgtagtggt   360
gttgattgtc tttctgtcgg cggagggacc gaggtggtcg tcgaaggtga tccagttgca   420
cctactgtcc tcatcttccc accatctgct gatcttgtgg caactggaac agtcaccatc   480
gtgtgtgtgg cgaataaata ctttcccgat gtcaccgtca cctgggaggt ggatggcacc   540
acccaaacaa ctggcatcga aacagtaaaa acaccgcaga attctgcaga ttgtacctac   600
aacctcagca gcactctgac actgaccagc acacagtaca cagccacaa agagtacacc   660
tgcaaggtga cccagggcac gacctcagtc gtccagagct caataggggt gactgttag   720
```

<210> SEQ ID NO 34
<211> LENGTH: 239
<212> TYPE: PRT
<213> ORGANISM: Artificial Sequence
<220> FEATURE:
<223> OTHER INFORMATION: chemically synthesized

<400> SEQUENCE: 34

```
Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Pro Pro Ser
            20                  25                  30

Val Ser Ala Ala Val Gly Gly Thr Val Thr Ile Asn Cys Gln Ala Ser
        35                  40                  45

Gln Ser Ile Tyr Asn Lys Asn Gln Leu Ser Trp Leu Gln Gln Lys Pro
    50                  55                  60

Gly Gln Pro Pro Lys Val Leu Ile His Tyr Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Asp Phe Ser Cys Ser Gly Val Asp Cys Leu Ser Val Gly Gly
        115                 120                 125

Gly Thr Glu Val Val Val Glu Gly Asp Pro Val Ala Pro Thr Val Leu
    130                 135                 140

Ile Phe Pro Pro Ser Ala Asp Leu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220
```

Gln Gly Thr Thr Ser Val Val Gln Ser Phe Asn Arg Gly Asp Cys
225                 230                 235

<210> SEQ ID NO 35
<211> LENGTH: 1412
<212> TYPE: DNA
<213> ORGANISM: Artificial Sequence
<220> FEATURE:
<223> OTHER INFORMATION: chemically synthesized

<400> SEQUENCE: 35

| | | | | |
|---|---|---|---|---|
| aagcttgtac | ccttcaccat | ggagactggg | ctgcgctggc | ttctcctggt | cgctgtgctc | 60 |
| aaaggtgtcc | agtgtcagtc | gctggaggag | tccggggggtc | acctggtcac | gcctgggaca | 120 |
| cccctgacac | tcacctgcaa | agcctctgga | ttctccctca | gtagctactg | catgagctgg | 180 |
| gtccgccagg | ctccagggaa | ggggctggaa | tggatcggaa | tcattggtgg | tatctgtagc | 240 |
| acatactacg | cagcctgggc | gaaaggccga | ttcaccatct | ccaaaacctc | gaccacggtg | 300 |
| gatctgaaaa | tcgccagtcc | gacaaccgag | gacacggcca | cctatttctg | tgccagacct | 360 |
| gcttataata | gtgacccaat | ctggggccca | ggcaccctgg | tcaccgtctc | ctcagggcaa | 420 |
| cctaaggctc | catcagtctt | cccactggcc | cctgctgcg | ggacacacc | cagctccacg | 480 |
| gtgaccctgg | gctgcctggt | caaagggtac | ctcccggagc | cagtgaccgt | gacctggaac | 540 |
| tcgggcaccc | tcaccaatgg | ggtacgcacc | ttccgtccg | tccggcagtc | ctcaggcctc | 600 |
| tactcgctga | gcagcgtggt | gagcgtgacc | tcaagcagcc | agcccgtcac | ctgcaacgtg | 660 |
| gcccacccag | ccaccaacac | caaagtggac | aagaccgttg | cgccctcgac | atgcagcaag | 720 |
| cccacgtgcc | caccccctga | actcctgggg | ggaccgtctg | tcttcatctt | ccccccaaaa | 780 |
| cccaaggaca | ccctcatgat | ctcacgcacc | cccgaggtca | catgcgtggt | ggtggacgtg | 840 |
| agccaggatg | accccgaggt | gcagttcaca | tggtacataa | caacgagca | ggtgcgcacc | 900 |
| gcccggccgc | cgctacggga | gcagcagttc | aacagcacga | tccgcgtggt | cagcacctc | 960 |
| cccatcgcgc | accaggactg | gctgaggggc | aaggagttca | agtgcaaagt | ccacaacaag | 1020 |
| gcactcccgg | cccccatcga | gaaaaccatc | tccaaagcca | gagggcagcc | cctggagccg | 1080 |
| aaggtctaca | ccatgggccc | tccccgggag | gagctgagca | gcaggtcggt | cagcctgacc | 1140 |
| tgcatgatca | acggcttcta | cccttccgac | atctcggtgg | agtgggagaa | gaacgggaag | 1200 |
| gcagaggaca | actacaagac | cacgccggcc | gtgctggaca | gcgacggctc | ctacttcctc | 1260 |
| tacagcaagc | tctcagtgcc | cacgagtgag | tggcagcggg | gcgacgtctt | cacctgctcc | 1320 |
| gtgatgcacg | aggccttgca | caaccactac | acgcagaagt | ccatctcccg | ctctccgggt | 1380 |
| aaatgagcgc | tgtgccggcg | agctgcggcc | gc | | | 1412 |

<210> SEQ ID NO 36
<211> LENGTH: 1368
<212> TYPE: DNA
<213> ORGANISM: Artificial Sequence
<220> FEATURE:
<223> OTHER INFORMATION: chemically synthesized

<400> SEQUENCE: 36

| | | | | |
|---|---|---|---|---|
| atggagactg | ggctgcgctg | gcttctcctg | gtcgctgtgc | tcaaaggtgt | ccagtgtcag | 60 |
| tcgctggagg | agtccggggg | gtcacctggt | cacgcctggg | acacccctga | cactcacctg | 120 |
| caaagcctctg | gattctccct | cagtagctac | tgcatgagct | gggtccgcca | ggctccaggg | 180 |
| aagggggctgg | aatggatcgg | aatcattggt | ggtatctgta | gcacatacta | cgcagcctgg | 240 |

```
gcgaaaggcc gattcaccat ctccaaaacc tcgaccacgg tggatctgaa aatcgccagt    300
ccgacaaccg aggacacggc cacctatttc tgtgccagac ctgcttataa tagtgaccca    360
atctggggcc caggcaccct ggtcaccgtc tcctcagggc aacctaaggc tccatcagtc    420
ttcccactgg cccccgctg cggggacaca cccagctcca cggtgaccct gggctgcctg     480
gtcaaagggt acctcccgga gccagtgacc gtgacctgga actcgggcac cctcaccaat    540
ggggtacgca ccttcccgtc cgtccggcag tcctcaggcc tctactcgct gagcagcgtg    600
gtgagcgtga cctcaagcag ccagcccgtc acctgcaacg tggcccaccc agccaccaac    660
accaaagtgg acaagaccgt tgcgccctcg acatgcagca gcccacgtg cccacccccct    720 gaactcctgg ggggaccgtc tgtcttcatc ttccccccaa acccaagga caccctcatg     780 atctcacgca cccccgaggt cacatgcgtg gtggtggacg tgagccagga tgaccccgag    840
gtgcagttca catggtacat aaacaacgag caggtgcgca ccgcccggcc gccgctacgg    900
gagcagcagt tcaacagcac gatccgcgtg tcagcaccc tccccatcgc gcaccaggac     960
tggctgaggg gcaaggagtt caagtgcaaa gtccacaaca aggcactccc ggcccccatc    1020
gagaaaacca tctccaaagc cagagggcag cccctggagc cgaaggtcta ccatgggc     1080 cctccccggg aggagctgag cagcaggtcg gtcagcctga cctgcatgat caacggcttc    1140 taccttccg acatctcggt ggagtgggag aagaacggga aggcagagga caactacaag     1200
accacgccgg ccgtgctgga cagcgacggc tcctacttcc tctacagcaa gctctcagtg    1260
cccacgagtg agtggcagcg gggcgacgtc ttcacctgct ccgtgatgca cgaggccttg    1320
cacaaccact acacgcagaa gtccatctcc cgctctccgg gtaaatga                 1368
```

<210> SEQ ID NO 37
<211> LENGTH: 455
<212> TYPE: PRT
<213> ORGANISM: Artificial Sequence
<220> FEATURE:
<223> OTHER INFORMATION: chemically synthesized

<400> SEQUENCE: 37

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly His Leu Val Thr Pro
            20                  25                  30

Gly Thr Pro Leu Thr Leu Thr Cys Lys Ala Ser Gly Phe Ser Leu Ser
        35                  40                  45

Ser Tyr Cys Met Ser Trp Val Arg Gln Ala Pro Gly Lys Gly Leu Glu
    50                  55                  60

Trp Ile Gly Ile Ile Gly Gly Ile Cys Ser Thr Tyr Tyr Ala Ala Trp
65                  70                  75                  80

Ala Lys Gly Arg Phe Thr Ile Ser Lys Thr Ser Thr Thr Val Asp Leu
                85                  90                  95

Lys Ile Ala Ser Pro Thr Thr Glu Asp Thr Ala Thr Tyr Phe Cys Ala
            100                 105                 110

Arg Pro Ala Tyr Asn Ser Asp Pro Ile Trp Gly Pro Gly Thr Leu Val
        115                 120                 125

Thr Val Ser Ser Gly Gln Pro Lys Ala Pro Ser Val Phe Pro Leu Ala
    130                 135                 140

Pro Cys Cys Gly Asp Thr Pro Ser Ser Thr Val Thr Leu Gly Cys Leu
145                 150                 155                 160
```

```
Val Lys Gly Tyr Leu Pro Glu Pro Val Thr Val Trp Asn Ser Gly
            165                 170                 175

Thr Leu Thr Asn Gly Val Arg Thr Phe Pro Ser Val Arg Gln Ser Ser
        180                 185                 190

Gly Leu Tyr Ser Leu Ser Ser Val Val Ser Val Thr Ser Ser Ser Gln
        195                 200                 205

Pro Val Thr Cys Asn Val Ala His Pro Ala Thr Asn Thr Lys Val Asp
        210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
                260                 265                 270

Asp Val Ser Gln Asp Asp Pro Glu Val Gln Phe Thr Trp Tyr Ile Asn
            275                 280                 285

Asn Glu Gln Val Arg Thr Ala Arg Pro Pro Leu Arg Glu Gln Gln Phe
290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
                340                 345                 350

Glu Pro Lys Val Tyr Thr Met Gly Pro Pro Arg Glu Glu Leu Ser Ser
            355                 360                 365

Arg Ser Val Ser Leu Thr Cys Met Ile Asn Gly Phe Tyr Pro Ser Asp
370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
        435                 440                 445

Ile Ser Arg Ser Pro Gly Lys
        450                 455

<210> SEQ ID NO 38
<211> LENGTH: 753
<212> TYPE: DNA
<213> ORGANISM: Artificial Sequence
<220> FEATURE:
<223> OTHER INFORMATION: chemically synthesized

<400> SEQUENCE: 38
aagcttgtac ccttcaccat ggacacgagg gcccccactc agctgctggg gctcctgctg    60
ctctggctcc caggtgccac atttgcccaa gtgctgaccc agactccatc ccctgtgtct   120
gtagctgtgg gaggcacagt caccatcaat tgccaggcca gtcagagtgt ttataataac   180
aactacttat cctggtatca gcagaaacca gggcagcctc ccaaagtcct gatctatgat   240
gctgccactc tggcatctgg ggtctcatcg cggttcagag cagtggatc tgggacacag   300 ttcactctca ccatcagcga cgtgcagtgt gacgatgctg ccacttacta ctgtctaggc   360
```

```
gaatttagtt gtggtagtgc tgattgtaat gctttcggcg agggaccga ggtggtcgtc    420 aaaggtgatc cagttgcacc tactgtcctc atcttcccac cagctgctga tcaggtggca    480
actggaacag tcaccatcgt gtgtgtggcg aataaatact ttcccgatgt caccgtcacc    540
tgggaggtgg atggcaccac ccaaacaact ggcatcgaga acagtaaaac accgcagaat    600
tctgcagatt gtacctacaa cctcagcagc actctgacac tgaccagcac acagtacaac    660
agccacaaag gtacacctg caaggtgacc cagggcacga cctcagtcgt ccagagcttc    720 aatagggtg actgttagag tgagagcggc cgc    753
```

<210> SEQ ID NO 39
<211> LENGTH: 735
<212> TYPE: DNA
<213> ORGANISM: Artificial Sequence
<220> FEATURE:
<223> OTHER INFORMATION: chemically synthesized

<400> SEQUENCE: 39

```
atggacacga gggcccccac tcagctgctg gggctcctgc tgctctggct cccaggtgcc     60
acatttgccc aagtgctgac ccagactcca tcccctgtgt ctgtagctgt gggaggcaca    120
gtcaccatca attgccaggc cagtcagagt gtttataata acaactactt atcctggtat    180
cagcagaaac cagggcagcc tcccaaagtc ctgatctatg atgctgccac tctggcatct    240 gggtctcat cgcggttcag aggcagtgga tctgggacac agttcactct caccatcagc    300
gacgtgcagt gtgacgatgc tgccacttac tactgtctag gcgaatttag ttgtggtagt    360
gctgattgta atgctttcgg cggagggacc gaggtggtcg tcaaaggtga tccagttgca    420
cctactgtcc tcatcttccc accagctgct gatcaggtgg caactggaac agtcaccatc    480
gtgtgtgtgg cgaataaata ctttcccgat gtcaccgtca cctgggaggt ggatggcacc    540
acccaaacaa ctggcatcga aacagtaaa acaccgcaga attctgcaga ttgtacctac    600
aacctcagca gcactctgac actgaccagc acacagtaca acagccacaa agagtacacc    660
tgcaaggtga cccagggcac gacctcagtc gtccagagct caatagggg tgactgttag    720 agtgagagcg gccgc    735
```

<210> SEQ ID NO 40
<211> LENGTH: 239
<212> TYPE: PRT
<213> ORGANISM: Artificial Sequence
<220> FEATURE:
<223> OTHER INFORMATION: chemically synthesized

<400> SEQUENCE: 40

```
Met Asp Thr Arg Ala Pro Thr Gln Leu Leu Gly Leu Leu Leu Leu Trp
  1               5                  10                  15

Leu Pro Gly Ala Thr Phe Ala Gln Val Leu Thr Gln Thr Pro Ser Pro
             20                  25                  30

Val Ser Val Ala Val Gly Gly Thr Val Thr Ile Asn Cys Gln Ala Ser
         35                  40                  45

Gln Ser Val Tyr Asn Asn Asn Tyr Leu Ser Trp Tyr Gln Gln Lys Pro
     50                  55                  60

Gly Gln Pro Pro Lys Val Leu Ile Tyr Asp Ala Ala Thr Leu Ala Ser
 65                  70                  75                  80

Gly Val Ser Ser Arg Phe Arg Gly Ser Gly Ser Gly Thr Gln Phe Thr
             85                  90                  95

Leu Thr Ile Ser Asp Val Gln Cys Asp Asp Ala Ala Thr Tyr Tyr Cys
```

| | | 100 | | | 105 | | | 110 | | | |
|---|---|---|---|---|---|---|---|---|---|---|---|

Leu Gly Glu Phe Ser Cys Gly Ser Ala Asp Cys Asn Ala Phe Gly Gly
               115                   120                 125

Gly Thr Glu Val Val Lys Gly Asp Pro Val Ala Pro Thr Val Leu
    130                  135                 140

Ile Phe Pro Pro Ala Ala Asp Gln Val Ala Thr Gly Thr Val Thr Ile
145               150                 155               160

Val Cys Val Ala Asn Lys Tyr Phe Pro Asp Val Thr Val Thr Trp Glu
               165                 170               175

Val Asp Gly Thr Thr Gln Thr Thr Gly Ile Glu Asn Ser Lys Thr Pro
         180                  185               190

Gln Asn Ser Ala Asp Cys Thr Tyr Asn Leu Ser Ser Thr Leu Thr Leu
        195                  200               205

Thr Ser Thr Gln Tyr Asn Ser His Lys Glu Tyr Thr Cys Lys Val Thr
    210                  215               220

Gln Gly Thr Thr Ser Val Val Gln Ser Phe Asn Arg Gly Asp Cys
225               230                 235

<210> SEQ ID NO 41
<211> LENGTH: 366
<212> TYPE: DNA
<213> ORGANISM: Artificial Sequence
<220> FEATURE:
<223> OTHER INFORMATION: chemically synthesized

<400> SEQUENCE: 41

```
cagtcgctgc aggagtccgg gggaggcctg ttccagcctg ggggatccct gacactcacc      60
tgcacagcct ctggattctc cctcagtaat tatgccgtga gtgctgggt  ccgccaggct     120
ccagggaagg ggctggagtg gatcgcatgt attgttcttg gtgatggtgg tactacttat    180
tacgcgagct gggcgagagg ccggttcacc atctccaaac cctcgtcgac cacggtgact    240
ctgcaaatga ccagtctgac ggccgcggac acggccacct atttctgtgc gagaagtttt    300
gctgctagta gccccattaa ctactttaac ttgtggggcc aggcaccct  ggtcaccgtc    360
tcctca                                                               366
```

<210> SEQ ID NO 42
<211> LENGTH: 122
<212> TYPE: PRT
<213> ORGANISM: Artificial Sequence
<220> FEATURE:
<223> OTHER INFORMATION: chemically synthesized

<400> SEQUENCE: 42

Gln Ser Leu Gln Glu Ser Gly Gly Gly Leu Phe Gln Pro Gly Gly Ser
1               5                    10                15

Leu Thr Leu Thr Cys Thr Ala Ser Gly Phe Ser Leu Ser Asn Tyr Ala
         20                  25               30

Val Met Cys Trp Val Arg Gln Ala Pro Gly Lys Gly Leu Glu Trp Ile
        35                  40               45

Ala Cys Ile Val Leu Gly Asp Gly Gly Thr Thr Tyr Tyr Ala Ser Trp
    50                  55               60

Ala Arg Gly Arg Phe Thr Ile Ser Lys Pro Ser Ser Thr Thr Val Thr
65               70                 75               80

Leu Gln Met Thr Ser Leu Thr Ala Ala Asp Thr Ala Thr Tyr Phe Cys
         85                  90               95

Ala Arg Ser Phe Ala Ala Ser Ser Pro Ile Asn Tyr Phe Asn Leu Trp 100                 105                 110
Gly Pro Gly Thr Leu Val Thr Val Ser Ser
            115                 120

<210> SEQ ID NO 43
<211> LENGTH: 327
<212> TYPE: DNA
<213> ORGANISM: Artificial Sequence
<220> FEATURE:
<223> OTHER INFORMATION: chemically synthesized

<400> SEQUENCE: 43
caagtgctga cccagacttc atccccgtg tctgcacctg tgggaggcac agtcaccatc      60
aagtgccagg ccagtcagcg cattagtacc tacctagcct ggtatcaaca gaaaccaggg     120
cagcctccca agctcctgat ctacaaggca tccactctgg catctggggt ctcatcgcgg     180
ttcaaaggca gtgcatctgg gacagagttc actctcacca tcaacgacct ggagtgtgac     240
gatgctgcca cttactactg tcagagctat tattttggtg atggtactac ttttgctttc     300
ggcggaggga ccgaggtggt ggtcaaa                                         327

<210> SEQ ID NO 44
<211> LENGTH: 109
<212> TYPE: PRT
<213> ORGANISM: Artificial Sequence
<220> FEATURE:
<223> OTHER INFORMATION: chemically synthesized

<400> SEQUENCE: 44

Gln Val Leu Thr Gln Thr Ser Ser Pro Val Ser Ala Pro Val Gly Gly
1               5                   10                  15

Thr Val Thr Ile Lys Cys Gln Ala Ser Gln Arg Ile Ser Thr Tyr Leu
            20                  25                  30

Ala Trp Tyr Gln Gln Lys Pro Gly Gln Pro Pro Lys Leu Leu Ile Tyr
        35                  40                  45

Lys Ala Ser Thr Leu Ala Ser Gly Val Ser Ser Arg Phe Lys Gly Ser
    50                  55                  60

Ala Ser Gly Thr Glu Phe Thr Leu Thr Ile Asn Asp Leu Glu Cys Asp
65                  70                  75                  80

Asp Ala Ala Thr Tyr Tyr Cys Gln Ser Tyr Tyr Phe Gly Asp Gly Thr
                85                  90                  95

Thr Phe Ala Phe Gly Gly Gly Thr Glu Val Val Val Lys
            100                 105

<210> SEQ ID NO 45
<211> LENGTH: 8
<212> TYPE: PRT
<213> ORGANISM: Artificial Sequence
<220> FEATURE:
<223> OTHER INFORMATION: chemically synthesized

<400> SEQUENCE: 45

Ile Ser Ser Gly Leu Leu Ser Ser
1               5

<210> SEQ ID NO 46
<211> LENGTH: 8
<212> TYPE: PRT
<213> ORGANISM: Artificial Sequence
<220> FEATURE:
<223> OTHER INFORMATION: chemically synthesized

```
<400> SEQUENCE: 46

Gln Asn Gln Ala Leu Arg Met Ala
1               5

<210> SEQ ID NO 47
<211> LENGTH: 8
<212> TYPE: PRT
<213> ORGANISM: Artificial Sequence
<220> FEATURE:
<223> OTHER INFORMATION: chemically synthesized

<400> SEQUENCE: 47

Ala Gln Asn Leu Leu Gly Met Val
1               5

<210> SEQ ID NO 48
<211> LENGTH: 8
<212> TYPE: PRT
<213> ORGANISM: Artificial Sequence
<220> FEATURE:
<223> OTHER INFORMATION: chemically synthesized

<400> SEQUENCE: 48

Ser Thr Phe Pro Phe Gly Met Phe
1               5

<210> SEQ ID NO 49
<211> LENGTH: 8
<212> TYPE: PRT
<213> ORGANISM: Artificial Sequence
<220> FEATURE:
<223> OTHER INFORMATION: chemically synthesized

<400> SEQUENCE: 49

Pro Val Gly Tyr Thr Ser Ser Leu
1               5

<210> SEQ ID NO 50
<211> LENGTH: 8
<212> TYPE: PRT
<213> ORGANISM: Artificial Sequence
<220> FEATURE:
<223> OTHER INFORMATION: chemically synthesized

<400> SEQUENCE: 50

Asp Trp Leu Tyr Trp Pro Gly Ile
1               5

<210> SEQ ID NO 51
<211> LENGTH: 8
<212> TYPE: PRT
<213> ORGANISM: Artificial Sequence
<220> FEATURE:
<223> OTHER INFORMATION: chemically synthesized

<400> SEQUENCE: 51

Met Ile Ala Pro Val Ala Tyr Arg
1               5

<210> SEQ ID NO 52
<211> LENGTH: 8
<212> TYPE: PRT
<213> ORGANISM: Artificial Sequence
<220> FEATURE:
<223> OTHER INFORMATION: chemically synthesized

<400> SEQUENCE: 52
```

Arg Pro Ser Pro Met Trp Ala Tyr
1               5

<210> SEQ ID NO 53
<211> LENGTH: 8
<212> TYPE: PRT
<213> ORGANISM: Artificial Sequence
<220> FEATURE:
<223> OTHER INFORMATION: chemically synthesized

<400> SEQUENCE: 53

Trp Ala Thr Pro Arg Pro Met Arg
1               5

<210> SEQ ID NO 54
<211> LENGTH: 8
<212> TYPE: PRT
<213> ORGANISM: Artificial Sequence
<220> FEATURE:
<223> OTHER INFORMATION: chemically synthesized

<400> SEQUENCE: 54

Phe Arg Leu Leu Asp Trp Gln Trp
1               5

<210> SEQ ID NO 55
<211> LENGTH: 342
<212> TYPE: DNA
<213> ORGANISM: Artificial Sequence
<220> FEATURE:
<223> OTHER INFORMATION: chemically synthesized

<400> SEQUENCE: 55
cagtcggtgg aggagtccgg gggtcgtctg gtcatgcctg gaggatccct gacactcacc      60
tgtacagtct ctggaatcga cctcagtcgc tatggaatgg cctggttccg ccaggctcca     120
gggaaggggc tgaaatacat cggagccatt agtagtagtg gtaatgaaga ctacgcgagc     180
tgggcgatag gccgatttac catctccaaa acctcgacca cggcggagct gaaaatgacc     240
agtctgacaa ccgaggacac ggccacctat ttctgtggca gaggttggct tagtaataac     300
gcttatatgt ggggcccagg caccctggtc accgtctcgt ca                        342

<210> SEQ ID NO 56
<211> LENGTH: 114
<212> TYPE: PRT
<213> ORGANISM: Artificial Sequence
<220> FEATURE:
<223> OTHER INFORMATION: chemically synthesized

<400> SEQUENCE: 56

Gln Ser Val Glu Glu Ser Gly Gly Arg Leu Val Met Pro Gly Gly Ser
1               5                   10                  15

Leu Thr Leu Thr Cys Thr Val Ser Gly Ile Asp Leu Ser Arg Tyr Gly
            20                  25                  30

Met Ala Trp Phe Arg Gln Ala Pro Gly Lys Gly Leu Lys Tyr Ile Gly
        35                  40                  45

Ala Ile Ser Ser Ser Gly Asn Glu Asp Tyr Ala Ser Trp Ala Ile Gly
    50                  55                  60

Arg Phe Thr Ile Ser Lys Thr Ser Thr Thr Ala Glu Leu Lys Met Thr
65                  70                  75                  80

Ser Leu Thr Thr Glu Asp Thr Ala Thr Tyr Phe Cys Gly Arg Gly Trp
                85                  90                  95

Leu Ser Asn Asn Ala Tyr Met Trp Gly Pro Gly Thr Leu Val Thr Val
            100                 105                 110

Ser Ser

<210> SEQ ID NO 57
<211> LENGTH: 336
<212> TYPE: DNA
<213> ORGANISM: Artificial Sequence
<220> FEATURE:
<223> OTHER INFORMATION: chemically synthesized

<400> SEQUENCE: 57
ccggtgctga cccagactcc aacgcccgtg tctgcagctg tgggaggcac agtcaccatc      60
aattgccagg ccagtcaaag tatttataat aaaaatcaat tatcctggtt tcagcagaaa     120
ccagggcagc ctcccaagct cctgatccat tatgcatcca ctctggcatc tggggtctca     180
tcgcggttca aaggcagtgg atctgggaca cagttcactc tcaccatcag cgacgtgcag     240
tgtgacgatg ctgccactta ctattgtcta ggcgatttta gttgtagtgg tgttgattgt     300
cttgttgtcg gcgagggac cgaggtggtc gtcgaa                                336

<210> SEQ ID NO 58
<211> LENGTH: 112
<212> TYPE: PRT
<213> ORGANISM: Artificial Sequence
<220> FEATURE:
<223> OTHER INFORMATION: chemically synthesized

<400> SEQUENCE: 58

Pro Val Leu Thr Gln Thr Pro Thr Pro Val Ser Ala Ala Val Gly Gly
1               5                   10                  15

Thr Val Thr Ile Asn Cys Gln Ala Ser Gln Ser Ile Tyr Asn Lys Asn
            20                  25                  30

Gln Leu Ser Trp Phe Gln Gln Lys Pro Gly Gln Pro Pro Lys Leu Leu
        35                  40                  45

Ile His Tyr Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Asp Phe Ser Cys Ser
                85                  90                  95

Gly Val Asp Cys Leu Val Val Gly Gly Gly Thr Glu Val Val Val Glu
            100                 105                 110

<210> SEQ ID NO 59
<211> LENGTH: 342
<212> TYPE: DNA
<213> ORGANISM: Artificial Sequence
<220> FEATURE:
<223> OTHER INFORMATION: chemically synthesized

<400> SEQUENCE: 59
cagtcggtgg aggagtccgg gggtcgtctg gtcatgcctg gaggatccct gacactcacc      60
tgcacagtct ctggaatcga cctcagtcac tatggaatgg cctggttccg ccaggctcca     120
gggaaggggc tggaatacat cggagccatt agtagtagtg gtaatgaaga ctacgcgagc     180
tggccgaaag gccgattcac catctccaaa acctcgacca cggtgactct gaaaatgacc     240
agtctgacaa ccgaggacac ggccacctat ttctgtggca gaggttggct tagtaataat     300
gtttatatgt ggggcccagg caccctggtc accgtctcgt ca   342

<210> SEQ ID NO 60
<211> LENGTH: 114
<212> TYPE: PRT
<213> ORGANISM: Artificial Sequence
<220> FEATURE:
<223> OTHER INFORMATION: chemically synthesized

<400> SEQUENCE: 60

Gln Ser Val Glu Glu Ser Gly Gly Arg Leu Val Met Pro Gly Gly Ser
1               5                   10                  15

Leu Thr Leu Thr Cys Thr Val Ser Gly Ile Asp Leu Ser His Tyr Gly
            20                  25                  30

Met Ala Trp Phe Arg Gln Ala Pro Gly Lys Gly Leu Glu Tyr Ile Gly
        35                  40                  45

Ala Ile Ser Ser Ser Gly Asn Glu Asp Tyr Ala Ser Trp Pro Lys Gly
    50                  55                  60

Arg Phe Thr Ile Ser Lys Thr Ser Thr Val Thr Leu Lys Met Thr
65                  70                  75                  80

Ser Leu Thr Thr Glu Asp Thr Ala Thr Tyr Phe Cys Gly Arg Gly Trp
                85                  90                  95

Leu Ser Asn Asn Val Tyr Met Trp Gly Pro Gly Thr Leu Val Thr Val
            100                 105                 110

Ser Ser

<210> SEQ ID NO 61
<211> LENGTH: 336
<212> TYPE: DNA
<213> ORGANISM: Artificial Sequence
<220> FEATURE:
<223> OTHER INFORMATION: chemically synthesized

<400> SEQUENCE: 61
caagtgctga cccagactcc accctccgtg tctgcagctg tgggaggcac agtcaccatc   60
aattgccagg ccagtcaaag tatttataat aaaaatcaat tatcctggct tcagcagaaa   120
ccagggcagc ctcccaaggt cctgatccat tatgcatcca ctctggcatc tggggtctca   180
tcgcggttca aaggcagtgg atctgggaca cagttcactc tcaccatcag cgacgtgcag   240
tgtgacgatg ctgccactta ctactgtcta ggcgatttta gttgtagtgg tgttgattgt   300
ctttctgtcg gcggagggac cgaggtggtc gtcgaa   336

<210> SEQ ID NO 62
<211> LENGTH: 112
<212> TYPE: PRT
<213> ORGANISM: Artificial Sequence
<220> FEATURE:
<223> OTHER INFORMATION: chemically synthesized

<400> SEQUENCE: 62

Gln Val Leu Thr Gln Thr Pro Pro Ser Val Ser Ala Ala Val Gly Gly
1               5                   10                  15

Thr Val Thr Ile Asn Cys Gln Ala Ser Gln Ser Ile Tyr Asn Lys Asn
            20                  25                  30

Gln Leu Ser Trp Leu Gln Gln Lys Pro Gly Gln Pro Pro Lys Val Leu
        35                  40                  45

Ile His Tyr Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Asp Phe Ser Cys Ser
                85                  90                  95

Gly Val Asp Cys Leu Ser Val Gly Gly Thr Glu Val Val Glu
            100                 105                 110

<210> SEQ ID NO 63
<211> LENGTH: 339
<212> TYPE: DNA
<213> ORGANISM: Artificial Sequence
<220> FEATURE:
<223> OTHER INFORMATION: chemically synthesized

<400> SEQUENCE: 63
cagtcgctgg aggagtccgg gggtcacctg gtcacgcctg ggacacccct gacactcacc    60
tgcaaagcct ctggattctc cctcagtagc tactgcatga gctgggtccg ccaggctcca   120
gggaaggggc tggaatggat cggaatcatt ggtggtatct gtagcacata ctacgcagcc   180
tgggcgaaag gccgattcac catctccaaa acctcgacca cggtggatct gaaaatcgcc   240
agtccgacaa ccgaggacac ggccacctat ttctgtgcca gacctgctta taatagtgac   300
ccaatctggg gcccaggcac cctggtcacc gtctcctca                          339

<210> SEQ ID NO 64
<211> LENGTH: 113
<212> TYPE: PRT
<213> ORGANISM: Artificial Sequence
<220> FEATURE:
<223> OTHER INFORMATION: chemically synthesized

<400> SEQUENCE: 64

Gln Ser Leu Glu Glu Ser Gly Gly His Leu Val Thr Pro Gly Thr Pro
1               5                   10                  15

Leu Thr Leu Thr Cys Lys Ala Ser Gly Phe Ser Leu Ser Ser Tyr Cys
                20                  25                  30

Met Ser Trp Val Arg Gln Ala Pro Gly Lys Gly Leu Glu Trp Ile Gly
            35                  40                  45

Ile Ile Gly Gly Ile Cys Ser Thr Tyr Tyr Ala Ala Trp Ala Lys Gly
50                  55                  60

Arg Phe Thr Ile Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Pro Ala
                85                  90                  95

Tyr Asn Ser Asp Pro Ile Trp Gly Pro Gly Thr Leu Val Thr Val Ser
            100                 105                 110

Ser

<210> SEQ ID NO 65
<211> LENGTH: 336
<212> TYPE: DNA
<213> ORGANISM: Artificial Sequence
<220> FEATURE:
<223> OTHER INFORMATION: chemically synthesized

<400> SEQUENCE: 65
caagtgctga cccagactcc atcccctgtg tctgtagctg tgggaggcac agtcaccatc    60
aattgccagg ccagtcagag tgtttataat aacaactact atcctggta tcagcagaaa   120 ccagggcagc ctcccaaagt cctgatctat gatgctgcca ctctggcatc tggggtctca   180
tcgcggttca gaggcagtgg atctgggaca cagttcactc tcaccatcag cgacgtgcag    240
tgtgacgatg ctgccactta ctactgtcta ggcgaattta gttgtggtag tgctgattgt    300
aatgctttcg gcggagggac cgaggtggtc gtcaaa    336

```
<210> SEQ ID NO 66
<211> LENGTH: 112
<212> TYPE: PRT
<213> ORGANISM: Artificial Sequence
<220> FEATURE:
<223> OTHER INFORMATION: chemically synthesized

<400> SEQUENCE: 66
```

Gln Val Leu Thr Gln Thr Pro Ser Pro Val Ser Val Ala Val Gly Gly
1               5                   10                  15

Thr Val Thr Ile Asn Cys Gln Ala Ser Gln Ser Val Tyr Asn Asn Asn
            20                  25                  30

Tyr Leu Ser Trp Tyr Gln Gln Lys Pro Gly Gln Pro Pro Lys Val Leu
        35                  40                  45

Ile Tyr Asp Ala Ala Thr Leu Ala Ser Gly Val Ser Ser Arg Phe Arg
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Glu Phe Ser Cys Gly
                85                  90                  95

Ser Ala Asp Cys Asn Ala Phe Gly Gly Gly Thr Glu Val Val Val Lys
            100                 105                 110

```
<210> SEQ ID NO 67
<211> LENGTH: 6
<212> TYPE: PRT
<213> ORGANISM: Artificial Sequence
<220> FEATURE:
<223> OTHER INFORMATION: chemically synthesized

<400> SEQUENCE: 67
```

Asn Tyr Ala Val Met Cys
1               5

```
<210> SEQ ID NO 68
<211> LENGTH: 18
<212> TYPE: PRT
<213> ORGANISM: Artificial Sequence
<220> FEATURE:
<223> OTHER INFORMATION: chemically synthesized

<400> SEQUENCE: 68
```

Cys Ile Val Leu Gly Asp Gly Gly Thr Thr Tyr Tyr Ala Ser Trp Ala
1               5                   10                  15

Arg Gly

```
<210> SEQ ID NO 69
<211> LENGTH: 13
<212> TYPE: PRT
<213> ORGANISM: Artificial Sequence
<220> FEATURE:
<223> OTHER INFORMATION: chemically synthesized

<400> SEQUENCE: 69
```

Ser Phe Ala Ala Ser Ser Pro Ile Asn Tyr Phe Asn Leu
1               5                   10

```
<210> SEQ ID NO 70
<211> LENGTH: 11
<212> TYPE: PRT
<213> ORGANISM: Artificial Sequence
<220> FEATURE:
<223> OTHER INFORMATION: chemically synthesized

<400> SEQUENCE: 70

Gln Ala Ser Gln Arg Ile Ser Thr Tyr Leu Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: chemically synthesized

<400> SEQUENCE: 71

Lys Ala Ser Thr Leu Ala Ser
1               5

<210> SEQ ID NO 72
<211> LENGTH: 12
<212> TYPE: PRT
<213> ORGANISM: Artificial Sequence
<220> FEATURE:
<223> OTHER INFORMATION: chemically synthesized

<400> SEQUENCE: 72

Gln Ser Tyr Tyr Phe Gly Asp Gly Thr Thr Phe Ala
1               5                   10

<210> SEQ ID NO 73
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (6)..(6)
<223> OTHER INFORMATION: X is Ala or Ser

<400> SEQUENCE: 73

Asn Tyr Ala Val Met Xaa
1               5

<210> SEQ ID NO 74
<211> LENGTH: 18
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: X is Ala or Ser

<400> SEQUENCE: 74

Xaa Ile Val Leu Gly Asp Gly Gly Thr Thr Tyr Tyr Ala Ser Trp Ala
1               5                   10                  15

Arg Gly

<210> SEQ ID NO 75
<211> LENGTH: 464
<212> TYPE: PRT
```

```
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (54)..(54)
<223> OTHER INFORMATION: X is Ala or Ser
<220> FEATURE:
<221> NAME/KEY: MISC_FEATURE
<222> LOCATION: (69)..(69)
<223> OTHER INFORMATION: X is Ala or Ser

<400> SEQUENCE: 75
```

| | | | | | | | | | | | | | | |
|---|---|---|---|---|---|---|---|---|---|---|---|---|---|---|
| Met | Glu | Thr | Gly | Leu | Arg | Trp | Leu | Leu | Leu | Val | Ala | Val | Leu | Lys | Gly |
| 1 | | | | 5 | | | | | 10 | | | | | 15 | |
| Val | Gln | Cys | Gln | Ser | Leu | Gln | Glu | Ser | Gly | Gly | Gly | Leu | Phe | Gln | Pro |
| | | | 20 | | | | | 25 | | | | | 30 | | |
| Gly | Gly | Ser | Leu | Thr | Leu | Thr | Cys | Thr | Ala | Ser | Gly | Phe | Ser | Leu | Ser |
| | | 35 | | | | | 40 | | | | | 45 | | | |
| Asn | Tyr | Ala | Val | Met | Xaa | Trp | Val | Arg | Gln | Ala | Pro | Gly | Lys | Gly | Leu |
| | 50 | | | | 55 | | | | | 60 | | | | | |
| Glu | Trp | Ile | Ala | Xaa | Ile | Val | Leu | Gly | Asp | Gly | Thr | Thr | Tyr | Tyr |
| 65 | | | | 70 | | | | | 75 | | | | | 80 |
| Ala | Ser | Trp | Ala | Arg | Gly | Arg | Phe | Thr | Ile | Ser | Lys | Pro | Ser | Ser | Thr |
| | | | 85 | | | | | 90 | | | | | 95 | | |
| Thr | Val | Thr | Leu | Gln | Met | Thr | Ser | Leu | Thr | Ala | Ala | Asp | Thr | Ala | Thr |
| | | | 100 | | | | | 105 | | | | | 110 | | |
| Tyr | Phe | Cys | Ala | Arg | Ser | Phe | Ala | Ala | Ser | Ser | Pro | Ile | Asn | Tyr | Phe |
| | | | 115 | | | | | 120 | | | | | 125 | | |
| Asn | Leu | Trp | Gly | Pro | Gly | Thr | Leu | Val | Thr | Val | Ser | Ser | Gly | Gln | Pro |
| | 130 | | | | 135 | | | | | 140 | | | | | |
| Lys | Ala | Pro | Ser | Val | Phe | Pro | Leu | Ala | Pro | Cys | Cys | Gly | Asp | Thr | Pro |
| 145 | | | | 150 | | | | | 155 | | | | | 160 | |
| Ser | Ser | Thr | Val | Thr | Leu | Gly | Cys | Leu | Val | Lys | Gly | Tyr | Leu | Pro | Glu |
| | | | 165 | | | | | 170 | | | | | 175 | | |
| Pro | Val | Thr | Val | Thr | Trp | Asn | Ser | Gly | Thr | Leu | Thr | Asn | Gly | Val | Arg |
| | | | 180 | | | | | 185 | | | | | 190 | | |
| Thr | Phe | Pro | Ser | Val | Arg | Gln | Ser | Ser | Gly | Leu | Tyr | Ser | Leu | Ser | Ser |
| | | 195 | | | | | 200 | | | | | 205 | | | |
| Val | Val | Ser | Val | Thr | Ser | Ser | Ser | Gln | Pro | Val | Thr | Cys | Asn | Val | Ala |
| | 210 | | | | 215 | | | | | 220 | | | | | |
| His | Pro | Ala | Thr | Asn | Thr | Lys | Val | Asp | Lys | Thr | Val | Ala | Pro | Ser | Thr |
| 225 | | | | 230 | | | | | 235 | | | | | 240 | |
| Cys | Ser | Lys | Pro | Thr | Cys | Pro | Pro | Glu | Leu | Leu | Gly | Gly | Pro | Ser |
| | | | 245 | | | | | 250 | | | | | 255 | |
| Val | Phe | Ile | Phe | Pro | Pro | Lys | Pro | Lys | Asp | Thr | Leu | Met | Ile | Ser | Arg |
| | | | 260 | | | | | 265 | | | | | 270 | | |
| Thr | Pro | Glu | Val | Thr | Cys | Val | Val | Val | Asp | Val | Ser | Gln | Asp | Asp | Pro |
| | | | 275 | | | | | 280 | | | | | 285 | | |
| Glu | Val | Gln | Phe | Thr | Trp | Tyr | Ile | Asn | Asn | Glu | Gln | Val | Arg | Thr | Ala |
| | | 290 | | | | | 295 | | | | | 300 | | | |
| Arg | Pro | Pro | Leu | Arg | Glu | Gln | Gln | Phe | Asn | Ser | Thr | Ile | Arg | Val | Val |
| 305 | | | | 310 | | | | | 315 | | | | | 320 | |
| Ser | Thr | Leu | Pro | Ile | Ala | His | Gln | Asp | Trp | Leu | Arg | Gly | Lys | Glu | Phe |
| | | | 325 | | | | | 330 | | | | | 335 | | |
| Lys | Cys | Lys | Val | His | Asn | Lys | Ala | Leu | Pro | Ala | Pro | Ile | Glu | Lys | Thr |
| | | | 340 | | | | | 345 | | | | | 350 | | |

```
Ile Ser Lys Ala Arg Gly Gln Pro Leu Glu Pro Lys Val Tyr Thr Met
        355                 360                 365

Gly Pro Pro Arg Glu Glu Leu Ser Ser Arg Ser Val Ser Leu Thr Cys
370                 375                 380

Met Ile Asn Gly Phe Tyr Pro Ser Asp Ile Ser Val Glu Trp Glu Lys
385                 390                 395                 400

Asn Gly Lys Ala Glu Asp Asn Tyr Lys Thr Thr Pro Ala Val Leu Asp
                405                 410                 415

Ser Asp Gly Ser Tyr Phe Leu Tyr Ser Lys Leu Ser Val Pro Thr Ser
                420                 425                 430

Glu Trp Gln Arg Gly Asp Val Phe Thr Cys Ser Val Met His Glu Ala
                435                 440                 445

Leu His Asn His Tyr Thr Gln Lys Ser Ile Ser Arg Ser Pro Gly Lys
        450                 455                 460

<210> SEQ ID NO 76
<211> LENGTH: 445
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (35)..(35)
<223> OTHER INFORMATION: X is Ala or Ser
<220> FEATURE:
<221> NAME/KEY: MISC_FEATURE
<222> LOCATION: (50)..(50)
<223> OTHER INFORMATION: X is Ala or Ser

<400> SEQUENCE: 76

Gln Ser Leu Gln Glu Ser Gly Gly Gly Leu Phe Gln Pro Gly Gly Ser
1               5                   10                  15

Leu Thr Leu Thr Cys Thr Ala Ser Gly Phe Ser Leu Ser Asn Tyr Ala
                20                  25                  30

Val Met Xaa Trp Val Arg Gln Ala Pro Gly Lys Gly Leu Glu Trp Ile
            35                  40                  45

Ala Xaa Ile Val Leu Gly Asp Gly Gly Thr Thr Tyr Tyr Ala Ser Trp
        50                  55                  60

Ala Arg Gly Arg Phe Thr Ile Ser Lys Pro Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Phe Ala Ala Ser Ser Pro Ile Asn Tyr Phe Asn Leu Trp
                100                 105                 110

Gly Pro Gly Thr Leu Val Thr Val Ser Ser Gly Gln Pro Lys Ala Pro
            115                 120                 125

Ser Val Phe Pro Leu Ala Pro Cys Cys Gly Asp Thr Pro Ser Ser Thr
130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                165                 170                 175

Ser Val Arg Gln Ser Ser Gly Leu Tyr Ser Leu Ser Ser Val Val Ser
                180                 185                 190

Val Thr Ser Ser Ser Gln Pro Val Thr Cys Asn Val Ala His Pro Ala
            195                 200                 205
```

```
Thr Asn Thr Lys Val Asp Lys Thr Val Ala Pro Ser Thr Cys Ser Lys
        210                 215                 220

Pro Thr Cys Pro Pro Glu Leu Leu Gly Gly Pro Ser Val Phe Ile
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Asp Asp Pro Glu Val Gln
            260                 265                 270

Phe Thr Trp Tyr Ile Asn Asn Glu Gln Val Arg Thr Ala Arg Pro Pro
            275                 280                 285

Leu Arg Glu Gln Gln Phe Asn Ser Thr Ile Arg Val Val Ser Thr Leu
290                 295                 300

Pro Ile Ala His Gln Asp Trp Leu Arg Gly Lys Glu Phe Lys Cys Lys
305                 310                 315                 320

Val His Asn Lys Ala Leu Pro Ala Pro Ile Glu Lys Thr Ile Ser Lys
                325                 330                 335

Ala Arg Gly Gln Pro Leu Glu Pro Lys Val Tyr Thr Met Gly Pro Pro
            340                 345                 350

Arg Glu Glu Leu Ser Ser Arg Ser Val Ser Leu Thr Cys Met Ile Asn
355                 360                 365

Gly Phe Tyr Pro Ser Asp Ile Ser Val Glu Trp Glu Lys Asn Gly Lys
370                 375                 380

Ala Glu Asp Asn Tyr Lys Thr Thr Pro Ala Val Leu Asp Ser Asp Gly
385                 390                 395                 400

Ser Tyr Phe Leu Tyr Ser Lys Leu Ser Val Pro Thr Ser Glu Trp Gln
            405                 410                 415

Arg Gly Asp Val Phe Thr Cys Ser Val Met His Glu Ala Leu His Asn
            420                 425                 430

His Tyr Thr Gln Lys Ser Ile Ser Arg Ser Pro Gly Lys
            435                 440                 445

<210> SEQ ID NO 77
<211> LENGTH: 122
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (35)..(35)
<223> OTHER INFORMATION: X is Ala or Ser
<220> FEATURE:
<221> NAME/KEY: MISC_FEATURE
<222> LOCATION: (50)..(50)
<223> OTHER INFORMATION: X is Ala or Ser

<400> SEQUENCE: 77

Gln Ser Leu Gln Glu Ser Gly Gly Gly Leu Phe Gln Pro Gly Gly Ser
1               5                   10                  15

Leu Thr Leu Thr Cys Thr Ala Ser Gly Phe Ser Leu Ser Asn Tyr Ala
            20                  25                  30

Val Met Xaa Trp Val Arg Gln Ala Pro Gly Lys Gly Leu Glu Trp Ile
        35                  40                  45

Ala Xaa Ile Val Leu Gly Asp Gly Gly Thr Thr Tyr Tyr Ala Ser Trp
    50                  55                  60

Ala Arg Gly Arg Phe Thr Ile Ser Lys Pro Ser Ser Thr Thr Val Thr
65                  70                  75                  80

Leu Gln Met Thr Ser Leu Thr Ala Ala Asp Thr Ala Thr Tyr Phe Cys
```

85                  90                  95
Ala Arg Ser Phe Ala Ala Ser Ser Pro Ile Asn Tyr Phe Asn Leu Trp
                100                 105                 110

Gly Pro Gly Thr Leu Val Thr Val Ser Ser
        115                 120

<210> SEQ ID NO 78
<211> LENGTH: 5
<212> TYPE: PRT
<213> ORGANISM: Artificial Sequence
<220> FEATURE:
<223> OTHER INFORMATION: chemically synthesized

<400> SEQUENCE: 78

Arg Tyr Gly Met Ala
1               5

<210> SEQ ID NO 79
<211> LENGTH: 16
<212> TYPE: PRT
<213> ORGANISM: Artificial Sequence
<220> FEATURE:
<223> OTHER INFORMATION: chemically synthesized

<400> SEQUENCE: 79

Ala Ile Ser Ser Ser Gly Asn Glu Asp Tyr Ala Ser Trp Ala Ile Gly
1               5                   10                  15

<210> SEQ ID NO 80
<211> LENGTH: 9
<212> TYPE: PRT
<213> ORGANISM: Artificial Sequence
<220> FEATURE:
<223> OTHER INFORMATION: chemically synthesized

<400> SEQUENCE: 80

Gly Trp Leu Ser Asn Asn Ala Tyr Met
1               5

<210> SEQ ID NO 81
<211> LENGTH: 13
<212> TYPE: PRT
<213> ORGANISM: Artificial Sequence
<220> FEATURE:
<223> OTHER INFORMATION: chemically synthesized

<400> SEQUENCE: 81

Gln Ala Ser Gln Ser Ile Tyr Asn Lys Asn Gln Leu Ser
1               5                   10

<210> SEQ ID NO 82
<211> LENGTH: 7
<212> TYPE: PRT
<213> ORGANISM: Artificial Sequence
<220> FEATURE:
<223> OTHER INFORMATION: chemically synthesized

<400> SEQUENCE: 82

Tyr Ala Ser Thr Leu Ala Ser
1               5

<210> SEQ ID NO 83
<211> LENGTH: 13
<212> TYPE: PRT
<213> ORGANISM: Artificial Sequence
<220> FEATURE:

<223> OTHER INFORMATION: chemically synthesized

<400> SEQUENCE: 83

Leu Gly Asp Phe Ser Cys Ser Gly Val Asp Cys Leu Val
1               5                   10

<210> SEQ ID NO 84
<211> LENGTH: 13
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (6)..(6)
<223> OTHER INFORMATION: X is Ala or Ser
<220> FEATURE:
<221> NAME/KEY: MISC_FEATURE
<222> LOCATION: (11)..(11)
<223> OTHER INFORMATION: X is Ala or Ser

<400> SEQUENCE: 84

Leu Gly Asp Phe Ser Xaa Ser Gly Val Asp Xaa Leu Val
1               5                   10

<210> SEQ ID NO 85
<211> LENGTH: 239
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (118)..(118)
<223> OTHER INFORMATION: X is Ala or Ser
<220> FEATURE:
<221> NAME/KEY: MISC_FEATURE
<222> LOCATION: (123)..(123)
<223> OTHER INFORMATION: X is Ala or Ser

<400> SEQUENCE: 85

Met Asp Thr Arg Ala Pro Thr Gln Leu Leu Gly Leu Leu Leu Leu Trp
1               5                   10                  15

Leu Pro Gly Ala Thr Phe Ala Pro Val Leu Thr Gln Thr Pro Thr Pro
                20                  25                  30

Val Ser Ala Ala Val Gly Gly Thr Val Thr Ile Asn Cys Gln Ala Ser
            35                  40                  45

Gln Ser Ile Tyr Asn Lys Asn Gln Leu Ser Trp Phe Gln Gln Lys Pro
        50                  55                  60

Gly Gln Pro Pro Lys Leu Leu Ile His Tyr Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Asp Phe Ser Xaa Ser Gly Val Asp Xaa Leu Val Val Gly Gly
        115                 120                 125

Gly Thr Glu Val Val Val Glu Gly Asp Pro Val Ala Pro Thr Val Leu
    130                 135                 140

Ile Phe Pro Pro Ser Ala Asp Leu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

```
Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 86
<211> LENGTH: 216
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (95)..(95)
<223> OTHER INFORMATION: X is Ala or Ser
<220> FEATURE:
<221> NAME/KEY: MISC_FEATURE
<222> LOCATION: (100)..(100)
<223> OTHER INFORMATION: X is Ala or Ser

<400> SEQUENCE: 86

```
Pro Val Leu Thr Gln Thr Pro Thr Pro Val Ser Ala Ala Val Gly Gly
1               5                   10                  15

Thr Val Thr Ile Asn Cys Gln Ala Ser Gln Ser Ile Tyr Asn Lys Asn
            20                  25                  30

Gln Leu Ser Trp Phe Gln Gln Lys Pro Gly Gln Pro Pro Lys Leu Leu
        35                  40                  45

Ile His Tyr Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Asp Phe Ser Xaa Ser
                85                  90                  95

Gly Val Asp Xaa Leu Val Val Gly Gly Thr Glu Val Val Val Glu
            100                 105                 110

Gly Asp Pro Val Ala Pro Thr Val Leu Ile Phe Pro Pro Ser Ala Asp
        115                 120                 125

Leu Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215
```

<210> SEQ ID NO 87
<211> LENGTH: 112
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (95)..(95)
<223> OTHER INFORMATION: X is Ala or Ser
<220> FEATURE:
<221> NAME/KEY: MISC_FEATURE
<222> LOCATION: (100)..(100)
<223> OTHER INFORMATION: X is Ala or Ser

<400> SEQUENCE: 87

Pro Val Leu Thr Gln Thr Pro Thr Pro Val Ser Ala Ala Val Gly Gly
1               5                   10                  15

Thr Val Thr Ile Asn Cys Gln Ala Ser Gln Ser Ile Tyr Asn Lys Asn
            20                  25                  30

Gln Leu Ser Trp Phe Gln Gln Lys Pro Gly Gln Pro Pro Lys Leu Leu
        35                  40                  45

Ile His Tyr Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Asp Phe Ser Xaa Ser
                85                  90                  95

Gly Val Asp Xaa Leu Val Val Gly Gly Thr Glu Val Val Val Glu
            100                 105                 110

<210> SEQ ID NO 88
<211> LENGTH: 5
<212> TYPE: PRT
<213> ORGANISM: Artificial Sequence
<220> FEATURE:
<223> OTHER INFORMATION: chemically synthesized

<400> SEQUENCE: 88

His Tyr Gly Met Ala
1               5

<210> SEQ ID NO 89
<211> LENGTH: 16
<212> TYPE: PRT
<213> ORGANISM: Artificial Sequence
<220> FEATURE:
<223> OTHER INFORMATION: chemically synthesized

<400> SEQUENCE: 89

Ala Ile Ser Ser Ser Gly Asn Glu Asp Tyr Ala Ser Trp Pro Lys Gly
1               5                   10                  15

<210> SEQ ID NO 90
<211> LENGTH: 9
<212> TYPE: PRT
<213> ORGANISM: Artificial Sequence
<220> FEATURE:
<223> OTHER INFORMATION: chemically synthesized

<400> SEQUENCE: 90

Gly Trp Leu Ser Asn Asn Val Tyr Met
1               5

<210> SEQ ID NO 91
<211> LENGTH: 13
<212> TYPE: PRT
<213> ORGANISM: Artificial Sequence
<220> FEATURE:
<223> OTHER INFORMATION: chemically synthesized

<400> SEQUENCE: 91

Leu Gly Asp Phe Ser Cys Ser Gly Val Asp Cys Leu Ser
1               5                   10

<210> SEQ ID NO 92
<211> LENGTH: 239
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (118)..(118)
<223> OTHER INFORMATION: X is Ala or Ser
<220> FEATURE:
<221> NAME/KEY: MISC_FEATURE
<222> LOCATION: (123)..(123)
<223> OTHER INFORMATION: X is Ala or Ser

<400> SEQUENCE: 92

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Pro Ser
                20                  25                  30

Val Ser Ala Ala Val Gly Gly Thr Val Thr Ile Asn Cys Gln Ala Ser
            35                  40                  45

Gln Ser Ile Tyr Asn Lys Asn Gln Leu Ser Trp Leu Gln Gln Lys Pro
        50                  55                  60

Gly Gln Pro Pro Lys Val Leu Ile His Tyr Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Asp Phe Ser Xaa Ser Gly Val Asp Xaa Leu Ser Val Gly Gly
        115                 120                 125

Gly Thr Glu Val Val Val Glu Gly Asp Pro Val Ala Pro Thr Val Leu
130                 135                 140

Ile Phe Pro Pro Ser Ala Asp Leu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
210                 215                 220

Gln Gly Thr Thr Ser Val Val Gln Ser Phe Asn Arg Gly Asp Cys
225                 230                 235

<210> SEQ ID NO 93
<211> LENGTH: 216
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (95)..(95)
<223> OTHER INFORMATION: X is Ala or Ser

```
<220> FEATURE:
<221> NAME/KEY: MISC_FEATURE
<222> LOCATION: (100)..(100)
<223> OTHER INFORMATION: X is Ala or Ser

<400> SEQUENCE: 93
```

Gln Val Leu Thr Gln Thr Pro Pro Ser Val Ser Ala Ala Val Gly Gly
1               5                   10                  15

Thr Val Thr Ile Asn Cys Gln Ala Ser Gln Ser Ile Tyr Asn Lys Asn
            20                  25                  30

Gln Leu Ser Trp Leu Gln Gln Lys Pro Gly Gln Pro Pro Lys Val Leu
        35                  40                  45

Ile His Tyr Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Asp Phe Ser Xaa Ser
                85                  90                  95

Gly Val Asp Xaa Leu Ser Val Gly Gly Thr Glu Val Val Val Glu
                100                 105                 110

Gly Asp Pro Val Ala Pro Thr Val Leu Ile Phe Pro Pro Ser Ala Asp
                115                 120                 125

Leu Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
                180                 185                 190

His Lys Glu Tyr Thr Cys Lys Val Thr Gln Gly Thr Thr Ser Val Val
                195                 200                 205

Gln Ser Phe Asn Arg Gly Asp Cys
        210                 215

```
<210> SEQ ID NO 94
<211> LENGTH: 112
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (95)..(95)
<223> OTHER INFORMATION: X is Ala or Ser
<220> FEATURE:
<221> NAME/KEY: MISC_FEATURE
<222> LOCATION: (100)..(100)
<223> OTHER INFORMATION: X is Ala or Ser

<400> SEQUENCE: 94
```

Gln Val Leu Thr Gln Thr Pro Pro Ser Val Ser Ala Ala Val Gly Gly
1               5                   10                  15

Thr Val Thr Ile Asn Cys Gln Ala Ser Gln Ser Ile Tyr Asn Lys Asn
            20                  25                  30

Gln Leu Ser Trp Leu Gln Gln Lys Pro Gly Gln Pro Pro Lys Val Leu
        35                  40                  45

Ile His Tyr Ala Ser Thr Leu Ala Ser Gly Val Ser Ser Arg Phe Lys
    50                  55                  60

```
Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Asp Phe Ser Xaa Ser
                85                  90                  95

Gly Val Asp Xaa Leu Ser Val Gly Gly Thr Glu Val Val Glu
            100                 105                 110

<210> SEQ ID NO 95
<211> LENGTH: 5
<212> TYPE: PRT
<213> ORGANISM: Artificial Sequence
<220> FEATURE:
<223> OTHER INFORMATION: chemically synthesized

<400> SEQUENCE: 95

Ser Tyr Cys Met Ser
1               5

<210> SEQ ID NO 96
<211> LENGTH: 16
<212> TYPE: PRT
<213> ORGANISM: Artificial Sequence
<220> FEATURE:
<223> OTHER INFORMATION: chemically synthesized

<400> SEQUENCE: 96

Ile Ile Gly Gly Ile Cys Ser Thr Tyr Tyr Ala Ala Trp Ala Lys Gly
1               5                   10                  15

<210> SEQ ID NO 97
<211> LENGTH: 8
<212> TYPE: PRT
<213> ORGANISM: Artificial Sequence
<220> FEATURE:
<223> OTHER INFORMATION: chemically synthesized

<400> SEQUENCE: 97

Pro Ala Tyr Asn Ser Asp Pro Ile
1               5

<210> SEQ ID NO 98
<211> LENGTH: 13
<212> TYPE: PRT
<213> ORGANISM: Artificial Sequence
<220> FEATURE:
<223> OTHER INFORMATION: chemically synthesized

<400> SEQUENCE: 98

Gln Ala Ser Gln Ser Val Tyr Asn Asn Asn Tyr Leu Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: chemically synthesized

<400> SEQUENCE: 99

Asp Ala Ala Thr Leu Ala Ser
1               5

<210> SEQ ID NO 100
<211> LENGTH: 13
<212> TYPE: PRT
<213> ORGANISM: Artificial Sequence
```

```
<220> FEATURE:
<223> OTHER INFORMATION: chemically synthesized

<400> SEQUENCE: 100

Leu Gly Glu Phe Ser Cys Gly Ser Ala Asp Cys Asn Ala
1               5                   10

<210> SEQ ID NO 101
<211> LENGTH: 5
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (3)..(3)
<223> OTHER INFORMATION: X is Ala or Ser

<400> SEQUENCE: 101

Ser Tyr Xaa Met Ser
1               5

<210> SEQ ID NO 102
<211> LENGTH: 16
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (6)..(6)
<223> OTHER INFORMATION: X is Ala or Ser

<400> SEQUENCE: 102

Ile Ile Gly Gly Ile Xaa Ser Thr Tyr Tyr Ala Ala Trp Ala Lys Gly
1               5                   10                  15

<210> SEQ ID NO 103
<211> LENGTH: 13
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (6)..(6)
<223> OTHER INFORMATION: X is Ala or Ser
<220> FEATURE:
<221> NAME/KEY: MISC_FEATURE
<222> LOCATION: (11)..(11)
<223> OTHER INFORMATION: X is Ala or Ser

<400> SEQUENCE: 103

Leu Gly Glu Phe Ser Xaa Gly Ser Ala Asp Xaa Asn Ala
1               5                   10

<210> SEQ ID NO 104
<211> LENGTH: 455
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (51)..(51)
<223> OTHER INFORMATION: X is Ala or Ser
<220> FEATURE:
<221> NAME/KEY: MISC_FEATURE
<222> LOCATION: (73)..(73)
<223> OTHER INFORMATION: X is Ala or Ser
```

-continued

<400> SEQUENCE: 104

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly His Leu Val Thr Pro
            20                  25                  30

Gly Thr Pro Leu Thr Leu Thr Cys Lys Ala Ser Gly Phe Ser Leu Ser
        35                  40                  45

Ser Tyr Xaa Met Ser Trp Val Arg Gln Ala Pro Gly Lys Gly Leu Glu
    50                  55                  60

Trp Ile Gly Ile Ile Gly Gly Ile Xaa Ser Thr Tyr Tyr Ala Ala Trp
65                  70                  75                  80

Ala Lys Gly Arg Phe Thr Ile Ser Lys Thr Ser Thr Val Asp Leu
                85                  90                  95

Lys Ile Ala Ser Pro Thr Thr Glu Asp Thr Ala Thr Tyr Phe Cys Ala
            100                 105                 110

Arg Pro Ala Tyr Asn Ser Asp Pro Ile Trp Gly Pro Gly Thr Leu Val
        115                 120                 125

Thr Val Ser Ser Gly Gln Pro Lys Ala Pro Ser Val Phe Pro Leu Ala
130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
        195                 200                 205

Pro Val Thr Cys Asn Val Ala His Pro Ala Thr Asn Thr Lys Val Asp
    210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
        275                 280                 285

Asn Glu Gln Val Arg Thr Ala Arg Pro Pro Leu Arg Glu Gln Gln Phe
290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
        355                 360                 365

Arg Ser Val Ser Leu Thr Cys Met Ile Asn Gly Phe Tyr Pro Ser Asp
    370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415
```

```
Lys Leu Ser Val Pro Thr Ser Glu Trp Gln Arg Gly Asp Val Phe Thr
                420                 425                 430

Cys Ser Val Met His Glu Ala Leu His Asn His Tyr Thr Gln Lys Ser
            435                 440                 445

Ile Ser Arg Ser Pro Gly Lys
        450                 455

<210> SEQ ID NO 105
<211> LENGTH: 436
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (32)..(32)
<223> OTHER INFORMATION: X is Ala or Ser
<220> FEATURE:
<221> NAME/KEY: MISC_FEATURE
<222> LOCATION: (54)..(54)
<223> OTHER INFORMATION: X is Ala or Ser

<400> SEQUENCE: 105

Gln Ser Leu Glu Glu Ser Gly Gly His Leu Val Thr Pro Gly Thr Pro
1               5                   10                  15

Leu Thr Leu Thr Cys Lys Ala Ser Gly Phe Ser Leu Ser Ser Tyr Xaa
            20                  25                  30

Met Ser Trp Val Arg Gln Ala Pro Gly Lys Gly Leu Glu Trp Ile Gly
        35                  40                  45

Ile Ile Gly Gly Ile Xaa Ser Thr Tyr Tyr Ala Ala Trp Ala Lys Gly
    50                  55                  60

Arg Phe Thr Ile Ser Lys Thr Ser Thr Val Asp Leu Lys Ile Ala
65                  70                  75                  80

Ser Pro Thr Thr Glu Asp Thr Ala Thr Tyr Phe Cys Ala Arg Pro Ala
                85                  90                  95

Tyr Asn Ser Asp Pro Ile Trp Gly Pro Gly Thr Leu Val Thr Val Ser
            100                 105                 110

Ser Gly Gln Pro Lys Ala Pro Ser Val Phe Pro Leu Ala Pro Cys Cys
        115                 120                 125

Gly Asp Thr Pro Ser Ser Thr Val Thr Leu Gly Cys Leu Val Lys Gly
130                 135                 140

Tyr Leu Pro Glu Pro Val Thr Val Thr Trp Asn Ser Gly Thr Leu Thr
145                 150                 155                 160

Asn Gly Val Arg Thr Phe Pro Ser Val Arg Gln Ser Ser Gly Leu Tyr
                165                 170                 175

Ser Leu Ser Ser Val Val Ser Val Thr Ser Ser Ser Gln Pro Val Thr
            180                 185                 190

Cys Asn Val Ala His Pro Ala Thr Asn Thr Lys Val Asp Lys Thr Val
        195                 200                 205

Ala Pro Ser Thr Cys Ser Lys Pro Thr Cys Pro Pro Pro Glu Leu Leu
    210                 215                 220

Gly Gly Pro Ser Val Phe Ile Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

Gln Asp Asp Pro Glu Val Gln Phe Thr Trp Tyr Ile Asn Asn Glu Gln
            260                 265                 270
```

Val Arg Thr Ala Arg Pro Pro Leu Arg Glu Gln Gln Phe Asn Ser Thr
            275                 280                 285

Ile Arg Val Val Ser Thr Leu Pro Ile Ala His Gln Asp Trp Leu Arg
    290                 295                 300

Gly Lys Glu Phe Lys Cys Lys Val His Asn Lys Ala Leu Pro Ala Pro
305                 310                 315                 320

Ile Glu Lys Thr Ile Ser Lys Ala Arg Gly Gln Pro Leu Glu Pro Lys
                325                 330                 335

Val Tyr Thr Met Gly Pro Pro Arg Glu Glu Leu Ser Ser Arg Ser Val
            340                 345                 350

Ser Leu Thr Cys Met Ile Asn Gly Phe Tyr Pro Ser Asp Ile Ser Val
            355                 360                 365

Glu Trp Glu Lys Asn Gly Lys Ala Glu Asp Asn Tyr Lys Thr Thr Pro
    370                 375                 380

Ala Val Leu Asp Ser Asp Gly Ser Tyr Phe Leu Tyr Ser Lys Leu Ser
385                 390                 395                 400

Val Pro Thr Ser Glu Trp Gln Arg Gly Asp Val Phe Thr Cys Ser Val
                405                 410                 415

Met His Glu Ala Leu His Asn His Tyr Thr Gln Lys Ser Ile Ser Arg
            420                 425                 430

Ser Pro Gly Lys
        435

<210> SEQ ID NO 106
<211> LENGTH: 113
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (32)..(32)
<223> OTHER INFORMATION: X is Ala or Ser
<220> FEATURE:
<221> NAME/KEY: MISC_FEATURE
<222> LOCATION: (54)..(54)
<223> OTHER INFORMATION: X is Ala or Ser

<400> SEQUENCE: 106

Gln Ser Leu Glu Glu Ser Gly Gly His Leu Val Thr Pro Gly Thr Pro
1               5                   10                  15

Leu Thr Leu Thr Cys Lys Ala Ser Gly Phe Ser Leu Ser Ser Tyr Xaa
            20                  25                  30

Met Ser Trp Val Arg Gln Ala Pro Gly Lys Gly Leu Glu Trp Ile Gly
        35                  40                  45

Ile Ile Gly Gly Ile Xaa Ser Thr Tyr Tyr Ala Ala Trp Ala Lys Gly
    50                  55                  60

Arg Phe Thr Ile Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Pro Ala
                85                  90                  95

Tyr Asn Ser Asp Pro Ile Trp Gly Pro Gly Thr Leu Val Thr Val Ser
            100                 105                 110

Ser

<210> SEQ ID NO 107
<211> LENGTH: 239
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (118)..(118)
<223> OTHER INFORMATION: X is Ala or Ser
<220> FEATURE:
<221> NAME/KEY: MISC_FEATURE
<222> LOCATION: (123)..(123)
<223> OTHER INFORMATION: X is Ala or Ser

<400> SEQUENCE: 107

Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Pro Ser Pro
            20                  25                  30

Val Ser Val Ala Val Gly Gly Thr Val Thr Ile Asn Cys Gln Ala Ser
        35                  40                  45

Gln Ser Val Tyr Asn Asn Tyr Leu Ser Trp Tyr Gln Gln Lys Pro
    50                  55                  60

Gly Gln Pro Pro Lys Val Leu Ile Tyr Asp Ala Ala Thr Leu Ala Ser
65                  70                  75                  80

Gly Val Ser Ser Arg Phe Arg Gly Ser Gly Ser Gly Thr Gln Phe Thr
                85                  90                  95

Leu Thr Ile Ser Asp Val Gln Cys Asp Asp Ala Ala Thr Tyr Tyr Cys
                100                 105                 110

Leu Gly Glu Phe Ser Xaa Gly Ser Ala Asp Xaa Asn Ala Phe Gly Gly
            115                 120                 125

Gly Thr Glu Val Val Lys Gly Asp Pro Val Ala Pro Thr Val Leu
130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 108
<211> LENGTH: 216
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (95)..(95)
<223> OTHER INFORMATION: X is Ala or Ser
<220> FEATURE:
<221> NAME/KEY: MISC_FEATURE
<222> LOCATION: (100)..(100)
<223> OTHER INFORMATION: X is Ala or Ser

<400> SEQUENCE: 108

Gln Val Leu Thr Gln Thr Pro Ser Pro Val Ser Val Ala Val Gly Gly
1               5                   10                  15

Thr Val Thr Ile Asn Cys Gln Ala Ser Gln Ser Val Tyr Asn Asn
            20                  25                  30

Tyr Leu Ser Trp Tyr Gln Gln Lys Pro Gly Gln Pro Pro Lys Val Leu
        35                  40                  45

Ile Tyr Asp Ala Ala Thr Leu Ala Ser Gly Val Ser Ser Arg Phe Arg
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Glu Phe Ser Xaa Gly
                85                  90                  95

Ser Ala Asp Xaa Asn Ala Phe Gly Gly Gly Thr Glu Val Val Val Lys
            100                 105                 110

Gly Asp Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215

<210> SEQ ID NO 109
<211> LENGTH: 112
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (95)..(95)
<223> OTHER INFORMATION: X is Ala or Ser
<220> FEATURE:
<221> NAME/KEY: MISC_FEATURE
<222> LOCATION: (100)..(100)
<223> OTHER INFORMATION: X is Ala or Ser

<400> SEQUENCE: 109

Gln Val Leu Thr Gln Thr Pro Ser Pro Val Ser Val Ala Val Gly Gly
1               5                   10                  15

Thr Val Thr Ile Asn Cys Gln Ala Ser Gln Ser Val Tyr Asn Asn Asn
            20                  25                  30

Tyr Leu Ser Trp Tyr Gln Gln Lys Pro Gly Gln Pro Pro Lys Val Leu
        35                  40                  45

Ile Tyr Asp Ala Ala Thr Leu Ala Ser Gly Val Ser Ser Arg Phe Arg
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Glu Phe Ser Xaa Gly
                85                  90                  95

Ser Ala Asp Xaa Asn Ala Phe Gly Gly Gly Thr Glu Val Val Val Lys
            100                 105                 110

```
<210> SEQ ID NO 110
<211> LENGTH: 13
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (6)..(6)
<223> OTHER INFORMATION: X is Ala or Ser
<220> FEATURE:
<221> NAME/KEY: MISC_FEATURE
<222> LOCATION: (11)..(11)
<223> OTHER INFORMATION: X is Ala or Ser

<400> SEQUENCE: 110

Leu Gly Asp Phe Ser Xaa Ser Gly Val Asp Xaa Leu Ser
1               5                   10

<210> SEQ ID NO 111
<211> LENGTH: 6
<212> TYPE: PRT
<213> ORGANISM: Artificial Sequence
<220> FEATURE:
<223> OTHER INFORMATION: chemically synthesized

<400> SEQUENCE: 111

Cys Ile Ser Pro Arg Gly
1               5

<210> SEQ ID NO 112
<211> LENGTH: 8
<212> TYPE: PRT
<213> ORGANISM: Artificial Sequence
<220> FEATURE:
<223> OTHER INFORMATION: chemically synthesized

<400> SEQUENCE: 112

Cys Ile Ser Pro Arg Gly Cys Gly
1               5

<210> SEQ ID NO 113
<211> LENGTH: 15
<212> TYPE: PRT
<213> ORGANISM: Artificial Sequence
<220> FEATURE:
<223> OTHER INFORMATION: chemically synthesized

<400> SEQUENCE: 113

Cys Ile Ser Pro Arg Gly Cys Pro Asp Gly Pro Tyr Val Met Tyr
1               5                   10                  15

<210> SEQ ID NO 114
<211> LENGTH: 14
<212> TYPE: PRT
<213> ORGANISM: Artificial Sequence
<220> FEATURE:
<223> OTHER INFORMATION: chemically synthesized

<400> SEQUENCE: 114

Cys Ile Ser Pro Arg Gly Cys Pro Asp Gly Pro Tyr Val Met
1               5                   10

<210> SEQ ID NO 115
<211> LENGTH: 15
<212> TYPE: PRT
<213> ORGANISM: Artificial Sequence
<220> FEATURE:
<223> OTHER INFORMATION: chemically synthesized
```

```
<400> SEQUENCE: 115

Cys Ile Ser Pro Arg Gly Cys Glu Pro Gly Thr Tyr Val Pro Thr
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: chemically synthesized

<400> SEQUENCE: 116

Cys Ile Ser Pro Arg Gly Cys Pro Gly Gln Ile Trp His Pro Pro
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: chemically synthesized

<400> SEQUENCE: 117

Gly Ser His Cys Leu Ile Pro Ile Asn Met Gly Ala Pro Ser Cys
1               5                   10                  15

<210> SEQ ID NO 118
<211> LENGTH: 32
<212> TYPE: PRT
<213> ORGANISM: Artificial Sequence
<220> FEATURE:
<223> OTHER INFORMATION: chemically synthesized

<400> SEQUENCE: 118

Cys Ile Ser Pro Arg Gly Cys Gly Gly Ser Ser Ala Ser Gln Ser Gly
1               5                   10                  15

Gln Gly Ser His Cys Leu Ile Pro Ile Asn Met Gly Ala Pro Ser Cys
            20                  25                  30

<210> SEQ ID NO 119
<211> LENGTH: 19
<212> TYPE: PRT
<213> ORGANISM: Artificial Sequence
<220> FEATURE:
<223> OTHER INFORMATION: chemically synthesized

<400> SEQUENCE: 119

Cys Asn His His Tyr Phe Tyr Thr Cys Gly Cys Ile Ser Pro Arg Gly
1               5                   10                  15

Cys Pro Gly

<210> SEQ ID NO 120
<211> LENGTH: 19
<212> TYPE: PRT
<213> ORGANISM: Artificial Sequence
<220> FEATURE:
<223> OTHER INFORMATION: chemically synthesized

<400> SEQUENCE: 120

Ala Asp His Val Phe Trp Gly Ser Tyr Gly Cys Ile Ser Pro Arg Gly
1               5                   10                  15

Cys Pro Gly
```

```
<210> SEQ ID NO 121
<211> LENGTH: 19
<212> TYPE: PRT
<213> ORGANISM: Artificial Sequence
<220> FEATURE:
<223> OTHER INFORMATION: chemically synthesized

<400> SEQUENCE: 121

Cys His His Val Tyr Trp Gly His Cys Gly Cys Ile Ser Pro Arg Gly
1               5                   10                  15

Cys Pro Gly

<210> SEQ ID NO 122
<211> LENGTH: 19
<212> TYPE: PRT
<213> ORGANISM: Artificial Sequence
<220> FEATURE:
<223> OTHER INFORMATION: chemically synthesized

<400> SEQUENCE: 122

Cys Pro His Phe Thr Thr Thr Ser Cys Gly Cys Ile Ser Pro Arg Gly
1               5                   10                  15

Cys Pro Gly

<210> SEQ ID NO 123
<211> LENGTH: 19
<212> TYPE: PRT
<213> ORGANISM: Artificial Sequence
<220> FEATURE:
<223> OTHER INFORMATION: chemically synthesized

<400> SEQUENCE: 123

Cys Asn His His Tyr His Tyr Tyr Cys Gly Cys Ile Ser Pro Arg Gly
1               5                   10                  15

Cys Pro Gly

<210> SEQ ID NO 124
<211> LENGTH: 19
<212> TYPE: PRT
<213> ORGANISM: Artificial Sequence
<220> FEATURE:
<223> OTHER INFORMATION: chemically synthesized

<400> SEQUENCE: 124

Cys Pro His Val Ser Phe Gly Ser Cys Gly Cys Ile Ser Pro Arg Gly
1               5                   10                  15

Cys Pro Gly

<210> SEQ ID NO 125
<211> LENGTH: 19
<212> TYPE: PRT
<213> ORGANISM: Artificial Sequence
<220> FEATURE:
<223> OTHER INFORMATION: chemically synthesized

<400> SEQUENCE: 125

Cys Pro Tyr Tyr Thr Leu Ser Tyr Cys Gly Cys Ile Ser Pro Arg Gly
1               5                   10                  15

Cys Pro Gly

<210> SEQ ID NO 126
<211> LENGTH: 19
<212> TYPE: PRT
<213> ORGANISM: Artificial Sequence
```

<220> FEATURE:
<223> OTHER INFORMATION: chemically synthesized

<400> SEQUENCE: 126

Cys Asn His Val Tyr Phe Gly Thr Cys Gly Cys Ile Ser Pro Arg Gly
1               5                   10                  15

Cys Pro Gly

<210> SEQ ID NO 127
<211> LENGTH: 19
<212> TYPE: PRT
<213> ORGANISM: Artificial Sequence
<220> FEATURE:
<223> OTHER INFORMATION: chemically synthesized

<400> SEQUENCE: 127

Cys Asn His Phe Thr Leu Thr Thr Cys Gly Cys Ile Ser Pro Arg Gly
1               5                   10                  15

Cys Pro Gly

<210> SEQ ID NO 128
<211> LENGTH: 19
<212> TYPE: PRT
<213> ORGANISM: Artificial Sequence
<220> FEATURE:
<223> OTHER INFORMATION: chemically synthesized

<400> SEQUENCE: 128

Cys His His Phe Thr Leu Thr Thr Cys Gly Cys Ile Ser Pro Arg Gly
1               5                   10                  15

Cys Pro Gly

<210> SEQ ID NO 129
<211> LENGTH: 18
<212> TYPE: PRT
<213> ORGANISM: Artificial Sequence
<220> FEATURE:
<223> OTHER INFORMATION: chemically synthesized

<400> SEQUENCE: 129

Tyr Asn Pro Cys Ala Thr Pro Met Cys Cys Ile Ser Pro Arg Gly Cys
1               5                   10                  15

Pro Gly

<210> SEQ ID NO 130
<211> LENGTH: 18
<212> TYPE: PRT
<213> ORGANISM: Artificial Sequence
<220> FEATURE:
<223> OTHER INFORMATION: chemically synthesized

<400> SEQUENCE: 130

Cys Asn His His Tyr Phe Tyr Thr Cys Gly Cys Ile Ser Pro Arg Gly
1               5                   10                  15

Cys Gly

<210> SEQ ID NO 131
<211> LENGTH: 18
<212> TYPE: PRT
<213> ORGANISM: Artificial Sequence
<220> FEATURE:
<223> OTHER INFORMATION: chemically synthesized

<400> SEQUENCE: 131

```
Cys Asn His Tyr His Tyr Tyr Cys Gly Cys Ile Ser Pro Arg Gly
1               5                   10                  15

Cys Gly

<210> SEQ ID NO 132
<211> LENGTH: 18
<212> TYPE: PRT
<213> ORGANISM: Artificial Sequence
<220> FEATURE:
<223> OTHER INFORMATION: chemically synthesized

<400> SEQUENCE: 132

Cys Asn His Val Tyr Phe Gly Thr Cys Gly Cys Ile Ser Pro Arg Gly
1               5                   10                  15

Cys Gly

<210> SEQ ID NO 133
<211> LENGTH: 18
<212> TYPE: PRT
<213> ORGANISM: Artificial Sequence
<220> FEATURE:
<223> OTHER INFORMATION: chemically synthesized

<400> SEQUENCE: 133

Cys His His Val Tyr Trp Gly His Cys Gly Cys Ile Ser Pro Arg Gly
1               5                   10                  15

Cys Gly

<210> SEQ ID NO 134
<211> LENGTH: 18
<212> TYPE: PRT
<213> ORGANISM: Artificial Sequence
<220> FEATURE:
<223> OTHER INFORMATION: chemically synthesized

<400> SEQUENCE: 134

Cys Pro His Phe Thr Thr Thr Ser Cys Gly Cys Ile Ser Pro Arg Gly
1               5                   10                  15

Cys Gly

<210> SEQ ID NO 135
<211> LENGTH: 18
<212> TYPE: PRT
<213> ORGANISM: Artificial Sequence
<220> FEATURE:
<223> OTHER INFORMATION: chemically synthesized

<400> SEQUENCE: 135

Cys Asn His Phe Thr Leu Thr Thr Cys Gly Cys Ile Ser Pro Arg Gly
1               5                   10                  15

Cys Gly

<210> SEQ ID NO 136
<211> LENGTH: 18
<212> TYPE: PRT
<213> ORGANISM: Artificial Sequence
<220> FEATURE:
<223> OTHER INFORMATION: chemically synthesized

<400> SEQUENCE: 136

Cys His His Phe Thr Leu Thr Thr Cys Gly Cys Ile Ser Pro Arg Gly
1               5                   10                  15
```

Cys Gly

<210> SEQ ID NO 137
<211> LENGTH: 18
<212> TYPE: PRT
<213> ORGANISM: Artificial Sequence
<220> FEATURE:
<223> OTHER INFORMATION: chemically synthesized

<400> SEQUENCE: 137

Cys Pro Tyr Tyr Thr Leu Ser Tyr Cys Gly Cys Ile Ser Pro Arg Gly
1               5                   10                  15

Cys Gly

<210> SEQ ID NO 138
<211> LENGTH: 18
<212> TYPE: PRT
<213> ORGANISM: Artificial Sequence
<220> FEATURE:
<223> OTHER INFORMATION: chemically synthesized

<400> SEQUENCE: 138

Cys Pro His Val Ser Phe Gly Ser Cys Gly Cys Ile Ser Pro Arg Gly
1               5                   10                  15

Cys Gly

<210> SEQ ID NO 139
<211> LENGTH: 18
<212> TYPE: PRT
<213> ORGANISM: Artificial Sequence
<220> FEATURE:
<223> OTHER INFORMATION: chemically synthesized

<400> SEQUENCE: 139

Ala Asp His Val Phe Trp Gly Ser Tyr Gly Cys Ile Ser Pro Arg Gly
1               5                   10                  15

Cys Gly

<210> SEQ ID NO 140
<211> LENGTH: 17
<212> TYPE: PRT
<213> ORGANISM: Artificial Sequence
<220> FEATURE:
<223> OTHER INFORMATION: chemically synthesized

<400> SEQUENCE: 140

Tyr Asn Pro Cys Ala Thr Pro Met Cys Cys Ile Ser Pro Arg Gly Cys
1               5                   10                  15

Gly

<210> SEQ ID NO 141
<211> LENGTH: 18
<212> TYPE: PRT
<213> ORGANISM: Artificial Sequence
<220> FEATURE:
<223> OTHER INFORMATION: chemically synthesized

<400> SEQUENCE: 141

Cys His His Val Tyr Trp Gly His Cys Gly Cys Ile Ser Pro Arg Gly
1               5                   10                  15

Cys Gly

<210> SEQ ID NO 142

```
<211> LENGTH: 18
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: X is Asn or Pro
<220> FEATURE:
<221> NAME/KEY: MISC_FEATURE
<222> LOCATION: (4)..(4)
<223> OTHER INFORMATION: X is His, Val, or Phe
<220> FEATURE:
<221> NAME/KEY: MISC_FEATURE
<222> LOCATION: (5)..(5)
<223> OTHER INFORMATION: X is Tyr or Thr
<220> FEATURE:
<221> NAME/KEY: MISC_FEATURE
<222> LOCATION: (6)..(6)
<223> OTHER INFORMATION: X is Phe, Trp, Thr, or Leu
<220> FEATURE:
<221> NAME/KEY: MISC_FEATURE
<222> LOCATION: (7)..(7)
<223> OTHER INFORMATION: X is Tyr, Gly, Thr, or Ser
<220> FEATURE:
<221> NAME/KEY: MISC_FEATURE
<222> LOCATION: (8)..(8)
<223> OTHER INFORMATION: X is Thr, Ser, Tyr, or His

<400> SEQUENCE: 142

Cys Xaa His Xaa Xaa Xaa Xaa Cys Gly Cys Ile Ser Pro Arg Gly
1               5                   10                  15

Cys Gly

<210> SEQ ID NO 143
<211> LENGTH: 15
<212> TYPE: PRT
<213> ORGANISM: Artificial Sequence
<220> FEATURE:
<223> OTHER INFORMATION: chemically synthesized

<400> SEQUENCE: 143

Cys Ile Ser Pro Arg Gly Cys Gly Gln Pro Ile Pro Ser Val Lys
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: chemically synthesized

<400> SEQUENCE: 144

Cys Ile Ser Pro Arg Gly Cys Thr Gln Pro Tyr His Val Ser Arg
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: chemically synthesized

<400> SEQUENCE: 145

Cys Ile Ser Pro Arg Gly Cys Asn Ala Val Ser Gly Leu Gly Ser
1               5                   10                  15

<210> SEQ ID NO 146
<211> LENGTH: 26
```

```
<212> TYPE: PRT
<213> ORGANISM: Artificial Sequence
<220> FEATURE:
<223> OTHER INFORMATION: chemically synthesized

<400> SEQUENCE: 146

Gln Gly Gln Ser Gly Gln Gly Gln Gln Trp Cys Asn Ile Trp Ile
1               5                   10                  15

Asn Gly Gly Asp Cys Arg Gly Trp Asn Gly
            20                  25

<210> SEQ ID NO 147
<211> LENGTH: 15
<212> TYPE: PRT
<213> ORGANISM: Artificial Sequence
<220> FEATURE:
<223> OTHER INFORMATION: chemically synthesized

<400> SEQUENCE: 147

Pro Trp Cys Met Gln Arg Gln Asp Phe Leu Arg Cys Pro Gln Pro
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: chemically synthesized

<400> SEQUENCE: 148

Gln Leu Gly Leu Pro Ala Tyr Met Cys Thr Phe Glu Cys Leu Arg
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: chemically synthesized

<400> SEQUENCE: 149

Cys Asn Leu Trp Val Ser Gly Gly Asp Cys Gly Gly Leu Gln Gly
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: chemically synthesized

<400> SEQUENCE: 150

Ser Cys Ser Leu Trp Thr Ser Gly Ser Cys Leu Pro His Ser Pro
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: chemically synthesized

<400> SEQUENCE: 151

Tyr Cys Leu Gln Leu Pro His Tyr Met Gln Ala Met Cys Gly Arg
1               5                   10                  15
```

```
<210> SEQ ID NO 152
<211> LENGTH: 15
<212> TYPE: PRT
<213> ORGANISM: Artificial Sequence
<220> FEATURE:
<223> OTHER INFORMATION: chemically synthesized

<400> SEQUENCE: 152

Cys Phe Leu Tyr Ser Cys Thr Asp Val Ser Tyr Trp Asn Asn Thr
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: chemically synthesized

<400> SEQUENCE: 153

Pro Trp Cys Met Gln Arg Gln Asp Tyr Leu Arg Cys Pro Gln Pro
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: chemically synthesized

<400> SEQUENCE: 154

Cys Asn Leu Trp Ile Ser Gly Gly Asp Cys Arg Gly Leu Ala Gly
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: chemically synthesized

<400> SEQUENCE: 155

Cys Asn Leu Trp Val Ser Gly Gly Asp Cys Arg Gly Val Gln Gly
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: chemically synthesized

<400> SEQUENCE: 156

Cys Asn Leu Trp Val Ser Gly Gly Asp Cys Arg Gly Leu Arg Gly
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: chemically synthesized

<400> SEQUENCE: 157

Cys Asn Leu Trp Ile Ser Gly Gly Asp Cys Arg Gly Leu Pro Gly
1               5                   10                  15

<210> SEQ ID NO 158
```

```
<211> LENGTH: 15
<212> TYPE: PRT
<213> ORGANISM: Artificial Sequence
<220> FEATURE:
<223> OTHER INFORMATION: chemically synthesized

<400> SEQUENCE: 158

Cys Asn Leu Trp Val Ser Gly Gly Asp Cys Arg Asp Ala Pro Trp
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: chemically synthesized

<400> SEQUENCE: 159

Cys Asn Leu Trp Val Ser Gly Gly Asp Cys Arg Asp Leu Leu Gly
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: chemically synthesized

<400> SEQUENCE: 160

Cys Asn Leu Trp Val Ser Gly Gly Asp Cys Arg Gly Leu Gln Gly
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: chemically synthesized

<400> SEQUENCE: 161

Cys Asn Leu Trp Leu His Gly Gly Asp Cys Arg Gly Trp Gln Gly
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: chemically synthesized

<400> SEQUENCE: 162

Cys Asn Ile Trp Leu Val Gly Gly Asp Cys Arg Gly Trp Gln Gly
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: chemically synthesized

<400> SEQUENCE: 163

Cys Thr Thr Trp Phe Cys Gly Gly Asp Cys Gly Val Met Arg Gly
1               5                   10                  15

<210> SEQ ID NO 164
<211> LENGTH: 15
```

```
<212> TYPE: PRT
<213> ORGANISM: Artificial Sequence
<220> FEATURE:
<223> OTHER INFORMATION: chemically synthesized

<400> SEQUENCE: 164

Cys Asn Ile Trp Gly Pro Ser Val Asp Cys Gly Ala Leu Leu Gly
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: chemically synthesized

<400> SEQUENCE: 165

Cys Asn Ile Trp Val Asn Gly Gly Asp Cys Arg Ser Phe Glu Gly
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: chemically synthesized

<400> SEQUENCE: 166

Tyr Cys Leu Asn Leu Pro Arg Tyr Met Gln Asp Met Cys Trp Ala
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: chemically synthesized

<400> SEQUENCE: 167

Tyr Cys Leu Ala Leu Pro His Tyr Met Gln Ala Asp Cys Ala Arg
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: chemically synthesized

<400> SEQUENCE: 168

Cys Phe Leu Tyr Ser Cys Gly Asp Val Ser Tyr Trp Gly Ser Ala
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: chemically synthesized

<400> SEQUENCE: 169

Cys Tyr Leu Tyr Ser Cys Thr Asp Ser Ala Phe Trp Asn Asn Arg
1               5                   10                  15

<210> SEQ ID NO 170
<211> LENGTH: 15
<212> TYPE: PRT
```

```
<213> ORGANISM: Artificial Sequence
<220> FEATURE:
<223> OTHER INFORMATION: chemically synthesized

<400> SEQUENCE: 170

Cys Tyr Leu Tyr Ser Cys Asn Asp Val Ser Tyr Trp Ser Asn Thr
1               5                   10                  15

<210> SEQ ID NO 171
<211> LENGTH: 12
<212> TYPE: PRT
<213> ORGANISM: Artificial Sequence
<220> FEATURE:
<223> OTHER INFORMATION: chemically synthesized

<400> SEQUENCE: 171

Cys Phe Leu Tyr Ser Cys Thr Asp Val Ser Tyr Trp
1               5                   10

<210> SEQ ID NO 172
<211> LENGTH: 15
<212> TYPE: PRT
<213> ORGANISM: Artificial Sequence
<220> FEATURE:
<223> OTHER INFORMATION: chemically synthesized

<400> SEQUENCE: 172

Cys Phe Leu Tyr Ser Cys Thr Asp Val Ala Tyr Trp Asn Ser Ala
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: chemically synthesized

<400> SEQUENCE: 173

Cys Phe Leu Tyr Ser Cys Thr Asp Val Ser Tyr Trp Gly Asp Thr
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: chemically synthesized

<400> SEQUENCE: 174

Cys Phe Leu Tyr Ser Cys Thr Asp Val Ser Tyr Trp Gly Asn Ser
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: chemically synthesized

<400> SEQUENCE: 175

Cys Phe Leu Tyr Ser Cys Thr Asp Val Ala Tyr Trp Asn Asn Thr
1               5                   10                  15

<210> SEQ ID NO 176
<211> LENGTH: 18
<212> TYPE: PRT
<213> ORGANISM: Artificial Sequence
```

```
<220> FEATURE:
<223> OTHER INFORMATION: chemically synthesized

<400> SEQUENCE: 176

Cys Phe Leu Tyr Ser Cys Gly Asp Val Ser Tyr Trp Gly Asn Pro Gly
1               5                   10                  15

Leu Ser

<210> SEQ ID NO 177
<211> LENGTH: 15
<212> TYPE: PRT
<213> ORGANISM: Artificial Sequence
<220> FEATURE:
<223> OTHER INFORMATION: chemically synthesized

<400> SEQUENCE: 177

Cys Phe Leu Tyr Ser Cys Thr Asp Val Ala Tyr Trp Ser Gly Leu
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: chemically synthesized

<400> SEQUENCE: 178

Cys Tyr Leu Tyr Ser Cys Thr Asp Gly Ser Tyr Trp Asn Ser Thr
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: chemically synthesized

<400> SEQUENCE: 179

Cys Phe Leu Tyr Ser Cys Ser Asp Val Ser Tyr Trp Gly Asn Ile
1               5                   10                  15

<210> SEQ ID NO 180
<211> LENGTH: 12
<212> TYPE: PRT
<213> ORGANISM: Artificial Sequence
<220> FEATURE:
<223> OTHER INFORMATION: chemically synthesized

<400> SEQUENCE: 180

Cys Phe Leu Tyr Ser Cys Thr Asp Val Ala Tyr Trp
1               5                   10

<210> SEQ ID NO 181
<211> LENGTH: 15
<212> TYPE: PRT
<213> ORGANISM: Artificial Sequence
<220> FEATURE:
<223> OTHER INFORMATION: chemically synthesized

<400> SEQUENCE: 181

Cys Phe Leu Tyr Ser Cys Thr Asp Val Ser Tyr Trp Gly Ser Thr
1               5                   10                  15

<210> SEQ ID NO 182
<211> LENGTH: 15
<212> TYPE: PRT
```

```
<213> ORGANISM: Artificial Sequence
<220> FEATURE:
<223> OTHER INFORMATION: chemically synthesized

<400> SEQUENCE: 182

Cys Phe Leu Tyr Ser Cys Thr Asp Val Ala Tyr Trp Gly Asp Thr
1               5                   10                  15

<210> SEQ ID NO 183
<211> LENGTH: 20
<212> TYPE: PRT
<213> ORGANISM: Artificial Sequence
<220> FEATURE:
<223> OTHER INFORMATION: chemically synthesized

<400> SEQUENCE: 183

Gly Cys Asn Ile Trp Leu Asn Gly Gly Asp Cys Arg Gly Trp Val Asp
1               5                   10                  15

Pro Leu Gln Gly
            20

<210> SEQ ID NO 184
<211> LENGTH: 20
<212> TYPE: PRT
<213> ORGANISM: Artificial Sequence
<220> FEATURE:
<223> OTHER INFORMATION: chemically synthesized

<400> SEQUENCE: 184

Gly Cys Asn Ile Trp Leu Val Gly Gly Asp Cys Arg Gly Trp Ile Gly
1               5                   10                  15

Asp Thr Asn Gly
            20

<210> SEQ ID NO 185
<211> LENGTH: 20
<212> TYPE: PRT
<213> ORGANISM: Artificial Sequence
<220> FEATURE:
<223> OTHER INFORMATION: chemically synthesized

<400> SEQUENCE: 185

Gly Cys Asn Ile Trp Leu Val Gly Gly Asp Cys Arg Gly Trp Ile Glu
1               5                   10                  15

Asp Ser Asn Gly
            20

<210> SEQ ID NO 186
<211> LENGTH: 20
<212> TYPE: PRT
<213> ORGANISM: Artificial Sequence
<220> FEATURE:
<223> OTHER INFORMATION: chemically synthesized

<400> SEQUENCE: 186

Gly Cys Asn Ile Trp Ala Asn Gly Gly Asp Cys Arg Gly Trp Ile Asp
1               5                   10                  15

Asn Ile Asp Gly
            20

<210> SEQ ID NO 187
<211> LENGTH: 20
<212> TYPE: PRT
<213> ORGANISM: Artificial Sequence
<220> FEATURE:
```

<223> OTHER INFORMATION: chemically synthesized

<400> SEQUENCE: 187

Gly Cys Asn Ile Trp Leu Val Gly Gly Asp Cys Arg Gly Trp Leu Gly
1               5                   10                  15

Glu Ala Val Gly
            20

<210> SEQ ID NO 188
<211> LENGTH: 20
<212> TYPE: PRT
<213> ORGANISM: Artificial Sequence
<220> FEATURE:
<223> OTHER INFORMATION: chemically synthesized

<400> SEQUENCE: 188

Gly Cys Asn Ile Trp Leu Val Gly Gly Asp Cys Arg Gly Trp Leu Glu
1               5                   10                  15

Glu Ala Val Gly
            20

<210> SEQ ID NO 189
<211> LENGTH: 20
<212> TYPE: PRT
<213> ORGANISM: Artificial Sequence
<220> FEATURE:
<223> OTHER INFORMATION: chemically synthesized

<400> SEQUENCE: 189

Gly Gly Pro Ala Leu Cys Asn Ile Trp Leu Asn Gly Gly Asp Cys Arg
1               5                   10                  15

Gly Trp Ser Gly
            20

<210> SEQ ID NO 190
<211> LENGTH: 20
<212> TYPE: PRT
<213> ORGANISM: Artificial Sequence
<220> FEATURE:
<223> OTHER INFORMATION: chemically synthesized

<400> SEQUENCE: 190

Gly Ala Pro Val Phe Cys Asn Ile Trp Leu Asn Gly Gly Asp Cys Arg
1               5                   10                  15

Gly Trp Met Gly
            20

<210> SEQ ID NO 191
<211> LENGTH: 20
<212> TYPE: PRT
<213> ORGANISM: Artificial Sequence
<220> FEATURE:
<223> OTHER INFORMATION: chemically synthesized

<400> SEQUENCE: 191

Gly Gln Gln Gln Trp Cys Asn Ile Trp Ile Asn Gly Gly Asp Cys Arg
1               5                   10                  15

Gly Trp Asn Gly
            20

<210> SEQ ID NO 192
<211> LENGTH: 20
<212> TYPE: PRT
<213> ORGANISM: Artificial Sequence

```
<220> FEATURE:
<223> OTHER INFORMATION: chemically synthesized

<400> SEQUENCE: 192

Gly Lys Ser Glu Phe Cys Asn Ile Trp Leu Asn Gly Gly Asp Cys Arg
1               5                   10                  15

Gly Trp Ile Gly
            20

<210> SEQ ID NO 193
<211> LENGTH: 20
<212> TYPE: PRT
<213> ORGANISM: Artificial Sequence
<220> FEATURE:
<223> OTHER INFORMATION: chemically synthesized

<400> SEQUENCE: 193

Gly Thr Pro Gly Gly Cys Asn Ile Trp Ala Asn Gly Gly Asp Cys Arg
1               5                   10                  15

Gly Trp Glu Gly
            20

<210> SEQ ID NO 194
<211> LENGTH: 20
<212> TYPE: PRT
<213> ORGANISM: Artificial Sequence
<220> FEATURE:
<223> OTHER INFORMATION: chemically synthesized

<400> SEQUENCE: 194

Gly Ala Ser Gln Tyr Cys Asn Leu Trp Ile Asn Gly Gly Asp Cys Arg
1               5                   10                  15

Gly Trp Arg Gly
            20

<210> SEQ ID NO 195
<211> LENGTH: 18
<212> TYPE: PRT
<213> ORGANISM: Artificial Sequence
<220> FEATURE:
<223> OTHER INFORMATION: chemically synthesized

<400> SEQUENCE: 195

Gly Cys Asn Ile Trp Leu Val Gly Gly Asp Cys Arg Pro Trp Val Glu
1               5                   10                  15

Gly Gly

<210> SEQ ID NO 196
<211> LENGTH: 18
<212> TYPE: PRT
<213> ORGANISM: Artificial Sequence
<220> FEATURE:
<223> OTHER INFORMATION: chemically synthesized

<400> SEQUENCE: 196

Gly Cys Asn Ile Trp Ala Val Gly Gly Asp Cys Arg Pro Phe Val Asp
1               5                   10                  15

Gly Gly

<210> SEQ ID NO 197
<211> LENGTH: 18
<212> TYPE: PRT
<213> ORGANISM: Artificial Sequence
<220> FEATURE:
```

<223> OTHER INFORMATION: chemically synthesized

<400> SEQUENCE: 197

Gly Cys Asn Ile Trp Leu Asn Gly Gly Asp Cys Arg Ala Trp Val Asp
1               5                   10                  15

Thr Gly

<210> SEQ ID NO 198
<211> LENGTH: 18
<212> TYPE: PRT
<213> ORGANISM: Artificial Sequence
<220> FEATURE:
<223> OTHER INFORMATION: chemically synthesized

<400> SEQUENCE: 198

Gly Cys Asn Ile Trp Ile Val Gly Gly Asp Cys Arg Pro Phe Ile Asn
1               5                   10                  15

Asp Gly

<210> SEQ ID NO 199
<211> LENGTH: 18
<212> TYPE: PRT
<213> ORGANISM: Artificial Sequence
<220> FEATURE:
<223> OTHER INFORMATION: chemically synthesized

<400> SEQUENCE: 199

Gly Cys Asn Ile Trp Leu Asn Gly Gly Asp Cys Arg Pro Val Val Phe
1               5                   10                  15

Gly Gly

<210> SEQ ID NO 200
<211> LENGTH: 18
<212> TYPE: PRT
<213> ORGANISM: Artificial Sequence
<220> FEATURE:
<223> OTHER INFORMATION: chemically synthesized

<400> SEQUENCE: 200

Gly Cys Asn Ile Trp Leu Ser Gly Gly Asp Cys Arg Met Phe Met Asn
1               5                   10                  15

Glu Gly

<210> SEQ ID NO 201
<211> LENGTH: 18
<212> TYPE: PRT
<213> ORGANISM: Artificial Sequence
<220> FEATURE:
<223> OTHER INFORMATION: chemically synthesized

<400> SEQUENCE: 201

Gly Cys Asn Ile Trp Val Asn Gly Gly Asp Cys Arg Ser Phe Val Tyr
1               5                   10                  15

Ser Gly

<210> SEQ ID NO 202
<211> LENGTH: 18
<212> TYPE: PRT
<213> ORGANISM: Artificial Sequence
<220> FEATURE:
<223> OTHER INFORMATION: chemically synthesized

<400> SEQUENCE: 202

Gly Cys Asn Ile Trp Leu Asn Gly Gly Asp Cys Arg Gly Trp Glu Ala
1               5                   10                  15

Ser Gly

<210> SEQ ID NO 203
<211> LENGTH: 18
<212> TYPE: PRT
<213> ORGANISM: Artificial Sequence
<220> FEATURE:
<223> OTHER INFORMATION: chemically synthesized

<400> SEQUENCE: 203

Gly Cys Asn Ile Trp Ala His Gly Gly Asp Cys Arg Gly Phe Ile Glu
1               5                   10                  15

Pro Gly

<210> SEQ ID NO 204
<211> LENGTH: 18
<212> TYPE: PRT
<213> ORGANISM: Artificial Sequence
<220> FEATURE:
<223> OTHER INFORMATION: chemically synthesized

<400> SEQUENCE: 204

Gly Cys Asn Ile Trp Leu Asn Gly Gly Asp Cys Arg Thr Phe Val Ala
1               5                   10                  15

Ser Gly

<210> SEQ ID NO 205
<211> LENGTH: 18
<212> TYPE: PRT
<213> ORGANISM: Artificial Sequence
<220> FEATURE:
<223> OTHER INFORMATION: chemically synthesized

<400> SEQUENCE: 205

Gly Cys Asn Ile Trp Ala His Gly Gly Asp Cys Arg Gly Phe Ile Glu
1               5                   10                  15

Pro Gly

<210> SEQ ID NO 206
<211> LENGTH: 18
<212> TYPE: PRT
<213> ORGANISM: Artificial Sequence
<220> FEATURE:
<223> OTHER INFORMATION: chemically synthesized

<400> SEQUENCE: 206

Gly Phe Leu Glu Asn Cys Asn Ile Trp Leu Asn Gly Gly Asp Cys Arg
1               5                   10                  15

Thr Gly

<210> SEQ ID NO 207
<211> LENGTH: 18
<212> TYPE: PRT
<213> ORGANISM: Artificial Sequence
<220> FEATURE:
<223> OTHER INFORMATION: chemically synthesized

<400> SEQUENCE: 207

Gly Ile Tyr Glu Asn Cys Asn Ile Trp Leu Asn Gly Gly Asp Cys Arg
1               5                   10                  15

Met Gly

```
<210> SEQ ID NO 208
<211> LENGTH: 18
<212> TYPE: PRT
<213> ORGANISM: Artificial Sequence
<220> FEATURE:
<223> OTHER INFORMATION: chemically synthesized

<400> SEQUENCE: 208

Gly Ile Pro Asp Asn Cys Asn Ile Trp Ile Asn Gly Gly Asp Cys Arg
1               5                   10                  15

Tyr Gly

<210> SEQ ID NO 209
<211> LENGTH: 21
<212> TYPE: PRT
<213> ORGANISM: Artificial Sequence
<220> FEATURE:
<223> OTHER INFORMATION: chemically synthesized

<400> SEQUENCE: 209

Gln Gly Gln Ser Gly Gln Tyr Gly Ser Cys Ser Trp Asn Tyr Val His
1               5                   10                  15

Ile Phe Met Asp Cys
            20

<210> SEQ ID NO 210
<211> LENGTH: 21
<212> TYPE: PRT
<213> ORGANISM: Artificial Sequence
<220> FEATURE:
<223> OTHER INFORMATION: chemically synthesized

<400> SEQUENCE: 210

Gln Gly Gln Ser Gly Gln Gly Asp Phe Asp Ile Pro Phe Pro Ala His
1               5                   10                  15

Trp Val Pro Ile Thr
            20

<210> SEQ ID NO 211
<211> LENGTH: 24
<212> TYPE: PRT
<213> ORGANISM: Artificial Sequence
<220> FEATURE:
<223> OTHER INFORMATION: chemically synthesized

<400> SEQUENCE: 211

Gln Gly Gln Ser Gly Gln Met Gly Val Pro Ala Gly Cys Val Trp Asn
1               5                   10                  15

Tyr Ala His Ile Phe Met Asp Cys
            20

<210> SEQ ID NO 212
<211> LENGTH: 15
<212> TYPE: PRT
<213> ORGANISM: Artificial Sequence
<220> FEATURE:
<223> OTHER INFORMATION: chemically synthesized

<400> SEQUENCE: 212

Tyr Arg Ser Cys Asn Trp Asn Tyr Val Ser Ile Phe Leu Asp Cys
1               5                   10                  15

<210> SEQ ID NO 213
```

```
<211> LENGTH: 16
<212> TYPE: PRT
<213> ORGANISM: Artificial Sequence
<220> FEATURE:
<223> OTHER INFORMATION: chemically synthesized

<400> SEQUENCE: 213

Pro Gly Ala Phe Asp Ile Pro Phe Pro Ala His Trp Val Pro Asn Thr
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: chemically synthesized

<400> SEQUENCE: 214

Glu Ser Ser Cys Val Trp Asn Tyr Val His Ile Tyr Met Asp Cys
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: chemically synthesized

<400> SEQUENCE: 215

Tyr Pro Gly Cys Lys Trp Asn Tyr Asp Arg Ile Phe Leu Asp Cys
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: chemically synthesized

<400> SEQUENCE: 216

Tyr Arg Thr Cys Ser Trp Asn Tyr Val Gly Ile Phe Leu Asp Cys
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: chemically synthesized

<400> SEQUENCE: 217

Tyr Gly Ser Cys Ser Trp Asn Tyr Val His Ile Phe Met Asp Cys
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: chemically synthesized

<400> SEQUENCE: 218

Tyr Gly Ser Cys Ser Trp Asn Tyr Val His Ile Phe Leu Asp Cys
1               5                   10                  15

<210> SEQ ID NO 219
<211> LENGTH: 15
```

<212> TYPE: PRT
<213> ORGANISM: Artificial Sequence
<220> FEATURE:
<223> OTHER INFORMATION: chemically synthesized

<400> SEQUENCE: 219

Tyr Gly Ser Cys Asn Trp Asn Tyr Val His Ile Phe Leu Asp Cys
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: chemically synthesized

<400> SEQUENCE: 220

Tyr Thr Ser Cys Asn Trp Asn Tyr Val His Ile Phe Met Asp Cys
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: chemically synthesized

<400> SEQUENCE: 221

Tyr Pro Gly Cys Lys Trp Asn Tyr Asp Arg Ile Phe Leu Asp Cys
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: chemically synthesized

<400> SEQUENCE: 222

Trp Arg Ser Cys Asn Trp Asn Tyr Ala His Ile Phe Leu Asp Cys
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: chemically synthesized

<400> SEQUENCE: 223

Trp Ser Asn Cys His Trp Asn Tyr Val His Ile Phe Leu Asp Cys
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: chemically synthesized

<400> SEQUENCE: 224

Asp Arg Ser Cys Thr Trp Asn Tyr Val Arg Ile Ser Tyr Asp Cys
1               5                   10                  15

<210> SEQ ID NO 225
<211> LENGTH: 15
<212> TYPE: PRT

<213> ORGANISM: Artificial Sequence
<220> FEATURE:
<223> OTHER INFORMATION: chemically synthesized

<400> SEQUENCE: 225

Ser Gly Ser Cys Lys Trp Asp Tyr Val His Ile Phe Leu Asp Cys
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: chemically synthesized

<400> SEQUENCE: 226

Ser Arg Ser Cys Ile Trp Asn Tyr Ala His Ile His Leu Asp Cys
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: chemically synthesized

<400> SEQUENCE: 227

Ser Met Ser Cys Tyr Trp Gln Tyr Glu Arg Ile Phe Leu Asp Cys
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: chemically synthesized

<400> SEQUENCE: 228

Tyr Arg Ser Cys Asn Trp Asn Tyr Val Ser Ile Phe Leu Asp Cys
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: chemically synthesized

<400> SEQUENCE: 229

Ser Gly Ser Cys Lys Trp Asp Tyr Val His Ile Phe Leu Asp Cys
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: chemically synthesized

<400> SEQUENCE: 230

Tyr Lys Ser Cys His Trp Asp Tyr Val His Ile Phe Leu Asp Cys
1               5                   10                  15

<210> SEQ ID NO 231
<211> LENGTH: 15
<212> TYPE: PRT
<213> ORGANISM: Artificial Sequence

```
<220> FEATURE:
<223> OTHER INFORMATION: chemically synthesized

<400> SEQUENCE: 231

Tyr Gly Ser Cys Thr Trp Asn Tyr Val His Ile Phe Met Glu Cys
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: chemically synthesized

<400> SEQUENCE: 232

Phe Ser Ser Cys Asn Trp Asn Tyr Val His Ile Phe Leu Asp Cys
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: chemically synthesized

<400> SEQUENCE: 233

Trp Arg Ser Cys Asn Trp Asn Tyr Ala His Ile Phe Leu Asp Cys
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: chemically synthesized

<400> SEQUENCE: 234

Tyr Gly Ser Cys Gln Trp Asn Tyr Val His Ile Phe Leu Asp Cys
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: chemically synthesized

<400> SEQUENCE: 235

Tyr Arg Ser Cys Asn Trp Asn Tyr Val His Ile Phe Leu Asp Cys
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: chemically synthesized

<400> SEQUENCE: 236

Asn Met Ser Cys His Trp Asp Tyr Val His Ile Phe Leu Asp Cys
1               5                   10                  15

<210> SEQ ID NO 237
<211> LENGTH: 15
<212> TYPE: PRT
<213> ORGANISM: Artificial Sequence
<220> FEATURE:
```

```
<223> OTHER INFORMATION: chemically synthesized

<400> SEQUENCE: 237

Phe Gly Pro Cys Thr Trp Asn Tyr Ala Arg Ile Ser Trp Asp Cys
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(2)
<223> OTHER INFORMATION: X is any amino acid
<220> FEATURE:
<221> NAME/KEY: MISC_FEATURE
<222> LOCATION: (5)..(5)
<223> OTHER INFORMATION: X is any amino acid
<220> FEATURE:
<221> NAME/KEY: MISC_FEATURE
<222> LOCATION: (7)..(7)
<223> OTHER INFORMATION: X is any amino acid
<220> FEATURE:
<221> NAME/KEY: MISC_FEATURE
<222> LOCATION: (13)..(13)
<223> OTHER INFORMATION: X is any amino acid

<400> SEQUENCE: 238

Xaa Xaa Ser Cys Xaa Trp Xaa Tyr Val His Ile Phe Xaa Asp Cys
1               5                   10                  15

<210> SEQ ID NO 239
<211> LENGTH: 18
<212> TYPE: PRT
<213> ORGANISM: Artificial Sequence
<220> FEATURE:
<223> OTHER INFORMATION: chemically synthesized

<400> SEQUENCE: 239

Met Gly Val Pro Ala Gly Cys Val Trp Asn Tyr Ala His Ile Phe Met
1               5                   10                  15

Asp Cys

<210> SEQ ID NO 240
<211> LENGTH: 18
<212> TYPE: PRT
<213> ORGANISM: Artificial Sequence
<220> FEATURE:
<223> OTHER INFORMATION: chemically synthesized

<400> SEQUENCE: 240

Arg Asp Thr Gly Gly Gln Cys Arg Trp Asp Tyr Val His Ile Phe Met
1               5                   10                  15

Asp Cys

<210> SEQ ID NO 241
<211> LENGTH: 18
<212> TYPE: PRT
<213> ORGANISM: Artificial Sequence
<220> FEATURE:
<223> OTHER INFORMATION: chemically synthesized

<400> SEQUENCE: 241

Ala Gly Val Pro Ala Gly Cys Thr Trp Asn Tyr Val His Ile Phe Met
1               5                   10                  15
```

Glu Cys

<210> SEQ ID NO 242
<211> LENGTH: 18
<212> TYPE: PRT
<213> ORGANISM: Artificial Sequence
<220> FEATURE:
<223> OTHER INFORMATION: chemically synthesized

<400> SEQUENCE: 242

Val Gly Val Pro Asn Gly Cys Val Trp Asn Tyr Ala His Ile Phe Met
1               5                   10                  15

Glu Cys

<210> SEQ ID NO 243
<211> LENGTH: 18
<212> TYPE: PRT
<213> ORGANISM: Artificial Sequence
<220> FEATURE:
<223> OTHER INFORMATION: chemically synthesized

<400> SEQUENCE: 243

Asp Gly Gly Pro Ala Gly Cys Ser Trp Asn Tyr Val His Ile Phe Met
1               5                   10                  15

Glu Cys

<210> SEQ ID NO 244
<211> LENGTH: 18
<212> TYPE: PRT
<213> ORGANISM: Artificial Sequence
<220> FEATURE:
<223> OTHER INFORMATION: chemically synthesized

<400> SEQUENCE: 244

Ala Val Gly Pro Ala Gly Cys Trp Trp Asn Tyr Val His Ile Phe Met
1               5                   10                  15

Glu Cys

<210> SEQ ID NO 245
<211> LENGTH: 18
<212> TYPE: PRT
<213> ORGANISM: Artificial Sequence
<220> FEATURE:
<223> OTHER INFORMATION: chemically synthesized

<400> SEQUENCE: 245

Cys Thr Trp Asn Tyr Val His Ile Phe Met Asp Cys Gly Glu Gly Glu
1               5                   10                  15

Gly Pro

<210> SEQ ID NO 246
<211> LENGTH: 18
<212> TYPE: PRT
<213> ORGANISM: Artificial Sequence
<220> FEATURE:
<223> OTHER INFORMATION: chemically synthesized

<400> SEQUENCE: 246

Gly Gly Val Pro Glu Gly Cys Thr Trp Asn Tyr Ala His Ile Phe Met
1               5                   10                  15

Glu Cys

<210> SEQ ID NO 247

```
<211> LENGTH: 18
<212> TYPE: PRT
<213> ORGANISM: Artificial Sequence
<220> FEATURE:
<223> OTHER INFORMATION: chemically synthesized

<400> SEQUENCE: 247

Ala Glu Val Pro Ala Gly Cys Trp Trp Asn Tyr Val His Ile Phe Met
1               5                   10                  15

Glu Cys

<210> SEQ ID NO 248
<211> LENGTH: 18
<212> TYPE: PRT
<213> ORGANISM: Artificial Sequence
<220> FEATURE:
<223> OTHER INFORMATION: chemically synthesized

<400> SEQUENCE: 248

Ala Gly Val Pro Ala Gly Cys Thr Trp Asn Tyr Val His Ile Phe Met
1               5                   10                  15

Glu Cys

<210> SEQ ID NO 249
<211> LENGTH: 18
<212> TYPE: PRT
<213> ORGANISM: Artificial Sequence
<220> FEATURE:
<223> OTHER INFORMATION: chemically synthesized

<400> SEQUENCE: 249

Ser Gly Ala Ser Gly Gly Cys Lys Trp Asn Tyr Val His Ile Phe Met
1               5                   10                  15

Asp Cys

<210> SEQ ID NO 250
<211> LENGTH: 18
<212> TYPE: PRT
<213> ORGANISM: Artificial Sequence
<220> FEATURE:
<223> OTHER INFORMATION: chemically synthesized

<400> SEQUENCE: 250

Thr Pro Gly Cys Arg Trp Asn Tyr Val His Ile Phe Met Glu Cys Glu
1               5                   10                  15

Ala Leu

<210> SEQ ID NO 251
<211> LENGTH: 18
<212> TYPE: PRT
<213> ORGANISM: Artificial Sequence
<220> FEATURE:
<223> OTHER INFORMATION: chemically synthesized

<400> SEQUENCE: 251

Val Gly Val Pro Asn Gly Cys Val Trp Asn Tyr Ala His Ile Phe Met
1               5                   10                  15

Glu Cys

<210> SEQ ID NO 252
<211> LENGTH: 16
<212> TYPE: PRT
<213> ORGANISM: Artificial Sequence
<220> FEATURE:
```

```
<223> OTHER INFORMATION: chemically synthesized

<400> SEQUENCE: 252

Pro Gly Ala Phe Asp Ile Pro Phe Pro Ala His Trp Val Pro Asn Thr
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: chemically synthesized

<400> SEQUENCE: 253

Arg Gly Ala Cys Asp Ile Pro Phe Pro Ala His Trp Ile Pro Asn Thr
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: chemically synthesized

<400> SEQUENCE: 254

Gln Gly Asp Phe Asp Ile Pro Phe Pro Ala His Trp Val Pro Ile Thr
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: X is any amino acid

<400> SEQUENCE: 255

Xaa Gly Ala Phe Asp Ile Pro Phe Pro Ala His Trp Val Pro Asn Thr
1               5                   10                  15

<210> SEQ ID NO 256
<211> LENGTH: 19
<212> TYPE: PRT
<213> ORGANISM: Artificial Sequence
<220> FEATURE:
<223> OTHER INFORMATION: chemically synthesized

<400> SEQUENCE: 256

Arg Gly Asp Gly Asn Asp Ser Asp Ile Pro Phe Pro Ala His Trp Val
1               5                   10                  15

Pro Arg Thr

<210> SEQ ID NO 257
<211> LENGTH: 19
<212> TYPE: PRT
<213> ORGANISM: Artificial Sequence
<220> FEATURE:
<223> OTHER INFORMATION: chemically synthesized

<400> SEQUENCE: 257

Ser Gly Val Gly Arg Asp Arg Asp Ile Pro Phe Pro Ala His Trp Val
1               5                   10                  15

Pro Arg Thr
```

```
<210> SEQ ID NO 258
<211> LENGTH: 19
<212> TYPE: PRT
<213> ORGANISM: Artificial Sequence
<220> FEATURE:
<223> OTHER INFORMATION: chemically synthesized

<400> SEQUENCE: 258

Trp Ala Gly Gly Asn Asp Cys Asp Ile Pro Phe Pro Ala His Trp Ile
1               5                   10                  15

Pro Asn Thr

<210> SEQ ID NO 259
<211> LENGTH: 19
<212> TYPE: PRT
<213> ORGANISM: Artificial Sequence
<220> FEATURE:
<223> OTHER INFORMATION: chemically synthesized

<400> SEQUENCE: 259

Trp Gly Asp Gly Met Asp Val Asp Ile Pro Phe Pro Ala His Trp Val
1               5                   10                  15

Pro Val Thr

<210> SEQ ID NO 260
<211> LENGTH: 19
<212> TYPE: PRT
<213> ORGANISM: Artificial Sequence
<220> FEATURE:
<223> OTHER INFORMATION: chemically synthesized

<400> SEQUENCE: 260

Ala Gly Ser Gly Asn Asp Ser Asp Ile Pro Phe Pro Ala His Trp Val
1               5                   10                  15

Pro Arg Thr

<210> SEQ ID NO 261
<211> LENGTH: 19
<212> TYPE: PRT
<213> ORGANISM: Artificial Sequence
<220> FEATURE:
<223> OTHER INFORMATION: chemically synthesized

<400> SEQUENCE: 261

Glu Ser Arg Ser Gly Tyr Ala Asp Ile Pro Phe Pro Ala His Trp Val
1               5                   10                  15

Pro Arg Thr

<210> SEQ ID NO 262
<211> LENGTH: 19
<212> TYPE: PRT
<213> ORGANISM: Artificial Sequence
<220> FEATURE:
<223> OTHER INFORMATION: chemically synthesized

<400> SEQUENCE: 262

Arg Glu Cys Gly Arg Cys Gly Asp Ile Pro Phe Pro Ala His Trp Val
1               5                   10                  15

Pro Arg Thr

<210> SEQ ID NO 263
<211> LENGTH: 8
```

```
<212> TYPE: PRT
<213> ORGANISM: Artificial Sequence
<220> FEATURE:
<223> OTHER INFORMATION: chemically synthesized

<400> SEQUENCE: 263

Thr Gly Arg Gly Pro Ser Trp Val
1               5

<210> SEQ ID NO 264
<211> LENGTH: 8
<212> TYPE: PRT
<213> ORGANISM: Artificial Sequence
<220> FEATURE:
<223> OTHER INFORMATION: chemically synthesized

<400> SEQUENCE: 264

Ser Ala Arg Gly Pro Ser Arg Trp
1               5

<210> SEQ ID NO 265
<211> LENGTH: 8
<212> TYPE: PRT
<213> ORGANISM: Artificial Sequence
<220> FEATURE:
<223> OTHER INFORMATION: chemically synthesized

<400> SEQUENCE: 265

Thr Ala Arg Gly Pro Ser Phe Lys
1               5

<210> SEQ ID NO 266
<211> LENGTH: 8
<212> TYPE: PRT
<213> ORGANISM: Artificial Sequence
<220> FEATURE:
<223> OTHER INFORMATION: chemically synthesized

<400> SEQUENCE: 266

Leu Ser Gly Arg Ser Asp Asn His
1               5

<210> SEQ ID NO 267
<211> LENGTH: 8
<212> TYPE: PRT
<213> ORGANISM: Artificial Sequence
<220> FEATURE:
<223> OTHER INFORMATION: chemically synthesized

<400> SEQUENCE: 267

Gly Gly Trp His Thr Gly Arg Asn
1               5

<210> SEQ ID NO 268
<211> LENGTH: 8
<212> TYPE: PRT
<213> ORGANISM: Artificial Sequence
<220> FEATURE:
<223> OTHER INFORMATION: chemically synthesized

<400> SEQUENCE: 268

His Thr Gly Arg Ser Gly Ala Leu
1               5

<210> SEQ ID NO 269
<211> LENGTH: 8
<212> TYPE: PRT
```

```
<213> ORGANISM: Artificial Sequence
<220> FEATURE:
<223> OTHER INFORMATION: chemically synthesized

<400> SEQUENCE: 269

Pro Leu Thr Gly Arg Ser Gly Gly
1               5

<210> SEQ ID NO 270
<211> LENGTH: 8
<212> TYPE: PRT
<213> ORGANISM: Artificial Sequence
<220> FEATURE:
<223> OTHER INFORMATION: chemically synthesized

<400> SEQUENCE: 270

Ala Ala Arg Gly Pro Ala Ile His
1               5

<210> SEQ ID NO 271
<211> LENGTH: 8
<212> TYPE: PRT
<213> ORGANISM: Artificial Sequence
<220> FEATURE:
<223> OTHER INFORMATION: chemically synthesized

<400> SEQUENCE: 271

Arg Gly Pro Ala Phe Asn Pro Met
1               5

<210> SEQ ID NO 272
<211> LENGTH: 8
<212> TYPE: PRT
<213> ORGANISM: Artificial Sequence
<220> FEATURE:
<223> OTHER INFORMATION: chemically synthesized

<400> SEQUENCE: 272

Ser Ser Arg Gly Pro Ala Tyr Leu
1               5

<210> SEQ ID NO 273
<211> LENGTH: 8
<212> TYPE: PRT
<213> ORGANISM: Artificial Sequence
<220> FEATURE:
<223> OTHER INFORMATION: chemically synthesized

<400> SEQUENCE: 273

Arg Gly Pro Ala Thr Pro Ile Met
1               5

<210> SEQ ID NO 274
<211> LENGTH: 4
<212> TYPE: PRT
<213> ORGANISM: Artificial Sequence
<220> FEATURE:
<223> OTHER INFORMATION: chemically synthesized

<400> SEQUENCE: 274

Arg Gly Pro Ala
1

<210> SEQ ID NO 275
<211> LENGTH: 10
<212> TYPE: PRT
<213> ORGANISM: Artificial Sequence
```

```
<220> FEATURE:
<223> OTHER INFORMATION: chemically synthesized

<400> SEQUENCE: 275

Gly Gly Gln Pro Ser Gly Met Trp Gly Trp
1               5                   10

<210> SEQ ID NO 276
<211> LENGTH: 10
<212> TYPE: PRT
<213> ORGANISM: Artificial Sequence
<220> FEATURE:
<223> OTHER INFORMATION: chemically synthesized

<400> SEQUENCE: 276

Phe Pro Arg Pro Leu Gly Ile Thr Gly Leu
1               5                   10

<210> SEQ ID NO 277
<211> LENGTH: 10
<212> TYPE: PRT
<213> ORGANISM: Artificial Sequence
<220> FEATURE:
<223> OTHER INFORMATION: chemically synthesized

<400> SEQUENCE: 277

Val His Met Pro Leu Gly Phe Leu Gly Pro
1               5                   10

<210> SEQ ID NO 278
<211> LENGTH: 8
<212> TYPE: PRT
<213> ORGANISM: Artificial Sequence
<220> FEATURE:
<223> OTHER INFORMATION: chemically synthesized

<400> SEQUENCE: 278

Ser Pro Leu Thr Gly Arg Ser Gly
1               5

<210> SEQ ID NO 279
<211> LENGTH: 8
<212> TYPE: PRT
<213> ORGANISM: Artificial Sequence
<220> FEATURE:
<223> OTHER INFORMATION: chemically synthesized

<400> SEQUENCE: 279

Ser Ala Gly Phe Ser Leu Pro Ala
1               5

<210> SEQ ID NO 280
<211> LENGTH: 9
<212> TYPE: PRT
<213> ORGANISM: Artificial Sequence
<220> FEATURE:
<223> OTHER INFORMATION: chemically synthesized

<400> SEQUENCE: 280

Leu Ala Pro Leu Gly Leu Gln Arg Arg
1               5

<210> SEQ ID NO 281
<211> LENGTH: 8
<212> TYPE: PRT
<213> ORGANISM: Artificial Sequence
<220> FEATURE:
```

<223> OTHER INFORMATION: chemically synthesized

<400> SEQUENCE: 281

Ser Gly Gly Pro Leu Gly Val Arg
1               5

<210> SEQ ID NO 282
<211> LENGTH: 4
<212> TYPE: PRT
<213> ORGANISM: Artificial Sequence
<220> FEATURE:
<223> OTHER INFORMATION: chemically synthesized

<400> SEQUENCE: 282

Pro Leu Gly Leu
1

<210> SEQ ID NO 283
<211> LENGTH: 7
<212> TYPE: PRT
<213> ORGANISM: Artificial Sequence
<220> FEATURE:
<223> OTHER INFORMATION: chemically synthesized

<400> SEQUENCE: 283

Gly Pro Arg Ser Phe Gly Leu
1               5

<210> SEQ ID NO 284
<211> LENGTH: 6
<212> TYPE: PRT
<213> ORGANISM: Artificial Sequence
<220> FEATURE:
<223> OTHER INFORMATION: chemically synthesized

<400> SEQUENCE: 284

Gly Pro Arg Ser Phe Gly
1               5

<210> SEQ ID NO 285
<211> LENGTH: 5
<212> TYPE: PRT
<213> ORGANISM: Artificial Sequence
<220> FEATURE:
<223> OTHER INFORMATION: chemically synthesized

<400> SEQUENCE: 285

Gly Ser Gly Gly Ser
1               5

<210> SEQ ID NO 286
<211> LENGTH: 4
<212> TYPE: PRT
<213> ORGANISM: Artificial Sequence
<220> FEATURE:
<223> OTHER INFORMATION: chemically synthesized

<400> SEQUENCE: 286

Gly Gly Gly Ser
1

<210> SEQ ID NO 287
<211> LENGTH: 4
<212> TYPE: PRT
<213> ORGANISM: Artificial Sequence
<220> FEATURE:
<223> OTHER INFORMATION: chemically synthesized

<400> SEQUENCE: 287

Gly Gly Ser Gly
1

<210> SEQ ID NO 288
<211> LENGTH: 5
<212> TYPE: PRT
<213> ORGANISM: Artificial Sequence
<220> FEATURE:
<223> OTHER INFORMATION: chemically synthesized

<400> SEQUENCE: 288

Gly Gly Ser Gly Gly
1               5

<210> SEQ ID NO 289
<211> LENGTH: 5
<212> TYPE: PRT
<213> ORGANISM: Artificial Sequence
<220> FEATURE:
<223> OTHER INFORMATION: chemically synthesized

<400> SEQUENCE: 289

Gly Ser Gly Ser Gly
1               5

<210> SEQ ID NO 290
<211> LENGTH: 5
<212> TYPE: PRT
<213> ORGANISM: Artificial Sequence
<220> FEATURE:
<223> OTHER INFORMATION: chemically synthesized

<400> SEQUENCE: 290

Gly Ser Gly Gly Gly
1               5

<210> SEQ ID NO 291
<211> LENGTH: 5
<212> TYPE: PRT
<213> ORGANISM: Artificial Sequence
<220> FEATURE:
<223> OTHER INFORMATION: chemically synthesized

<400> SEQUENCE: 291

Gly Gly Gly Ser Gly
1               5

<210> SEQ ID NO 292
<211> LENGTH: 5
<212> TYPE: PRT
<213> ORGANISM: Artificial Sequence
<220> FEATURE:
<223> OTHER INFORMATION: chemically synthesized

<400> SEQUENCE: 292

Gly Ser Ser Ser Gly
1               5

<210> SEQ ID NO 293
<211> LENGTH: 13
<212> TYPE: PRT
<213> ORGANISM: Artificial Sequence
<220> FEATURE:
<223> OTHER INFORMATION: chemically synthesized

```
<400> SEQUENCE: 293

Gly Ser Ser Gly Gly Ser Gly Gly Ser Gly Gly Ser Gly
1               5                   10

<210> SEQ ID NO 294
<211> LENGTH: 5
<212> TYPE: PRT
<213> ORGANISM: Artificial Sequence
<220> FEATURE:
<223> OTHER INFORMATION: chemically synthesized

<400> SEQUENCE: 294

Gly Ser Ser Gly Thr
1               5

<210> SEQ ID NO 295
<211> LENGTH: 4
<212> TYPE: PRT
<213> ORGANISM: Artificial Sequence
<220> FEATURE:
<223> OTHER INFORMATION: chemically synthesized

<400> SEQUENCE: 295

Gly Ser Ser Gly
1

<210> SEQ ID NO 296
<211> LENGTH: 6
<212> TYPE: PRT
<213> ORGANISM: Artificial Sequence
<220> FEATURE:
<223> OTHER INFORMATION: chemically synthesized

<400> SEQUENCE: 296

Gln Gly Gln Ser Gly Gln
1               5

<210> SEQ ID NO 297
<211> LENGTH: 60
<212> TYPE: DNA
<213> ORGANISM: Artificial Sequence
<220> FEATURE:
<223> OTHER INFORMATION: chemically synthesized

<400> SEQUENCE: 297
atgtacagga tgcaactcct gtcttgcatt gcactaagtc ttgcacttgt cacgaattcg    60

<210> SEQ ID NO 298
<211> LENGTH: 1350
<212> TYPE: DNA
<213> ORGANISM: Artificial Sequence
<220> FEATURE:
<223> OTHER INFORMATION: chemically synthesized

<400> SEQUENCE: 298
caggtgcagc tgaaacagag cggcccgggc ctggtgcagc cgagccagag cctgagcatt    60
acctgcaccg tgagcggctt tagcctgacc aactatggcg tgcattgggt gcgccagagc   120
ccgggcaaag cctggaatg gctgggcgtg atttggagcg gcggcaacac cgattataac   180
accccgttta ccagccgcct gagcattaac aaagataaca gcaaaagcca ggtgtttttt   240
aaaatgaaca gcctgcaaag ccaggatacc gcgatttatt attgcgcgcg cgcgctgacc   300
tattatgatt atgaatttgc gtattggggc cagggcaccc tggtgaccgt gagcgcggct   360
agcaccaagg gcccatcggt cttccccctg gcaccctcct ccaagagcac ctctggggc    420
```

```
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggatgaactg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaatga                                      1350

<210> SEQ ID NO 299
<211> LENGTH: 1410
<212> TYPE: DNA
<213> ORGANISM: Artificial Sequence
<220> FEATURE:
<223> OTHER INFORMATION: chemically synthesized

<400> SEQUENCE: 299
atgtacagga tgcaactcct gtcttgcatt gcactaagtc ttgcacttgt cacgaattcg       60
caggtgcagc tgaaacagag cggcccgggc ctggtgcagc cgagccagag cctgagcatt      120
acctgcaccg tgagcggctt tagcctgacc aactatggcg tgcattgggt gcgccagagc      180
ccgggcaaag gcctggaatg gctgggcgtg atttggagcg gcggcaacac cgattataac      240
accccgttta gcagccgcct gagcattaac aaagataaca gcaaaagcca ggtgttttttt      300 aaaatgaaca gcctgcaaag ccaggatacc gcgatttatt attgcgcgcg cgcgctgacc      360
tattatgatt atgaatttgc gtattggggc cagggcaccc tggtgaccgt gagcgcggct      420
agcaccaagg gcccatcggt cttccccctg gcaccctcct ccaagagcac ctctgggggc      480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac ccagacctac      660
atctgcaacg tgaatcacaa gcccagcaac accaaggtgg acaagaaagt tgagcccaaa      720
tcttgtgaca aaactcacac atgcccaccg tgcccagcac ctgaactcct ggggggaccg      780
tcagtcttcc tcttcccccc aaaacccaag gacaccctca tgatctcccg gacccctgag      840
gtcacatgcg tggtggtgga cgtgagccac gaagaccctg aggtcaagtt caactggtac      900
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080
```

```
gccaaagggc agccccgaga accacaggtg tacaccctgc ccccatcccg ggatgaactg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                    1410

<210> SEQ ID NO 300
<211> LENGTH: 20
<212> TYPE: PRT
<213> ORGANISM: Artificial Sequence
<220> FEATURE:
<223> OTHER INFORMATION: chemically synthesized

<400> SEQUENCE: 300

Met Tyr Arg Met Gln Leu Leu Ser Cys Ile Ala Leu Ser Leu Ala Leu
1               5                   10                  15

Val Thr Asn Ser
            20

<210> SEQ ID NO 301
<211> LENGTH: 449
<212> TYPE: PRT
<213> ORGANISM: Artificial Sequence
<220> FEATURE:
<223> OTHER INFORMATION: chemically synthesized

<400> SEQUENCE: 301

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 302
<211> LENGTH: 469
<212> TYPE: PRT
<213> ORGANISM: Artificial Sequence
<220> FEATURE:
<223> OTHER INFORMATION: chemically synthesized

<400> SEQUENCE: 302

Met Tyr Arg Met Gln Leu Leu Ser Cys Ile Ala Leu Ser Leu Ala Leu
1               5                   10                  15

Val Thr Asn Ser Gln Val Gln Leu Lys Gln Ser Gly Pro Gly Leu Val
            20                  25                  30

Gln Pro Ser Gln Ser Leu Ser Ile Thr Cys Thr Val Ser Gly Phe Ser
        35                  40                  45

Leu Thr Asn Tyr Gly Val His Trp Val Arg Gln Ser Pro Gly Lys Gly
    50                  55                  60

Leu Glu Trp Leu Gly Val Ile Trp Ser Gly Gly Asn Thr Asp Tyr Asn
65                  70                  75                  80

Thr Pro Phe Thr Ser Arg Leu Ser Ile Asn Lys Asp Asn Ser Lys Ser
                85                  90                  95

Gln Val Phe Phe Lys Met Asn Ser Leu Gln Ser Gln Asp Thr Ala Ile
            100                 105                 110

Tyr Tyr Cys Ala Arg Ala Leu Thr Tyr Tyr Asp Tyr Glu Phe Ala Tyr
        115                 120                 125

```
Trp Gly Gln Gly Thr Leu Val Thr Val Ser Ala Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
450                 455                 460

Leu Ser Pro Gly Lys
465

<210> SEQ ID NO 303
<211> LENGTH: 45
<212> TYPE: DNA
<213> ORGANISM: Artificial Sequence
<220> FEATURE:
<223> OTHER INFORMATION: chemically synthesized

<400> SEQUENCE: 303
tgcatctcac ctcgtggttg tccggacggc ccatacgtca tgtac                45
```

```
<210> SEQ ID NO 304
<211> LENGTH: 18
<212> TYPE: DNA
<213> ORGANISM: Artificial Sequence
<220> FEATURE:
<223> OTHER INFORMATION: chemically synthesized

<400> SEQUENCE: 304
caaggccagt ctggccag                                                  18

<210> SEQ ID NO 305
<211> LENGTH: 39
<212> TYPE: DNA
<213> ORGANISM: Artificial Sequence
<220> FEATURE:
<223> OTHER INFORMATION: chemically synthesized

<400> SEQUENCE: 305
ggctcgagcg gtggcagcgg tggctctggt ggatccggt                           39

<210> SEQ ID NO 306
<211> LENGTH: 24
<212> TYPE: DNA
<213> ORGANISM: Artificial Sequence
<220> FEATURE:
<223> OTHER INFORMATION: chemically synthesized

<400> SEQUENCE: 306
ctgagcggcc gttccgataa tcat                                           24

<210> SEQ ID NO 307
<211> LENGTH: 15
<212> TYPE: DNA
<213> ORGANISM: Artificial Sequence
<220> FEATURE:
<223> OTHER INFORMATION: chemically synthesized

<400> SEQUENCE: 307
ggcagtagcg gtacc                                                     15

<210> SEQ ID NO 308
<211> LENGTH: 645
<212> TYPE: DNA
<213> ORGANISM: Artificial Sequence
<220> FEATURE:
<223> OTHER INFORMATION: chemically synthesized

<400> SEQUENCE: 308
cagatcttgc tgacccagag cccggtgatt ctgagcgtga gcccgggcga acgtgtgagc     60
tttagctgcc gcgcgagcca gagcattggc accaacattc attggtatca gcagcgcacc   120
aacggcagcc cgcgcctgct gattaaatat gcgagcgaaa gcattagcgg cattccgagc   180
cgctttagcg gcagcggcag cggcaccgat tttaccctga gcattaacag cgtggaaagc   240
gaagatattg cggattatta ttgccagcag aacaacaact ggccgaccac ctttggcgcg   300
ggcaccaaac tggaactgaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactccag    480 gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 309
<211> LENGTH: 846
<212> TYPE: DNA
<213> ORGANISM: Artificial Sequence
<220> FEATURE:
<223> OTHER INFORMATION: chemically synthesized

<400> SEQUENCE: 309

```
atgtacagga tgcaactcct gtcttgcatt gcactaagtc ttgcacttgt cacgaattcg      60
caaggccagt ctggccagtg catctcacct cgtggttgtc cggacggccc atacgtcatg     120
tacggctcga gcggtggcag cggtggctct ggtggatccg gtctgagcgg ccgttccgat     180
aatcatggca gtagcggtac ccagatcttg ctgacccaga gcccggtgat tctgagcgtg     240
agcccgggcg aacgtgtgag ctttagctgc cgcgcgagcc agagcattgg caccaacatt     300
cattggtatc agcagcgcac caacggcagc ccgcgcctgc tgattaaata tgcgagcgaa     360
agcattagcg gcattccgag ccgctttagc ggcagcggca gcggcaccga ttttaccctg     420
agcattaaca gcgtggaaag cgaagatatt gcggattatt attgccagca gaacaacaac     480
tggccgacca cctttggcgc gggcaccaaa ctggaactga acgtacggt ggctgcacca      540
tctgtcttca tcttcccgcc atctgatgag cagttgaaat ctggaactgc ctctgttgtg     600
tgcctgctga ataacttcta tcccagagag gccaaagtac agtggaaggt ggataacgcc     660
ctccaatcgg gtaactccca ggagagtgtc acagagcagg acagcaagga cagcacctac     720
agcctcagca gcaccctgac gctgagcaaa gcagactacg agaaacacaa agtctacgcc     780
tgcgaagtca cccatcaggg cctgagctcg cccgtcacaa agagcttcaa caggggagag     840
tgttag                                                                846
```

<210> SEQ ID NO 310
<211> LENGTH: 214
<212> TYPE: PRT
<213> ORGANISM: Artificial Sequence
<220> FEATURE:
<223> OTHER INFORMATION: chemically synthesized

<400> SEQUENCE: 310

```
Gln Ile Leu Leu Thr Gln Ser Pro Val Ile Leu Ser Val Ser Pro Gly
1               5                   10                  15
Glu Arg Val Ser Phe Ser Cys Arg Ala Ser Gln Ser Ile Gly Thr Asn
            20                  25                  30
Ile His Trp Tyr Gln Gln Arg Thr Asn Gly Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Asn Asn Asn Trp Pro Thr
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 311
<211> LENGTH: 281
<212> TYPE: PRT
<213> ORGANISM: Artificial Sequence
<220> FEATURE:
<223> OTHER INFORMATION: chemically synthesized

<400> SEQUENCE: 311

Met Tyr Arg Met Gln Leu Leu Ser Cys Ile Ala Leu Ser Leu Ala Leu
1               5                   10                  15

Val Thr Asn Ser Gln Gly Gln Ser Gly Gln Cys Ile Ser Pro Arg Gly
            20                  25                  30

Cys Pro Asp Gly Pro Tyr Val Met Tyr Gly Ser Ser Gly Ser Gly
        35                  40                  45

Gly Ser Gly Gly Ser Gly Leu Ser Gly Arg Ser Asp Asn His Gly Ser
    50                  55                  60

Ser Gly Thr Gln Ile Leu Leu Thr Gln Ser Pro Val Ile Leu Ser Val
65                  70                  75                  80

Ser Pro Gly Glu Arg Val Ser Phe Ser Cys Arg Ala Ser Gln Ser Ile
                85                  90                  95

Gly Thr Asn Ile His Trp Tyr Gln Gln Arg Thr Asn Gly Ser Pro Arg
            100                 105                 110

Leu Leu Ile Lys Tyr Ala Ser Glu Ser Ile Ser Gly Ile Pro Ser Arg
        115                 120                 125

Phe Ser Gly Ser Gly Ser Gly Thr Asp Phe Thr Leu Ser Ile Asn Ser
    130                 135                 140

Val Glu Ser Glu Asp Ile Ala Asp Tyr Tyr Cys Gln Gln Asn Asn Asn
145                 150                 155                 160

Trp Pro Thr Thr Phe Gly Ala Gly Thr Lys Leu Glu Leu Lys Arg Thr
                165                 170                 175

Val Ala Ala Pro Ser Val Phe Ile Phe Pro Pro Ser Asp Glu Gln Leu
            180                 185                 190

Lys Ser Gly Thr Ala Ser Val Val Cys Leu Leu Asn Asn Phe Tyr Pro
        195                 200                 205

Arg Glu Ala Lys Val Gln Trp Lys Val Asp Asn Ala Leu Gln Ser Gly
    210                 215                 220

Asn Ser Gln Glu Ser Val Thr Glu Gln Asp Ser Lys Asp Ser Thr Tyr
225                 230                 235                 240

Ser Leu Ser Ser Thr Leu Thr Leu Ser Lys Ala Asp Tyr Glu Lys His
                245                 250                 255

Lys Val Tyr Ala Cys Glu Val Thr His Gln Gly Leu Ser Ser Pro Val
            260                 265                 270

Thr Lys Ser Phe Asn Arg Gly Glu Cys
        275                 280

<210> SEQ ID NO 312

<211> LENGTH: 786
<212> TYPE: DNA
<213> ORGANISM: Artificial Sequence
<220> FEATURE:
<223> OTHER INFORMATION: chemically synthesized

<400> SEQUENCE: 312

```
caaggccagt ctggccagtg catctcacct cgtggttgtc cggacggccc atacgtcatg      60
tacggctcga gcggtggcag cggtggctct ggtggatccg gtctgagcgg ccgttccgat     120
aatcatggca gtagcggtac ccagatcttg ctgacccaga gcccggtgat tctgagcgtg     180
agcccgggcg aacgtgtgag ctttagctgc cgcgcgagcc agagcattgg caccaacatt     240
cattggtatc agcagcgcac caacggcagc ccgcgcctgc tgattaaata tgcgagcgaa     300
agcattagcg gcattccgag ccgctttagc ggcagcggca gcggcaccga ttttaccctg     360
agcattaaca gcgtggaaag cgaagatatt gcggattatt attgccagca gaacaacaac     420
tggccgacca cctttggcgc gggcaccaaa ctggaactga acgtacggt ggctgcacca     480
tctgtcttca tcttcccgcc atctgatgag cagttgaaat ctggaactgc ctctgttgtg     540
tgcctgctga ataacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                               786
```

<210> SEQ ID NO 313
<211> LENGTH: 261
<212> TYPE: PRT
<213> ORGANISM: Artificial Sequence
<220> FEATURE:
<223> OTHER INFORMATION: chemically synthesized

<400> SEQUENCE: 313

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Asp Asn His Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175
```

```
Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260
```

<210> SEQ ID NO 314
<211> LENGTH: 1350
<212> TYPE: DNA
<213> ORGANISM: Artificial Sequence
<220> FEATURE:
<223> OTHER INFORMATION: chemically synthesized

<400> SEQUENCE: 314

```
caggtgcagc tgaaacagag cggcccgggc ctggtgcagc cgagccagag cctgagcatt    60
acctgcaccg tgagcggctt tagcctgacc aactatggcg tgcattgggt gcgccagagc   120
ccgggcaaag cctggaatg gctgggcgtg atttggagcg gcggcaacac cgattataac   180
accccgttta ccagccgcct gagcattaac aaagataaca gcaaaagcca ggtgttttt    240
aaaatgaaca gcctgcaaag caacgatacc gcgatttatt attgcgcgcg cgcgctgacc   300
tattatgatt atgaatttgc gtattggggc cagggcaccc tggtgaccgt gagcgcggct   360
agcaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagaaagt tgagcccaaa   660
tcttgtgaca aaactcacac atgcccaccg tgcccagcac ctgaactcct ggggggaccg   720
tcagtcttcc tcttcccccc aaaacccaag gacaccctca tgatctcccg gaccccctgag   780
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccgtg tggtcagcgt cctcaccgtc ctgcaccagg actggctgaa tggcaaggag   960
tacaagtgca aggtctccaa caaagccctc ccagccccca tcgagaaaac catctccaaa  1020
gccaaagggc agccccgaga accacaggtg tacaccctgc ccccatcccg ggatgaactg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                    1350
```

<210> SEQ ID NO 315
<211> LENGTH: 1410
<212> TYPE: DNA
<213> ORGANISM: Artificial Sequence
<220> FEATURE:
<223> OTHER INFORMATION: chemically synthesized

<400> SEQUENCE: 315

```
atgtacagga tgcaactcct gtcttgcatt gcactaagtc ttgcacttgt cacgaattcg      60
caggtgcagc tgaaacagag cggcccgggc ctggtgcagc cgagccagag cctgagcatt     120
acctgcaccg tgagcggctt tagcctgacc aactatggcg tgcattgggt gcgccagagc     180
ccgggcaaag gcctggaatg gctgggcgtg atttggagcg gcggcaacac cgattataac     240
accccgttta ccagccgcct gagcattaac aaagataaca gcaaaagcca ggtgtttttt     300
aaaatgaaca gcctgcaaag caacgatacc gcgatttatt attgcgcgcg cgcgctgacc     360
tattatgatt atgaatttgc gtattggggc cagggcaccc tggtgaccgt gagcgcggct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggatgaactg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                     1410
```

<210> SEQ ID NO 316
<211> LENGTH: 449
<212> TYPE: PRT
<213> ORGANISM: Artificial Sequence
<220> FEATURE:
<223> OTHER INFORMATION: chemically synthesized

<400> SEQUENCE: 316

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
```

```
                    85                  90                  95
Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 317
<211> LENGTH: 469
<212> TYPE: PRT
<213> ORGANISM: Artificial Sequence
<220> FEATURE:
<223> OTHER INFORMATION: chemically synthesized

<400> SEQUENCE: 317
```

-continued

```
Met Tyr Arg Met Gln Leu Leu Ser Cys Ile Ala Leu Ser Leu Ala Leu
1               5                   10                  15

Val Thr Asn Ser Gln Val Gln Leu Lys Gln Ser Gly Pro Gly Leu Val
            20                  25                  30

Gln Pro Ser Gln Ser Leu Ser Ile Thr Cys Thr Val Ser Gly Phe Ser
            35                  40                  45

Leu Thr Asn Tyr Gly Val His Trp Val Arg Gln Ser Pro Gly Lys Gly
        50                  55                  60

Leu Glu Trp Leu Gly Val Ile Trp Ser Gly Gly Asn Thr Asp Tyr Asn
65                  70                  75                  80

Thr Pro Phe Thr Ser Arg Leu Ser Ile Asn Lys Asp Asn Ser Lys Ser
                85                  90                  95

Gln Val Phe Phe Lys Met Asn Ser Leu Gln Ser Asn Asp Thr Ala Ile
            100                 105                 110

Tyr Tyr Cys Ala Arg Ala Leu Thr Tyr Tyr Asp Tyr Glu Phe Ala Tyr
        115                 120                 125

Trp Gly Gln Gly Thr Leu Val Thr Val Ser Ala Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415
```

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 318
<211> LENGTH: 846
<212> TYPE: DNA
<213> ORGANISM: Artificial Sequence
<220> FEATURE:
<223> OTHER INFORMATION: chemically synthesized

<400> SEQUENCE: 318
atgtacagga tgcaactcct gtcttgcatt gcactaagtc ttgcacttgt cacgaattcg    60
caaggccagt ctggccagtg catctcacct cgtggttgtc cggacggccc atacgtcatg   120
tacggctcga gcggtggcag cggtggctct ggtggatccg gtctgagcgg ccgttccgat   180
aatcatggca gtagcggtac ccagatcttg ctgacccaga gccggtgat tctgagcgtg    240
agcccgggcg aacgtgtgag ctttagctgc cgcgcgagcc agagcattgg caccaacatt   300
cattggtatc agcagcgcac caacggcagc cgcgcctgc tgattaaata tgcgagcgaa    360
agcattagcg gcattccgag ccgctttagc ggcagcggca gcggcaccga ttttaccctg   420
agcattaaca gcgtggaaag cgaagatatt gcggattatt attgccagca gaacaacaac   480
tggccgacca ccttttggcgc gggcaccaaa ctggaactga acgtacggt ggctgcacca    540
tctgtcttca tcttcccgcc atctgatgag cagttgaaat ctggaactgc ctctgttgtg   600
tgcctgctga ataacttcta tcccagagag gccaaagtac agtggaaggt ggataacgcc   660
ctccaatcgg gtaactccca ggagagtgtc acagagcagg acagcaagga cagcacctac   720
agcctcagca gcaccctgac gctgagcaaa gcagactacg agaaacacaa agtctacgcc   780
tgcgaagtca cccatcaggg cctgagctcg cccgtcacaa agagcttcaa caggggagag   840
tgttag                                                              846

<210> SEQ ID NO 319
<211> LENGTH: 281
<212> TYPE: PRT
<213> ORGANISM: Artificial Sequence
<220> FEATURE:
<223> OTHER INFORMATION: chemically synthesized

<400> SEQUENCE: 319

Met Tyr Arg Met Gln Leu Leu Ser Cys Ile Ala Leu Ser Leu Ala Leu
1               5                   10                  15

Val Thr Asn Ser Gln Gly Gln Ser Gly Gln Cys Ile Ser Pro Arg Gly
            20                  25                  30

Cys Pro Asp Gly Pro Tyr Val Met Tyr Gly Ser Ser Gly Gly Ser Gly
        35                  40                  45

Gly Ser Gly Gly Ser Gly Leu Ser Gly Arg Ser Asp Asn His Gly Ser
    50                  55                  60

Ser Gly Thr Gln Ile Leu Leu Thr Gln Ser Pro Val Ile Leu Ser Val
65                  70                  75                  80

Ser Pro Gly Glu Arg Val Ser Phe Ser Cys Arg Ala Ser Gln Ser Ile
                85                  90                  95

Gly Thr Asn Ile His Trp Tyr Gln Gln Arg Thr Asn Gly Ser Pro Arg
            100                 105                 110

Leu Leu Ile Lys Tyr Ala Ser Glu Ser Ile Ser Gly Ile Pro Ser Arg
        115                 120                 125

Phe Ser Gly Ser Gly Ser Gly Thr Asp Phe Thr Leu Ser Ile Asn Ser
    130                 135                 140

Val Glu Ser Glu Asp Ile Ala Asp Tyr Tyr Cys Gln Gln Asn Asn Asn
145                 150                 155                 160

Trp Pro Thr Thr Phe Gly Ala Gly Thr Lys Leu Glu Leu Lys Arg Thr
                165                 170                 175

Val Ala Ala Pro Ser Val Phe Ile Phe Pro Pro Ser Asp Glu Gln Leu
            180                 185                 190

Lys Ser Gly Thr Ala Ser Val Val Cys Leu Leu Asn Asn Phe Tyr Pro
        195                 200                 205

Arg Glu Ala Lys Val Gln Trp Lys Val Asp Asn Ala Leu Gln Ser Gly
    210                 215                 220

Asn Ser Gln Glu Ser Val Thr Glu Gln Asp Ser Lys Asp Ser Thr Tyr
225                 230                 235                 240

Ser Leu Ser Ser Thr Leu Thr Leu Ser Lys Ala Asp Tyr Glu Lys His
                245                 250                 255

Lys Val Tyr Ala Cys Glu Val Thr His Gln Gly Leu Ser Ser Pro Val
            260                 265                 270

Thr Lys Ser Phe Asn Arg Gly Glu Cys
        275                 280

<210> SEQ ID NO 320
<211> LENGTH: 786
<212> TYPE: DNA
<213> ORGANISM: Artificial Sequence
<220> FEATURE:
<223> OTHER INFORMATION: chemically synthesized

<400> SEQUENCE: 320
caaggccagt ctggccagtg catctcacct cgtggttgtc cggacggccc atacgtcatg      60
tacggctcga gcggtggcag cggtggctct ggtggatccg gtctgagcgg ccgttccgat     120
aatcatggca gtagcggtac ccagatcttg ctgacccaga gcccggtgat tctgagcgtg     180
agcccgggcg aacgtgtgag ctttagctgc cgcgcgagcc agagcattgg caccaacatt     240
cattggtatc agcagcgcac caacggcagc ccgcgcctgc tgattaaata tgcgagcgaa     300
agcattagcg gcattccgag ccgctttagc ggcagcggca cgggcaccga ttttaccctg     360
agcattaaca gcgtggaaag cgaagatatt gcggattatt attgccagca gaacaacaac     420
tggccgacca ccttttggcgc gggcaccaaa ctggaactga acgtacggt ggctgcacca     480 tctgtcttca tcttcccgcc atctgatgag cagttgaaat ctggaactgc ctctgttgtg     540
tgcctgctga ataacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                               786

<210> SEQ ID NO 321
<211> LENGTH: 261
<212> TYPE: PRT

<213> ORGANISM: Artificial Sequence
<220> FEATURE:
<223> OTHER INFORMATION: chemically synthesized

<400> SEQUENCE: 321

Gln Gly Gln Ser Gly Gln Cys Ile Ser Pro Arg Gly Cys Pro Asp Gly
1               5                   10                  15
Pro Tyr Val Met Tyr Gly Ser Ser Gly Ser Gly Gly Ser Gly Gly
            20                  25                  30
Ser Gly Leu Ser Gly Arg Ser Asp Asn His Gly Ser Ser Gly Thr Gln
        35                  40                  45
Ile Leu Leu Thr Gln Ser Pro Val Ile Leu Ser Val Ser Pro Gly Glu
50                  55                  60
Arg Val Ser Phe Ser Cys Arg Ala Ser Gln Ser Ile Gly Thr Asn Ile
65                  70                  75                  80
His Trp Tyr Gln Gln Arg Thr Asn Gly Ser Pro Arg Leu Leu Ile Lys
            85                  90                  95
Tyr Ala Ser Glu Ser Ile Ser Gly Ile Pro Ser Arg Phe Ser Gly Ser
            100                 105                 110
Gly Ser Gly Thr Asp Phe Thr Leu Ser Ile Asn Ser Val Glu Ser Glu
        115                 120                 125
Asp Ile Ala Asp Tyr Tyr Cys Gln Gln Asn Asn Asn Trp Pro Thr Thr
130                 135                 140
Phe Gly Ala Gly Thr Lys Leu Glu Leu Lys Arg Thr Val Ala Ala Pro
145                 150                 155                 160
Ser Val Phe Ile Phe Pro Pro Ser Asp Glu Gln Leu Lys Ser Gly Thr
            165                 170                 175
Ala Ser Val Val Cys Leu Leu Asn Asn Phe Tyr Pro Arg Glu Ala Lys
            180                 185                 190
Val Gln Trp Lys Val Asp Asn Ala Leu Gln Ser Gly Asn Ser Gln Glu
        195                 200                 205
Ser Val Thr Glu Gln Asp Ser Lys Asp Ser Thr Tyr Ser Leu Ser Ser
    210                 215                 220
Thr Leu Thr Leu Ser Lys Ala Asp Tyr Glu Lys His Lys Val Tyr Ala
225                 230                 235                 240
Cys Glu Val Thr His Gln Gly Leu Ser Ser Pro Val Thr Lys Ser Phe
            245                 250                 255
Asn Arg Gly Glu Cys
            260

<210> SEQ ID NO 322
<211> LENGTH: 1350
<212> TYPE: DNA
<213> ORGANISM: Artificial Sequence
<220> FEATURE:
<223> OTHER INFORMATION: chemically synthesized

<400> SEQUENCE: 322
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag cctggaatg gctgggcgtg atttggagcg gcggcaacac cgattataac     180
accccgttta ccagccgcct gagcattaac aaagataaca gcaaaagcca ggtgttttt      240 aaaatgaaca gcctgcaaag ccaggatacc gcgatttatt attgcgcgcg cgcgctgacc     300
tattatgatt atgaatttgc gtattggggc cagggcaccc tggtgaccgt gagcgcggct     360

| | |
|---|---|
| agcaccaagg gcccatcggt cttcccctg gcaccctcct ccaagagcac ctctgggggc | 420 |
| acagcggccc tgggctgcct ggtcaaggac tacttccccg aaccggtgac ggtgtcgtgg | 480 |
| aactcaggcg ccctgaccag cggcgtgcac accttcccgg ctgtcctaca gtcctcagga | 540 |
| ctctactccc tcagcagcgt ggtgaccgtg ccctccagca gcttgggcac ccagacctac | 600 |
| atctgcaacg tgaatcacaa gcccagcaac accaaggtgg acaagaaagt tgagcccaaa | 660 |
| tcttgtgaca aaactcacac atgcccaccg tgcccagcac ctgaactcct ggggggaccg | 720 |
| tcagtcttcc tcttccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacgccagc | 900 |
| acgtaccgtg tggtcagcgt cctcaccgtc ctgcaccagg actggctgaa tggcaaggag | 960 |
| tacaagtgca aggtctccaa caaagccctc ccagccccca tcgagaaaac catctccaaa | 1020 |
| gccaaagggc agccccgaga accacaggtg tacaccctgc ccccatcccg ggatgaactg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaatga | 1350 |

<210> SEQ ID NO 323
<211> LENGTH: 1410
<212> TYPE: DNA
<213> ORGANISM: Artificial Sequence
<220> FEATURE:
<223> OTHER INFORMATION: chemically synthesized

<400> SEQUENCE: 323

| | |
|---|---|
| atgtacagga tgcaactcct gtcttgcatt gcactaagtc ttgcacttgt cacgaattcg | 60 |
| caggtgcagc tgaaacagag cggcccgggc ctggtgcagc cgagccagag cctgagcatt | 120 |
| acctgcaccg tgagcggctt tagcctgacc aactatggcg tgcattgggt gcgccagagc | 180 |
| ccgggcaaag gcctggaatg gctgggcgtg atttggagcg gcggcaacac cgattataac | 240 |
| accccgttta ccagccgcct gagcattaac aaagataaca gcaaaagcca ggtgtttttt | 300 |
| aaaatgaaca gcctgcaaag ccaggatacc gcgatttatt attgcgcgcg cgcgctgacc | 360 |
| tattatgatt atgaatttgc gtattggggc cagggcaccc tggtgaccgt gagcgcggct | 420 |
| agcaccaagg gcccatcggt cttcccctg gcaccctcct ccaagagcac ctctgggggc | 480 |
| acagcggccc tgggctgcct ggtcaaggac tacttccccg aaccggtgac ggtgtcgtgg | 540 |
| aactcaggcg ccctgaccag cggcgtgcac accttcccgg ctgtcctaca gtcctcagga | 600 |
| ctctactccc tcagcagcgt ggtgaccgtg ccctccagca gcttgggcac ccagacctac | 660 |
| atctgcaacg tgaatcacaa gcccagcaac accaaggtgg acaagaaagt tgagcccaaa | 720 |
| tcttgtgaca aaactcacac atgcccaccg tgcccagcac ctgaactcct ggggggaccg | 780 |
| tcagtcttcc tcttccccc aaaacccaag gacaccctca tgatctcccg gacccctgag | 840 |
| gtcacatgcg tggtggtgga cgtgagccac gaagaccctg aggtcaagtt caactggtac | 900 |
| gtggacggcg tggaggtgca taatgccaag acaaagccgc gggaggagca gtacgccagc | 960 |
| acgtaccgtg tggtcagcgt cctcaccgtc ctgcaccagg actggctgaa tggcaaggag | 1020 |
| tacaagtgca aggtctccaa caaagccctc ccagccccca tcgagaaaac catctccaaa | 1080 |

```
gccaaagggc agccccgaga accacaggtg tacaccctgc ccccatcccg ggatgaactg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                     1410
```

<210> SEQ ID NO 324
<211> LENGTH: 449
<212> TYPE: PRT
<213> ORGANISM: Artificial Sequence
<220> FEATURE:
<223> OTHER INFORMATION: chemically synthesized

<400> SEQUENCE: 324

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 325
<211> LENGTH: 469
<212> TYPE: PRT
<213> ORGANISM: Artificial Sequence
<220> FEATURE:
<223> OTHER INFORMATION: chemically synthesized

<400> SEQUENCE: 325

Met Tyr Arg Met Gln Leu Leu Ser Cys Ile Ala Leu Ser Leu Ala Leu
1               5                   10                  15

Val Thr Asn Ser Gln Val Gln Leu Lys Gln Ser Gly Pro Gly Leu Val
            20                  25                  30

Gln Pro Ser Gln Ser Leu Ser Ile Thr Cys Thr Val Ser Gly Phe Ser
        35                  40                  45

Leu Thr Asn Tyr Gly Val His Trp Val Arg Gln Ser Pro Gly Lys Gly
    50                  55                  60

Leu Glu Trp Leu Gly Val Ile Trp Ser Gly Gly Asn Thr Asp Tyr Asn
65                  70                  75                  80

Thr Pro Phe Thr Ser Arg Leu Ser Ile Asn Lys Asp Asn Ser Lys Ser
                85                  90                  95

Gln Val Phe Phe Lys Met Asn Ser Leu Gln Ser Gln Asp Thr Ala Ile
            100                 105                 110

Tyr Tyr Cys Ala Arg Ala Leu Thr Tyr Tyr Asp Tyr Glu Phe Ala Tyr
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

```
Thr Val Pro Ser Ser Ser Leu Gly Thr Gln Thr Tyr Ile Cys Asn Val
    210                 215                 220
Asn His Lys Pro Ser Asn Thr Lys Val Asp Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
290                 295                 300
Glu Val His Asn Ala Lys Thr Lys Pro Arg Glu Glu Gln Tyr Ala Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 326
<211> LENGTH: 846
<212> TYPE: DNA
<213> ORGANISM: Artificial Sequence
<220> FEATURE:
<223> OTHER INFORMATION: chemically synthesized

<400> SEQUENCE: 326
atgtacagga tgcaactcct gtcttgcatt gcactaagtc ttgcacttgt cacgaattcg      60
caaggccagt ctggccagtg catctcacct cgtggttgtc cggacggccc atacgtcatg     120
tacggctcga gcggtggcag cggtggctct ggtggatccg gtctgagcgg ccgttccgat     180
aatcatggca gtagcggtac ccagatcttg ctgacccaga gcccggtgat tctgagcgtg     240
agcccgggcg aacgtgtgag ctttagctgc cgcgcgagcc agagcattgg caccaacatt     300
cattggtatc agcagcgcac caacggcagc ccgcgcctgc tgattaaata tgcgagcgaa     360
agcattagcg gcattccgag ccgctttagc ggcagcggca gcggcaccga ttttaccctg     420
agcattaaca gcgtggaaag cgaagatatt gcggattatt attgccagca gaacaacaac     480
tggccgacca cctttggcgc gggcaccaaa ctggaactga acgtacggt ggctgcacca     540
```

-continued

```
tctgtcttca tcttcccgcc atctgatgag cagttgaaat ctggaactgc ctctgttgtg    600
tgcctgctga ataacttcta tcccagagag gccaaagtac agtggaaggt ggataacgcc    660
ctccaatcgg gtaactccca ggagagtgtc acagagcagg acagcaagga cagcacctac    720
agcctcagca gcaccctgac gctgagcaaa gcagactacg agaaacacaa agtctacgcc    780
tgcgaagtca cccatcaggg cctgagctcg cccgtcacaa agagcttcaa caggggagag    840
tgttag                                                                846
```

```
<210> SEQ ID NO 327
<211> LENGTH: 281
<212> TYPE: PRT
<213> ORGANISM: Artificial Sequence
<220> FEATURE:
<223> OTHER INFORMATION: chemically synthesized

<400> SEQUENCE: 327

Met Tyr Arg Met Gln Leu Leu Ser Cys Ile Ala Leu Ser Leu Ala Leu
1               5                   10                  15

Val Thr Asn Ser Gln Gly Gln Ser Gly Gln Cys Ile Ser Pro Arg Gly
            20                  25                  30

Cys Pro Asp Gly Pro Tyr Val Met Tyr Gly Ser Ser Gly Gly Ser Gly
        35                  40                  45

Gly Ser Gly Gly Ser Gly Leu Ser Gly Arg Ser Asp Asn His Gly Ser
    50                  55                  60

Ser Gly Thr Gln Ile Leu Leu Thr Gln Ser Pro Val Ile Leu Ser Val
65                  70                  75                  80

Ser Pro Gly Glu Arg Val Ser Phe Ser Cys Arg Ala Ser Gln Ser Ile
                85                  90                  95

Gly Thr Asn Ile His Trp Tyr Gln Gln Arg Thr Asn Gly Ser Pro Arg
            100                 105                 110

Leu Leu Ile Lys Tyr Ala Ser Glu Ser Ile Ser Gly Ile Pro Ser Arg
        115                 120                 125

Phe Ser Gly Ser Gly Ser Gly Thr Asp Phe Thr Leu Ser Ile Asn Ser
    130                 135                 140

Val Glu Ser Glu Asp Ile Ala Asp Tyr Tyr Cys Gln Gln Asn Asn Asn
145                 150                 155                 160

Trp Pro Thr Thr Phe Gly Ala Gly Thr Lys Leu Glu Leu Lys Arg Thr
                165                 170                 175

Val Ala Ala Pro Ser Val Phe Ile Phe Pro Pro Ser Asp Glu Gln Leu
            180                 185                 190

Lys Ser Gly Thr Ala Ser Val Val Cys Leu Leu Asn Asn Phe Tyr Pro
        195                 200                 205

Arg Glu Ala Lys Val Gln Trp Lys Val Asp Asn Ala Leu Gln Ser Gly
    210                 215                 220

Asn Ser Gln Glu Ser Val Thr Glu Gln Asp Ser Lys Asp Ser Thr Tyr
225                 230                 235                 240

Ser Leu Ser Ser Thr Leu Thr Leu Ser Lys Ala Asp Tyr Glu Lys His
                245                 250                 255

Lys Val Tyr Ala Cys Glu Val Thr His Gln Gly Leu Ser Ser Pro Val
            260                 265                 270

Thr Lys Ser Phe Asn Arg Gly Glu Cys
        275                 280

<210> SEQ ID NO 328
<211> LENGTH: 786
```

<212> TYPE: DNA
<213> ORGANISM: Artificial Sequence
<220> FEATURE:
<223> OTHER INFORMATION: chemically synthesized

<400> SEQUENCE: 328

```
caaggccagt ctggccagtg catctcacct cgtggttgtc cggacggccc atacgtcatg    60
tacggctcga gcggtggcag cggtggctct ggtggatccg gtctgagcgg ccgttccgat   120
aatcatggca gtagcggtac ccagatcttg ctgacccaga gcccggtgat tctgagcgtg   180
agcccgggcg aacgtgtgag ctttagctgc cgcgcgagcc agagcattgg caccaacatt   240
cattggtatc agcagcgcac caacggcagc ccgcgcctgc tgattaaata tgcgagcgaa   300
agcattagcg gcattccgag ccgctttagc ggcagcggca gcggcaccga ttttaccctg   360
agcattaaca gcgtggaaag cgaagatatt gcggattatt attgccagca gaacaacaac   420
tggccgacca cctttggcgc gggcaccaaa ctggaactga acgtacggt ggctgcacca   480
tctgtcttca tcttcccgcc atctgatgag cagttgaaat ctggaactgc ctctgttgtg   540
tgcctgctga ataacttcta tcccagagag gccaaagtac agtggaaggt ggataacgcc   600
ctccaatcgg gtaactccca ggagagtgtc acagagcagg acagcaagga cagcacctac   660
agcctcagca gcaccctgac gctgagcaaa gcagactacg agaaacacaa agtctacgcc   720
tgcgaagtca cccatcaggg cctgagctcg cccgtcacaa agagcttcaa caggggagag   780
tgttag                                                              786
```

<210> SEQ ID NO 329
<211> LENGTH: 261
<212> TYPE: PRT
<213> ORGANISM: Artificial Sequence
<220> FEATURE:
<223> OTHER INFORMATION: chemically synthesized

<400> SEQUENCE: 329

```
Gln Gly Gln Ser Gly Gln Cys Ile Ser Pro Arg Gly Cys Pro Asp Gly
1               5                   10                  15
Pro Tyr Val Met Tyr Gly Ser Ser Gly Gly Ser Gly Gly Ser Gly Gly
            20                  25                  30
Ser Gly Leu Ser Gly Arg Ser Asp Asn His Gly Ser Ser Gly Thr Gln
        35                  40                  45
Ile Leu Leu Thr Gln Ser Pro Val Ile Leu Ser Val Ser Pro Gly Glu
    50                  55                  60
Arg Val Ser Phe Ser Cys Arg Ala Ser Gln Ser Ile Gly Thr Asn Ile
65                  70                  75                  80
His Trp Tyr Gln Gln Arg Thr Asn Gly Ser Pro Arg Leu Leu Ile Lys
                85                  90                  95
Tyr Ala Ser Glu Ser Ile Ser Gly Ile Pro Ser Arg Phe Ser Gly Ser
            100                 105                 110
Gly Ser Gly Thr Asp Phe Thr Leu Ser Ile Asn Ser Val Glu Ser Glu
        115                 120                 125
Asp Ile Ala Asp Tyr Tyr Cys Gln Gln Asn Asn Asn Trp Pro Thr Thr
    130                 135                 140
Phe Gly Ala Gly Thr Lys Leu Glu Leu Lys Arg Thr Val Ala Ala Pro
145                 150                 155                 160
Ser Val Phe Ile Phe Pro Pro Ser Asp Glu Gln Leu Lys Ser Gly Thr
                165                 170                 175
Ala Ser Val Val Cys Leu Leu Asn Asn Phe Tyr Pro Arg Glu Ala Lys
```

```
                180                 185                 190
Val Gln Trp Lys Val Asp Asn Ala Leu Gln Ser Gly Asn Ser Gln Glu
            195                 200                 205
Ser Val Thr Glu Gln Asp Ser Lys Asp Ser Thr Tyr Ser Leu Ser Ser
        210                 215                 220
Thr Leu Thr Leu Ser Lys Ala Asp Tyr Glu Lys His Lys Val Tyr Ala
225                 230                 235                 240
Cys Glu Val Thr His Gln Gly Leu Ser Ser Pro Val Thr Lys Ser Phe
                245                 250                 255
Asn Arg Gly Glu Cys
            260

<210> SEQ ID NO 330
<211> LENGTH: 449
<212> TYPE: PRT
<213> ORGANISM: Artificial Sequence
<220> FEATURE:
<223> OTHER INFORMATION: chemically synthesized

<400> SEQUENCE: 330

Gln Val Gln Leu Gln Glu Ser Gly Pro Gly Leu Val Arg Pro Ser Gln
1               5                   10                  15
Thr Leu Ser Leu Thr Cys Thr Val Ser Gly Tyr Ser Ile Thr Ser Asp
            20                  25                  30
His Ala Trp Ser Trp Val Arg Gln Pro Pro Gly Arg Gly Leu Glu Trp
        35                  40                  45
Ile Gly Tyr Ile Ser Tyr Ser Gly Ile Thr Thr Tyr Asn Pro Ser Leu
    50                  55                  60
Lys Ser Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Gln Gly
            100                 105                 110
Ser Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 331
<211> LENGTH: 214
<212> TYPE: PRT
<213> ORGANISM: Artificial Sequence
<220> FEATURE:
<223> OTHER INFORMATION: chemically synthesized

<400> SEQUENCE: 331

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 332
<211> LENGTH: 15
<212> TYPE: PRT
<213> ORGANISM: Artificial Sequence
<220> FEATURE:
<223> OTHER INFORMATION: chemically synthesized

<400> SEQUENCE: 332

Tyr Gly Ser Cys Ser Trp Asn Tyr Val His Ile Phe Met Asp Cys
1               5                   10                  15

<210> SEQ ID NO 333
<211> LENGTH: 16
<212> TYPE: PRT
<213> ORGANISM: Artificial Sequence
<220> FEATURE:
<223> OTHER INFORMATION: chemically synthesized

<400> SEQUENCE: 333

Gln Gly Asp Phe Asp Ile Pro Phe Pro Ala His Trp Val Pro Ile Thr
1               5                   10                  15

<210> SEQ ID NO 334
<211> LENGTH: 18
<212> TYPE: PRT
<213> ORGANISM: Artificial Sequence
<220> FEATURE:
<223> OTHER INFORMATION: chemically synthesized

<400> SEQUENCE: 334

Met Gly Val Pro Ala Gly Cys Val Trp Asn Tyr Ala His Ile Phe Met
1               5                   10                  15

Asp Cys

<210> SEQ ID NO 335
<211> LENGTH: 21
<212> TYPE: PRT
<213> ORGANISM: Artificial Sequence
<220> FEATURE:
<223> OTHER INFORMATION: chemically synthesized

<400> SEQUENCE: 335

Gln Gly Gln Ser Gly Gln Tyr Gly Ser Cys Ser Trp Asn Tyr Val His
1               5                   10                  15

Ile Phe Met Asp Cys
            20

<210> SEQ ID NO 336
<211> LENGTH: 21
<212> TYPE: PRT
<213> ORGANISM: Artificial Sequence
<220> FEATURE:
<223> OTHER INFORMATION: chemically synthesized

<400> SEQUENCE: 336

Gln Gly Gln Ser Gly Gln Gly Asp Phe Asp Ile Pro Phe Pro Ala His
1               5                   10                  15

Trp Val Pro Ile Thr
            20

<210> SEQ ID NO 337
<211> LENGTH: 24
<212> TYPE: PRT
<213> ORGANISM: Artificial Sequence
<220> FEATURE:
<223> OTHER INFORMATION: chemically synthesized

<400> SEQUENCE: 337

Gln Gly Gln Ser Gly Gln Met Gly Val Pro Ala Gly Cys Val Trp Asn
1               5                   10                  15

Tyr Ala His Ile Phe Met Asp Cys
            20

<210> SEQ ID NO 338
<211> LENGTH: 108
<212> TYPE: PRT
<213> ORGANISM: Artificial Sequence
<220> FEATURE:
<223> OTHER INFORMATION: chemically synthesized

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 339
<211> LENGTH: 119
<212> TYPE: PRT
<213> ORGANISM: Artificial Sequence
<220> FEATURE:
<223> OTHER INFORMATION: chemically synthesized

<400> SEQUENCE: 339

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Arg Ala Phe Asp Tyr Trp Gly Gln Gly
            100                 105                 110

```
Thr Leu Val Thr Val Ser Ser
        115

<210> SEQ ID NO 340
<211> LENGTH: 108
<212> TYPE: PRT
<213> ORGANISM: Artificial Sequence
<220> FEATURE:
<223> OTHER INFORMATION: chemically synthesized

<400> SEQUENCE: 340

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 341
<211> LENGTH: 119
<212> TYPE: PRT
<213> ORGANISM: Artificial Sequence
<220> FEATURE:
<223> OTHER INFORMATION: chemically synthesized

<400> SEQUENCE: 341

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr His Gly Gln Phe Asp Tyr Trp Gly Gln Gly
            100                 105                 110

Thr Leu Val Thr Val Ser Ser
        115

<210> SEQ ID NO 342
<211> LENGTH: 108
<212> TYPE: PRT
<213> ORGANISM: Artificial Sequence
<220> FEATURE:
<223> OTHER INFORMATION: chemically synthesized

<400> SEQUENCE: 342

Asp Ile Gln Met Thr Gln Ser Pro Ser Ser Leu Ser Ala Ser Val Gly
```

-continued

```
                1               5                  10                  15
Asp Arg Val Thr Ile Thr Cys Arg Ala Ser Gln Ser Ile Ser Ser Tyr
                    20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 343
<211> LENGTH: 119
<212> TYPE: PRT
<213> ORGANISM: Artificial Sequence
<220> FEATURE:
<223> OTHER INFORMATION: chemically synthesized

<400> SEQUENCE: 343

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                    20                  25                  30

Ala Met Ser Trp Val Arg Gln Ala Pro Gly Lys Gly Leu Glu Trp Val
            35                  40                  45

Ser Ser Ile Glu Gln Met Gly Trp Gln Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115
```

<210> SEQ ID NO 344
<211> LENGTH: 108
<212> TYPE: PRT
<213> ORGANISM: Artificial Sequence
<220> FEATURE:
<223> OTHER INFORMATION: chemically synthesized

<400> SEQUENCE: 344

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                    20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 345
<211> LENGTH: 119
<212> TYPE: PRT
<213> ORGANISM: Artificial Sequence
<220> FEATURE:
<223> OTHER INFORMATION: chemically synthesized

<400> SEQUENCE: 345

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Ile Gly Arg Thr Asn Pro Phe Asp Tyr Trp Gly Gln Gly
            100                 105                 110

Thr Leu Val Thr Val Ser Ser
        115
```

<210> SEQ ID NO 346
<211> LENGTH: 108
<212> TYPE: PRT
<213> ORGANISM: Artificial Sequence
<220> FEATURE:
<223> OTHER INFORMATION: chemically synthesized

<400> SEQUENCE: 346

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 347
<211> LENGTH: 116
<212> TYPE: PRT
<213> ORGANISM: Artificial Sequence
<220> FEATURE:
<223> OTHER INFORMATION: chemically synthesized

<400> SEQUENCE: 347

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
            115

<210> SEQ ID NO 348
<211> LENGTH: 108
<212> TYPE: PRT
<213> ORGANISM: Artificial Sequence
<220> FEATURE:
<223> OTHER INFORMATION: chemically synthesized

<400> SEQUENCE: 348

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 349
<211> LENGTH: 119
<212> TYPE: PRT
<213> ORGANISM: Artificial Sequence
<220> FEATURE:
<223> OTHER INFORMATION: chemically synthesized

<400> SEQUENCE: 349

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr Tyr Gly Gln Phe Asp Tyr Trp Gly Gln Gly
            100                 105                 110

Thr Leu Val Thr Val Ser Ser
        115

<210> SEQ ID NO 350
<211> LENGTH: 108
<212> TYPE: PRT
<213> ORGANISM: Artificial Sequence
<220> FEATURE:
<223> OTHER INFORMATION: chemically synthesized

<400> SEQUENCE: 350

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 351
<211> LENGTH: 119
<212> TYPE: PRT
<213> ORGANISM: Artificial Sequence
<220> FEATURE:
<223> OTHER INFORMATION: chemically synthesized

<400> SEQUENCE: 351

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115

<210> SEQ ID NO 352

```
<211> LENGTH: 108
<212> TYPE: PRT
<213> ORGANISM: Artificial Sequence
<220> FEATURE:
<223> OTHER INFORMATION: chemically synthesized

<400> SEQUENCE: 352

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 353
<211> LENGTH: 119
<212> TYPE: PRT
<213> ORGANISM: Artificial Sequence
<220> FEATURE:
<223> OTHER INFORMATION: chemically synthesized

<400> SEQUENCE: 353

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 354
<211> LENGTH: 108
<212> TYPE: PRT
<213> ORGANISM: Artificial Sequence
<220> FEATURE:
<223> OTHER INFORMATION: chemically synthesized

<400> SEQUENCE: 354

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
            100                 105
```

```
<210> SEQ ID NO 355
<211> LENGTH: 116
<212> TYPE: PRT
<213> ORGANISM: Artificial Sequence
<220> FEATURE:
<223> OTHER INFORMATION: chemically synthesized

<400> SEQUENCE: 355

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Glu Glu Met Gly Trp Gln Thr Leu Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ala Ala Ala Phe Asp Tyr Trp Gly Gln Gly Thr Leu Val
            100                 105                 110

Thr Val Ser Ser
       115
```

```
<210> SEQ ID NO 356
<211> LENGTH: 108
<212> TYPE: PRT
<213> ORGANISM: Artificial Sequence
<220> FEATURE:
<223> OTHER INFORMATION: chemically synthesized

<400> SEQUENCE: 356

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
            100                 105
```

<210> SEQ ID NO 357
<211> LENGTH: 119
<212> TYPE: PRT
<213> ORGANISM: Artificial Sequence
<220> FEATURE:
<223> OTHER INFORMATION: chemically synthesized

<400> SEQUENCE: 357

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115
```

<210> SEQ ID NO 358
<211> LENGTH: 108
<212> TYPE: PRT
<213> ORGANISM: Artificial Sequence
<220> FEATURE:
<223> OTHER INFORMATION: chemically synthesized

<400> SEQUENCE: 358

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 359
<211> LENGTH: 119
<212> TYPE: PRT
<213> ORGANISM: Artificial Sequence
<220> FEATURE:
<223> OTHER INFORMATION: chemically synthesized

<400> SEQUENCE: 359

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Pro Pro Phe Tyr Gly Gln Phe Asp Tyr Trp Gly Gln Gly
            100                 105                 110

Thr Leu Val Thr Val Ser Ser
            115
```

```
<210> SEQ ID NO 360
<211> LENGTH: 108
<212> TYPE: PRT
<213> ORGANISM: Artificial Sequence
<220> FEATURE:
<223> OTHER INFORMATION: chemically synthesized

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
            85                  90                  95

Thr Phe Gly Gln Gly Thr Lys Val Glu Ile Lys Arg
            100                 105
```

```
<210> SEQ ID NO 361
<211> LENGTH: 119
<212> TYPE: PRT
<213> ORGANISM: Artificial Sequence
<220> FEATURE:
<223> OTHER INFORMATION: chemically synthesized

<400> SEQUENCE: 361

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95
```

```
Ala Lys Ser Pro Pro Phe Phe Gly Gln Phe Asp Tyr Trp Gly Gln Gly
            100                 105                 110
Thr Leu Val Thr Val Ser Ser
        115

<210> SEQ ID NO 362
<211> LENGTH: 108
<212> TYPE: PRT
<213> ORGANISM: Artificial Sequence
<220> FEATURE:
<223> OTHER INFORMATION: chemically synthesized

<400> SEQUENCE: 362

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Val Val Ala Pro Leu
                85                  90                  95
Thr Phe Gly Gln Gly Thr Lys Val Glu Ile Lys Arg
            100                 105

<210> SEQ ID NO 363
<211> LENGTH: 115
<212> TYPE: PRT
<213> ORGANISM: Artificial Sequence
<220> FEATURE:
<223> OTHER INFORMATION: chemically synthesized

<400> SEQUENCE: 363

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ser Ile Glu Glu Met Gly Trp Gln Thr Leu Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Ala
                85                  90                  95
Lys Ser Ala Ala Ala Phe Asp Tyr Trp Gly Gln Gly Thr Leu Val Thr
            100                 105                 110
Val Ser Ser
        115

<210> SEQ ID NO 364
<211> LENGTH: 108
<212> TYPE: PRT
<213> ORGANISM: Artificial Sequence
<220> FEATURE:
<223> OTHER INFORMATION: chemically synthesized
```

<400> SEQUENCE: 364

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 365
<211> LENGTH: 119
<212> TYPE: PRT
<213> ORGANISM: Artificial Sequence
<220> FEATURE:
<223> OTHER INFORMATION: chemically synthesized

<400> SEQUENCE: 365

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 366
<211> LENGTH: 108
<212> TYPE: PRT
<213> ORGANISM: Artificial Sequence
<220> FEATURE:
<223> OTHER INFORMATION: chemically synthesized

<400> SEQUENCE: 366

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
            100                 105

<210> SEQ ID NO 367
<211> LENGTH: 116
<212> TYPE: PRT
<213> ORGANISM: Artificial Sequence
<220> FEATURE:
<223> OTHER INFORMATION: chemically synthesized

<400> SEQUENCE: 367

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ser Ile Asp Pro Glu Gly Trp Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 368
<211> LENGTH: 108
<212> TYPE: PRT
<213> ORGANISM: Artificial Sequence
<220> FEATURE:
<223> OTHER INFORMATION: chemically synthesized

<400> SEQUENCE: 368

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
            100                 105

<210> SEQ ID NO 369
<211> LENGTH: 119
<212> TYPE: PRT
```

<213> ORGANISM: Artificial Sequence
<220> FEATURE:
<223> OTHER INFORMATION: chemically synthesized

<400> SEQUENCE: 369

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro His Asn Gly Gln Phe Asp Tyr Trp Gly Gln Gly
            100                 105                 110

Thr Leu Val Thr Val Ser Ser
            115

<210> SEQ ID NO 370
<211> LENGTH: 108
<212> TYPE: PRT
<213> ORGANISM: Artificial Sequence
<220> FEATURE:
<223> OTHER INFORMATION: chemically synthesized

<400> SEQUENCE: 370

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 371
<211> LENGTH: 116
<212> TYPE: PRT
<213> ORGANISM: Artificial Sequence
<220> FEATURE:
<223> OTHER INFORMATION: chemically synthesized

<400> SEQUENCE: 371

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Ser Ile Glu Gln Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
            115

<210> SEQ ID NO 372
<211> LENGTH: 108
<212> TYPE: PRT
<213> ORGANISM: Artificial Sequence
<220> FEATURE:
<223> OTHER INFORMATION: chemically synthesized

<400> SEQUENCE: 372

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 373
<211> LENGTH: 119
<212> TYPE: PRT
<213> ORGANISM: Artificial Sequence
<220> FEATURE:
<223> OTHER INFORMATION: chemically synthesized

<400> SEQUENCE: 373

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
```

```
                115

<210> SEQ ID NO 374
<211> LENGTH: 108
<212> TYPE: PRT
<213> ORGANISM: Artificial Sequence
<220> FEATURE:
<223> OTHER INFORMATION: chemically synthesized

<400> SEQUENCE: 374

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 375
<211> LENGTH: 116
<212> TYPE: PRT
<213> ORGANISM: Artificial Sequence
<220> FEATURE:
<223> OTHER INFORMATION: chemically synthesized

<400> SEQUENCE: 375

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Glu Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Phe Asp Tyr Trp Gly Gln Gly Thr Leu Val
            100                 105                 110

Thr Val Ser Ser
        115

<210> SEQ ID NO 376
<211> LENGTH: 108
<212> TYPE: PRT
<213> ORGANISM: Artificial Sequence
<220> FEATURE:
<223> OTHER INFORMATION: chemically synthesized

<400> SEQUENCE: 376

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Leu Asp Ala Pro Pro
                85                  90                  95

Gln Phe Gly Gln Gly Thr Lys Val Glu Ile Lys Arg
            100                 105
```

<210> SEQ ID NO 377
<211> LENGTH: 119
<212> TYPE: PRT
<213> ORGANISM: Artificial Sequence
<220> FEATURE:
<223> OTHER INFORMATION: chemically synthesized

<400> SEQUENCE: 377

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115
```

<210> SEQ ID NO 378
<211> LENGTH: 108
<212> TYPE: PRT
<213> ORGANISM: Artificial Sequence
<220> FEATURE:
<223> OTHER INFORMATION: chemically synthesized

<400> SEQUENCE: 378

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Val Val Ala Pro Pro
```

85                  90                  95

Leu Phe Gly Gln Gly Thr Lys Val Glu Ile Lys Arg
            100                 105

<210> SEQ ID NO 379
<211> LENGTH: 119
<212> TYPE: PRT
<213> ORGANISM: Artificial Sequence
<220> FEATURE:
<223> OTHER INFORMATION: chemically synthesized

<400> SEQUENCE: 379

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 380
<211> LENGTH: 108
<212> TYPE: PRT
<213> ORGANISM: Artificial Sequence
<220> FEATURE:
<223> OTHER INFORMATION: chemically synthesized

<400> SEQUENCE: 380

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Val Ala Pro Leu
                85                  90                  95

Thr Phe Gly Gln Gly Thr Lys Val Glu Ile Lys Arg
            100                 105

<210> SEQ ID NO 381
<211> LENGTH: 116
<212> TYPE: PRT
<213> ORGANISM: Artificial Sequence
<220> FEATURE:
<223> OTHER INFORMATION: chemically synthesized

<400> SEQUENCE: 381

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
            115

<210> SEQ ID NO 382
<211> LENGTH: 108
<212> TYPE: PRT
<213> ORGANISM: Artificial Sequence
<220> FEATURE:
<223> OTHER INFORMATION: chemically synthesized

<400> SEQUENCE: 382

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Asp Ala Pro Leu
                85                  90                  95

Met Phe Gly Gln Gly Thr Lys Val Glu Ile Lys Arg
            100                 105

<210> SEQ ID NO 383
<211> LENGTH: 119
<212> TYPE: PRT
<213> ORGANISM: Artificial Sequence
<220> FEATURE:
<223> OTHER INFORMATION: chemically synthesized

<400> SEQUENCE: 383

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Glu Pro Met Gly Gln Leu Thr Glu Tyr Ala Asp Ser Val
50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Lys Asp Ile Gly Gly Arg Ser Ala Phe Asp Tyr Trp Gly Gln Gly
                100                 105                 110

Thr Leu Val Thr Val Ser Ser
            115

<210> SEQ ID NO 384
<211> LENGTH: 108
<212> TYPE: PRT
<213> ORGANISM: Artificial Sequence
<220> FEATURE:
<223> OTHER INFORMATION: chemically synthesized

<400> SEQUENCE: 384

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Val Ala Pro Leu
                85                  90                  95

Thr Phe Gly Gln Gly Thr Lys Val Glu Ile Lys Arg
                100                 105

<210> SEQ ID NO 385
<211> LENGTH: 116
<212> TYPE: PRT
<213> ORGANISM: Artificial Sequence
<220> FEATURE:
<223> OTHER INFORMATION: chemically synthesized

<400> SEQUENCE: 385

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ser Ile Asp Glu Met Gly Trp Gln Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Phe Asp Tyr Trp Gly Gln Gly Thr Leu Val
                100                 105                 110

Thr Val Ser Ser
            115

<210> SEQ ID NO 386
<211> LENGTH: 108
```

```
<212> TYPE: PRT
<213> ORGANISM: Artificial Sequence
<220> FEATURE:
<223> OTHER INFORMATION: chemically synthesized

<400> SEQUENCE: 386

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Val Ala Pro Leu
                85                  90                  95

Thr Phe Gly Gln Gly Thr Lys Val Glu Ile Lys Arg
            100                 105

<210> SEQ ID NO 387
<211> LENGTH: 116
<212> TYPE: PRT
<213> ORGANISM: Artificial Sequence
<220> FEATURE:
<223> OTHER INFORMATION: chemically synthesized

<400> SEQUENCE: 387

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Glu Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 388
<211> LENGTH: 214
<212> TYPE: PRT
<213> ORGANISM: Artificial Sequence
<220> FEATURE:
<223> OTHER INFORMATION: chemically synthesized

<400> SEQUENCE: 388

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

-continued

```
                 35                  40                  45
Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Val Val Ala Pro Pro
                 85                  90                  95

Leu Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 389
<211> LENGTH: 449
<212> TYPE: PRT
<213> ORGANISM: Artificial Sequence
<220> FEATURE:
<223> OTHER INFORMATION: chemically synthesized

<400> SEQUENCE: 389

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
                 35                  40                  45

Ser Ser Ile Asp Pro Glu Gly Arg Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ile Gly Gly Arg Ser Ala Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180                 185                 190
    Ser Ser Leu Gly Thr Gln Thr Tyr Ile Cys Asn Val Asn His Lys Pro
            195                 200                 205
    Ser Asn Thr Lys Val Asp Lys Lys Val Glu Pro Lys Ser Cys Asp Lys
            210                 215                 220
    Thr His Thr Cys Pro Pro Cys Pro Ala Pro Glu Leu Leu Gly Gly Pro
225                 230                 235                 240
    Ser Val Phe Leu Phe Pro Pro Lys Pro Lys Asp Thr Leu Met Ile Ser
            245                 250                 255
    Arg Thr Pro Glu Val Thr Cys Val Val Val Asp Val Ser His Glu Asp
            260                 265                 270
    Pro Glu Val Lys Phe Asn Trp Tyr Val Asp Gly Val Glu Val His Asn
            275                 280                 285
    Ala Lys Thr Lys Pro Arg Glu Glu Gln Tyr Asn Ser Thr Tyr Arg Val
            290                 295                 300
    Val Ser Val Leu Thr Val Leu His Gln Asp Trp Leu Asn Gly Lys Glu
305                 310                 315                 320
    Tyr Lys Cys Lys Val Ser Asn Lys Ala Leu Pro Ala Pro Ile Glu Lys
            325                 330                 335
    Thr Ile Ser Lys Ala Lys Gly Gln Pro Arg Glu Pro Gln Val Tyr Thr
            340                 345                 350
    Leu Pro Pro Ser Arg Glu Glu Met Thr Lys Asn Gln Val Ser Leu Thr
            355                 360                 365
    Cys Leu Val Lys Gly Phe Tyr Pro Ser Asp Ile Ala Val Glu Trp Glu
370                 375                 380
    Ser Asn Gly Gln Pro Glu Asn Asn Tyr Lys Thr Thr Pro Pro Val Leu
385                 390                 395                 400
    Asp Ser Asp Gly Ser Phe Phe Leu Tyr Ser Lys Leu Thr Val Asp Lys
                405                 410                 415
    Ser Arg Trp Gln Gln Gly Asn Val Phe Ser Cys Ser Val Met His Glu
                420                 425                 430
    Ala Leu His Asn His Tyr Thr Gln Lys Ser Leu Ser Leu Ser Pro Gly
            435                 440                 445
    Lys

<210> SEQ ID NO 390
<211> LENGTH: 449
<212> TYPE: PRT
<213> ORGANISM: Artificial Sequence
<220> FEATURE:
<223> OTHER INFORMATION: chemically synthesized

<400> SEQUENCE: 390

Glu Val His Leu Leu Glu Ser Gly Gly Gly Leu Val Gln Pro Gly Gly
1               5                   10                  15
    Ser Leu Arg Leu Ser Cys Ala Ala Ser Gly Phe Thr Phe Ser Ser Tyr
                20                  25                  30
    Ala Met Ser Trp Val Arg Gln Ala Pro Gly Lys Gly Leu Glu Trp Val
                35                  40                  45
    Ser Ser Ile Asp Pro Glu Gly Arg Gln Thr Tyr Tyr Ala Asp Ser Val
            50                  55                  60
    Lys Gly Arg Phe Thr Ile Ser Arg Asp Asn Ser Lys Asn Thr Leu Tyr
65                  70                  75                  80
    Leu Gln Met Asn Ser Leu Arg Ala Glu Asp Thr Ala Val Tyr Tyr Cys
                85                  90                  95
```

```
Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 391
<211> LENGTH: 214
<212> TYPE: PRT
<213> ORGANISM: Artificial Sequence
<220> FEATURE:
<223> OTHER INFORMATION: chemically synthesized

<400> SEQUENCE: 391
```

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 392
<211> LENGTH: 48
<212> TYPE: PRT
<213> ORGANISM: Artificial Sequence
<220> FEATURE:
<223> OTHER INFORMATION: chemically synthesized

<400> SEQUENCE: 392

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Ser Gly Gly Gly
            20                  25                  30

Ser Gly Leu Ser Gly Arg Ser Asp Asn His Gly Ser Ser Gly Thr Gln
            35                  40                  45

<210> SEQ ID NO 393
<211> LENGTH: 10
<212> TYPE: PRT
<213> ORGANISM: Artificial Sequence
<220> FEATURE:
<223> OTHER INFORMATION: chemically synthesized

<400> SEQUENCE: 393

Ser Asp Asn His Gly Ser Ser Gly Thr Gln
1               5                   10

<210> SEQ ID NO 394
<211> LENGTH: 7
<212> TYPE: PRT
<213> ORGANISM: Artificial Sequence
<220> FEATURE:
<223> OTHER INFORMATION: chemically synthesized

<400> SEQUENCE: 394

His Gly Ser Ser Gly Thr Gln
1               5

<210> SEQ ID NO 395
<211> LENGTH: 31
<212> TYPE: PRT
<213> ORGANISM: Artificial Sequence
<220> FEATURE:
<223> OTHER INFORMATION: chemically synthesized

<400> SEQUENCE: 395

Gln Gly Gln Ser Gly Gln Cys Ile Ser Pro Arg Gly Cys Pro Asp Gly
1               5                   10                  15

Pro Tyr Val Met Tyr Gly Ser Ser Gly Ser Gly Gly Ser Lys
            20                  25                  30

<210> SEQ ID NO 396
<211> LENGTH: 23
<212> TYPE: PRT
<213> ORGANISM: Artificial Sequence
<220> FEATURE:
<223> OTHER INFORMATION: chemically synthesized

<400> SEQUENCE: 396

Gly Ser Ser Gly Gly Ser Gly Gly Ser Gly Gly Ser Gly Gly Ser Gly
1               5                   10                  15

Gly Gly Gly Ser Gly Gly Ser
            20

<210> SEQ ID NO 397
<211> LENGTH: 45
<212> TYPE: PRT
<213> ORGANISM: Artificial Sequence
<220> FEATURE:
<223> OTHER INFORMATION: chemically synthesized

<400> SEQUENCE: 397

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly Ser Gly Gly
            20                  25                  30

Leu Ser Gly Arg Ser Asp Asn His Gly Gly Ser Lys
        35                  40                  45

<210> SEQ ID NO 398
<211> LENGTH: 8
<212> TYPE: PRT
<213> ORGANISM: Artificial Sequence
<220> FEATURE:
<223> OTHER INFORMATION: chemically synthesized

<400> SEQUENCE: 398

Leu Lys Ala Ala Pro Arg Trp Ala
1               5

<210> SEQ ID NO 399
<211> LENGTH: 8
<212> TYPE: PRT
<213> ORGANISM: Artificial Sequence
<220> FEATURE:
<223> OTHER INFORMATION: chemically synthesized

```
<400> SEQUENCE: 399

Gly Pro Ser His Leu Val Leu Thr
1               5

<210> SEQ ID NO 400
<211> LENGTH: 8
<212> TYPE: PRT
<213> ORGANISM: Artificial Sequence
<220> FEATURE:
<223> OTHER INFORMATION: chemically synthesized

<400> SEQUENCE: 400

Leu Pro Gly Gly Leu Ser Pro Trp
1               5

<210> SEQ ID NO 401
<211> LENGTH: 8
<212> TYPE: PRT
<213> ORGANISM: Artificial Sequence
<220> FEATURE:
<223> OTHER INFORMATION: chemically synthesized

<400> SEQUENCE: 401

Met Gly Leu Phe Ser Glu Ala Gly
1               5

<210> SEQ ID NO 402
<211> LENGTH: 8
<212> TYPE: PRT
<213> ORGANISM: Artificial Sequence
<220> FEATURE:
<223> OTHER INFORMATION: chemically synthesized

<400> SEQUENCE: 402

Ser Pro Leu Pro Leu Arg Val Pro
1               5

<210> SEQ ID NO 403
<211> LENGTH: 8
<212> TYPE: PRT
<213> ORGANISM: Artificial Sequence
<220> FEATURE:
<223> OTHER INFORMATION: chemically synthesized

<400> SEQUENCE: 403

Arg Met His Leu Arg Ser Leu Gly
1               5

<210> SEQ ID NO 404
<211> LENGTH: 8
<212> TYPE: PRT
<213> ORGANISM: Artificial Sequence
<220> FEATURE:
<223> OTHER INFORMATION: chemically synthesized

<400> SEQUENCE: 404

Leu Ala Ala Pro Leu Gly Leu Leu
1               5

<210> SEQ ID NO 405
<211> LENGTH: 8
<212> TYPE: PRT
<213> ORGANISM: Artificial Sequence
<220> FEATURE:
<223> OTHER INFORMATION: chemically synthesized
```

<400> SEQUENCE: 405

Ala Val Gly Leu Leu Ala Pro Pro
1               5

<210> SEQ ID NO 406
<211> LENGTH: 8
<212> TYPE: PRT
<213> ORGANISM: Artificial Sequence
<220> FEATURE:
<223> OTHER INFORMATION: chemically synthesized

<400> SEQUENCE: 406

Leu Leu Ala Pro Ser His Arg Ala
1               5

<210> SEQ ID NO 407
<211> LENGTH: 8
<212> TYPE: PRT
<213> ORGANISM: Artificial Sequence
<220> FEATURE:
<223> OTHER INFORMATION: chemically synthesized

<400> SEQUENCE: 407

Pro Ala Gly Leu Trp Leu Asp Pro
1               5

<210> SEQ ID NO 408
<211> LENGTH: 7
<212> TYPE: PRT
<213> ORGANISM: Artificial Sequence
<220> FEATURE:
<223> OTHER INFORMATION: chemically synthesized

<400> SEQUENCE: 408

Ile Ser Ser Gly Leu Ser Ser
1               5

<210> SEQ ID NO 409
<211> LENGTH: 768
<212> TYPE: DNA
<213> ORGANISM: Artificial Sequence
<220> FEATURE:
<223> OTHER INFORMATION: chemically synthesized

<400> SEQUENCE: 409

| | | | | | |
|---|---|---|---|---|---|
| tgcatctcac | ctcgtggttg | tccggacggc | ccatacgtca | tgtacggctc | gagcggtggc | 60 |
| agcggtggct | ctggtggatc | cggtctgagc | ggccgttccg | ataatcatgg | cagtagcggt | 120 |
| acccagatct | tgctgaccca | gagcccggtg | attctgagcg | tgagcccggg | cgaacgtgtg | 180 |
| agctttagct | gccgcgcgag | ccagagcatt | ggcaccaaca | ttcattggta | tcagcagcgc | 240 |
| accaacggca | gcccgcgcct | gctgattaaa | tatgcgagcg | aaagcattag | cggcattccg | 300 |
| agccgcttta | gcggcagcgg | cagcggcacc | gattttaccc | tgagcattaa | cagcgtggaa | 360 |
| agcgaagata | ttgcggatta | ttattgccag | cagaacaaca | actggccgac | cacctttggc | 420 |
| gcgggcacca | aactggaact | gaaacgtacg | gtggctgcac | catctgtctt | catcttcccg | 480 |
| ccatctgatg | agcagttgaa | atctggaact | gcctctgttg | tgtgcctgct | gaataacttc | 540 |
| tatcccagag | aggccaaagt | acagtggaag | gtggataacg | ccctccaatc | gggtaactcc | 600 |
| caggagagtg | tcacagagca | ggacagcaag | gacagcacct | acagcctcag | cagcaccctg | 660 |
| acgctgagca | aagcagacta | cgagaaacac | aaagtctacg | cctgcgaagt | cacccatcag | 720 |
| ggcctgagct | cgcccgtcac | aaagagcttc | aacaggggag | agtgttag | | 768 |

<210> SEQ ID NO 410
<211> LENGTH: 255
<212> TYPE: PRT
<213> ORGANISM: Artificial Sequence
<220> FEATURE:
<223> OTHER INFORMATION: chemically synthesized

<400> SEQUENCE: 410

Cys Ile Ser Pro Arg Gly Cys Pro Asp Gly Pro Tyr Val Met Tyr Gly
1               5                   10                  15

Ser Ser Gly Gly Ser Gly Gly Ser Gly Ser Gly Leu Ser Gly Arg
            20                  25                  30

Ser Asp Asn His Gly Ser Ser Gly Thr Gln Ile Leu Leu Thr Gln Ser
        35                  40                  45

Pro Val Ile Leu Ser Val Ser Pro Gly Glu Arg Val Ser Phe Ser Cys
    50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
    130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255

<210> SEQ ID NO 411
<211> LENGTH: 768
<212> TYPE: DNA
<213> ORGANISM: Artificial Sequence
<220> FEATURE:
<223> OTHER INFORMATION: chemically synthesized

<400> SEQUENCE: 411
tgcatctcac ctcgtggttg tccggacggc ccatacgtca gtacggctc gagcggtggc        60 agcggtggct ctggtggatc cggtctgagc ggccgttccg ataatcatgg cagtagcggt       120
acccagatct tgctgaccca gagcccggtg attctgagcg tgagcccggg cgaacgtgtg       180
agctttagct gccgcgcgag ccagagcatt ggcaccaaca ttcattggta tcagcagcgc       240
accaacggca gcccgcgcct gctgattaaa tatgcgagcg aaagcattag cggcattccg       300

```
agccgcttta gcggcagcgg cagcggcacc gattttaccc tgagcattaa cagcgtggaa    360
agcgaagata ttgcggatta ttattgccag cagaacaaca actggccgac cacctttggc    420
gcgggcacca aactggaact gaaacgtacg gtggctgcac atctgtctt catcttcccg    480 ccatctgatg agcagttgaa atctggaact gcctctgttg tgtgcctgct gaataacttc    540
tatcccagag aggccaaagt acagtggaag gtggataacg ccctccaatc gggtaactcc    600
caggagagtg tcacagagca ggacagcaag gacagcacct acagcctcag cagcaccctg    660
acgctgagca agcagactca cgagaaacac aaagtctacg cctgcgaagt cacccatcag    720
ggcctgagct cgcccgtcac aaagagcttc aacaggggag agtgttag                768
```

<210> SEQ ID NO 412
<211> LENGTH: 255
<212> TYPE: PRT
<213> ORGANISM: Artificial Sequence
<220> FEATURE:
<223> OTHER INFORMATION: chemically synthesized

<400> SEQUENCE: 412

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Leu Ser Gly Arg
            20                  25                  30

Ser Asp Asn His Gly Ser Ser Gly Thr Gln Ile Leu Leu Thr Gln Ser
        35                  40                  45

Pro Val Ile Leu Ser Val Ser Pro Gly Glu Arg Val Ser Phe Ser Cys
    50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
    130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255
```

<210> SEQ ID NO 413
<211> LENGTH: 768
<212> TYPE: DNA
<213> ORGANISM: Artificial Sequence
<220> FEATURE:
<223> OTHER INFORMATION: chemically synthesized

<400> SEQUENCE: 413

```
tgcatctcac ctcgtggttg tccggacggc ccatacgtca tgtacggctc gagcggtggc    60
agcggtggct ctggtggatc cggtctgagc ggccgttccg ataatcatgg cagtagcggt   120
acccagatct tgctgaccca gagcccggtg attctgagcg tgagcccggg cgaacgtgtg   180
agctttagct gccgcgcgag ccagagcatt ggcaccaaca ttcattggta tcagcagcgc   240
accaacggca gcccgcgcct gctgattaaa tatgcgagcg aaagcattag cggcattccg   300
agccgcttta gcggcagcgg cagcggcacc gattttaccc tgagcattaa cagcgtggaa   360
agcgaagata ttgcggatta ttattgccag cagaacaaca actggccgac cacctttggc   420
gcgggcacca aactggaact gaaacgtacg gtggctgcac catctgtctt catcttcccg   480
ccatctgatg agcagttgaa atctggaact gcctctgttg tgtgcctgct gaataacttc   540
tatcccagag aggccaaagt acagtggaag gtggataacg ccctccaatc gggtaactcc   600
caggagagtg tcacagagca ggacagcaag gacagcacct acagcctcag cagcaccctg   660
acgctgagca agcagactac gagaaacac aaagtctacg cctgcgaagt cacccatcag   720
ggcctgagct cgcccgtcac aaagagcttc aacaggggag agtgttag                768
```

<210> SEQ ID NO 414
<211> LENGTH: 255
<212> TYPE: PRT
<213> ORGANISM: Artificial Sequence
<220> FEATURE:
<223> OTHER INFORMATION: chemically synthesized

<400> SEQUENCE: 414

```
Cys Ile Ser Pro Arg Gly Cys Pro Asp Gly Pro Tyr Val Met Tyr Gly
1               5                   10                  15
Ser Ser Gly Gly Ser Gly Gly Ser Gly Gly Ser Gly Leu Ser Gly Arg
                20                  25                  30
Ser Asp Asn His Gly Ser Ser Gly Thr Gln Ile Leu Leu Thr Gln Ser
            35                  40                  45
Pro Val Ile Leu Ser Val Ser Pro Gly Glu Arg Val Ser Phe Ser Cys
        50                  55                  60
Arg Ala Ser Gln Ser Ile Gly Thr Asn Ile His Trp Tyr Gln Gln Arg
65                  70                  75                  80
Thr Asn Gly Ser Pro Arg Leu Leu Ile Lys Tyr Ala Ser Glu Ser Ile
                85                  90                  95
Ser Gly Ile Pro Ser Arg Phe Ser Gly Ser Gly Ser Gly Thr Asp Phe
            100                 105                 110
Thr Leu Ser Ile Asn Ser Val Glu Ser Glu Asp Ile Ala Asp Tyr Tyr
        115                 120                 125
Cys Gln Gln Asn Asn Asn Trp Pro Thr Thr Phe Gly Ala Gly Thr Lys
    130                 135                 140
Leu Glu Leu Lys Arg Thr Val Ala Ala Pro Ser Val Phe Ile Phe Pro
145                 150                 155                 160
Pro Ser Asp Glu Gln Leu Lys Ser Gly Thr Ala Ser Val Val Cys Leu
                165                 170                 175
Leu Asn Asn Phe Tyr Pro Arg Glu Ala Lys Val Gln Trp Lys Val Asp
            180                 185                 190
Asn Ala Leu Gln Ser Gly Asn Ser Gln Glu Ser Val Thr Glu Gln Asp
        195                 200                 205
```

```
Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
            245                 250                 255
```

<210> SEQ ID NO 415
<211> LENGTH: 1347
<212> TYPE: DNA
<213> ORGANISM: Artificial Sequence
<220> FEATURE:
<223> OTHER INFORMATION: chemically synthesized

<400> SEQUENCE: 415

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtgtcaagt attgacccgg aaggtcggca gacatattac     180
gcagactccg tgaagggccg gttcaccatc tccagagaca attccaagaa cacgctgtat     240
ctgcaaatga acagcctgag agccgaggac acggccgtat attactgtgc gaaagacatc     300
ggcggcaggt cggcctttga ctactggggc cagggaaccc tggtcaccgt ctcctcagct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gacccctgag      780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 416
<211> LENGTH: 449
<212> TYPE: PRT
<213> ORGANISM: Artificial Sequence
<220> FEATURE:
<223> OTHER INFORMATION: chemically synthesized

<400> SEQUENCE: 416

```
Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly

Lys

<210> SEQ ID NO 417
<211> LENGTH: 774
<212> TYPE: DNA
<213> ORGANISM: Artificial Sequence
<220> FEATURE:
<223> OTHER INFORMATION: chemically synthesized

<400> SEQUENCE: 417

```
caaggccagt ctggccagtg caatatttgg ctcgtaggtg gtgattgcag gggctggcag      60
gggggctcga gcggtggcag cggtggctct ggtggtctga gcggccgttc cgataatcat     120
ggcggcggtt ctgacatcca gatgacccag tctccatcct ccctgtctgc atctgtagga     180
gacagagtca ccatcacttg ccgggcaagt cagagcatta gcagctattt aaattggtat     240
cagcagaaac cagggaaagc ccctaagctc ctgatctatg cggcatccag tttgcaaagt     300
ggggtcccat caaggttcag tggcagtgga tctgggacag atttcactct caccatcagc     360
agtctgcaac ctgaagattt tgcaacttac tactgtcaac agacggttgt ggcgcctccg     420
ttattcggcc aagggaccaa ggtggaaatc aaacgtacgg tggctgcacc atctgtcttc     480
atcttcccgc catctgatga gcagttgaaa tctggaactg cctctgttgt gtgcctgctg     540
aataacttct atcccagaga ggccaaagta cagtggaagg tggataacgc cctccaatcg     600
ggtaactccc aggagagtgt cacagagcag gacagcaagg acagcaccta cagcctcagc     660
agcaccctga cgctgagcaa agcagactac gagaaacaca agtctacgc ctgcgaagtc      720
acccatcagg gcctgagctc gcccgtcaca aagagcttca caggggaga gtgt            774
```

<210> SEQ ID NO 418
<211> LENGTH: 258
<212> TYPE: PRT
<213> ORGANISM: Artificial Sequence
<220> FEATURE:
<223> OTHER INFORMATION: chemically synthesized

<400> SEQUENCE: 418

```
Gln Gly Gln Ser Gly Gln Cys Asn Ile Trp Leu Val Gly Gly Asp Cys
1               5                   10                  15
Arg Gly Trp Gln Gly Gly Ser Ser Gly Gly Ser Gly Ser Gly Gly
            20                  25                  30
Leu Ser Gly Arg Ser Asp Asn His Gly Gly Gly Ser Asp Ile Gln Met
        35                  40                  45
Thr Gln Ser Pro Ser Ser Leu Ser Ala Ser Val Gly Asp Arg Val Thr
    50                  55                  60
Ile Thr Cys Arg Ala Ser Gln Ser Ile Ser Ser Tyr Leu Asn Trp Tyr
65                  70                  75                  80
Gln Gln Lys Pro Gly Lys Ala Pro Lys Leu Leu Ile Tyr Ala Ala Ser
                85                  90                  95
Ser Leu Gln Ser Gly Val Pro Ser Arg Phe Ser Gly Ser Gly Ser Gly
            100                 105                 110
Thr Asp Phe Thr Leu Thr Ile Ser Ser Leu Gln Pro Glu Asp Phe Ala
        115                 120                 125
Thr Tyr Tyr Cys Gln Gln Thr Val Val Ala Pro Pro Leu Phe Gly Gln
    130                 135                 140
Gly Thr Lys Val Glu Ile Lys Arg Thr Val Ala Ala Pro Ser Val Phe
145                 150                 155                 160
```

Ile Phe Pro Pro Ser Asp Glu Gln Leu Lys Ser Gly Thr Ala Ser Val
              165                 170                 175

Val Cys Leu Leu Asn Asn Phe Tyr Pro Arg Glu Ala Lys Val Gln Trp
          180                 185                 190

Lys Val Asp Asn Ala Leu Gln Ser Gly Asn Ser Gln Glu Ser Val Thr
      195                 200                 205

Glu Gln Asp Ser Lys Asp Ser Thr Tyr Ser Leu Ser Ser Thr Leu Thr
  210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
              245                 250                 255

Glu Cys

<210> SEQ ID NO 419
<211> LENGTH: 756
<212> TYPE: DNA
<213> ORGANISM: Artificial Sequence
<220> FEATURE:
<223> OTHER INFORMATION: chemically synthesized

<400> SEQUENCE: 419
tgcaatattt ggctcgtagg tggtgattgc aggggctggc aggggggctc gagcggtggc        60
agcggtggct ctggtggtct gagcggccgt tccgataatc atggcggcgg ttctgacatc       120
cagatgaccc agtctccatc ctccctgtct gcatctgtag gagacagagt caccatcact       180
tgccgggcaa gtcagagcat tagcagctat ttaaattggt atcagcagaa accagggaaa       240
gcccctaagc tcctgatcta tgcggcatcc agtttgcaaa gtggggtccc atcaaggttc       300
agtggcagtg gatctgggac agatttcact ctcaccatca gcagtctgca acctgaagat       360
tttgcaactt actactgtca acagacggtt gtggcgcctc cgttattcgg ccaagggacc       420
aaggtggaaa tcaaacgtac ggtggctgca ccatctgtct tcatcttccc gccatctgat       480
gagcagttga aatctggaac tgcctctgtt gtgtgcctgc tgaataactt ctatcccaga       540
gaggccaaag tacagtggaa ggtggataac gccctccaat cgggtaactc ccaggagagt       600
gtcacagagc aggacagcaa ggacagcacc tacagcctca gcagcaccct gacgctgagc       660
aaagcagact acgagaaaca caaagtctac gcctgcgaag tcacccatca gggcctgagc       720
tcgcccgtca caaagagctt caacagggga gagtgt                                  756

<210> SEQ ID NO 420
<211> LENGTH: 252
<212> TYPE: PRT
<213> ORGANISM: Artificial Sequence
<220> FEATURE:
<223> OTHER INFORMATION: chemically synthesized

<400> SEQUENCE: 420

Cys Asn Ile Trp Leu Val Gly Gly Asp Cys Arg Gly Trp Gln Gly Gly
1               5                   10                  15

Ser Ser Gly Gly Ser Gly Gly Ser Gly Gly Leu Ser Gly Arg Ser Asp
              20                  25                  30

Asn His Gly Gly Gly Ser Asp Ile Gln Met Thr Gln Ser Pro Ser Ser
          35                  40                  45

Leu Ser Ala Ser Val Gly Asp Arg Val Thr Ile Thr Cys Arg Ala Ser
      50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250

<210> SEQ ID NO 421
<211> LENGTH: 267
<212> TYPE: PRT
<213> ORGANISM: Artificial Sequence
<220> FEATURE:
<223> OTHER INFORMATION: chemically synthesized

<400> SEQUENCE: 421

Cys Asn Ile Trp Leu Val Gly Gly Asp Cys Arg Gly Trp Gln Gly Gly
1               5                   10                  15

Ser Ser Gly Gly Ser Gly Gly Ser Gly Gly Ser Gly Gly Ser Gly Ser
                20                  25                  30

Gly Gly Ser Gly Gly Ser Gly Gly Ser Gly Gly Ser Gly Gly Ser Gly Gly
            35                  40                  45

Ser Gly Gly Ser Asp Ile Gln Met Thr Gln Ser Pro Ser Ser Leu
        50                  55                  60

Ser Ala Ser Val Gly Asp Arg Val Thr Ile Thr Cys Arg Ala Ser Gln
65                  70                  75                  80

Ser Ile Ser Ser Tyr Leu Asn Trp Tyr Gln Gln Lys Pro Gly Lys Ala
                85                  90                  95

Pro Lys Leu Leu Ile Tyr Ala Ala Ser Ser Leu Gln Ser Gly Val Pro
            100                 105                 110

Ser Arg Phe Ser Gly Ser Gly Ser Gly Thr Asp Phe Thr Leu Thr Ile
        115                 120                 125

Ser Ser Leu Gln Pro Glu Asp Phe Ala Thr Tyr Tyr Cys Gln Gln Thr
130                 135                 140

Val Val Ala Pro Pro Leu Phe Gly Gln Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 422
<211> LENGTH: 252
<212> TYPE: PRT
<213> ORGANISM: Artificial Sequence
<220> FEATURE:
<223> OTHER INFORMATION: chemically synthesized

<400> SEQUENCE: 422

Cys Asn Ile Trp Leu Val Gly Gly Asp Cys Arg Gly Trp Gln Gly Gly
1               5                   10                  15

Ser Ser Gly Gly Ser Gly Gly Ser Gly Thr Gly Arg Gly Pro Ser
            20                  25                  30

Trp Val Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
    50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250

<210> SEQ ID NO 423
<211> LENGTH: 252

<212> TYPE: PRT
<213> ORGANISM: Artificial Sequence
<220> FEATURE:
<223> OTHER INFORMATION: chemically synthesized

<400> SEQUENCE: 423

Cys Asn Ile Trp Leu Val Gly Gly Asp Cys Arg Gly Trp Gln Gly Gly
1               5                   10                  15

Ser Ser Gly Gly Ser Gly Gly Ser Gly Gly Gly Ser Pro
            20                  25                  30

Leu Gly Leu Gly Gly Ser Asp Ile Gln Met Thr Gln Ser Pro Ser Ser
            35                  40                  45

Leu Ser Ala Ser Val Gly Asp Arg Val Thr Ile Thr Cys Arg Ala Ser
50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
            115                 120                 125

Thr Val Val Ala Pro Pro Leu Phe Gly Gln Gly Thr Lys Val Glu Ile
130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
            195                 200                 205

Ser Thr Tyr Ser Leu Ser Ser Thr Leu Thr Leu Ser Lys Ala Asp Tyr
210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250

<210> SEQ ID NO 424
<211> LENGTH: 257
<212> TYPE: PRT
<213> ORGANISM: Artificial Sequence
<220> FEATURE:
<223> OTHER INFORMATION: chemically synthesized

<400> SEQUENCE: 424

Gly Cys Asn Ile Trp Leu Asn Gly Gly Asp Cys Arg Gly Trp Val Asp
1               5                   10                  15

Pro Leu Gln Gly Gly Ser Gly Gly Ser Gly Gly Ser Gly Gly Leu
            20                  25                  30

Ser Gly Arg Ser Asp Asn His Gly Gly Ser Asp Ile Gln Met Thr
            35                  40                  45

Gln Ser Pro Ser Ser Leu Ser Ala Ser Val Gly Asp Arg Val Thr Ile
50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys

<210> SEQ ID NO 425
<211> LENGTH: 1350
<212> TYPE: DNA
<213> ORGANISM: Artificial Sequence
<220> FEATURE:
<223> OTHER INFORMATION: chemically synthesized

<400> SEQUENCE: 425

```
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag gcctggaatg gctgggcgtg atttggagcg gcggcaacac cgattataac     180
accccgttta ccagccgcct gagcattaac aaagataaca gcaaaagcca ggtgtttttt     240
aaaatgaaca gcctgcaaag ccaggatacc gcgatttatt attgcgcgcg cgcgctgacc     300
tattatgatt atgaatttgc gtattggggc cagggcaccc tggtgaccgt gagcgcggct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtaccagagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
```

```
gccaaagggc agccccgaga accacaggtg tacaccctgc ccccatcccg ggatgaactg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                    1350

<210> SEQ ID NO 426
<211> LENGTH: 1410
<212> TYPE: DNA
<213> ORGANISM: Artificial Sequence
<220> FEATURE:
<223> OTHER INFORMATION: chemically synthesized

<400> SEQUENCE: 426
atgtacagga tgcaactcct gtcttgcatt gcactaagtc ttgcacttgt cacgaattcg     60
caggtgcagc tgaaacagag cggcccgggc ctggtgcagc cgagccagag cctgagcatt    120
acctgcaccg tgagcggctt tagcctgacc aactatggcg tgcattgggt gcgccagagc    180
ccgggcaaag gcctggaatg gctgggcgtg atttggagcg gcggcaacac cgattataac    240
accccgttta ccagccgcct gagcattaac aaagataaca gcaaaagcca ggtgtttttt    300
aaaatgaaca gcctgcaaag ccaggatacc gcgatttatt attgcgcgcg cgcgctgacc    360
tattatgatt atgaatttgc gtattggggc cagggcaccc tggtgaccgt gagcgcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtaccaragc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggatgaactg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga                                    1410

<210> SEQ ID NO 427
<211> LENGTH: 449
<212> TYPE: PRT
<213> ORGANISM: Artificial Sequence
<220> FEATURE:
<223> OTHER INFORMATION: chemically synthesized
```

<400> SEQUENCE: 427

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 428
<211> LENGTH: 469
<212> TYPE: PRT
<213> ORGANISM: Artificial Sequence
<220> FEATURE:
<223> OTHER INFORMATION: chemically synthesized

<400> SEQUENCE: 428

Met Tyr Arg Met Gln Leu Leu Ser Cys Ile Ala Leu Ser Leu Ala Leu
1               5                   10                  15

Val Thr Asn Ser Gln Val Gln Leu Lys Gln Ser Gly Pro Gly Leu Val
            20                  25                  30

Gln Pro Ser Gln Ser Leu Ser Ile Thr Cys Thr Val Ser Gly Phe Ser
        35                  40                  45

Leu Thr Asn Tyr Gly Val His Trp Val Arg Gln Ser Pro Gly Lys Gly
    50                  55                  60

Leu Glu Trp Leu Gly Val Ile Trp Ser Gly Gly Asn Thr Asp Tyr Asn
65                  70                  75                  80

Thr Pro Phe Thr Ser Arg Leu Ser Ile Asn Lys Asp Asn Ser Lys Ser
                85                  90                  95

Gln Val Phe Phe Lys Met Asn Ser Leu Gln Ser Gln Asp Thr Ala Ile
            100                 105                 110

Tyr Tyr Cys Ala Arg Ala Leu Thr Tyr Tyr Asp Tyr Glu Phe Ala Tyr
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Gln Ser
305                 310                 315                 320
```

```
Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly Lys
465
```

What is claimed is:

1. A method of detecting the presence or absence of an activatable antibody or conjugated activatable antibody in a subject or a sample, the method comprising:
    contacting a subject or a sample with an antibody or fragment thereof that binds an activatable antibody or conjugated activatable antibody; and
    determining the level of activatable antibody or conjugated activatable antibody in the subject or sample,
    wherein the antibody or fragment thereof comprises a combination of a VH CDR1 sequence, a VH CDR2 sequence, a VH CDR3 sequence, a VL CDR1 sequence, a VL CDR2 sequence, and a VL CDR3 sequence,
    wherein the VH CDR1 sequence comprises an amino acid sequence selected from the group consisting of SEQ ID NOs: 67, 73, 78, 88, 95, and 101; the VH CDR2 sequence comprises an amino acid sequence selected from the group consisting of SEQ ID NOs: 68, 74, 79, 89, 96, and 102; the VH CDR3 sequence comprises an amino acid sequence selected from the group consisting of SEQ ID NOs: 69, 80, 90, and 97; the VL CDR1 sequence comprises an amino acid sequence selected from the group consisting of SEQ ID NOs: 70, 81, and 98; the VL CDR2 sequence comprises an amino acid sequence selected from the group consisting of SEQ ID NOs: 71, 82, and 99; and the VL CDR3 sequence comprises an amino acid sequence selected from the group consisting of SEQ ID NOs: 72, 83, 84, 91, 110, 100, and 103.

2. The method of claim 1, wherein the antibody or fragment thereof has an equilibrium dissociation constant of about 100 nM or less for binding to the activatable antibody or conjugated activatable antibody.

3. The method of claim 1, wherein the antibody or fragment thereof is a monoclonal antibody, domain antibody, single chain, Fab fragment, a F(ab')$_2$ fragment, a scFv, a scAb, a dAb, a single domain heavy chain antibody, or a single domain light chain antibody.

4. The method of claim 1, wherein the antibody or fragment thereof is a rabbit, mouse, chimeric, humanized or fully human monoclonal antibody.

5. The method of claim 1, wherein the antibody or fragment thereof comprises a combination of a VH CDR1 sequence, a VH CDR2 sequence, a VH CDR3 sequence, a VL CDR1 sequence, a VL CDR2 sequence, and a VL CDR3 sequence selected from the group consisting of:
    (a) a VH CDR1 sequence comprising the amino acid sequence of SEQ ID NO: 67; a VH CDR2 sequence comprising the amino acid sequence of SEQ ID NO: 68; a VH CDR3 sequence comprising the amino acid sequence of SEQ ID NO: 69; a VL CDR1 sequence comprising the amino acid sequence of SEQ ID NO: 70; a VL CDR2 sequence comprising the amino acid of SEQ ID NO: 71; and a VL CDR3 sequence comprising the amino acid sequence of SEQ ID NO: 72;
    (b) a VH CDR1 sequence comprising the amino acid sequence of SEQ ID NO: 73; a VH CDR2 sequence comprising the amino acid sequence of SEQ ID NO: 74; a VH CDR3 sequence comprising the amino acid sequence of SEQ ID NO: 69; a VL CDR1 sequence comprising the amino acid sequence of SEQ ID NO: 70; a VL CDR2 sequence comprising the amino acid sequence of SEQ ID NO: 71; and a VL CDR3 sequence comprising the amino acid sequence of SEQ ID NO: 72;
    (c) a VH CDR1 sequence comprising the amino acid sequence of SEQ ID NO: 78; a VH CDR2 sequence comprising the amino acid sequence of SEQ ID NO: 79; a VH CDR3 sequence comprising the amino acid sequence of SEQ ID NO: 80; a VL CDR1 sequence comprising the amino acid sequence of SEQ ID NO: 81; a VL CDR2 sequence comprising the amino acid sequence of SEQ ID NO: 82; and a VL CDR3 sequence comprising the amino acid sequence of SEQ ID NO: 83;
    (d) a VH CDR1 sequence comprising the amino acid sequence of SEQ ID NO: 78; a VH CDR2 sequence comprising the amino acid sequence of SEQ ID NO: 79; a VH CDR3 sequence comprising the amino acid sequence of SEQ ID NO: 80; a VL CDR1 sequence comprising the amino acid sequence of SEQ ID NO: 81; a VL CDR2 sequence comprising the amino acid sequence of SEQ ID NO: 82; and a VL CDR3 sequence comprising the amino acid sequence of SEQ ID NO: 84;

(e) a VH CDR1 sequence comprising the amino acid sequence of SEQ ID NO: 88; a VH CDR2 sequence comprising the amino acid sequence of SEQ ID NO: 89; a VH CDR3 sequence comprising the amino acid sequence of SEQ ID NO: 90; a VL CDR1 sequence comprising the amino acid sequence of SEQ ID NO: 81; a VL CDR2 sequence comprising the amino acid sequence of SEQ ID NO: 82; and a VL CDR3 sequence comprising the amino acid sequence of SEQ ID NO: 91;

(f) a VH CDR1 sequence comprising the amino acid sequence of SEQ ID NO: 88; a VH CDR2 sequence comprising the amino acid sequence of SEQ ID NO: 89; a VH CDR3 sequence comprising the amino acid sequence of SEQ ID NO: 90; a VL CDR1 sequence comprising the amino acid sequence of SEQ ID NO: 81; a VL CDR2 sequence comprising the amino acid sequence of SEQ ID NO: 82; and a VL CDR3 sequence comprising the amino acid sequence of SEQ ID NO: 110;

(g) a VH CDR1 sequence comprising the amino acid sequence of SEQ ID NO: 95; a VH CDR2 sequence comprising the amino acid sequence of SEQ ID NO: 96; a VH CDR3 sequence comprising the amino acid sequence of SEQ ID NO: 97; a VL CDR1 sequence comprising the amino acid sequence of SEQ ID NO: 98; a VL CDR2 sequence comprising the amino acid sequence of SEQ ID NO: 99; and a VL CDR3 sequence comprising the amino acid sequence of SEQ ID NO: 100; and (h) a VH CDR1 sequence comprising the amino acid sequence of SEQ ID NO: 101; a VH CDR2 sequence comprising the amino acid sequence of SEQ ID NO: 102; a VH CDR3 sequence comprising the amino acid sequence of SEQ ID NO: 97; a VL CDR1 sequence comprising the amino acid sequence of SEQ ID NO: 98; a VL CDR2 sequence comprising the amino acid sequence of SEQ ID NO: 99; and a VL CDR3 sequence comprising the amino acid sequence of SEQ ID NO: 103.

6. The method of claim 1, wherein the antibody or fragment thereof comprises a heavy chain variable region amino acid sequence selected from the group consisting of SEQ ID NOs: 42, 56, 60, 64, 77, and 106.

7. The method of claim 1, wherein the antibody or fragment thereof comprises a light chain variable region amino acid sequence selected from the group consisting of SEQ ID NOs: 44, 58, 62, 66, 87, 94, and 109.

8. The method of claim 1, wherein the antibody or fragment thereof comprises a heavy chain variable region amino acid sequence selected from the group consisting of SEQ ID NOs: 42, 56, 60, 64, 77, and 106 and a light chain variable region amino acid sequence selected from the group consisting of SEQ ID NOs: 44, 58, 62, 66, 87, 94, and 109.

9. The method of claim 1, wherein the antibody comprises a heavy chain amino acid sequence selected from the group consisting of SEQ ID NOs: 2, 6, 10, 14, 76, and 105.

10. The method of claim 1, wherein the antibody comprises a light chain amino acid sequence selected from the group consisting of SEQ ID NOs: 4, 8, 12, 16, 86, 93, and 108.

11. The method of claim 1, wherein the antibody comprises a heavy chain amino acid sequence selected from the group consisting of SEQ ID NOs: 2, 6, 10, 14, 76, and 105, and a light chain amino acid sequence selected from the group consisting of SEQ ID NOs: 4, 8, 12, 16, 86, 93, and 108.

12. The method of claim 1, wherein the antibody comprises a combination of a heavy chain and a light chain selected from the group consisting of:
  (a) a heavy chain comprising the amino acid sequence of SEQ ID NO: 2 and a light chain comprising the amino acid sequence of SEQ ID NO: 4;
  (b) a heavy chain comprising the amino acid sequence of SEQ ID NO: 6 and a light chain comprising the amino acid sequence of SEQ ID NO: 8;
  (c) a heavy chain comprising the amino acid sequence of SEQ ID NO: 10 and a light chain comprising the amino acid sequence of SEQ ID NO: 12; and
  (d) a heavy chain comprising the amino acid sequence of SEQ ID NO: 14 and a light chain comprising the amino acid sequence of SEQ ID NO: 16.

13. The method of claim 1, wherein the antibody comprises a combination of a heavy chain variable region and a light chain variable region selected from the group consisting of:
  (a) a heavy chain variable region comprising the amino acid sequence of SEQ ID NO: 42 and a light chain variable region comprising the amino acid sequence of SEQ ID NO: 44;
  (b) a heavy chain variable region comprising the amino acid sequence of SEQ ID NO: 56 and a light chain variable region comprising the amino acid sequence of SEQ ID NO: 58;
  (c) a heavy chain variable region comprising the amino acid sequence of SEQ ID NO: 60 and a light chain variable region comprising the amino acid sequence of SEQ ID NO: 62; and
  (d) a heavy chain variable region comprising the amino acid sequence of SEQ ID NO: 64 and a light chain variable region comprising the amino acid sequence of SEQ ID NO: 66.

14. The method of claim 1, wherein the antibody or fragment thereof is conjugated to an agent.

15. The method of claim 14, wherein the agent is conjugated to the antibody or fragment thereof via a linker.

16. The method of claim 15, wherein the linker is a cleavable linker.

17. The method of claim 15, wherein the linker is a non-cleavable linker.

18. The method of claim 1, wherein the antibody or fragment thereof comprises a detectable moiety.

19. The method of claim 18, wherein the detectable moiety is a diagnostic agent.

20. The method of claim 18, wherein the detectable moiety is an imaging agent, a contrasting agent, an enzyme, a fluorescent label, a chromophore, a dye, one or more metal ions, a radioisotope, or a ligand-based label.

* * * * *